United States Patent
Hanna et al.

(10) Patent No.: US 9,169,279 B2
(45) Date of Patent: *Oct. 27, 2015

(54) CRYSTALLIZATION METHOD AND BIOAVAILABILITY

(75) Inventors: Mazen Hanna, Lutz, FL (US); Ning Shan, Tampa, FL (US); Miranda L. Cheney, Tampa, FL (US); David R. Weyna, Tampa, FL (US); Raymond Houck, Oakmont, PA (US)

(73) Assignee: THAR PHARMACEUTICALS, INC., Pittsburgh, PA (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/567,827

(22) Filed: Aug. 6, 2012

(65) Prior Publication Data

US 2013/0035315 A1 Feb. 7, 2013

Related U.S. Application Data

(63) Continuation-in-part of application No. 12/847,568, filed on Jul. 30, 2010, now Pat. No. 8,399,023, and a continuation-in-part of application No. 13/387,490, filed as application No. PCT/US2010/043916 on Jul.

(Continued)

(51) Int. Cl.
| | |
|---|---|
| A61K 31/675 | (2006.01) |
| A61K 31/195 | (2006.01) |
| A61K 9/14 | (2006.01) |
| C07F 9/6506 | (2006.01) |
| A61K 31/6615 | (2006.01) |

(52) U.S. Cl.
CPC ............... *C07F 9/65061* (2013.01); *A61K 9/14* (2013.01); *A61K 31/6615* (2013.01); *A61K 31/675* (2013.01)

(58) Field of Classification Search
CPC ... A61K 31/675; A61K 31/6615; A61K 9/14; A61K 9/16
USPC .................................... 514/94, 561; 424/489
See application file for complete search history.

(56) References Cited

U.S. PATENT DOCUMENTS

| | | | |
|---|---|---|---|
| 3,959,361 | A | 5/1976 | Krueger et al. |
| 3,961,934 | A | 6/1976 | Ratts |
| 4,939,130 | A | 7/1990 | Jaeggi et al. |
| 5,431,920 | A | 7/1995 | Bechard |
| 5,512,552 | A | 4/1996 | Sohda et al. |

(Continued)

FOREIGN PATENT DOCUMENTS

| | | |
|---|---|---|
| AR | 080072 | 3/2012 |
| AU | 2010278860 A1 | 2/2011 |

(Continued)

OTHER PUBLICATIONS

Vippagunta et al. "Crystalline solid." Advanced Drug Delivery, 2001, vol. 48 pp. 3-26.*

(Continued)

*Primary Examiner* — Shengjun Wang
(74) *Attorney, Agent, or Firm* — J.A. Lindeman & Co., PLLC

(57) ABSTRACT

Preparation and in vitro and in vivo characterization of novel forms of active pharmaceutical ingredients, suitable for pharmaceutical compositions in drug delivery systems for humans.

9 Claims, 47 Drawing Sheets

Related U.S. Application Data 30, 2010, now Pat. No. 8,980,868, application No. 13/567,827, which is a continuation-in-part of application No. PCT/US2011/023427, filed on Feb. 2, 2011, which is a continuation-in-part of application No. 12/847,568, and a continuation-in-part of application No. PCT/US2010/043916, filed on Jul. 30, 2010, and a continuation-in-part of application No. PCT/US2010/043892, filed on Jul. 30, 2010.

(60) Provisional application No. 61/230,222, filed on Jul. 31, 2009, provisional application No. 61/288,036, filed on Dec. 18, 2009, provisional application No. 61/302,110, filed on Feb. 6, 2010, provisional application No. 61/312,879, filed on Mar. 11, 2010, provisional application No. 61/318,503, filed on Mar. 29, 2010, provisional application No. 61/359,544, filed on Jun. 29, 2010, provisional application No. 61/230,234, filed on Jul. 31, 2009, provisional application No. 61/333,041, filed on May 10, 2010, provisional application No. 61/333,028, filed on May 10, 2010, provisional application No. 61/379,814, filed on Sep. 3, 2010, provisional application No. 61/455,778, filed on Oct. 26, 2010, provisional application No. 61/522,116, filed on Aug. 10, 2011.

(56) References Cited

U.S. PATENT DOCUMENTS

| | | |
|---|---|---|
| 6,468,559 B1 | 10/2002 | Chen et al. |
| 6,476,006 B2 | 11/2002 | Flashner-Barak et al. |
| 6,541,454 B1 | 4/2003 | Breuer et al. |
| 6,676,965 B1 | 1/2004 | Lulla et al. |
| 6,676,970 B2 | 1/2004 | Bader et al. |
| 6,677,320 B2 | 1/2004 | Diederich et al. |
| 6,936,275 B2 | 8/2005 | Fassihi et al. |
| 7,008,640 B2 | 3/2006 | Watanabe et al. |
| 7,011,847 B2 | 3/2006 | Lulla et al. |
| 7,038,083 B2 | 5/2006 | Lidor-Hadas et al. |
| 7,192,938 B2 | 3/2007 | Bauss et al. |
| 7,309,698 B2 | 12/2007 | Boyd et al. |
| 7,332,603 B2 | 2/2008 | De Ferra et al. |
| 7,345,088 B2 | 3/2008 | Green et al. |
| 7,354,912 B2 | 4/2008 | Lichtenberger |
| 7,410,957 B2 | 8/2008 | Bauss et al. |
| 7,411,087 B2 | 8/2008 | Patel et al. |
| 7,425,549 B2 | 9/2008 | Little et al. |
| 7,435,827 B2 * | 10/2008 | Aronhime et al. ............ 548/112 |
| 7,439,385 B2 | 10/2008 | Deshpande et al. |
| 7,473,684 B2 | 1/2009 | Harrison et al. |
| 7,528,280 B2 | 5/2009 | Danda et al. |
| 7,582,768 B2 * | 9/2009 | Aronhime et al. ............ 548/112 |
| 7,589,211 B2 | 9/2009 | Aronhime et al. |
| 7,645,459 B2 | 1/2010 | Dansereau et al. |
| 7,645,460 B2 | 1/2010 | Dansereau et al. |
| 7,687,636 B2 * | 3/2010 | Aronhime et al. ............ 548/112 |
| 7,704,977 B2 | 4/2010 | Leonard |
| 7,718,634 B2 | 5/2010 | Bauss et al. |
| 7,820,722 B2 | 10/2010 | Raoof et al. |
| 8,053,429 B2 | 11/2011 | Cumming et al. |
| 8,119,159 B2 | 2/2012 | Cumming et al. |
| 8,158,153 B2 | 4/2012 | Liversidge et al. |
| 8,399,023 B2 * | 3/2013 | Hanna et al. .................. 424/489 |
| 2002/0142996 A1 | 10/2002 | Okuno et al. |
| 2003/0064966 A1 | 4/2003 | Palepu |
| 2003/0091623 A1 | 5/2003 | Cumming et al. |
| 2003/0181421 A1 | 9/2003 | Horowitz et al. |
| 2004/0127466 A1 | 7/2004 | Palepu |
| 2004/0157798 A1 | 8/2004 | Little |
| 2004/0157799 A1 | 8/2004 | Seaman |
| 2004/0176327 A1 | 9/2004 | Okuno et al. |
| 2004/0220264 A1 | 11/2004 | Yu et al. |
| 2004/0230076 A1 | 11/2004 | Lifshitz-Liron et al. |
| 2005/0054616 A1 | 3/2005 | Aronhime et al. |
| 2005/0260262 A1 | 11/2005 | Dansereau et al. |
| 2006/0068010 A1 | 3/2006 | Turner et al. |
| 2006/0069069 A1 | 3/2006 | Kajander et al. |
| 2006/0173009 A1 | 8/2006 | Kanoh et al. |
| 2006/0178439 A1 * | 8/2006 | Mohakhud et al. ............ 514/678 |
| 2006/0210639 A1 | 9/2006 | Liversidge |
| 2007/0015736 A1 | 1/2007 | Glausch et al. |
| 2007/0021389 A1 * | 1/2007 | Aronhime et al. ............... 514/94 |
| 2007/0021616 A1 | 1/2007 | Aronhime et al. |
| 2007/0021617 A1 | 1/2007 | Aronhime et al. |
| 2007/0021618 A1 | 1/2007 | Aronhime et al. |
| 2007/0021619 A1 | 1/2007 | Aronhime et al. |
| 2007/0049557 A1 | 3/2007 | Ahmed et al. |
| 2007/0088161 A1 | 4/2007 | Stockel et al. |
| 2007/0134319 A1 | 6/2007 | Zannou et al. |
| 2007/0196464 A1 | 8/2007 | Cumming et al. |
| 2007/0218130 A1 | 9/2007 | Ahmed et al. |
| 2007/0225258 A1 | 9/2007 | Walsh |
| 2007/0238707 A1 | 10/2007 | Leonard |
| 2008/0090784 A1 | 4/2008 | Labriola et al. |
| 2008/0139514 A1 | 6/2008 | Gore et al. |
| 2008/0153784 A1 | 6/2008 | Zhang et al. |
| 2008/0153785 A1 | 6/2008 | Shin et al. |
| 2008/0167271 A1 | 7/2008 | Masini-Eteve |
| 2008/0249069 A1 | 10/2008 | Bauss et al. |
| 2008/0254089 A1 | 10/2008 | Glausch et al. |
| 2008/0255366 A1 | 10/2008 | Mohakhud et al. |
| 2008/0275001 A1 | 11/2008 | Cumming et al. |
| 2008/0286359 A1 | 11/2008 | Dansereau et al. |
| 2008/0287400 A1 | 11/2008 | Dansereau et al. |
| 2009/0023683 A1 | 1/2009 | Kocherlakota et al. |
| 2009/0075941 A1 | 3/2009 | Selander et al. |
| 2009/0082312 A1 | 3/2009 | Czarnik |
| 2009/0137808 A1 | 5/2009 | Samsel et al. |
| 2009/0209763 A1 | 8/2009 | Lidor-Hadas et al. |
| 2009/0215729 A1 | 8/2009 | Johnson et al. |
| 2009/0238876 A1 | 9/2009 | Danenberg et al. |
| 2009/0281064 A1 | 11/2009 | Ahmed et al. |
| 2010/0029596 A1 | 2/2010 | Ryu et al. |
| 2010/0047306 A1 | 2/2010 | Loeffler et al. |
| 2010/0056481 A1 | 3/2010 | Glausch et al. |
| 2010/0086593 A1 | 4/2010 | Dansereau et al. |
| 2010/0113394 A1 | 5/2010 | Dansereau et al. |
| 2010/0113395 A1 | 5/2010 | Dansereau et al. |
| 2010/0119559 A1 | 5/2010 | Dansereau et al. |
| 2010/0215743 A1 | 8/2010 | Leonard |
| 2010/0248640 A1 | 9/2010 | Macnaughtan et al. |
| 2011/0028435 A1 | 2/2011 | Hanna et al. |
| 2011/0182985 A1 | 7/2011 | Coughlan et al. |
| 2011/0263537 A1 | 10/2011 | Desai |

FOREIGN PATENT DOCUMENTS

| | | |
|---|---|---|
| AU | 2011218625 A1 | 9/2011 |
| CN | 102070668 B | 7/2013 |
| CN | 103070668 | 7/2013 |
| EP | 1154761 A1 | 11/2001 |
| EP | 1392325 A1 | 3/2004 |
| EP | 1567533 A2 | 8/2005 |
| EP | 1591122 A1 | 11/2005 |
| EP | 1612212 A1 | 1/2006 |
| EP | 1880744 A1 | 1/2008 |
| EP | 1925621 A1 | 5/2008 |
| JP | 2003-520240 | 7/2003 |
| JP | 2004-528303 A | 9/2004 |
| JP | 2008-533173 A | 8/2008 |
| WO | WO 92/14474 A1 | 9/1992 |
| WO | WO 95/08331 A1 | 3/1995 |
| WO | WO 96/07417 A1 | 3/1996 |
| WO | WO 97/05903 A2 | 2/1997 |
| WO | WO 98/52547 A1 | 11/1998 |
| WO | WO 98/56360 A2 | 12/1998 |
| WO | WO 00/21541 A1 | 4/2000 |
| WO | WO 00/50012 A1 | 8/2000 |
| WO | 00/61111 | 10/2000 |
| WO | WO 00/64516 A1 | 11/2000 |
| WO | WO 01/52859 A1 | 7/2001 |

(56) References Cited

FOREIGN PATENT DOCUMENTS

| | | |
|---|---|---|
| WO | WO 01/82903 A1 | 11/2001 |
| WO | WO 01/97788 A2 | 12/2001 |
| WO | WO 02/080933 A1 | 10/2002 |
| WO | WO 02/087554 A2 | 11/2002 |
| WO | WO 02/089816 A1 | 11/2002 |
| WO | 03/007916 A1 | 1/2003 |
| WO | WO 03/051373 A1 | 6/2003 |
| WO | WO 2004/024165 A1 | 3/2004 |
| WO | WO 2004/035061 A1 | 4/2004 |
| WO | WO 2004/056373 A1 | 7/2004 |
| WO | WO 2004/075860 A2 | 9/2004 |
| WO | WO 2004/078161 A1 | 9/2004 |
| WO | WO 2004/078163 A2 | 9/2004 |
| WO | WO 2004/100941 A1 | 11/2004 |
| WO | WO 2005/000404 A2 | 1/2005 |
| WO | WO 2005/005447 A2 | 1/2005 |
| WO | WO 2005/025551 A2 | 3/2005 |
| WO | WO 2005/037157 A1 | 4/2005 |
| WO | WO 2005/044831 A2 | 5/2005 |
| WO | WO 2005/048979 A2 | 6/2005 |
| WO | WO 2005/063218 A2 | 7/2005 |
| WO | WO 2005/063717 A1 | 7/2005 |
| WO | WO 2005/099676 A2 | 10/2005 |
| WO | 2005/115331 A2 | 12/2005 |
| WO | 2006/020009 A1 | 2/2006 |
| WO | WO 2006/018033 A1 | 2/2006 |
| WO | WO 2006/019843 A1 | 2/2006 |
| WO | 2006/039499 A2 | 4/2006 |
| WO | WO 2006/066067 A2 | 6/2006 |
| WO | WO 2006/080780 A1 | 8/2006 |
| WO | WO 2006/102117 A1 | 9/2006 |
| WO | 2006/112889 A1 | 10/2006 |
| WO | WO 2007/016982 A1 | 2/2007 |
| WO | WO 2007/023342 A2 | 3/2007 |
| WO | WO 2007/032808 A1 | 3/2007 |
| WO | WO 2007/069049 A2 | 6/2007 |
| WO | WO 2007/093226 A1 | 8/2007 |
| WO | WO 2007/117706 A2 | 10/2007 |
| WO | WO 2007/125521 A2 | 11/2007 |
| WO | WO 2007/146234 A2 | 12/2007 |
| WO | WO 2008/040763 A1 | 4/2008 |
| WO | WO 2008/058722 A1 | 5/2008 |
| WO | WO 2008/064849 A1 | 6/2008 |
| WO | WO 2008/085281 A1 | 7/2008 |
| WO | WO 2008/100767 A1 | 8/2008 |
| WO | WO 2008/113177 A1 | 9/2008 |
| WO | WO 2009/018834 A1 | 2/2009 |
| WO | WO 2009/035265 A2 | 3/2009 |
| WO | WO 2009/040818 A1 | 4/2009 |
| WO | WO 2009/042179 A1 | 4/2009 |
| WO | WO 2009/056952 A1 | 5/2009 |
| WO | WO 2009/068567 A1 | 6/2009 |
| WO | WO 2009/072119 A2 | 6/2009 |
| WO | WO 2009/107850 A2 | 9/2009 |
| WO | WO 2009/112493 A1 | 9/2009 |
| WO | WO 2009/121935 A2 | 10/2009 |
| WO | 2010/014765 A1 | 2/2010 |
| WO | 2010/014766 A1 | 2/2010 |
| WO | WO 2010/060619 A1 | 6/2010 |
| WO | WO 2010/071866 A2 | 6/2010 |
| WO | WO 2010/099255 A1 | 9/2010 |
| WO | WO 2011/014781 A1 | 2/2011 |
| WO | WO 2011/097269 A1 | 8/2011 |
| WO | WO 2011/097269 A9 | 8/2011 |
| WO | WO 2011/132826 A1 | 10/2011 |
| WO | WO 2012/071517 A2 | 5/2012 |

OTHER PUBLICATIONS

Ulrich "Crystallization" Chaptor 4, Kirk-Othmer Encyclopedia of Cheimical Technology, John Wiley and Sons, 2002.*
International Search Report and Written Opinion for PCT International Application No. PCT/US2010/043916, dated Sep. 27, 2010.
European Search Report for PCT/US2010/043916 dated Jan. 15, 2013.
Supplemental European Search Report for PCT/US2011/023427, dated Dec. 10, 2013.
McNamara et al. "Use of Glutaric Acid Cocrystal to Improve Bioavailability of a Low Solubility API," Pharmaceutical Research, Aug. 2006, vol. 23, No. 8, pp. 1888-1897; p. 1899, para. 4; p. 1889, para 8 to p. 1890, para 1; p. 1891, Fig. 4; p. 1894, para 2.
Bronner, "Intestinal Calcium Absorption: Mechanisms and Applications," J. Nutr. 1347-1352 (1987).
Bronner, "Current Concepts of Calcium Absorption: An Overview," J. Nutr. 122:642-643 (1992).
Dupuis et al., "Does the Inihbition of Microvillus Protein Phosphorylation by Lysine Explain the Activity of the Latter on Calcium Transfer?" J. Biochem. 13:1163-1170 (1981).
Dupuis et al., "Enterocyte Microvillus Can Phosphorylate Molecules Which Inhibit Endogenous Phosphorylation of its Proteins," Archives Internationales de Physiologie et de Biochimie 92:1-11 (1984).
Gueguen et al., "The Bioavailability of Dietary Calcium," J. Am. Col. Nutr. 19(2):119S-136S (2000).
Wasserman et al., "The Influence of Amino Acids and Other Organic Compounds on the Gastrointestinal Absorption of Calcium and Strontium in the Rat," J. Nutr. 371-383 (1956).
Atelvia Prescribing Information.
International Search Report and Written Opinion of PCT PCT/US11/23427 dated Apr. 22, 2011.
PCT International Search Report of PCT International Application No. PCT/US2010/043892, dated Feb. 11, 2011.
Written Opinion of the International Searching Authority of PCT International Application No. PCT/US2020/043892, dated Feb. 11, 2011.
PCT International Search Report and Written Opinion of PCT International Application No. PCT/US2011/062050, dated Apr. 10, 2012.
Coleman et al., "The Effects of Adding Zoledronic Acid to Neoadjuvant Chemotherapy on Tumor Response: Exploratory Evidence for Direct Anti-Tumor Activity in Breast Cancer," British J Cancer 102(7):1099-1105 (2010).
Davies et al., "Evaluating the Effects of Zolendronic Acid (ZOL) on Overall Survival (OS) in Patients (Pts) with Multiple Myeloma (MM): Results of the Medical Research Council (MRC) Myeloma IX Study," J Clinical Oncology 28(15): Abstract 8021 (2010).
Gnant et al., "Endocrine Therapy Plus Zolendronic Acid in Premenopausal Breast Cancer," New Englang J Medicine 360(17):679-691 2009).
Sorbera et al., "Zolendronate Disodium. Treatment of Tumor-Induced Hypercalcemia, Angiogenesis Inhibitor," Drugs of the Future, 25(3):259-268 (2000).
Patent Examination Report in Australian Application No. 2012216632 dated Aug. 14, 2014.
Office Action for JP Application No. 2012-552048 dated Sep. 17, 2014.
International Preliminary Report on Patentability in PCT application No. PCT/US2010/043892 dated Feb. 9, 2012.
International Search Report in PCT application No. PCT/US2011/023427 dated Aug. 11, 2011.
International Preliminary Report on Patentability in PCT application No. PCT/US2011/023427 dated Aug. 7, 2012.
International Preliminary Report on Patentability in PCT application No. PCT/US2011/062050 dated Mar. 6, 2014.
Office Action for JP Application No. 2012-523084 dated Aug. 1, 2014.
Examination Report in Australian Application No. 2010278860 dated Aug. 14, 2014.

* cited by examiner

CRYSTALLIZATION METHOD AND BIOAVAILABILITY

CROSS-REFERENCE TO RELATED APPLICATIONS

This application claims priority under 35 USC 120 as a Continuation-in-Part of U.S. patent application Ser. No. 12/847,568, filed Jul. 30, 2010, which claims the benefit of U.S. Provisional Application Nos. 61/230,222 filed Jul. 31, 2009, 61/288,036 filed Dec. 18, 2009, 61/302,110 filed Feb. 6, 2010, 61/312,879 filed Mar. 11, 2010, 61/318,503 filed Mar. 29, 2010, and 61/359,544 filed Jun. 29, 2010; and a Continuation-in-Part of U.S. patent application Ser. No. 13/387,490, filed Apr. 13, 2012, which claims the benefit of PCT International Application No. PCT/US2010/043916 filed Jul. 30, 2010, and 61/230,234 filed Jul. 31, 2009; and a Continuation-in-Part of PCT International Application No. PCT/US2011/023427 filed Feb. 2, 2011, which claims the benefit of U.S. Provisional Application Nos. 61/302,110 filed Feb. 6, 2010, 61/333,041 filed May 10, 2010, 61/333,028 filed May 10, 2010, 61/379,814 filed Sep. 3, 2010, 61/455,778 filed Oct. 26, 2010, 61/312,879 filed Mar. 11, 2010, 61/318,503 filed Mar. 29, 2010, 61/359,544 filed Jun. 29, 2010, Ser. No. 12/847,568 filed Jul. 30, 2010, PCT/US10/43916 filed Jul. 30, 2010, and PCT/US10/43892 filed Jul. 30, 2010; and also claims priority under 35 USC §119 to U.S. Provisional Application No. 61/522,116 filed Aug. 10, 2011. The disclosures of each are incorporated herein by reference.

FIELD OF THE INVENTION

This disclosure pertains to improvement of the aqueous solubility and permeability of poorly permeable and sparingly water soluble drug compounds through generating novel crystalline forms of such drugs. The novel forms include but are not limited to cocrystals, salts, hydrates, solvates, solvates of salts, and mixtures thereof. Methods for the preparation and pharmaceutical compositions suitable for drug delivery systems that include one or more of these new forms are disclosed.

BACKGROUND OF THE INVENTION

Many Biopharmaceutics Classification System (BCS) class III or IV drugs suffer from the lack of gastrointestinal (GI) tract membrane permeability leading to poor oral bioavailability. Different strategies have been implemented to improve the permeability and subsequently the oral bioavailability of such drugs. For example, the U.S. patent application 20060068010 describes a formulation method for improving the permeability of drugs and subsequently increasing their bioavailability by granulation of the physical solid mixture of the drug with one or more amino acids, at least one intergranular hydrophilic polymer, and an additional immediate release excipient. Another application WO 200602009 A1 disclosed an increase in the oral bioavailability of poorly permeable bisphosphonate drugs; risedronate, an exemplary bisphosphonate, was mixed with a chelating agent such as ethylenediaminetetraacetic acid (EDTA) and other excipients to make an oral dosage form with enhanced bioavailability. In another application, WO 2007093226 describes a method for improving the bioavailability of ibandronate by generating a physical mixture of the drug together with a modified amino acid (acylation or sulphonation of the amino group with phenyl or cyclohexyl) and other excipients. Another application, WO 2003007916 A1, reports a gastric retention system to improve the bioavailability of a poorly permeable drug, alendronate, which was orally formulated with vitamin D and released an hour after the immediate release of vitamin D. WO 2006080780 discloses yet another method to improve the permeability and bioavailability of alendronate by mixing it with a biocompatible cationic polymer (i.e. water soluble chitosan) with up to a 10:1 weight ratio of the chitosan to the drug, while the resulting mixture can be formulated into a solid or liquid oral dosage form. An additional method of improving permeability of drug materials was discussed in the U.S. patent application 2007/014319 A1, where an oral dosage form was formulated by a powder mixture of a bisphosphonic acid (e.g. zoledronic acid) together with an inactive ingredient (either an ester of a medium chain fatty acid or a lipophilic polyethylene glycol ester). A similar approach was disclosed in the US application 2007/0238707 A1 where a medium chain length fatty acid or its derivative (6-20 carbon atom fatty acid chain) was physically mixed with a poorly permeable drug (e.g. zoledronic acid) in a capsule that was enterically coated.

Zoledronic acid, known as (1-hydroxy-2-imidazol-1-yl-1-phosphono-ethyl)phosphonic acid, is depicted by the following chemical structure:

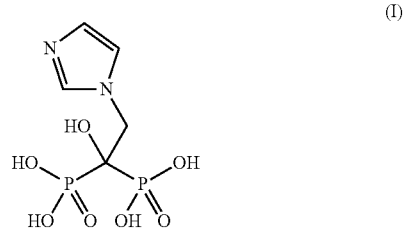 [SMILES: O=P(O)(O)C(O)(Cn1ccnc1)P(=O)(O)O]

(I)

Zoledronic acid is a third generation bisphosphonate which far exceeds the previous generations in terms of efficacy and is used predominately for indications of osteoporosis, Paget's disease, hypercalcemia, and inhibition of bone metastasis. It was originally developed by Novartis and marketed as the monohydrate under the brand names Zometa® and Reclast®. Zoledronic acid was first approved in 2000 for the treatment of hypercalcemia in Canada. It was later approved for use in the US for hypercalcemia in 2001, for multiple myeloma and bone metastases from solid tumors in 2002, and for osteoporosis and Paget's disease in 2007. Clinical trials have also been conducted and are on-going to explore the use of zoledronic acid in neoadjuvant or adjuvant cancer therapy, Coleman, et al., *British J Cancer* 2010; 102(7):1099-1105, Gnant, et al., *New England J Medicine.* 2009, 360 (17):679-691 and Davies, et al. *J Clinical Oncology,* 2010, 28(7s): Abstract 8021. Zoledronic acid is administered as an intravenous (IV) dose of 4 mg over 15 minutes for hypercalcemia of malignancy, multiple myeloma, and bone metastases from solid tumors, while an IV dose of 5 mg over 15 minutes is used for osteoporosis and Paget's disease.

Zoledronic acid is sparingly soluble in water and 0.1 N HCl solution but is freely soluble in 0.1 N NaOH. Zoledronic acid is practically insoluble in various organic solvents. Much effort has been taken to generate novel oral formulations of zoledronic acid through crystallization and metal salt formation to improve its aqueous solubility, permeability, and subsequent oral bioavailability. A crystalline trihydrate was disclosed in the U.S. Patent application 2006/0178439 A1 and world patent application WO2007/032808. Seven hydrated forms, an amorphous form, three monosodium salts, and eleven disodium salts with varying degrees of hydration of zoledronic acid were also disclosed in the patent application WO2005/005447 A2. Zoledronate metal salts including Na$^+$, Mg$^{2+}$, Zn$^{2+}$ were reported in the journal of Drugs of the Future (Sorbera et al, *Drugs of the Future*, 2000, 25(3): 259-268). Zoledronate, zoledronic, or zoledronic salt represents the ionic form of zoledronic acid. Patent application WO2008/064849 A1 from Novartis disclosed additional metal salts including two Ca$^{2+}$ salts, two Zn$^{2+}$ salts, one Mg$^{2+}$ salt, as well as a monohydrate, a trihydrate, an amorphous form, and an anhydrous form.

According to the US Food and Drug Administration (FDA) Summary Basis of Approval (SBA) for zoledronic acid, the poor oral bioavailability (approximately 1%), is partially due to its poor permeability in the GI tract. It was also noted that insoluble metal complexes were formed in the upper intestines, most commonly with calcium. Zoledronic acid has also been shown to cause severe gastric and intestinal irritations.

All of the above attempts to improve the oral bioavailability of zoledronic acid were either focused on improving the aqueous solubility by generating novel solid forms, or by mixing the drug with an inactive ingredient that has enhanced GI tract permeability. The improvement of aqueous solubility failed to improve the bioavailability of zoledronic acid, since the formation of insoluble zoledronate calcium complexes is unlikely to be prevented. On the other hand, powder mixtures of the poorly permeable drug with inactive permeability enhancers improved the bioavailability of the drug. This approach of mixing different materials with different particle sizes and size distributions could result in poor blend/physical mixture uniformity. Constituents of the mixture could also segregate during transportation or with shaking and vibration. Additionally, the powder blends require rigorous batch-to-batch consistency to ensure the uniformity of the blend batches.

The upward trend in the use of oral drugs continues especially in light of the goal to decrease the overall cost of healthcare. Orally administered drugs are becoming more preferred in various therapeutic areas including oncology. Clearly, there is an opportunity to create oral dosage forms of drugs with poor aqueous solubility and/or poor permeability. One such example is zoledronic acid which is only approved for intravenous administration due to its low oral bioavailability, resulting from poor permeability. By using pharmaceutically acceptable and/or approved coformers to hydrogen or ionically bond with an API, novel molecular complexes (e.g. cocrystals, salts, solvates, and mixtures thereof) with improved solubility and/or permeability can be created. These novel molecular complexes could be used in the development of novel oral dosage forms of BCS Class III and IV drugs.

SUMMARY OF THE INVENTION

The present invention addresses the issue of low oral bioavailability using two approaches. The first approach represents a deliberate molecular design in the form of a molecular complex comprising drug and certain excipient(s) (coformer(s)) in a single crystalline structure. The benefit of such a design can reduce batch to batch blend uniformity and particle segregation problems that powder blends often suffer from. In addition, this invention simplifies the manufacturing of a solid dosage form (comprised of drug and excipient) such that the final solid dosage form is, in one embodiment, a particulate or powder of the molecular complex. Additionally, the resulting molecular complexes possess very different physicochemical properties compared to the parent drug or coformer or the physical mixture thereof. These properties include but are not limited to melting point, thermal and electrical conductivity, aqueous solubility, rate of dissolution and permeability across the GI tract membrane. The second approach targets the issue of low permeability of BCS class III and IV drugs. The approach involves combining a low permeability drug with an amino acid which can increase permeability and subsequent oral bioavailability.

The present disclosure is directed towards generating new forms of APIs, e.g., zoledronic acid, with improved physicochemical properties, such as improved aqueous solubility, rate of dissolution, and, particularly, improved permeability resulting in enhanced bioavailability.

One aspect of the present invention includes novel molecular complexes of APIs (e.g., zoledronic acid) in the form of cocrystals, salts, cocrystals of salts and solvates (including hydrates and mixed solvates) thereof. In addition, the disclosure further includes processes of making and methods for using the molecular complexes. The present invention is further directed to compositions comprising a molecular complex and additional or excess coformer, including processes of making and methods of using the same.

The present invention is still further directed to compositions comprising BCS Class III and IV drugs and an 'additional' or 'excess' coformer. In this aspect the role of the coformer is as a functional excipient. The additional coformer of the invention is particularly an amino acid, more particularly lysine or glycine, and more particularly lysine, wherein the coformer, particularly lysine or glycine, more particularly lysine, increases the oral bioavailability of BCS Class III and IV drugs.

In another aspect the present invention provides for a composition comprising a molecular complex, wherein the molecular complex comprises an API and at least one coformer. In one embodiment the molecular complex is a salt. In one embodiment the salt is a crystal. In another embodiment the molecular complex is a cocrystal. In another embodiment the molecular complex is a cocrystal of a salt. In another embodiment the molecular complex is a crystalline two-component molecular complex between the API and a single coformer. In another embodiment the molecular complex is a crystalline three-component molecular complex comprising the API and the at least one coformer. In a further embodiment the crystalline three-component molecular complex consists of the API, a first coformer and a second (different) coformer. In a further embodiment the crystalline three-component molecular complex consists of the API, a coformer and a solvent. In a further embodiment the solvent is water.

In one aspect the molar ratio of coformer to API is about 1:1. In another aspect the coformer is in molar excess to the API. In one embodiment the molar ratio of coformer to API is between about 2:1 and 10:1. In one embodiment the molar ratio of coformer to API is between about 1:1 and 4:1. In one embodiment the molar ratio of coformer to API is between about 1:1 and 3:1. In one embodiment the molar ratio of coformer to API is between about 1:1 and 2:1. In another embodiment the ratio is between about 2:1 and about 5:1. In another embodiment the ratio is about 1.5:1. In another embodiment the ratio is about 2:1. In another embodiment the ratio is about 3:1. In another embodiment the ratio is about 4:1. In another embodiment the ratio is about 5:1

In one aspect the API is in molar excess to the coformer. In one embodiment the molar ration of API to coformer is between about 2:1 and about 10:1. In one embodiment the molar ratio of coformer to API is between about 1:1 and 4:1. In one embodiment the molar ratio of coformer to API is between about 1:1 and 3:1. In one embodiment the molar ratio of coformer to API is between about 1:1 and 2:1 In another embodiment the molar ratio is between about 2:1 and about 5:1. In another embodiment the ratio is about 1.5:1 In another embodiment the molar ratio is about 2:1. In another embodiment the molar ratio is about 3:1. In another embodiment the molar ratio is about 4:1. In another embodiment the molar ratio is about 5:1.

In another aspect the composition of the present invention further comprises 'additional coformer' that is not in the form of a molecular complex with the API. In one embodiment the additional coformer and the coformer that forms a molecular complex with the API (i.e., the 'molecular complex coformer') are the same. In another embodiment the additional coformer and the molecular complex coformer are different. In another embodiment the additional coformer is crystalline. In another embodiment the additional coformer is amorphous. In one embodiment the amount of additional coformer in the composition is greater than the amount of molecular complex coformer. In another embodiment the mass ratio of the additional coformer to the molecular complex coformer is between about 2:1 to about 5000:1. In another embodiment the ratio is between about 1000:1 to about 5000:1. In another embodiment the ratio is between about 1000:1 to about 4000:1. In another embodiment the ratio is between about 2000:1 to about 4000:1. In another embodiment the ratio is between about 1000:1 to about 2000:1. In another embodiment the ratio is between about 100:1 to about 2000:1. In another embodiment the ratio is between about 100:1 to about 1000:1. In another embodiment the ratio is between about 100:1 to about 750:1. In another embodiment the ratio is between about 100:1 to about 500:1. In another embodiment the ratio is between about 100:1 to about 275:1. In another embodiment the ratio is between about 200:1 to about 275:1. In another embodiment the ratio is between about 175:1 to about 275:1. In another embodiment the ratio is between about 150:1 to about 250:1. In another embodiment the ratio is between about 100:1 to about 250:1. In another embodiment the ratio is between about 100:1 to about 200:1. In another embodiment the ratio is between about 50:1 to about 200:1. In another embodiment the ratio is between about 50:1 to about 150:1. In another embodiment the ratio is between about 50:1 to about 100:1. In another embodiment the ratio is between about 2:1 to about 100:1. In another embodiment the ratio is between about 5:1 to about 100:1. In another embodiment the ratio is between about 10:1 to about 100:1. In another embodiment the ratio is between about 11:1 to about 100:1. In another embodiment the ratio is between about 25:1 to about 100:1. In another embodiment the ratio is between about 50:1 to about 100:1. In another embodiment the ratio is between about 75:1 to about 100:1. In another embodiment the ratio is between about 2:1 to about 50:1. In another embodiment the ratio is between about 2:1 to about 25:1. In another embodiment the ratio is between about 2:1 to about 20:1. In another embodiment the ratio is between about 2:1 to about 15:1. In another embodiment the ratio is between about 2:1 to about 10:1. In another embodiment the ratio is between about 2:1 to about 5:1 In another embodiment the ratio is between about 5:1 to about 50:1. In another embodiment the ratio is between about 5:1 to about 25:1. In another embodiment the ratio is between about 5:1 to about 20:1. In another embodiment the ratio is between about 5:1 to about 15:1. In another embodiment the ratio is between about 5:1 to about 10:1. In another embodiment the ratio is between about 10:1 to about 50:1. In another embodiment the ratio is between about 10:1 to about 25:1. In another embodiment the ratio is between about 10:1 to about 20:1. In another embodiment the ratio is between about 10:1 to about 15:1. In another embodiment the ratio is between about 11:1 to about 50:1. In another embodiment the ratio is between about 12:1 to about 50:1. In another embodiment the ratio is between about 13:1 to about 50:1. In another embodiment the ratio is between about 14:1 to about 50:1. In another embodiment the ratio is between about 15:1 to about 50:1. In another embodiment the ratio is between about 25:1 to about 50:1. In another embodiment the ratio is between about 35:1 to about 50:1. In another embodiment the ratio is at least 2:1. In another embodiment the ratio is at least 5:1. In another embodiment the ratio is at least 7.5:1. In another embodiment the ratio is at least 9:1. In another embodiment the ratio is at least 10:1. In another embodiment the ratio is at least 11:1. In another embodiment the ratio is at least 12:1. In another embodiment the ratio is at least 13:1. In another embodiment the ratio is at least 14:1. In another embodiment the ratio is at least 15:1. In another embodiment the ratio is at least 25:1. In another embodiment the ratio is at least 35:1. In another embodiment the ratio is at least 50:1. In another embodiment the ratio is at least 65:1. In another embodiment the ratio is at least 75:1. In another embodiment the ratio is at least 85:1. In another embodiment the ratio is at least 100:1. In another embodiment the ratio is at least 125:1. In another embodiment the ratio is at least 150:1. In another embodiment the ratio is at least 175:1. In another embodiment the ratio is at least 200:1. In another embodiment the ratio is at least 225:1. In another embodiment the ratio is at least 250:1. In another embodiment the ratio is at least 275:1. In another embodiment the ratio is at least 500:1. In another embodiment the ratio is at least 750:1. In another embodiment the ratio is at least 100:1. In another embodiment the ratio is at least 2000:1. In another embodiment the ratio is at least 3000:1. In another embodiment the ratio is at least 4000:1.

In another aspect the invention provides for a composition comprising an API and additional coformer, wherein the API is present in its free form, as a free acid or free base, or present as a salt or cocrystal with one or more coformers that are different from the additional coformer. In one embodiment the amount of additional coformer present in the composition is in excess to the amount of API present in the composition. In another embodiment the mass ratio of the additional coformer to API is between about 2:1 to about 5000:1. In another embodiment the ratio is between about 1000:1 to about 5000:1. In another embodiment the ratio is between about 1000:1 to about 4000:1. In another embodiment the ratio is between about 2000:1 to about 4000:1. In another embodiment the ratio is between about 1000:1 to about 2000:1. In another embodiment the ratio is between about 100:1 to about 2000:1. In another embodiment the ratio is between about 100:1 to about 1000:1. In another embodiment the ratio is between about 100:1 to about 750:1. In another embodiment the ratio is between about 100:1 to about 500:1. In another embodiment the ratio is between about 100:1 to about 275:1. In another embodiment the ratio is between about 200:1 to about 275:1. In another embodiment the ratio is between about 175:1 to about 275:1. In another embodiment the ratio is between about 150:1 to about 250:1. In another embodiment the ratio is between about 100:1 to about 250:1. In another embodiment the ratio is between about 100:1 to about 200:1. In another embodiment the ratio is between about 50:1 to about 200:1. In another embodiment the ratio is between about 50:1 to about 150:1. In another embodiment the ratio is between about 50:1 to about 100:1. In another embodiment the ratio is between about 2:1 to about 100:1. In another embodiment the ratio is between about 5:1 to about 100:1. In another embodiment the ratio is between about 10:1 to about 100:1. In another embodiment the ratio is between about 11:1 to about 100:1. In another embodiment the ratio is between about 11:1 to about 100:1. In another embodiment the ratio is between about 12:1 to about 100:1. In another embodiment the ratio is between about 13:1 to about 100:1. In another embodiment the ratio is between about 14:1 to about 100:1. In another embodiment the ratio is between about 15:1 to about 100:1. In another embodiment the ratio is between about 25:1 to about 100:1. In another embodiment the ratio is between about 50:1 to about 100:1. In another embodiment the ratio is between about 75:1 to about 100:1. In another embodiment the ratio is between about 2:1 to about 50:1. In another embodiment the ratio is between about 2:1 to about 25:1. In another embodiment the ratio is between about 2:1 to about 20:1. In another embodiment the ratio is between about 2:1 to about 15:1. In another embodiment the ratio is between about 2:1 to about 10:1. In another embodiment the ratio is between about 2:1 to about 5:1. In another embodiment the ratio is between about 5:1 to about 50:1. In another embodiment the ratio is between about 5:1 to about 25:1. In another embodiment the ratio is between about 5:1 to about 20:1. In another embodiment the ratio is between about 5:1 to about 15:1. In another embodiment the ratio is between about 5:1 to about 10:1. In another embodiment the ratio is between about 10:1 to about 50:1. In another embodiment the ratio is between about 10:1 to about 25:1. In another embodiment the ratio is between about 10:1 to about 20:1. In another embodiment the ratio is between about 10:1 to about 15:1. In another embodiment the ratio is between about 11:1 to about 50:1. In another embodiment the ratio is between about 12:1 to about 50:1. In another embodiment the ratio is between about 13:1 to about 50:1. In another embodiment the ratio is between about 14:1 to about 50:1. In another embodiment the ratio is between about 15:1 to about 50:1. In another embodiment the ratio is between about 25:1 to about 50:1. In another embodiment the ratio is between about 35:1 to about 50:1. In another embodiment the ratio is at least 2:1. In another embodiment the ratio is at least 5:1. In another embodiment the ratio is at least 7.5:1. In another embodiment the ratio is at least 9:1. In another embodiment the ratio is at least 10:1. In another embodiment the ratio is at least 11:1. In another embodiment the ratio is at least 12:1. In another embodiment the ratio is at least 13:1. In another embodiment the ratio is at least 14:1. In another embodiment the ratio is at least 15:1. In another embodiment the ratio is at least 17.5:1. In another embodiment the ratio is at least 20:1. In another embodiment the ratio is at least 25:1. In another embodiment the ratio is at least 30:1. In another embodiment the ratio is at least 35:1. In another embodiment the ratio is at least 40:1. In another embodiment the ratio is at least 50:1. In another embodiment the ratio is at least 65:1. In another embodiment the ratio is at least 75:1. In another embodiment the ratio is at least 85:1. In another embodiment the ratio is at least 100:1. In another embodiment the ratio is at least 125:1. In another embodiment the ratio is at least 150:1. In another embodiment the ratio is at least 175:1. In another embodiment the ratio is at least 200:1. In another embodiment the ratio is at least 225:1. In another embodiment the ratio is at least 250:1. In another embodiment the ratio is at least 275:1. In another embodiment the ratio is at least 500:1. In another embodiment the ratio is at least 750:1. In another embodiment the ratio is at least 1000:1. In another embodiment the ratio is at least 2000:1. In another embodiment the ratio is at least 3000:1. In another embodiment the ratio is at least 4000:1.

In particular embodiments the invention provides for a composition of Tables 11-15.

In another aspect the coformer of the present invention increases the oral bioavailability of the API. In one embodiment the coformer increases oral bioavailability of the API by at least 10%. In one embodiment the coformer increases oral bioavailability of the API by at least 25%. In one embodiment the coformer increases oral bioavailability of the API by at least 75%. In one embodiment the coformer increases oral bioavailability of the API by at least two fold. In one embodiment the coformer increases oral bioavailability of the API by at least three fold. In one embodiment the coformer increases oral bioavailability of the API by at least five fold.

In another aspect the coformer increases the $C_{max}$ of the API. In one embodiment the coformer increases $C_{max}$ of the API by at least 10%. In one embodiment the coformer increases $C_{max}$ of the API by at least 25%. In one embodiment the coformer increases $C_{max}$ of the API by at least 75%. In one embodiment the coformer increases $C_{max}$ of the API by at least two fold. In one embodiment the coformer increases $C_{max}$ of the API by at least three fold. In one embodiment the coformer increases $C_{max}$ of the API by at least five fold.

In another aspect the coformer reduces the time to the $T_{max}$ of the API. In one embodiment the coformer reduces the time to the $T_{max}$ of the API by at least 10%. In one embodiment the coformer reduces the time to the $T_{max}$ of the API by at least 25%. In one embodiment the coformer reduces the time to the $T_{max}$ of the API by at least 75%. In one embodiment the coformer reduces the time to the $T_{max}$ of the API by at least two fold. In one embodiment the coformer reduces the time to the $T_{max}$ of the API by at least three fold. In one embodiment the coformer reduces the time to the $T_{max}$ of the API by at least five fold.

In another aspect the coformer increases the permeability of the API in the small intestine. In one embodiment the coformer increases the permeability of the API by at least 10%. In one embodiment the coformer increases the permeability of the API by at least 25%. In one embodiment the coformer increases the permeability of the API by at least 75%. In one embodiment the coformer increases the permeability of the API by at least two fold. In one embodiment the coformer increases the permeability of the API by at least three fold. In one embodiment the coformer increases the permeability of the API by at least five fold.

Another aspect of the present invention provides for a method of enhancing the permeability of an API comprising the step of contacting the API with a coformer to form the molecular complex of the present invention.

Another aspect of the present invention provides for a method of enhancing the oral bioavailability of an API comprising the step of contacting the API with a coformer to form the molecular complex of the present invention.

Another aspect of the present invention provides for a method of enhancing the permeability of an API comprising the step of combining the API with a coformer to form a pharmaceutical composition of the present invention.

Another aspect of the present invention provides for a method of enhancing the oral bioavailability of an API comprising the step of combining the API with a coformer to form a pharmaceutical composition of the present invention.

In particular embodiments of the present invention, the API is abacavir, acarbose, acetazolamide, acyclovir, albuterol (salbutamol), allopurinol, amiloride, amisulpride, amlodipine, amoxicillin, amphetamine, atenolol, atropine, azathioprine, benserazide, benznidazole, camostat, captopril, cefdinir, cefotiam hexetil hydrochloride, cefprozil, cefuroxime axetil, chloramphenicol, cimetidine, ciprofloxacin, codeine, colchicine, cyclophosphamide, dapsone, dexamethasone, didanosine, diethylcarbamazine, methionine, dolasetron, doxifluridine, doxycycline, ergonovine, erythromycin ethylsuccinate, ethambutol, ethosuximide, famotidine, fluconazole, folic acid, furosemide, fursultiamine, gabapentin, glipizide, granisetron, griseofulvin, hydralazine, hydrochlorothiazide, imidapril, isoniazid, lamivudine, 1-carbocysteine, levetiracetam, levofloxacin, linezolid, lisinopril, losartan, methotrexate, methyldopa, s-methylmethionine, metoclopramide, metronidazole, moxifloxacin, nalidixic acid, nicorandil, nifurtimox, nitrofurantoin, nizatidine, nystatin, ondansetron, oseltamivir, oxcarbazepine, penicillamine, perindopril, phenobarbital, phenoxymethylpenicillin, pravastatin sodium, prednisolone, primaquine, procaterol, propylthiouracil, pseudoephedrine, pyrazinamide, pyridostigmine bromide, pyridoxine hydrochloride, ranitidine, ribavirin, riboflavin, rizatriptan, stavudine, sulfadiazine, sulfamethoxazole, sultamicillin, sumatriptan, taltirelin, tegafur, tenofovir disoproxil, theophylline, thiamine, trimetazidine, trimethoprim, voglibose, zidovudine, zolmitriptan, acetylcarnitine, capecitabine, cefaclor, cefixime, cefmetazole, cefpodoxime proxetil, cefroxadine, alfoscerate, cilazapril, cimetropium bromide, diacerein, erdosteine, famciclovir, gemifloxacin, levosulpiride, nabumetone, oxiracetam, phendimetrazine, rabeprazole, roxatidine acetate, tamsulosin, terazosin, thioctic, tosufloxacin, triflusal, zaltoprofen, etidronic acid, zoledronic acid, clodronic acid, tiludronic acid, pamidronic acid, alendronic acid, risedronic acid or ibandronic acid.

In one aspect of the present invention the conformer is selected from the group consisting of sodium, ammonium, ammonia, L-lysine, DL-lysine, nicotinamide, adenine, and glycine.

In one aspect of the present invention the coformer is an amino acid. In one embodiment the coformer is L-lysine. In another embodiment the coformer is DL-lysine. In another embodiment the coformer is D-lysine. In another embodiment the coformer is glycine.

Another aspect of the present invention provides for a pharmaceutical composition, wherein the pharmaceutical composition comprises a composition of the present invention. In one aspect the pharmaceutical composition further comprises at least one pharmaceutically acceptable excipient. In another aspect the pharmaceutical composition consists of a molecular complex of the present invention. In another aspect the pharmaceutical composition consists of a molecular complex and an additional coformer of the present invention. In another aspect the pharmaceutical composition is an oral dosage form. In another aspect the pharmaceutical composition is a unit dose.

Another aspect of the present invention provides for a method of treating or preventing a disease for which the API is indicated, the method comprising the step of administering to a patient in need of the API a therapeutically effective amount of a pharmaceutical composition of the present invention. In one aspect the method is for treating such a disease. In another aspect the method is for preventing such as disease.

Another aspect of the present invention provides for a medicament comprising a pharmaceutical composition of the present invention for use in treating or preventing a disease for which the API is indicated. In one aspect the medicament is for use in treating such a disease. In another aspect the medicament is for use in preventing such a disease.

Obvious variants of the disclosed forms in the disclosure, including those described by the drawings, tables and examples, will be readily apparent to the person of ordinary skill in the art having the present disclosure and such variants are considered to be a part of the current invention.

The various aspects and embodiments of the present invention expressly provide for combinations in any consistent manner since providing for all such combinations would unduly lengthen the specification. For example, the ranges provided for the amount of API or coformer apply to any one of the individual API-coformer combination and accordingly, each of which should be considered a specific embodiment of the present invention. To list each such API or coformer combination for each range would needlessly lengthen the specification.

The following detailed description, including Examples, which proceeds with reference to the accompanying drawings and tables are meant to be illustrative, not limiting, of the invention.

DETAILED DESCRIPTION OF THE PREFERRED EMBODIMENTS

Figure 1:
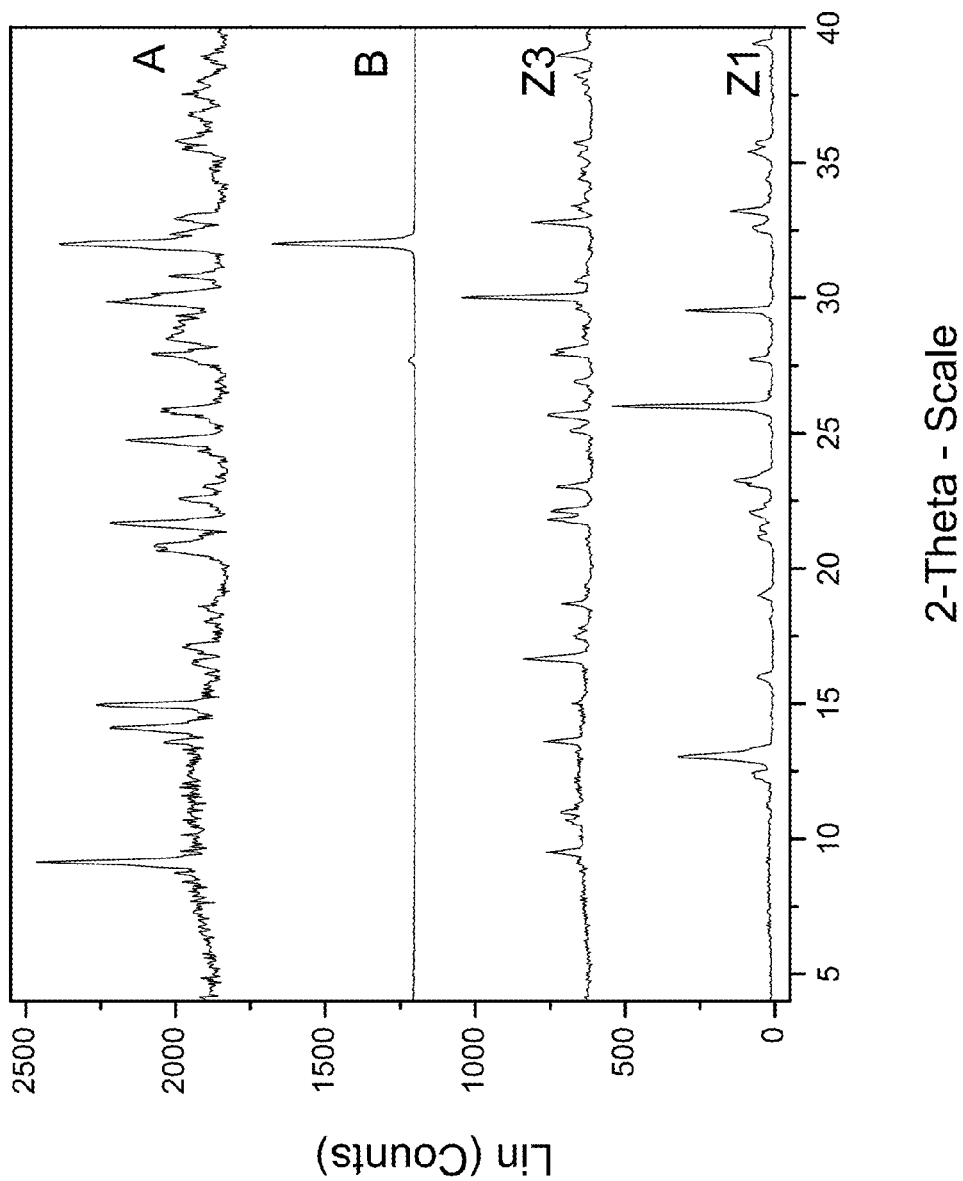
FIG. 1 shows PXRD diffractograms of: (A=zoledronic acid, sodium zoledronic salt and water complex), (B=NaCl), (Z1=Zoledronic acid monohydrate), (Z3=Zoledronic acid trihydrate).

Novel API forms and formulations provide an opportunity to improve the performance characteristics of a pharmaceutical product. The present disclosure is directed to new forms of active pharmaceutical ingredients (APIs) with improved physicochemical properties, such as improved aqueous solubility, rate of dissolution, and, particularly, increased permeability and bioavailability.

The term 'active pharmaceutical ingredient(s)' or 'API(s)' refers to the substance in a pharmaceutical drug that is biologically active.

As used herein, the terms 'treat', 'treating' or 'treatment' means to alleviate, reduce or abrogate one or more symptoms or characteristics of a disease and may be curative, palliative, prophylactic or slow the progression of the disease. The term 'therapeutically effective amount' is intended to mean that amount of drug that will elicit a desired biological or pharmacological response, i.e., an amount sufficient to treat said disease.

The term 'patient' includes mammals, especially humans. In one embodiment the patient is a human. In another embodiment the patient is a human male. In another embodiment the patient is a human female.

The term 'excipient' refers to a pharmaceutically acceptable, inactive substance used as a carrier for the pharmaceutically active ingredient(s) and includes antiadherents, binders, coatings, disintegrants, fillers, diluents, flavors, bulkants, colours, glidants, dispersing agents, wetting agents, lubricants, preservatives, sorbents and sweeteners. The choice of excipient(s) will depend on factors such as the particular mode of administration and the nature of the dosage form. The term 'functional excipient' refers to an excipient that improves the oral bioavailability of a drug, e.g., by increasing absorption, e.g., increasing paracellular and/or transcellular permeability, or increasing aqueous solubility.

The term 'oral bioavailability' is defined as $AUC_{oral} \cdot dose_{i.v.} / AUC_{i.v.} \cdot dose_{oral} \cdot 100\%$.

The term 'significant' or 'significantly' is determined by t-test at 0.05 level of significance.

The term 'molecular complex' refers to a material comprised of two or more unique molecules (in the case of a cocrystal) or ions (in the case of a salt) that are bonded together, and wherein one of the molecule/ions is an API and another of the molecule/ions is a coformer. The API and coformer are bonded either through ionic bonds (in the case of a salt) or hydrogen bonds (in the case of a cocrystal), or a combination of both ionic and hydrogen bonds in the case of a cocrystal of a salt. Other modes of molecular recognition may also be present including, pi-stacking, guest-host complexation and van der Waals interactions. The term also includes solvates, including hydrates, thereof.

The term 'cocrystal' refers to a crystalline material comprised of two or more unique molecules that are solids at room temperature, wherein one of the molecules is an API and one of the molecules is a coformer, wherein the API and coformer are both solids at room temperature and are bonded together by hydrogen bonds. Other modes of molecular recognition may also be present including, pi-stacking, guest-host complexation and van der Waals interactions. The term includes solvates of cocrystals, i.e., a solvated cocrystal, including hydrates of the same.

The term 'salt' refers to an ionic compound resulting from the neutralization reaction of an acid and a base, and in the case of a composition of the present invention, whereby one of the ions is an API and one of the ions, of an opposite charge, is a coformer, whereby the product is neutral (without a net charge).

The term 'coformer' refers to either (or both) a 'molecular complex coformer' or an 'additional coformer' (excess coformer'). The term 'molecular complex coformer' refers to a coformer that is a component of a molecular complex with an API. The terms 'additional coformer' or 'excess coformer' refers to a coformer of the present invention that is not bound to the API as part of a molecular complex, i.e., wherein the coformer is a 'functional excipient'. An 'additional coformer' or 'excess coformer' may be present in addition to a 'molecular complex coformer' or may be present in the absence of a 'molecular complex coformer' (e.g., when an API is a free acid or free base).

The term 'unit dose' refers to the amount of API administered to a patient in a single dose.

The present invention is directed in part to pharmaceutical compositions with increased permeability. In one aspect increased permeability is achieved through the addition of a coformer to a pharmaceutical composition comprising an API, wherein the coformer is an amino acid.

In one aspect the API is in the form of a molecular complex with the amino acid or other coformer. In another aspect a portion of the amino acid is in the form of a molecular complex with the API (as a molecular complex coformer) and a portion is not bound to the API (as an additional coformer). In one embodiment the API-amino acid molecular complex is a cocrystal. In another embodiment the API and amino acid molecular complex is a salt. In one embodiment the salt is crystalline. In another embodiment the amino acid not bound to the API is crystalline (as an additional coformer only).

In another aspect the invention provides for a pharmaceutical composition comprising an amino acid and an API, wherein the API is a BCS Class III or IV drug. In one embodiment the API is abacavir. In another embodiment the API is acarbose. In another embodiment the API is acetazolamide. In another embodiment the API is acyclovir. In another embodiment the API is albuterol (salbutamol). In another embodiment the API is allopurinol. In another embodiment the API is amiloride. In another embodiment the API is amisulpride. In another embodiment the API is amlodipine. In another embodiment the API is amoxicillin. In another embodiment the API is amphetamine. In another embodiment the API is atenolol. In another embodiment the API is atropine. In another embodiment the API is azathioprine. In another embodiment the API is benserazide. In another embodiment the API is benznidazole. In another embodiment the API is camostat. In another embodiment the API is captopril. In another embodiment the API is cefdinir. In another embodiment the API is cefotiam hexetil hydrochloride. In another embodiment the API is cefprozil. In another embodiment the API is cefuroxime axetil. In another embodiment the API is chloramphenicol. In another embodiment the API is cimetidine. In another embodiment the API is ciprofloxacin. In another embodiment the API is codeine. In another embodiment the API is colchicine. In another embodiment the API is cyclophosphamide. In another embodiment the API is dapsone. In another embodiment the API is dexamethasone. In another embodiment the API is didanosine. In another embodiment the API is diethylcarbamazine. In another embodiment the API is methionine. In another embodiment the API is dolasetron. In another embodiment the API is doxifluridine. In another embodiment the API is doxycycline. In another embodiment the API is ergonovine. In another embodiment the API is erythromycin ethylsuccinate. In another embodiment the API is ethambutol. In another embodiment the API is ethosuximide. In another embodiment the API is famotidine. In another embodiment the API is fluconazole. In another embodiment the API is folic acid. In another embodiment the API is furosemide. In another embodiment the API is fursultiamine. In another embodiment the API is gabapentin. In another embodiment the API is glipizide. In another embodiment the API is granisetron. In another embodiment the API is griseofulvin. In another embodiment the API is hydralazine. In another embodiment the API is hydrochlorothiazide. In another embodiment the API is imidapril. In another embodiment the API is isoniazid. In another embodiment the API is lamivudine. In another embodiment the API is 1-carbocysteine. In another embodiment the API is levetiracetam. In another embodiment the API is levofloxacin. In another embodiment the API is linezolid. In another embodiment the API is lisinopril. In another embodiment the API is losartan. In another embodiment the API is methotrexate. In another embodiment the API is methyldopa. In another embodiment the API is s-methylmethionine. In another embodiment the API is metoclopramide. In another embodiment the API is metronidazole. In another embodiment the API is moxifloxacin. In another embodiment the API is nalidixic acid. In another embodiment the API is nicorandil. In another embodiment the API is nifurtimox. In another embodiment the API is nitrofurantoin. In another embodiment the API is nizatidine. In another embodiment the API is nystatin. In another embodiment the API is ondansetron. In another embodiment the API is oseltamivir. In another embodiment the API is oxcarbazepine. In another embodiment the API is penicillamine. In another embodiment the API is perindopril. In another embodiment the API is phenobarbital. In another embodiment the API is phenoxymethylpenicillin. In another embodiment the API is pravastatin sodium. In another embodiment the API is prednisolone. In another embodiment the API is primaquine. In another embodiment the API is procaterol. In another embodiment the API is propylthiouracil. In another embodiment the API is pseudoephedrine. In another embodiment the API is pyrazinamide. In another embodiment the API is pyridostigmine bromide. In another embodiment the API is pyridoxine hydrochloride. In another embodiment the API is ranitidine. In another embodiment the API is ribavirin. In another embodiment the API is riboflavin. In another embodiment the API is rizatriptan. In another embodiment the API is stavudine. In another embodiment the API is sulfadiazine. In another embodiment the API is sulfamethoxazole. In another embodiment the API is sultamicillin. In another embodiment the API is sumatriptan. In another embodiment the API is taltirelin. In another embodiment the API is tegafur. In another embodiment the API is tenofovir disoproxil. In another embodiment the API is theophylline. In another embodiment the API is thiamine. In another embodiment the API is trimetazidine. In another embodiment the API is trimethoprim. In another embodiment the API is voglibose. In another embodiment the API is zidovudine. In another embodiment the API is zolmitriptan. In another embodiment the API is acetylcarnitine. In another embodiment the API is capecitabine. In another embodiment the API is cefaclor. In another embodiment the API is cefixime. In another embodiment the API is cefmetazole. In another embodiment the API is cefpodoxime proxetil. In another embodiment the API is cefroxadine. In another embodiment the API is alfoscerate. In another embodiment the API is cilazapril. In another embodiment the API is cimetropium bromide. In another embodiment the API is diacerein. In another embodiment the API is erdosteine. In another embodiment the API is famciclovir. In another embodiment the API is gemifloxacin. In another embodiment the API is levosulpiride. In another embodiment the API is nabumetone. In another embodiment the API is oxiracetam. In another embodiment the API is phendimetrazine. In another embodiment the API is rabeprazole. In another embodiment the API is roxatidine acetate. In another embodiment the API is tamsulosin. In another embodiment the API is terazosin. In another embodiment the API is thioctic. In another embodiment the API is tosufloxacin. In another embodiment the API is triflusal. In another embodiment the API is zaltoprofen. In another embodiment the API is etidronic acid. In another embodiment the API is zoledronic acid. In another embodiment the API is clodronic acid. In another embodiment the API is tiludronic acid. In another embodiment the API is pamidronic acid. In another embodiment the API is alendronic acid. In another embodiment the API is risedronic acid. In another embodiment the API is ibandronic acid. For each of the above APIs the name includes the free form as well as salts, cocrystals, and/or solvates where consistent with the invention.

In one aspect the amino acid is a standard amino acid. In particular embodiments the amino acid is isoleucine, alanine, leucine, asparagine, lysine, aspartic acid, methionine, cysteine, phenylalanine, glutamic acid, threonine, glutamine, tryptophan, glycine, valine, proline, serine, tyrosine arginine or histidine. In another embodiment the amino acid is selenocysteine, ornithine or taurine. In further particular embodiments the amino acid is the L-form (e.g., L-lysine). In other particular embodiments the amino acid is the D-form (e.g., D-lysine). In other particular embodiments the amino acid is the DL-form (e.g., DL-lysine).

In one embodiment the API is a BCS Class III or IV drug and the amino acid is lysine or glycine. In another embodiment the API is a BCS Class III or IV drug and the amino acid is L-lysine. In further particular embodiments the L-lysine is an L-lysine hydrate. In further particular embodiments the L-lysine is an L-lysine salt. In further particular embodiments the L-lysine salt is an L-lysine HCl salt. In another embodiment the API is a BCS Class III or IV drug and the amino acid is D-lysine. In further particular embodiments the D-lysine is a D-lysine hydrate. In further particular embodiments the D-lysine is a D-lysine salt. In further particular embodiments the D-lysine salt is a D-lysine HCl salt. In another embodiment the API is a BCS Class III or IV drug and the amino acid is DL-lysine. In further particular embodiments the DL-lysine is a DL-lysine hydrate. In further particular embodiments the DL-lysine is a DL-lysine monohydrate. In further particular embodiments the DL-lysine is a DL-lysine salt. In further particular embodiments the DL-lysine salt is a DL-lysine HCl salt. In other particular embodiments the composition is a composition of Tables 11-15.

In one aspect, compositions of the present invention comprising an amino acid have increased permeability of the API (compared to the corresponding composition without the amino acid). In one embodiment the compositions comprising an amino acid have increased paracellular transport of the API. In another embodiment the compositions comprising an amino acid have increased transcellular transport of the API. The increase in permeability results in an increase in bioavailability of the API. Thus the compositions of the present invention are particularly advantageous for oral dosage forms.

In one aspect the pharmaceutical compositions of the present invention comprising an amino acid have increased the oral bioavailability of the API (compared to the corresponding composition without the amino acid). In one embodiment the increase in oral bioavailability is at least 10%. In another embodiment the increase in oral bioavailability is at least 25%. In another embodiment the increase in oral bioavailability is at least 50%. In another embodiment the increase in oral bioavailability is at least 75%. In another embodiment the increase in oral bioavailability is at least two fold. In another embodiment the increase in oral bioavailability is at least three fold.

In one aspect the majority of the increase in oral bioavailability is due to the presence of the amino acid. In one embodiment the amino acid as a molecular complex coformer and/or as an additional coformer is the only component of a pharmaceutical composition that significantly increases the oral bioavailability of the API. In one embodiment the increase in oral bioavailability is achieved without the need of additional excipients, e.g., an intra-granular hydrophilic polymer.

Another aspect of the present invention provides for a method of enhancing the permeability of an API comprising the step of combining the API with an amino acid to form a pharmaceutical composition of the present invention. In another aspect the API is a BCS Class III or IV drug. In one embodiment the API is a BCS Class III or IV drug and the amino acid is L-lysine. In a further particular embodiments the L-lysine is a L-lysine salt or hydrate, including L-lysine HCl. In another embodiment the API is a BCS Class III or IV drug and the amino acid is DL-lysine. In a further particular embodiments the DL-lysine is a DL-lysine salt or hydrate, including DL-lysine monohydrate. In another embodiment the API is a BCS Class III or IV drug and the amino acid is D-lysine. In another embodiment the API is a BCS Class III or IV drug and the amino acid is glycine.

In one aspect the pharmaceutical composition consists of or consists essentially of an API and an amino acid. In one embodiment the pharmaceutical composition consists of or consists essentially of a BCS Class III or IV drug and one or more amino acids. In one embodiment the pharmaceutical composition consists of or consists essentially of a BCS Class III or IV drug and L-lysine. In another embodiment the pharmaceutical composition consists of or consists essentially of a BCS Class III or IV drug and DL-lysine. In a further aspect the pharmaceutical composition consists of or consists essentially of a BCS Class III or IV drug and D-lysine. In one embodiment of the present invention the coformer is glycine. In another embodiment the pharmaceutical composition further includes at least one pharmaceutically acceptable excipient.

In one aspect the pharmaceutical composition is an oral dosage form. In one embodiment the oral dosage form is a solid oral dosage form. In one embodiment the oral dosage form is a liquid oral dosage form. In one embodiment the liquid oral dosage form is a solution. In another embodiment the liquid oral dosage form is a suspension. In one embodiment the oral dosage form is a semi-solid oral dosage form.

In another aspect the pharmaceutical composition is a unit dose. In one embodiment the unit dose comprises at least 100 mg of amino acid. In another embodiment the unit dose comprises at least 250 mg of amino acid. In another embodiment the unit dose comprises at least 500 mg of amino acid. In another embodiment the unit dose comprises at least 750 mg of amino acid. In another embodiment the unit dose comprises at least 800 mg of amino acid. In another embodiment the unit dose comprises at least 900 mg of amino acid. In another embodiment the unit dose comprises at least 1000 mg of amino acid. In another embodiment the unit dose comprises at least 1100 mg of amino acid. In another embodiment the unit dose comprises at least 1250 mg of amino acid. In another embodiment the unit dose comprises at least 1750 mg of amino acid. In another embodiment the unit dose comprises at least 2000 mg of amino acid. In another embodiment the unit dose comprises at least 2250 mg of amino acid. In another embodiment the unit dose comprises at least 2500 mg of amino acid. In another embodiment the unit dose comprises at least 2750 mg of amino acid. In another embodiment the unit dose comprises at least 3000 mg of amino acid. In another embodiment the unit dose comprises at least 3250 mg of amino acid. In another embodiment the unit dose comprises at least 3500 mg of amino acid. In another embodiment the unit dose comprises at least 4000 mg of amino acid. In another embodiment the unit dose comprises at least 4500 mg of amino acid. In another embodiment the unit dose comprises at least 5000 mg of amino acid. In another embodiment the unit dose comprises at least 6000 mg of amino acid. In another embodiment the unit dose comprises at least 7000 mg of amino acid. In another embodiment the unit dose comprises at least 8000 mg of amino acid. In another embodiment the unit dose comprises at least 9000 mg of amino acid. In another embodiment the unit dose comprises at least 10 g of amino acid. In another embodiment the unit dose comprises at least 11 g of amino acid. In another embodiment the unit dose comprises at least 12 g of amino acid. In another embodiment the unit dose comprises at least 13 g of amino acid. In another embodiment the unit dose comprises at least 14 g of amino acid. In another embodiment the unit dose comprises at least 15 g of amino acid. In another embodiment the unit dose comprises at least 16 g of amino acid. In another embodiment the unit dose comprises at least 17 g of amino acid. In another embodiment the unit dose comprises at least 18 g of amino acid. In another embodiment the unit dose comprises at least 19 g of amino acid. In another embodiment the unit dose comprises at least 20 g of amino acid. In another embodiment the unit dose comprises between about 50 to about 5000 mg of amino acid. In another embodiment the unit dose comprises between about 100 to about 1000 mg of amino acid. In another embodiment the unit dose comprises between about 500 to about 1000 mg of amino acid. In another embodiment the unit dose comprises between about 750 to about 1000 mg of amino acid. In another embodiment the unit dose comprises between about 500 to about 1500 mg of amino acid. In another embodiment the unit dose comprises between about 500 to about 1250 mg of amino acid. In another embodiment the unit dose comprises between about 750 to about 1500 mg of amino acid. In another embodiment the unit dose comprises between about 750 to about 1250 mg of amino acid. In another embodiment the unit dose comprises between about 1000 to about 5000 mg of amino acid. In another embodiment the unit dose comprises between about 1000 to about 4500 mg of amino acid. In another embodiment the unit dose comprises between about 1000 to about 4000 mg of amino acid. In another embodiment the unit dose comprises between about 1000 to about 3500 mg of amino acid. In another embodiment the unit dose comprises between about 1000 to about 3000 mg of amino acid. In another embodiment the unit dose comprises between about 1000 to about 2500 mg of amino acid. In another embodiment the unit dose comprises between about 1000 to about 2000 mg of amino acid. In another embodiment the unit dose comprises between about 1000 to about 1500 mg of amino acid. In another embodiment the unit dose comprises between about 1250 to about 5000 mg of amino acid. In another embodiment the unit dose comprises between about 1250 to about 4500 mg of amino acid. In another embodiment the unit dose comprises between about 1250 to about 4000 mg of amino acid. In another embodiment the unit dose comprises between about 1250 to about 3500 mg of amino acid. In another embodiment the unit dose comprises between about 1250 to about 3000 mg of amino acid. In another embodiment the unit dose comprises between about 1250 to about 2500 mg of amino acid. In another embodiment the unit dose comprises between about 1250 to about 2000 mg of amino acid. In another embodiment the unit dose comprises between about 1250 to about 1750 mg of amino acid. In another embodiment the unit dose comprises between about 2000 to about 5000 mg of amino acid. In another embodiment the unit dose comprises between about 2000 to about 4500 mg of amino acid. In another embodiment the unit dose comprises between about 2000 to about 4000 mg of amino acid. In another embodiment the unit dose comprises between about 2000 to about 3500 mg of amino acid. In another embodiment the unit dose comprises between about 2000 to about 3000 mg of amino acid. In another embodiment the unit dose comprises between about 2000 to about 2500 mg of amino acid. In another embodiment the unit dose comprises between about 3000 to about 5000 mg of amino acid. In another embodiment the unit dose comprises between about 3000 to about 4500 mg of amino acid. In another embodiment the unit dose comprises between about 3000 to about 4000 mg of amino acid. In another embodiment the unit dose comprises between about 3000 to about 3500 mg of amino acid. In another embodiment the unit dose comprises between about 1 g to about 20 g of amino acid. In another embodiment the unit dose comprises between about 1250 mg to about 20 g of amino acid. In another embodiment the unit dose comprises between about 1500 mg to about 20 g of amino acid. In another embodiment the unit dose comprises between about 1 g to about 10 g of amino acid. In another embodiment the unit dose comprises between about 1250 mg to about 10 g of amino acid. In another embodiment the unit dose comprises between about 1500 mg to about 10 g of amino acid. In another embodiment the unit dose comprises between about 1 g to about 5 g of amino acid. In another embodiment the unit dose comprises between about 1250 mg to about 5 g of amino acid. In another embodiment the unit dose comprises between about 1500 mg to about 5 g of amino acid. In another embodiment the unit dose comprises between about 5 g to about 15 g of amino acid. In another embodiment the unit dose comprises between about 5 g to about 10 g of amino acid. In another embodiment the unit dose comprises between about 7 g to about 10 g of amino acid. In another embodiment the unit dose comprises between about 10 g to about 20 g of amino acid. In another embodiment the unit dose comprises between about 10 g to about 15 g of amino acid. In another embodiment the unit dose comprises between about 10 g to about 12.5 g of amino acid. In another embodiment the unit dose comprises between about 12.5 g to about 20 g of amino acid. In another embodiment the unit dose comprises between about 12.5 g to about 17.5 g of amino acid. In another embodiment the unit dose comprises between about 15 g to about 20 g of amino acid. In another embodiment the unit dose comprises between about 17.5 g to about 20 g of amino acid. In another embodiment the unit dose comprises between about 1 g to about 2 g of amino acid. In another embodiment the lysine is a lysine salt. In another embodiment the lysine is a lysine hydrate. In another embodiment the lysine salt is a lysine HCl salt. In another embodiment the lysine HCl salt is a lysine monohydrochloride salt.

In another embodiment the lysine HCl salt is a lysine dihydrochloride salt. In another embodiment the lysine hydrate is a lysine monohydrate. In another embodiment the amino acid is L-lysine. In another embodiment the L-lysine is a L-lysine salt. In another embodiment the L-lysine is a L-lysine hydrate. In another embodiment the L-lysine salt is a L-lysine HCl salt. In another embodiment the L-lysine HCl salt is a L-lysine monohydrochloride salt. In another embodiment the L-lysine HCl salt is a L-lysine dihydrochloride salt. In another embodiment the L-lysine hydrate is a L-lysine monohydrate. In another embodiment the amino acid is DL-lysine. In another embodiment the DL-lysine is a DL-lysine salt. In another embodiment the DL-lysine is a DL-lysine hydrate. In another embodiment the DL-lysine salt is a DL-lysine HCl salt. In another embodiment the DL-lysine HCl salt is a DL-lysine monohydrochloride salt. In another embodiment the DL-lysine HCl salt is a DL-lysine dihydrochloride salt. In another embodiment the DL-lysine hydrate is a DL-lysine monohydrate. In another embodiment the amino acid is D-lysine. In another embodiment the D-lysine is a D-lysine salt. In another embodiment the D-lysine is a D-lysine hydrate. In another embodiment the D-lysine salt is a D-lysine HCl salt. In another embodiment the D-lysine HCl salt is a D-lysine monohydrochloride salt. In another embodiment the D-lysine HCl salt is a D-lysine dihydrochloride salt. In another embodiment the D-lysine hydrate is a D-lysine monohydrate. In another embodiment the amino acid is glycine. In another embodiment the API is a BCS Class III or IV drug. In one embodiment the drug is a BCS Class III or IV drug and the amino acid is lysine or glycine. In one embodiment the drug is a BCS Class III or IV drug and the amino acid is L-lysine. In one embodiment the drug is a BCS Class III or IV drug and the amino acid is DL-lysine. In one embodiment the drug is a BCS Class III or IV drug and the amino acid is D-lysine. In one embodiment the drug is a BCS Class III or IV drug and the amino acid is glycine. In certain individual embodiments the BCS Class III or IV drug is abacavir, acarbose, acetazolamide, acyclovir, albuterol (salbutamol), allopurinol, amiloride, amisulpride, amlodipine, amoxicillin, amphetamine, atenolol, atropine, azathioprine, benserazide, benznidazole, camostat, captopril, cefdinir, cefotiam hexetil hydrochloride, cefprozil, cefuroxime axetil, chloramphenicol, cimetidine, ciprofloxacin, codeine, colchicine, cyclophosphamide, dapsone, dexamethasone, didanosine, diethylcarbamazine, methionine, dolasetron, doxifluridine, doxycycline, ergonovine, erythromycin ethylsuccinate, ethambutol, ethosuximide, famotidine, fluconazole, folic acid, furosemide, fursultiamine, gabapentin, glipizide, granisetron, griseofulvin, hydralazine, hydrochlorothiazide, imidapril, isoniazid, lamivudine, 1-carbocysteine, levetiracetam, levofloxacin, linezolid, lisinopril, losartan, methotrexate, methyldopa, s-methylmethionine, metoclopramide, metronidazole, moxifloxacin, nalidixic acid, nicorandil, nifurtimox, nitrofurantoin, nizatidine, nystatin, ondansetron, oseltamivir, oxcarbazepine, penicillamine, perindopril, phenobarbital, phenoxymethylpenicillin, pravastatin sodium, prednisolone, primaquine, procaterol, propylthiouracil, pseudoephedrine, pyrazinamide, pyridostigmine bromide, pyridoxine hydrochloride, ranitidine, ribavirin, riboflavin, rizatriptan, stavudine, sulfadiazine, sulfamethoxazole, sultamicillin, sumatriptan, taltirelin, tegafur, tenofovir disoproxil, theophylline, thiamine, trimetazidine, trimethoprim, voglibose, zidovudine, zolmitriptan, acetylcarnitine, capecitabine, cefaclor, cefixime, cefmetazole, cefpodoxime proxetil, cefroxadine, alfoscerate, cilazapril, cimetropium bromide, diacerein, erdosteine, famciclovir, gemifloxacin, levosulpiride, nabumetone, oxiracetam, phendimetrazine, rabeprazole, roxatidine acetate, tamsulosin, terazosin, thioctic, tosufloxacin, triflusal, zaltoprofen, etidronic acid, zoledronic acid, clodronic acid, tiludronic acid, pamidronic acid, alendronic acid, risedronic acid or ibandronic acid.

Another aspect of the present invention provides for a method of treating or preventing a disease for which an API is indicated, the method comprising the step of administering to a patient in need of the API a therapeutically effective amount of a pharmaceutical composition of the present invention comprising the API. In one embodiment the method is for treating such a disease. In another embodiment the method is for preventing such as disease. Another aspect of the present invention provides for a medicament comprising a pharmaceutical composition of the present invention for use in treating or preventing a disease for which the API is indicated. In one embodiment the medicament is for use in treating such a disease. In another embodiment the medicament is for use in preventing such a disease.

Bisphosphonic Acids

One aspect of the present invention relates to new crystalline forms and compositions of bisphosphonic acids. Bisphosphonic acids of the present invention include but are not limited to zoledronic acid, clodronic acid, tiludronic acid, pamidronic acid, alendronic acid, risedronic acid or ibandronic acid. In one aspect the invention relates to zoledronic acid. In another aspect the invention relates to clodronic acid. In another aspect the invention relates to tiludronic acid. In another aspect the invention relates to pamidronic acid. In another aspect the invention relates to alendronic acid. In another aspect the invention relates to risedronic acid. In another aspect the invention relates to ibandronic acid.

For example, a number of novel zoledronic acid forms and compositions with improved properties have been synthesized, characterized, and disclosed herein. Of particular interest are novel crystalline forms of zoledronic acid and compositions comprising zoledronic acid and a standard amino acid with enhanced permeability.

The results with bisphosphonic acids, e.g., zoledronic acid, are both surprising and unexpected. For example, it is known that bisphosphonic acids form insoluble complexes with metal ions such as $Ca^{2+}$. Two means of depleting $Ca^{2+}$ in the small intestine would be to either chelate the metal ion or cause its absorption before it could bind the bisphosphonic acid. Lysine and glycine however, are unable to form a coordinate covalent bond with $Ca^{2+}$ based on their structure. At the physiological pH of the small intestine, which is about 6-6.5 in the duodenum and about 7.5 in the jejunum and ileum, lysine has a net positive charge. Even at a pH of $\geq 10.5$, it will carry only a net negative charge of −1. Similarly, glycine can at most have a net negative charge of −1, occurring at about pH of $\geq 9.7$, and thus, cannot form a coordinate covalent bond with $Ca^{2+}$. At physiological pH, glycine is neutral. Alternatively, if lysine or glycine were acting to increase absorption of $Ca^{2+}$ in the intestine, one would expect that the amino acid would have to be released into the small intestine long before the bisphosphonic acid in order provide enough time for the small intestine to absorb the $Ca^{2+}$ present in the GI tract. PCT publication WO 03/007916 teaches that a $Ca^{2+}$ absorption activator needs to be released into the small intestine at least one hour before the bisphosphonic acid. The compositions of the present invention, on the other hand, do not have additional formulation requirements. The compositions do not require the bisphosphonic acid to be formulated as a delayed release. Further the compositions do not have particular granulation requirements. For example, the compositions do not have to be granulated with a hydrophilic polymer as do the compositions of PCT publication WO 06/039499.

Further unexpected and surprising is the extent to which the compositions of the present invention improve the oral bioavailability of bisphosphonic acids. For example, an oral bioavailability of greater than 8% has been achieved with zoledronic acid (see Leg 37). The data predicts an oral bioavailability well over this with increasing amounts of amino acid. The ability to achieve such high levels of oral bioavailability has the distinct advantage of being able to lower the dose of the drug, thereby increasing safety to the patient. In the case of bisphosphonic acids, side effects center on severe esophageal and GI irritation and ulceration that are worse when stringent dosing guidelines are not followed. A lower dose of bisphosphonic acid should result in reduced esophageal and GI irritation or ulceration and thus, increased safety to the patient. Accordingly, one aspect of the invention is an oral dosage form of a pharmaceutical composition of the present invention comprising a bisphosphonic acid, wherein said pharmaceutical composition has an improved safety profile over the corresponding marketed formulation: in the case of alendronate sodium, marketed as FOSAMAX; etidronate disodium, marketed as DIDRONEL; ibandronate sodium, marketed as BONIVA; pamidronate disodium, marketed as AREDIA; risedronate sodium, marketed as ACTONEL; tiludronate disodium, marketed as SKELID; zoledronic acid, marketed as ZOMETA as a 4 mg dose for hypercalcemia of malignancy, metastatic bone disease, osteoporosis, and Paget's disease and marketed as RECLAST as a 5 mg annual dose for postmenopausal osteoporosis. Another aspect of the invention is an oral dosage form of a pharmaceutical composition of the present invention comprising a bisphosphonic acid, wherein said pharmaceutical composition has reduced esophageal and GI irritation or ulceration over the corresponding bisphosphonic acid or marketed formulation. Another aspect of the invention is an oral dosage form of a pharmaceutical composition of the present invention comprising a bisphosphonic acid, wherein the permeability of said pharmaceutical composition is less affected by food, i.e., wherein said pharmaceutical composition has a reduced food effect, compared to that of the corresponding marketed oral formulation.

In one aspect the pharmaceutical composition comprises a bisphosphonic acid and an amino acid. In one embodiment the pharmaceutical composition comprises zoledronic acid and an amino acid. In one embodiment the amino acid is lysine or glycine. In another embodiment the lysine is a lysine salt. In another embodiment the lysine is a lysine hydrate. In another embodiment the lysine salt is a lysine HCl salt. In another embodiment the lysine HCl salt is a lysine monohydrochloride salt. In another embodiment the lysine HCl salt is a lysine dihydrochloride salt. In another embodiment the lysine hydrate is a lysine monohydrate. In another embodiment the amino acid is L-lysine. In another embodiment the L-lysine is a L-lysine salt. In another embodiment the L-lysine is a L-lysine hydrate. In another embodiment the L-lysine salt is a L-lysine HCl salt. In another embodiment the L-lysine HCl salt is a L-lysine monohydrochloride salt. In another embodiment the L-lysine HCl salt is a L-lysine dihydrochloride salt. In another embodiment the L-lysine hydrate is a L-lysine monohydrate. In another embodiment the amino acid is DL-lysine. In another embodiment the DL-lysine is a DL-lysine salt. In another embodiment the DL-lysine is a DL-lysine hydrate. In another embodiment the DL-lysine salt is a DL-lysine HCl salt. In another embodiment the DL-lysine HCl salt is a DL-lysine monohydrochloride salt. In another embodiment the DL-lysine HCl salt is a DL-lysine dihydrochloride salt. In another embodiment the DL-lysine hydrate is a DL-lysine monohydrate. In another embodiment the amino acid is D-lysine. In another embodiment the D-lysine is a D-lysine salt. In another embodiment the D-lysine is a D-lysine hydrate. In another embodiment the D-lysine salt is a D-lysine HCl salt. In another embodiment the D-lysine HCl salt is a D-lysine monohydrochloride salt. In another embodiment the D-lysine HCl salt is a D-lysine dihydrochloride salt. In another embodiment the D-lysine hydrate is a D-lysine monohydrate. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

One aspect provides for pharmaceutical composition comprising zoledronic acid and an amino acid. In one embodiment the amino acid is lysine or glycine. In another embodiment the lysine is a lysine salt. In another embodiment the lysine is a lysine hydrate. In another embodiment the lysine salt is a lysine HCl salt. In another embodiment the lysine HCl salt is a lysine monohydrochloride salt. In another embodiment the lysine HCl salt is a lysine dihydrochloride salt. In another embodiment the lysine hydrate is a lysine monohydrate. In another embodiment the amino acid is L-lysine. In another embodiment the L-lysine is a L-lysine salt. In another embodiment the L-lysine is a L-lysine hydrate. In another embodiment the L-lysine salt is a L-lysine HCl salt. In another embodiment the L-lysine HCl salt is a L-lysine monohydrochloride salt. In another embodiment the L-lysine HCl salt is a L-lysine dihydrochloride salt. In another embodiment the L-lysine hydrate is a L-lysine monohydrate. In another embodiment the amino acid is DL-lysine. In another embodiment the DL-lysine is a DL-lysine salt. In another embodiment the DL-lysine is a DL-lysine hydrate. In another embodiment the DL-lysine salt is a DL-lysine HCl salt. In another embodiment the DL-lysine HCl salt is a DL-lysine monohydrochloride salt. In another embodiment the DL-lysine HCl salt is a DL-lysine dihydrochloride salt. In another embodiment the DL-lysine hydrate is a DL-lysine monohydrate. In another embodiment the amino acid is D-lysine. In another embodiment the D-lysine is a D-lysine salt. In another embodiment the D-lysine is a D-lysine hydrate. In another embodiment the D-lysine salt is a D-lysine HCl salt. In another embodiment the D-lysine HCl salt is a D-lysine monohydrochloride salt. In another embodiment the D-lysine HCl salt is a D-lysine dihydrochloride salt. In another embodiment the D-lysine hydrate is a D-lysine monohydrate. In another embodiment the amino acid is glycine. In another embodiment the pharmaceutical composition has an improved safety profile over the marketed form. In another embodiment the pharmaceutical composition has reduced esophageal and GI irritation or ulceration over the marketed form. In another embodiment the pharmaceutical composition has reduced food effect over the marketed form. In another embodiment the pharmaceutical composition has reduced esophageal and GI irritation or ulceration over the same pharmaceutical composition except without the amino acid. In another embodiment the pharmaceutical composition has reduced food effect over the same pharmaceutical composition except without the amino acid.

Schematic diagrams for zoledronic acid:amino acid complexes (a zoledronic acid:lysine complex and a zoledronic acid:glycine complex, two embodiments of the invention) are shown below. The diagrams show a molecular structure of the complex and possible interactions between the constituents of the complex which is different from the physical mix of the constituents.

Zoledronic Acid:Lysine Complex

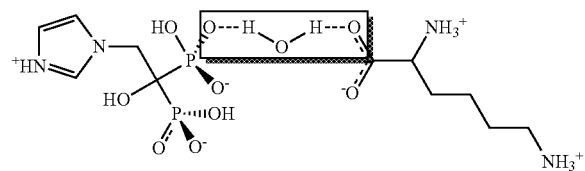

Zoledronic Acid:Glycine Complex

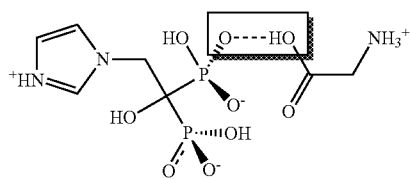

These represent one of the arrangements in which the molecules of the drug and the standard amino acids coformers could interact to form a stable complex that, even when stressed thermally in an elevated relative humidity (RH) environment, have not displayed any signs of deterioration or disintegration to its original constituents. Such stability can be attributed to the hydrogen bonding (dashed line in the box) or ionic interactions in these molecular complexes. When packing in a crystal structure these complexes exhibit a very different spatial arrangement in comparison to that of its constituents or their physical mix as indicated by their powder X-ray diffraction (PXRD) patterns and therefore would possess different, unpredictable physicochemical properties.

The present invention includes new forms and formulations of bisphosphonic acids including zoledronic acid, with improved physicochemical properties, such as improved, safety, stability, aqueous solubility, rate of dissolution, permeability, and/or enhanced bioavailability.

One aspect of the present invention includes novel molecular complexes of bisphosphonic acids (e.g., zoledronic acid) in the form of cocrystals, salts, mixed cocrystal-salts and solvates (e.g. hydrates), as well as combinations of such materials. In addition, the disclosure further includes methods for the preparation of such molecular complexes.

In another aspect the present invention provides for a composition comprising a molecular complex, wherein the molecular complex comprises a bisphosphonic acid or salt thereof and at least one coformer. In one embodiment the molecular complex is a salt. In another embodiment the salt is crystalline. In another embodiment the molecular complex is a cocrystal. In another embodiment the molecular complex is a crystalline two-component molecular complex between the bisphosphonic acid and a single coformer. In another embodiment the molecular complex is a crystalline three-component molecular complex comprising the bisphosphonic acid and at least one coformer. In a further embodiment the crystalline three-component molecular complex consists of the bisphosphonic acid, a first coformer and a second (different) coformer. In a further embodiment the crystalline three-component molecular complex consists of the bisphosphonic acid, a coformer and a solvent. In a further embodiment the solvent is water. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

In one aspect the molar ratio of coformer to bisphosphonic acid in the molecular complex is about 1:1. In another aspect the coformer is in molar excess to the bisphosphonic acid. In one embodiment the molar ratio of coformer to bisphosphonic acid is between about 1:1 and about 5:1. In one embodiment the molar ratio of coformer to bisphosphonic acid is between about 1:1 and about 4:1. In one embodiment the molar ratio of coformer to bisphosphonic acid is between about 1:1 and about 3:1. In one embodiment the molar ratio of coformer to bisphosphonic acid is between about 1:1 and about 2:1. In one embodiment the molar ratio of coformer to bisphosphonic acid is between about 2:1 and about 3:1. In one embodiment the molar ratio of coformer to bisphosphonic acid is between about 2:1 and about 10:1. In a further embodiment the molar ratio is between about 2:1 and about 5:1. In a further embodiment the molar ratio is about 2:1. In another embodiment the molar ratio is about 3:1. In another embodiment the molar ratio is about 4:1. In another embodiment the molar ratio is about 5:1. In another aspect the bisphosphonic acid is in molar excess to the coformer. In one embodiment the molar ratio is between about 1:1 and about 5:1. In one embodiment the molar ratio is between about 1:1 and about 4:1. In one embodiment the molar ratio is between about 1:1 and about 3:1. In one embodiment the molar ratio is between about 1:1 and about 2:1. In one embodiment the molar ratio is between about 2:1 and about 3:1. In one embodiment the molar ratio is between about 2:1 and about 10:1. In another embodiment the molar ratio is between about 2:1 and about 5:1. In another embodiment the molar ratio is about 2:1. In another embodiment the molar ratio is about 3:1. In another embodiment the molar ratio is about 4:1. In another embodiment the molar ratio is about 5:1. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

In one aspect the composition of the present invention further comprises additional coformer. In one embodiment the additional coformer and the coformer that forms a molecular complex with the bisphosphonic acid, i.e., the molecular complex coformer, are the same. In another embodiment the additional coformer and the molecular complex coformer are different. In another embodiment the additional coformer is crystalline. In another embodiment the additional coformer is amorphous. In another embodiment the amount of additional coformer is in excess to the amount of molecular complex coformer. In another embodiment the mass ratio of the additional coformer to the molecular complex coformer is between about 2:1 to about 5000:1. In another embodiment the mass ratio of additional coformer to molecular complex coformer is between about 1000:1 to about 5000:1. In another embodiment the mass ratio of additional coformer to molecular complex coformer is between about 1000:1 to about 4000:1. In another embodiment the mass ratio of additional coformer to molecular complex coformer is between about 2000:1 to about 4000:1. In another embodiment the mass ratio of additional coformer to molecular complex coformer is between about 1000:1 to about 2000:1. In another embodiment the mass ratio of additional coformer to molecular complex coformer is between about 100:1 to about 2000:1. In another embodiment the mass ratio of additional coformer to molecular complex coformer is between about 100:1 to about 1000:1. In another embodiment the mass ratio of additional coformer to molecular complex coformer is between about 100:1 to about 750:1. In another embodiment the mass ratio of additional coformer to molecular complex coformer is between about 100:1 to about 500:1. In another embodiment the mass ratio of additional coformer to molecular complex coformer is between about 100:1 to about 275:1. In another embodiment the mass ratio of additional coformer to molecular complex coformer is between about 200:1 to about 275:1. In another embodiment the mass ratio of additional coformer to molecular complex coformer is between about 175:1 to about 275:1. In another embodiment the mass ratio of additional coformer to molecular complex coformer is between about 150:1 to about 250:1. In another embodiment the mass ratio of additional coformer to molecular complex coformer is between about 100:1 to about 250:1. In another embodiment the mass ratio of additional coformer to molecular complex coformer is between about 100:1 to about 200:1. In another embodiment the mass ratio of additional coformer to molecular complex coformer is between about 50:1 to about 200:1. In another embodiment the mass ratio of additional coformer to molecular complex coformer is between about 50:1 to about 150:1. In another embodiment the mass ratio of additional coformer to molecular complex coformer is between about 50:1 to about 100:1. In another embodiment the mass ratio of additional coformer to molecular complex coformer is between about 2:1 to about 100:1. In another embodiment the mass ratio of additional coformer to molecular complex coformer is between about 5:1 to about 100:1. In another embodiment the mass ratio of additional coformer to molecular complex coformer is between about 10:1 to about 100:1. In another embodiment the mass ratio of additional coformer to molecular complex coformer is between about 11:1 to about 100:1. In another embodiment the mass ratio of additional coformer to molecular complex coformer is between about 25:1 to about 100:1. In another embodiment the mass ratio of additional coformer to molecular complex coformer is between about 50:1 to about 100:1. In another embodiment the mass ratio of additional coformer to molecular complex coformer is between about 75:1 to about 100:1. In another embodiment the mass ratio of additional coformer to molecular complex coformer is between about 2:1 to about 50:1. In another embodiment the mass ratio of additional coformer to molecular complex coformer is between about 2:1 to about 25:1. In another embodiment the mass ratio of additional coformer to molecular complex coformer is between about 2:1 to about 20:1. In another embodiment the mass ratio of additional coformer to molecular complex coformer is between about 2:1 to about 15:1. In another embodiment the mass ratio of additional coformer to molecular complex coformer is between about 2:1 to about 10:1. In another embodiment the mass ratio of additional coformer to molecular complex coformer is between about 2:1 to about 5:1. In another embodiment the mass ratio of additional coformer to molecular complex coformer is between about 5:1 to about 50:1. In another embodiment the mass ratio of additional coformer to molecular complex coformer is between about 5:1 to about 25:1. In another embodiment the mass ratio of additional coformer to molecular complex coformer is between about 5:1 to about 20:1. In another embodiment the mass ratio of additional coformer to molecular complex coformer is between about 5:1 to about 15:1. In another embodiment the mass ratio of additional coformer to molecular complex coformer is between about 5:1 to about 10:1. In another embodiment the mass ratio of additional coformer to molecular complex coformer is between about 10:1 to about 50:1. In another embodiment the mass ratio of additional coformer to molecular complex coformer is between about 10:1 to about 25:1. In another embodiment the mass ratio of additional coformer to molecular complex coformer is between about 10:1 to about 20:1. In another embodiment the mass ratio of additional coformer to molecular complex coformer is between about 10:1 to about 15:1. In another embodiment the mass ratio of additional coformer to molecular complex coformer is between about 11:1 to about 50:1. In another embodiment the mass ratio of additional coformer to molecular complex coformer is between about 15:1 to about 50:1. In another embodiment the mass ratio of additional coformer to molecular complex coformer is between about 25:1 to about 50:1. In another embodiment the mass ratio of additional coformer to molecular complex coformer is between about 35:1 to about 50:1. In another embodiment the mass ratio of additional coformer to molecular complex coformer is at least 2:1. In another embodiment the mass ratio of additional coformer to molecular complex coformer is at least 5:1. In another embodiment the mass ratio of additional coformer to molecular complex coformer is at least 7.5:1. In another embodiment the ratio is at least 9:1. In another embodiment the mass ratio of additional coformer to molecular complex coformer is at least 10:1. In another embodiment the mass ratio of additional coformer to molecular complex coformer is at least 11:1. In another embodiment the mass ratio of additional coformer to molecular complex coformer is at least 15:1. In another embodiment the mass ratio of additional coformer to molecular complex coformer is at least 25:1. In another embodiment the mass ratio of additional coformer to molecular complex coformer is at least 35:1. In another embodiment the mass ratio of additional coformer to molecular complex coformer is at least 50:1. In another embodiment the mass ratio of additional coformer to molecular complex coformer is at least 65:1. In another embodiment the mass ratio of additional coformer to molecular complex coformer is at least 75:1. In another embodiment the mass ratio of additional coformer to molecular complex coformer is at least 85:1. In another embodiment the mass ratio of additional coformer to molecular complex coformer is at least 100:1. In another embodiment the mass ratio of additional coformer to molecular complex coformer is at least 125:1. In another embodiment the mass ratio of additional coformer to molecular complex coformer is at least 150:1. In another embodiment the mass ratio of additional coformer to molecular complex coformer is at least 175:1. In another embodiment the mass ratio of additional coformer to molecular complex coformer is at least 200:1. In another embodiment the mass ratio of additional coformer to molecular complex coformer is at least 225:1. In another embodiment the mass ratio of additional coformer to molecular complex coformer is at least 250:1. In another embodiment the mass ratio of additional coformer to molecular complex coformer is at least 275:1. In another embodiment the mass ratio of additional coformer to molecular complex coformer is at least 500:1. In another embodiment the mass ratio of additional coformer to molecular complex coformer is at least 750:1. In another embodiment the mass ratio of additional coformer to molecular complex coformer is at least 1000:1. In another embodiment the mass ratio of additional coformer to molecular complex coformer is at least 2000:1. In another embodiment the mass ratio of additional coformer to molecular complex coformer is at least 3000:1. In another embodiment the mass ratio of additional coformer to molecular complex coformer is at least 4000:1.

Another aspect of the invention provides for a composition comprising a bisphosphonic acid and a coformer, wherein the bisphosphonic acid and coformer are not associated in a molecular complex, i.e., a composition comprising additional conformer but not a molecular complex coformer. In one embodiment the amount of additional coformer present in the composition is in excess to the amount of bisphosphonic acid present in the composition. In another embodiment the mass ratio of the additional coformer to bisphosphonic acid is between about 2:1 to about 5000:1. In another embodiment the mass ratio of additional coformer to bisphosphonic acid is between about 1000:1 to about 5000:1. In another embodiment the mass ratio of additional coformer to bisphosphonic acid is between about 1000:1 to about 4000:1. In another embodiment the mass ratio of additional coformer to bisphosphonic acid is between about 2000:1 to about 4000:1. In another embodiment the mass ratio of additional coformer to bisphosphonic acid is between about 1000:1 to about 2000:1. In another embodiment the mass ratio of additional coformer to bisphosphonic acid is between about 100:1 to about 2000:1. In another embodiment the mass ratio of additional coformer to bisphosphonic acid is between about 100:1 to about 1000:1. In another embodiment the mass ratio of additional coformer to bisphosphonic acid is between about 100:1 to about 750:1. In another embodiment the mass ratio of additional coformer to bisphosphonic acid is between about 100:1 to about 500:1. In another embodiment the mass ratio of additional coformer to bisphosphonic acid is between about 100:1 to about 275:1. In another embodiment the mass ratio of additional coformer to bisphosphonic acid is between about 200:1 to about 275:1. In another embodiment the mass ratio of additional coformer to bisphosphonic acid is between about 175:1 to about 275:1. In another embodiment the mass ratio of additional coformer to bisphosphonic acid is between about 150:1 to about 250:1. In another embodiment the mass ratio of additional coformer to bisphosphonic acid is between about 100:1 to about 250:1. In another embodiment the mass ratio of additional coformer to bisphosphonic acid is between about 100:1 to about 200:1. In another embodiment the mass ratio of additional coformer to bisphosphonic acid is between about 50:1 to about 200:1. In another embodiment the mass ratio of additional coformer to bisphosphonic acid is between about 50:1 to about 150:1. In another embodiment the mass ratio of additional coformer to bisphosphonic acid is between about 50:1 to about 100:1. In another embodiment the mass ratio of additional coformer to bisphosphonic acid is between about 2:1 to about 100:1. In another embodiment the mass ratio of additional coformer to bisphosphonic acid is between about 5:1 to about 100:1. In another embodiment the mass ratio of additional coformer to bisphosphonic acid is between about 10:1 to about 100:1. In another embodiment the mass ratio of additional coformer to bisphosphonic acid is between about 11:1 to about 100:1. In another embodiment the mass ratio of additional coformer to bisphosphonic acid is between about 25:1 to about 100:1. In another embodiment the mass ratio of additional coformer to bisphosphonic acid is between about 50:1 to about 100:1. In another embodiment the mass ratio of additional coformer to bisphosphonic acid is between about 75:1 to about 100:1. In another embodiment the mass ratio of additional coformer to bisphosphonic acid is between about 2:1 to about 50:1. In another embodiment the mass ratio of additional coformer to bisphosphonic acid is between about 2:1 to about 25:1. In another embodiment the mass ratio of additional coformer to bisphosphonic acid is between about 2:1 to about 20:1. In another embodiment the mass ratio of additional coformer to bisphosphonic acid is between about 2:1 to about 15:1. In another embodiment the mass ratio of additional coformer to bisphosphonic acid is between about 2:1 to about 10:1. In another embodiment the mass ratio of additional coformer to bisphosphonic acid is between about 2:1 to about 5:1. In another embodiment the mass ratio of additional coformer to bisphosphonic acid is between about 5:1 to about 50:1. In another embodiment the mass ratio of additional coformer to bisphosphonic acid is between about 5:1 to about 25:1. In another embodiment the mass ratio of additional coformer to bisphosphonic acid is between about 5:1 to about 20:1. In another embodiment the mass ratio of additional coformer to bisphosphonic acid is between about 5:1 to about 15:1. In another embodiment the mass ratio of additional coformer to bisphosphonic acid is between about 5:1 to about 10:1. In another embodiment the mass ratio of additional coformer to bisphosphonic acid is between about 10:1 to about 50:1. In another embodiment the mass ratio of additional coformer to bisphosphonic acid is between about 10:1 to about 25:1. In another embodiment the mass ratio of additional coformer to bisphosphonic acid is between about 10:1 to about 20:1. In another embodiment the mass ratio of additional coformer to bisphosphonic acid is between about 10:1 to about 15:1. In another embodiment the mass ratio of additional coformer to bisphosphonic acid is between about 11:1 to about 50:1. In another embodiment the mass ratio of additional coformer to bisphosphonic acid is between about 15:1 to about 50:1. In another embodiment the mass ratio of additional coformer to bisphosphonic acid is between about 25:1 to about 50:1. In another embodiment the mass ratio of additional coformer to bisphosphonic acid is between about 35:1 to about 50:1. In another embodiment the mass ratio of additional coformer to bisphosphonic acid is at least 2:1. In another embodiment the mass ratio of additional coformer to bisphosphonic acid is at least 5:1. In another embodiment the mass ratio of additional coformer to bisphosphonic acid is at least 7.5:1. In another embodiment the mass ratio of additional coformer to bisphosphonic acid is at least 9:1. In another embodiment the mass ratio of additional coformer to bisphosphonic acid is at least 10:1. In another embodiment the mass ratio of additional coformer to bisphosphonic acid is at least 11:1. In another embodiment the mass ratio of additional coformer to bisphosphonic acid is at least 15:1. In another embodiment the mass ratio of additional coformer to bisphosphonic acid is at least 25:1. In another embodiment the mass ratio of additional coformer to bisphosphonic acid is at least 35:1. In another embodiment the mass ratio of additional coformer to bisphosphonic acid is at least 50:1. In another embodiment the mass ratio of additional coformer to bisphosphonic acid is at least 65:1. In another embodiment the mass ratio of additional coformer to bisphosphonic acid is at least 75:1. In another embodiment the mass ratio of additional coformer to bisphosphonic acid is at least 85:1. In another embodiment the mass ratio of additional coformer to bisphosphonic acid is at least 100:1. In another embodiment the mass ratio of additional coformer to bisphosphonic acid is at least 125:1. In another embodiment the mass ratio of additional coformer to bisphosphonic acid is at least 150:1. In another embodiment the mass ratio of additional coformer to bisphosphonic acid is at least 175:1. In another embodiment the mass ratio of additional coformer to bisphosphonic acid is at least 200:1. In another embodiment the mass ratio of additional coformer to bisphosphonic acid is at least 225:1. In another embodiment the mass ratio of additional coformer to bisphosphonic acid is at least 250:1. In another embodiment the mass ratio of additional coformer to bisphosphonic acid is at least 275:1. In another embodiment the mass ratio of additional coformer to bisphosphonic acid is at least 500:1. In another embodiment the mass ratio of additional coformer to bisphosphonic acid is at least 750:1. In another embodiment the mass ratio of additional coformer to bisphosphonic acid is at least 1000:1. In another embodiment the mass ratio of additional coformer to bisphosphonic acid is at least 2000:1. In another embodiment the mass ratio of additional coformer to bisphosphonic acid is at least 3000:1. In another embodiment the mass ratio of additional coformer to bisphosphonic acid is at least 4000:1. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

In particular embodiments the invention provides for a composition of Table 12

In other particular embodiments the invention provides for a composition of Table 13.

In other particular embodiments the invention provides for a composition of Table 14.

In other particular embodiments the invention provides for a composition of Table 15.

Another aspect of the invention provides for a method of increasing aqueous solubility of a bisphosphonic acid (e.g., zoledronic acid), compared with the free acid, comprising the step of combining a bisphosphonic acid with a coformer and forming a composition of the present invention. In one embodiment the method comprises the step of forming a molecular complex of the present invention. In another embodiment the method comprises the step of combining a bisphosphonic acid (including salts, cocrystals, solvates and prodrugs) with an amino acid. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In another embodiment the bisphosphonic acid is zoledronic acid and the amino acid is lysine or glycine. In another embodiment the bisphosphonic acid is zoledronic acid and the amino acid is L-lysine. In another embodiment the bisphosphonic acid is zoledronic acid and the L-lysine is an L-lysine salt. In another embodiment the bisphosphonic acid is zoledronic acid and the L-lysine is an L-lysine hydrate. In another embodiment the bisphosphonic acid is zoledronic acid and the L-lysine salt is an L-lysine HCl salt. In another embodiment the bisphosphonic acid is zoledronic acid and the L-lysine hydrate is an L-lysine monohydrate. In another embodiment the bisphosphonic acid is zoledronic acid and the amino acid is DL-lysine. In another embodiment the bisphosphonic acid is zoledronic acid and the DL-lysine is a DL-lysine salt. In another embodiment the bisphosphonic acid is zoledronic acid and the DL-lysine is a DL-lysine hydrate. In another embodiment the bisphosphonic acid is zoledronic acid and the DL-lysine salt is a DL-lysine HCl salt. In another embodiment the bisphosphonic acid is zoledronic acid and the DL-lysine hydrate is a DL-lysine monohydrate. In another embodiment the bisphosphonic acid is zoledronic acid and the amino acid is D-lysine. In another embodiment the bisphosphonic acid is zoledronic acid and the D-lysine is a D-lysine salt. In another embodiment the bisphosphonic acid is zoledronic acid and the D-lysine is a D-lysine hydrate. In another embodiment the bisphosphonic acid is zoledronic acid and the D-lysine salt is a D-lysine HCl salt. In another embodiment the bisphosphonic acid is zoledronic acid and the D-lysine hydrate is a D-lysine monohydrate. In another embodiment the aqueous solubility of the composition comprising zoledronic acid is at least 5 mg/ml. In another embodiment the aqueous solubility of the composition comprising zoledronic acid is at least 10 mg/ml. In another embodiment the aqueous solubility of the composition comprising zoledronic acid is at least 13 mg/ml.

In another aspect the coformer of the present invention significantly increases the oral bioavailability of the bisphosphonic acid, as compared to the corresponding marketed form or the corresponding composition without the coformer. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In one embodiment the oral bioavailability of the bisphosphonic acid in a pharmaceutical composition of the present invention is at least 3%. In another embodiment the oral bioavailability of the bisphosphonic acid is at least 4%. In another embodiment the oral bioavailability of the bisphosphonic acid is at least 5%. In another embodiment the oral bioavailability of the bisphosphonic acid is at least 6%. In another embodiment the oral bioavailability of the bisphosphonic acid is at least 7%. In another embodiment the oral bioavailability of the bisphosphonic acid is at least 8%. In another embodiment the oral bioavailability of the bisphosphonic acid is at least 9%. In another embodiment the oral bioavailability of the bisphosphonic acid is at least 10%.

In another aspect the coformer significantly increases the $C_{max}$ of the bisphosphonic acid as compared to the corresponding marketed form or the corresponding composition without the coformer. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

In another aspect the coformer significantly increases the gastrointestinal permeability of the bisphosphonic acid, as compared to the corresponding marketed formulation or the corresponding composition without the coformer. In one embodiment the coformer significantly increases the paracellular transport of the bisphosphonic acid across the intestinal epithelium. In another embodiment the coformer significantly increases the transcellular transport of the bisphosphonic acid through the intestinal epithelium. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

Another aspect of the present invention provides for a method of significantly enhancing the bioavailabilty or permeability of a bisphosphonic acid comprising the step of combining the bisphosphonic acid with a coformer to form a pharmaceutical composition of the present invention. In one embodiment the method comprises the step of contacting the bisphosphonic acid with a coformer to form a molecular complex of the present invention. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

In one aspect the coformer is an amino acid. In one embodiment the coformer is an amino acid and the bisphosphonic acid is zoledronic acid. In another embodiment the coformer is an amino acid and the bisphosphonic acid is clodronic acid. In another embodiment the coformer is an amino acid and the bisphosphonic acid is tiludronic acid. In another embodiment the coformer is an amino acid and the bisphosphonic acid is pamidronic acid. In another embodiment the coformer is an amino acid and the bisphosphonic acid is alendronic acid. In another embodiment the coformer is an amino acid and the bisphosphonic acid is risedronic acid. In another embodiment the coformer is an amino acid and the bisphosphonic acid is ibandronic acid. In particular embodiments the amino acid is isoleucine, alanine, leucine, asparagine, lysine, aspartic acid, methionine, cysteine, phenylalanine, glutamic acid, threonine, glutamine, tryptophan, glycine, valine, proline, serine, tyrosine arginine, histidine, selenocysteine, ornithine or taurine. In another embodiment of the present invention the coformer is selected from the group consisting of sodium, ammonium, ammonia, L-lysine, DL-lysine, nicotinamide, adenine, and glycine. In one embodiment the coformer is L-lysine. In another embodiment the coformer is DL-lysine. In another embodiment the coformer is D-lysine. In another embodiment the coformer is glycine. In one particular embodiment of the present invention the bisphosphonic acid is zoledronic acid and the coformer is lysine. In another particular embodiment the molecular complex of the present invention consists of zoledronic acid, lysine and water. In another particular embodiment the molecular complex of the present invention consists of zoledronic acid and lysine. In another particular embodiment the molecular complex of the present invention consists of zoledronic acid and L-lysine. In another particular embodiment the molecular complex of the present invention consists of zoledronic acid and DL-lysine. In another particular embodiment the molecular complex of the present invention consists of zoledronic acid and D-lysine. In another particular embodiment the molecular complex of the present invention consists of zoledronic acid, water and L-lysine. In another particular embodiment the molecular complex of the present invention consists of zoledronic acid, water and DL-lysine. In another particular embodiment the molecular complex of the present invention consists of zoledronic acid, water and D-lysine.

One aspect of the invention provides for a molecular complex comprising a bisphosphonic acid and lysine. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In one embodiment the molecular complex comprising the bisphosphonic acid and lysine is crystalline.

Another aspect provides for molecular complexes that are crystalline forms of a bisphosphonic acid comprising a bisphosphonic acid, water, and a compound selected from L-lysine; DL-lysine, nicotinamide, adenine or glycine. In one embodiment the compound is L-lysine. In another embodiment the compound is DL-lysine. In another embodiment the compound is D-lysine. In another embodiment the compound is glycine. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid.

In one embodiment the molecular complex is a crystalline zoledronic acid, sodium zoledronate and water complex characterized by an X-ray powder diffraction pattern having peaks at about 8.1, 13.3, 21.5, 24.6, and 25.6±0.2 degrees two-theta.

In another embodiment the molecular complex is a crystalline ammonium zoledronic acid salt and water complex characterized by an X-ray powder diffraction pattern having strong peaks at about 11.0, 14.6, 15.4, 19.9, and 29.4±0.2 degrees two-theta.

In another embodiment the molecular complex is a zoledronic acid diammonia water complex characterized by an X-ray powder diffraction pattern having strong peaks at about 12.2, 13.0, 14.1, 17.1, and 19.3±0.2 degrees two-theta.

In another embodiment the molecular complex is a crystalline zoledronic acid, L-lysine, and water complex characterized by an X-ray powder diffraction pattern having peaks at about 9.0, 14.4, 18.1, 26.0, and 29.6±0.2 degrees two-theta.

In another embodiment the molecular complex is a crystalline zoledronic acid, L-lysine, and water complex characterized by an X-ray powder diffraction pattern comprising peaks at about 9.6, 10.7, 14.3, 21.4, 23.5±0.2 degrees two theta.

In another embodiment the molecular complex is a crystalline zoledronic acid, DL-lysine and water complex characterized by an X-ray powder diffraction pattern comprising peaks at about 8.3, 11.8, 12.3, 15.8, and 20.8±0.2 degrees two-theta.

In another embodiment the molecular complex is a crystalline zoledronic acid, DL-lysine, and water complex characterized by an X-ray powder diffraction pattern comprising peaks at about 9.1, 14.7, 18.0, 21.2, and 26.0±0.2 degrees two-theta.

In another embodiment the molecular complex is a crystalline zoledronic acid, DL-lysine, and water complex characterized by an X-ray powder diffraction pattern comprising peaks at about 9.7, 10.8, 14.4, 18.9, 21.4±0.2 degrees two theta.

In another embodiment the molecular complex is a crystalline zoledronic acid, DL-lysine, ethanol, and water complex characterized by an X-ray powder diffraction pattern comprising peaks at about 8.8, 9.7, 17.6, 23.1, and 26.5±0.2 degrees two-theta.

In another embodiment the molecular complex is a crystalline zoledronic acid, adenine, and water complex characterized by an X-ray powder diffraction pattern comprising peaks at about 13.6, 15.9, 19.7, 27.9, and 29.5±0.2 degrees two-theta.

In another embodiment the molecular complex is a crystalline zoledronic acid, nicotinamide, and water complex characterized by an X-ray powder diffraction pattern comprising peaks at about 13.1, 15.2, 21.0, 23.9, and 26.5±0.2 degrees two-theta.

Another embodiment provides for a molecular complex comprising zoledronic acid and glycine. In one embodiment the molecular complex is crystalline. In another particular embodiment the zoledronic and glycine crystalline form is characterized by an X-ray powder diffraction pattern comprising peaks at about 10.2, 17.8, 19.9, 22.9, and 28.1±0.2 degrees two-theta.

Another aspect provides for a molecular complex comprising zoledronic acid; water; a compound selected from L-lysine, D,L-lysine, nicotinamide, adenine or glycine; and optionally further comprising a zoledronic acid salt. In one embodiment the molecular complex is a zoledronic acid, sodium zoledronate and water complex. In another embodiment the molecular complex is an ammonium zoledronic acid salt and water complex. In another embodiment the molecular complex is a zoledronic diammonia water complex. In another embodiment the molecular complex is a zoledronic acid, L-lysine, and water complex. In another embodiment the molecular complex is a zoledronic acid DL-lysine and water complex. In another embodiment the molecular complex is a zoledronic acid, zoledronic, DL-lysine, ethanol, and water complex. In another embodiment the molecular complex is a zoledronic acid, adenine, and water complex. In another embodiment the molecular complex is a zoledronic acid, nicotinamide, and water complex. In another embodiment the molecular complex is a zoledronic acid glycine complex.

In another aspect the composition of the present invention comprising a bisphosphonic acid and coformer is a pharmaceutical composition. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In one embodiment the pharmaceutical composition comprises a molecular complex. In another embodiment the pharmaceutical composition comprises a molecular complex and an additional coformer. In another embodiment the pharmaceutical composition comprises an additional coformer. In another embodiment the pharmaceutical composition consists of or consists essentially of a molecular complex. In another embodiment the pharmaceutical composition consists of or consists essentially of a molecular complex and an additional coformer. In another embodiment the pharmaceutical composition consists of or consists essentially of an additional coformer. In another embodiment the pharmaceutical composition is a solid dosage form. In another embodiment the pharmaceutical composition is a liquid dosage form. In another embodiment the pharmaceutical composition further includes at least one pharmaceutically acceptable excipient. In another embodiment the pharmaceutical composition is an oral dosage form. In another embodiment the oral dosage form is a tablet which can be manufactured in any shape such as a caplet (an oval shaped medicinal tablet in the shape of a capsule). In another embodiment the oral dosage form is an enteric coated tablet or caplet. In another embodiment the oral dosage form is a capsule. In another embodiment the oral dosage form is an enteric coated capsule. In another embodiment the pharmaceutical composition is a unit dose. In another embodiment the unit dose is a single tablet, caplet or capsule. In another embodiment the unit dose is two tablets or capsules. In another embodiment the unit dose is in the form of a particulate material, e.g., a granulated particulate material or powder. In another embodiment the unit dose is enclosed in a sachet, a disposable one time use package. In another embodiment the unit dose is in the form of a solution. In another embodiment the unit dose is in the form of a suspension. In another embodiment the unit dose is an effervescent formulation. In one aspect of an oral dosage form comprising a bisphosphonic acid and an additional coformer, both the bisphosphonic acid and the additional coformer are formulated to have the same release profile. In another embodiment both the bisphosphonic acid and the additional coformer are formulated to have an enteric release profile. In another embodiment the bisphosphonic acid is formulated to have an enteric release profile. In another embodiment both the bisphosphonic acid and the additional coformer are formulated to have a sustained release profile. In another embodiment the bisphosphonic acid is formulated to have a sustained release profile. In another embodiment both the additional coformer is formulated to have a sustained release profile. In another embodiment both the bisphosphonic acid and the additional coformer are formulated to have a delayed+sustained release profile. In another embodiment the bisphosphonic acid is formulated to have a delayed+sustained release profile. In another embodiment the additional coformer is formulated to have a delayed+sustained release profile. In one embodiment, the sustained release is a first-order release. In another embodiment the sustained release is a zero-order release. In another embodiment the bisphosphonic acid and the additional coformer are formulated a biphasic release. In one embodiment the $T_{max}$ of the bisphosphonic acid is reached within one hour of the $T_{max}$ of the coformer. In another embodiment the $T_{max}$ of the bisphosphonic acid is reached within 45 minutes of the $T_{max}$ of the coformer. In another embodiment the $T_{max}$ of the bisphosphonic acid is reached within 30 minutes of the $T_{max}$ of the coformer. In another embodiment the $C_{max}$ of the bisphosphonic acid is reached within one hour of the $C_{max}$ of the coformer. In another embodiment the $C_{max}$ of the bisphosphonic acid is reached within 45 minutes of the $C_{max}$ of the coformer. In another embodiment the $C_{max}$ of the bisphosphonic acid is reached within 30 minutes of the $C_{max}$ of the coformer. In another embodiment the $C_{max}$ and $T_{max}$ for the coformer occurs less than one hour before the $C_{max}$ and $T_{max}$ of the bisphosphonic acid. In another embodiment, the $C_{max}$ and $T_{max}$ for the coformer occur less than 45 minutes before the $C_{max}$ and $T_{max}$ of the bisphosphonic acid. In another embodiment, the $C_{max}$ and $T_{max}$ for the coformer occur less than 30 minutes before the $C_{max}$ and $T_{max}$ of the bisphosphonic acid. In another embodiment, the $C_{max}$ and $T_{max}$ for the bisphosphonic acid occurs before the $C_{max}$ and $T_{max}$ of the coformer.

The pharmaceutical compositions generally contain about 1% to about 99% by weight of at least one novel molecular complex of a bisphosphonic acid (e.g., zoledronic acid) of the invention with the remaining 99% to 1% by weight of a comprising one or more coformers and, optionally, one or more suitable pharmaceutical excipients. Pharmaceutical compositions comprising excess coformer generally comprise excess coformer in the range from 0.001 to 99.999%, particularly, 0.01 to 99.99% more particularly 0.1 to 99.9% by weight of the coformer to the bisphosphonic acid (e.g., zoledronic acid). In one embodiment the pharmaceutical composition comprises about 50% to about 99% coformer. In another embodiment the pharmaceutical composition comprises about 60% to about 98% coformer. In another embodiment the pharmaceutical composition comprises about 70% to about 95% coformer. In another embodiment the pharmaceutical composition comprises about 80% to about 95% coformer. In another embodiment the pharmaceutical composition comprises about 85% to about 95% coformer. In another embodiment the pharmaceutical composition comprises about 90% to about 98% coformer. In another embodiment the pharmaceutical composition comprises about 90% to about 95% coformer.

In one aspect the pharmaceutical composition of the present invention is a unit dose comprising a bisphosphonic acid and an amino acid. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In one embodiment the amino acid is selected from isoleucine, alanine, leucine, asparagine, lysine, aspartic acid, methionine, cysteine, phenylalanine, glutamic acid, threonine, glutamine, tryptophan, glycine, valine, proline, serine, tyrosine arginine, histidine, selenocysteine, ornithine or taurine. In one embodiment the unit dose of bisphosphonic acid comprises at least 100 mg of an amino acid. In one embodiment the amino acid is present as a component of a molecular complex with the bisphosphonic acid. In another embodiment the amino acid is present both as a component of a molecular complex with the bisphosphonic acid and as an additional coformer. In another embodiment the amino acid is present only as an additional coformer. In one embodiment the unit dose comprises between about 50 to about 5000 mg of amino acid. In another embodiment the unit dose comprises between about 100 to about 1000 mg of amino acid. In another embodiment the unit dose comprises between about 500 to about 1000 mg of amino acid. In another embodiment the unit dose comprises between about 750 to about 1000 mg of amino acid. In another embodiment the unit dose comprises between about 500 to about 1500 mg of amino acid. In another embodiment the unit dose comprises between about 500 to about 1250 mg of amino acid. In another embodiment the unit dose comprises between about 750 to about 1500 mg of amino acid. In another embodiment the unit dose comprises between about 750 to about 1250 mg of amino acid. In another embodiment the unit dose comprises between about 1000 to about 5000 mg of amino acid. In another embodiment the unit dose comprises between about 1000 to about 4500 mg of amino acid. In another embodiment the unit dose comprises between about 1000 to about 4000 mg of amino acid. In another embodiment the unit dose comprises between about 1000 to about 3500 mg of amino acid. In another embodiment the unit dose comprises between about 1000 to about 3000 mg of amino acid. In another embodiment the unit dose comprises between about 1000 to about 2500 mg of amino acid. In another embodiment the unit dose comprises between about 1000 to about 2000 mg of amino acid. In another embodiment the unit dose comprises between about 1000 to about 1500 mg of amino acid. In another embodiment the unit dose comprises between about 1250 to about 5000 mg of amino acid. In another embodiment the unit dose comprises between about 1250 to about 4500 mg of amino acid. In another embodiment the unit dose comprises between about 1250 to about 4000 mg of amino acid. In another embodiment the unit dose comprises between about 1250 to about 3500 mg of amino acid. In another embodiment the unit dose comprises between about 1250 to about 3000 mg of amino acid. In another embodiment the unit dose comprises between about 1250 to about 2500 mg of amino acid. In another embodiment the unit dose comprises between about 1250 to about 2000 mg of amino acid. In another embodiment the unit dose comprises between about 1250 to about 1750 mg of amino acid. In another embodiment the unit dose comprises between about 1500 to about 5000 mg of amino acid. In another embodiment the unit dose comprises between about 2000 to about 5000 mg of amino acid. In another embodiment the unit dose comprises between about 2000 to about 4500 mg of amino acid. In another embodiment the unit dose comprises between about 2000 to about 4000 mg of amino acid. In another embodiment the unit dose comprises between about 2000 to about 3500 mg of amino acid. In another embodiment the unit dose comprises between about 2000 to about 3000 mg of amino acid. In another embodiment the unit dose comprises between about 2000 to about 2500 mg of amino acid. In another embodiment the unit dose comprises between about 3000 to about 5000 mg of amino acid. In another embodiment the unit dose comprises between about 3000 to about 4500 mg of amino acid. In another embodiment the unit dose comprises between about 3000 to about 4000 mg of amino acid. In another embodiment the unit dose comprises between about 3000 to about 3500 mg of amino acid. In another embodiment the unit dose comprises between about 1 g to about 20 g of amino acid. In another embodiment the unit dose comprises between about 5 g to about 20 g of amino acid. In another embodiment the unit dose comprises between about 10 g to about 20 g of amino acid. In another embodiment the unit dose comprises between about 1 g to about 10 g of amino acid. In another embodiment the unit dose comprises between about 5 g to about 10 g of amino acid. In another embodiment the unit dose comprises between about 7.5 g to about 10 g of amino acid. In another embodiment the unit dose comprises between about 5 g to about 15 g of amino acid. In another embodiment the unit dose comprises between about 10 g to about 15 g of amino acid. In another embodiment the unit dose comprises between about 10 g to about 12.5 g of amino acid. In another embodiment the unit dose comprises between about 12.5 g to about 20 g of amino acid. In another embodiment the unit dose comprises between about 12.5 g to about 17.5 g of amino acid. In another embodiment the unit dose comprises between about 15 g to about 20 g of amino acid. In another embodiment the unit dose comprises between about 17.5 g to about 20 g of amino acid. In another embodiment the unit dose comprises at least 250 mg of an amino acid. In another embodiment the unit dose comprises at least 500 mg of an amino acid. In another embodiment the unit dose comprises at least 600 mg of an amino acid. In another embodiment the unit dose comprises at least 700 mg of an amino acid. In another embodiment the unit dose comprises at least 750 mg of an amino acid. In another embodiment the unit dose comprises at least 800 mg of an amino acid. In another embodiment the unit dose comprises at least 900 mg of an amino acid. In another embodiment the unit dose comprises at least 1000 mg of an amino acid. In another embodiment the unit dose comprises at least 1100 mg of an amino acid. In another embodiment the unit dose comprises at least 1200 mg of an amino acid. In another embodiment the unit dose comprises at least 1250 mg of an amino acid. In another embodiment the unit dose comprises at least 1500 mg of an amino acid. In another embodiment the unit dose comprises at least 1750 mg of an amino acid. In another embodiment the unit dose comprises at least 1900 mg of an amino acid. In another embodiment the unit dose comprises at least 2000 mg of an amino acid. In another embodiment the unit dose comprises at least 2500 mg of an amino acid. In another embodiment the unit dose comprises at least 3000 mg of an amino acid. In another embodiment the unit dose comprises at least 3500 mg of an amino acid. In another embodiment the unit dose comprises at least 4000 mg of an amino acid. In another embodiment the unit dose comprises at least 4500 mg of an amino acid. In another embodiment the unit dose comprises at least 5000 mg of an amino acid. In another embodiment the unit dose comprises at least 6000 mg of amino acid. In another embodiment the unit dose comprises at least 7000 mg of amino acid. In another embodiment the unit dose comprises at least 8000 mg of amino acid. In another embodiment the unit dose comprises at least 9000 mg of amino acid. In another embodiment the unit dose comprises at least 10 g of amino acid. In another embodiment the unit dose comprises at least 11 g of amino acid. In another embodiment the unit dose comprises at least 12 g of amino acid. In another embodiment the unit dose comprises at least 13 g of amino acid. In another embodiment the unit dose comprises at least 14 g of amino acid. In another embodiment the unit dose comprises at least 15 g of amino acid. In another embodiment the unit dose comprises at least 16 g of amino acid. In another embodiment the unit dose comprises at least 17 g of amino acid. In another embodiment the unit dose comprises at least 18 g of amino acid. In another embodiment the unit dose comprises at least 19 g of amino acid. In another embodiment the unit dose comprises at least 20 g of amino acid. In one embodiment the bisphosphonic acid is zoledronic acid. In one embodiment the amino acid is lysine or glycine. In one embodiment the unit dose of zoledronic acid comprises between about 50 to about 5000 mg of lysine. In another embodiment the unit dose of zoledronic acid comprises between about 100 to about 1000 mg of lysine. In another embodiment the unit dose of zoledronic acid comprises between about 500 to about 1000 mg of lysine. In another embodiment the unit dose of zoledronic acid comprises between about 750 to about 1000 mg of lysine. In another embodiment the unit dose of zoledronic acid comprises between about 500 to about 1500 mg of lysine. In another embodiment the unit dose of zoledronic acid comprises between about 500 to about 1250 mg of lysine. In another embodiment the unit dose of zoledronic acid comprises between about 750 to about 1500 mg of lysine. In another embodiment the unit dose of zoledronic acid comprises between about 750 to about 1250 mg of lysine. In another embodiment the unit dose of zoledronic acid comprises between about 1000 to about 5000 mg of lysine. In another embodiment the unit dose of zoledronic acid comprises between about 1000 to about 4500 mg of lysine. In another embodiment the unit dose of zoledronic acid comprises between about 1000 to about 4000 mg of lysine. In another embodiment the unit dose of zoledronic acid comprises between about 1000 to about 3500 mg of lysine. In another embodiment the unit dose of zoledronic acid comprises between about 1000 to about 3000 mg of lysine. In another embodiment the unit dose of zoledronic acid comprises between about 1000 to about 2500 mg of lysine. In another embodiment the unit dose of zoledronic acid comprises between about 1000 to about 2000 mg of lysine. In another embodiment the unit dose of zoledronic acid comprises between about 1000 to about 1500 mg of lysine. In another embodiment the unit dose of zoledronic acid comprises between about 1250 to about 5000 mg of lysine. In another embodiment the unit dose of zoledronic acid comprises between about 1250 to about 4500 mg of lysine. In another embodiment the unit dose of zoledronic acid comprises between about 1250 to about 4000 mg of lysine. In another embodiment the unit dose of zoledronic acid comprises between about 1250 to about 3500 mg of lysine. In another embodiment the unit dose of zoledronic acid comprises between about 1250 to about 3000 mg of lysine. In another embodiment the unit dose of zoledronic acid comprises between about 1250 to about 2500 mg of lysine. In another embodiment the unit dose of zoledronic acid comprises between about 1250 to about 2000 mg of lysine. In another embodiment the unit dose of zoledronic acid comprises between about 1250 to about 1750 mg of lysine. In another embodiment the unit dose of zoledronic acid comprises between about 1500 to about 2500 mg of lysine. In another embodiment the unit dose of zoledronic acid comprises between about 1500 to about 2000 mg of lysine. In another embodiment the unit dose of zoledronic acid comprises between about 1500 to about 5000 mg of lysine. In another embodiment the unit dose of zoledronic acid comprises between about 2000 to about 5000 mg of lysine. In another embodiment the unit dose of zoledronic acid comprises between about 2000 to about 4500 mg of lysine. In another embodiment the unit dose of zoledronic acid comprises between about 2000 to about 4000 mg of lysine. In another embodiment the unit dose of zoledronic acid comprises between about 2000 to about 3500 mg of lysine. In another embodiment the unit dose of zoledronic acid comprises between about 2000 to about 3000 mg of lysine. In another embodiment the unit dose of zoledronic acid comprises between about 2000 to about 2500 mg of lysine. In another embodiment the unit dose of zoledronic acid comprises between about 3000 to about 5000 mg of lysine. In another embodiment the unit dose of zoledronic acid comprises between about 3000 to about 4500 mg of lysine. In another embodiment the unit dose of zoledronic acid comprises between about 3000 to about 4000 mg of lysine. In another embodiment the unit dose of zoledronic acid comprises between about 3000 to about 3500 mg of lysine. In another embodiment the unit dose of zoledronic acid comprises between about 1 g to about 20 g of lysine. In another embodiment the unit dose of zoledronic acid comprises between about 5 g to about 20 g of lysine. In another embodiment the unit dose of zoledronic acid comprises between about 10 g to about 20 g of lysine. In another embodiment the unit dose of zoledronic acid comprises between about 15 g to about 20 g of lysine. In another embodiment the unit dose of zoledronic acid comprises between about 17.5 g to about 20 g of lysine. In another embodiment the unit dose of zoledronic acid comprises between about 1 g to about 10 g of lysine. In another embodiment the unit dose of zoledronic acid comprises between about 2.5 g to about 10 g of lysine. In another embodiment the unit dose of zoledronic acid comprises between about 5 g to about 10 g of lysine. In another embodiment the unit dose of zoledronic acid comprises between about 7 g to about 10 g of lysine. In another embodiment the unit dose of zoledronic acid comprises between about 7.5 g to about 10 g of lysine. In another embodiment the unit dose of zoledronic acid comprises between about 7.5 g to about 15 g of lysine. In another embodiment the unit dose of zoledronic acid comprises between about 10 g to about 15 g of lysine. In another embodiment the unit dose of zoledronic acid comprises between about 12.5 g to about 15 g of lysine. In another embodiment the unit dose of zoledronic acid comprises between about 10 g to about 12.5 g of lysine. In another embodiment the unit dose of zoledronic acid comprises between about 12.5 g to about 20 g of lysine. In another embodiment the unit dose of zoledronic acid comprises between about 12.5 g to about 17.5 g of lysine. In another embodiment a unit dose of a zoledronic acid pharmaceutical composition comprises at least 100 mg of lysine. In another embodiment the unit dose of zoledronic acid comprises at least 250 mg of lysine. In another embodiment the unit dose of zoledronic acid comprises at least 500 mg of lysine. In another embodiment the unit dose of zoledronic acid comprises at least 600 mg of lysine. In another embodiment the unit dose of zoledronic acid comprises at least 700 mg of lysine. In another embodiment the unit dose of zoledronic acid comprises at least 750 mg of lysine. In another embodiment the unit dose of zoledronic acid comprises at least 800 mg of lysine. In another embodiment the unit dose of zoledronic acid comprises at least 900 mg of lysine. In another embodiment the unit dose of zoledronic acid comprises at least 1000 mg of lysine. In another embodiment the unit dose of zoledronic acid comprises at least 1100 mg of lysine. In another embodiment the unit dose of zoledronic acid comprises at least 1200 mg of lysine. In another embodiment the unit dose of zoledronic acid comprises at least 1250 mg of lysine. In another embodiment the unit dose of zoledronic acid comprises at least 1500 mg of lysine. In another embodiment the unit dose of zoledronic acid comprises at least 1750 mg of lysine. In another embodiment the unit dose of zoledronic acid comprises at least 1900 mg of lysine. In another embodiment the unit dose of zoledronic acid comprises at least 2000 mg of lysine. In another embodiment the unit dose of zoledronic acid comprises at least 2500 mg of lysine. In another embodiment the unit dose of zoledronic acid comprises at least 3000 mg of lysine. In another embodiment the unit dose of zoledronic acid comprises at least 3500 mg of lysine. In another embodiment the unit dose of zoledronic acid comprises at least 4000 mg of lysine. In another embodiment the unit dose of zoledronic acid comprises at least 4500 mg of lysine. In another embodiment the unit dose of zoledronic acid comprises at least 5000 mg of lysine. In another embodiment the unit dose of zoledronic acid comprises at least 6000 mg of lysine. In another embodiment the unit dose of zoledronic acid comprises at least 7000 mg of lysine. In another embodiment the unit dose of zoledronic acid comprises at least 8000 mg of lysine. In another embodiment the unit dose of zoledronic acid comprises at least 9000 mg of lysine. In another embodiment the unit dose of zoledronic acid comprises at least 10 g of lysine. In another embodiment the unit dose of zoledronic acid comprises at least 11 g of lysine. In another embodiment the unit dose of zoledronic acid comprises at least 12 g of lysine. In another embodiment the unit dose of zoledronic acid comprises at least 13 g of lysine. In another embodiment the unit dose of zoledronic acid comprises at least 14 g of lysine. In another embodiment the unit dose of zoledronic acid comprises at least 15 g of lysine. In another embodiment the unit dose of zoledronic acid comprises at least 16 g of lysine. In another embodiment the unit dose of zoledronic acid comprises at least 17 g of lysine. In another embodiment the unit dose of zoledronic acid comprises at least 18 g of lysine. In another embodiment the unit dose of zoledronic acid comprises at least 19 g of lysine. In another embodiment the unit dose of zoledronic acid comprises at least 20 g of lysine. In one embodiment the lysine in the unit dose of zoledronic acid is L-lysine. In one embodiment the L-lysine in the unit dose of zoledronic acid comprises an L-lysine salt. In one embodiment the L-lysine in the unit dose of zoledronic acid comprises an L-lysine hydrate. In one embodiment the L-lysine salt in the unit dose of zoledronic acid comprises an L-lysine HCl salt. In one embodiment the L-lysine hydrate in the unit dose of zoledronic acid comprises a L-lysine monohydrate. In another embodiment the lysine in the unit dose of zoledronic acid is DL-lysine. In one embodiment the DL-lysine in the unit dose of zoledronic acid comprises a DL-lysine salt. In one embodiment the DL-lysine salt in the unit dose of zoledronic acid comprises a DL-lysine HCl salt. In one embodiment the DL-lysine in the unit dose of zoledronic acid comprises a DL-lysine hydrate. In one embodiment the DL-lysine hydrate in the unit dose of zoledronic acid comprises a DL-lysine monohydrate. In another embodiment the lysine in the unit dose of zoledronic acid is D-lysine. In one embodiment the D-lysine in the unit dose of zoledronic acid comprises a D-lysine salt. In one embodiment the D-lysine salt in the unit dose of zoledronic acid comprises a D-lysine HCl salt. In one embodiment the D-lysine in the unit dose of zoledronic acid comprises a D-lysine hydrate. In one embodiment the D-lysine hydrate in the unit dose of zoledronic acid comprises D-lysine monohydrate. In one embodiment a unit dose of a zoledronic acid pharmaceutical composition comprises at least 100 mg of glycine. In another embodiment the unit dose of zoledronic acid comprises at least 250 mg of glycine. In another embodiment the unit dose of zoledronic acid comprises at least 500 mg of glycine. In another embodiment the unit dose of zoledronic acid comprises at least 750 mg of glycine. In another embodiment the unit dose of zoledronic acid comprises at least 1000 mg of glycine. In another embodiment the unit dose of zoledronic acid comprises at least 1100 mg of glycine. In another embodiment the unit dose of zoledronic acid comprises at least 1200 mg of glycine. In another embodiment the unit dose of zoledronic acid comprises at least 1250 mg of glycine. In another embodiment the unit dose of zoledronic acid comprises at least 1500 mg of glycine. In another embodiment the unit dose of zoledronic acid comprises at least 1750 mg of glycine. In another embodiment the unit dose of zoledronic acid comprises at least 1900 mg of glycine. In another embodiment the unit dose of zoledronic acid comprises at least 2000 mg of glycine. In another embodiment the unit dose of zoledronic acid comprises at least 2500 mg of glycine. In another embodiment the unit dose of zoledronic acid comprises at least 3000 mg of glycine. In another embodiment the unit dose of zoledronic acid comprises at least 3500 mg of glycine. In another embodiment the unit dose of zoledronic acid comprises at least 4000 mg of glycine. In another embodiment the unit dose of zoledronic acid comprises at least 4500 mg of glycine. In another embodiment the unit dose of zoledronic acid comprises at least 5000 mg of glycine. In another embodiment the unit dose of zoledronic acid comprises at least 6000 mg of glycine. In another embodiment the unit dose of zoledronic acid comprises at least 7000 mg of glycine. In another embodiment the unit dose of zoledronic acid comprises at least 8000 mg of glycine. In another embodiment the unit dose of zoledronic acid comprises at least 9000 mg of glycine. In another embodiment the unit dose of zoledronic acid comprises at least 10 g of glycine. In another embodiment the unit dose of zoledronic acid comprises at least 11 g of glycine. In another embodiment the unit dose of zoledronic acid comprises at least 12 g of glycine. In another embodiment the unit dose of zoledronic acid comprises at least 13 g of glycine. In another embodiment the unit dose of zoledronic acid comprises at least 14 g of glycine. In another embodiment the unit dose of zoledronic acid comprises at least 15 g of glycine. In another embodiment the unit dose of zoledronic acid comprises at least 16 g of glycine. In another embodiment the unit dose of zoledronic acid comprises at least 17 g of glycine. In another embodiment the unit dose of zoledronic acid comprises at least 18 g of glycine. In another embodiment the unit dose of zoledronic acid comprises at least 19 g of glycine. In another embodiment the unit dose of zoledronic acid comprises at least 20 g of glycine. In another embodiment the unit dose of zoledronic acid comprises between about 50 to about 5000 mg of glycine. In another embodiment the unit dose of zoledronic acid comprises between about 100 to about 1000 mg of glycine. In another embodiment the unit dose of zoledronic acid comprises between about 1250 to about 5000 mg of glycine. In another embodiment the unit dose of zoledronic acid comprises between about 2000 to about 5000 mg of glycine. In another embodiment the unit dose of zoledronic acid comprises between about 3000 to about 5000 mg of glycine. In another embodiment the unit dose of zoledronic acid comprises between about 1250 to about 3000 mg of glycine. In another embodiment the unit dose of zoledronic acid comprises between about 1250 to about 2500 mg of glycine. In another embodiment the unit dose of zoledronic acid comprises between about 1 g to about 20 g of glycine. In another embodiment the unit dose of zoledronic acid comprises between about 1250 mg to about 20 g of glycine. In another embodiment the unit dose of zoledronic acid comprises between about 1500 mg to about 20 g of glycine. In another embodiment the unit dose of zoledronic acid comprises between about 1 g to about 10 g of glycine. In another embodiment the unit dose of zoledronic acid comprises between about 1250 mg to about 10 g of glycine. In another embodiment the unit dose of zoledronic acid comprises between about 1500 mg to about 10 g of glycine. In another embodiment the unit dose of zoledronic acid comprises between about 1 g to about 5 g of glycine. In another embodiment the unit dose of zoledronic acid comprises between about 1250 mg to about 5 g of glycine. In another embodiment the unit dose of zoledronic acid comprises between about 1500 mg to about 5 g of glycine. In another embodiment the unit dose of zoledronic acid comprises between about 5 g to about 15 g of glycine. In another embodiment the unit dose of zoledronic acid comprises between about 5 g to about 10 g of glycine. In another embodiment the unit dose of zoledronic acid comprises between about 7 g to about 10 g of glycine. In another embodiment the unit dose of zoledronic acid comprises between about 10 g to about 20 g of glycine. In another embodiment the unit dose of zoledronic acid comprises between about 10 g to about 15 g of glycine. In another embodiment the unit dose of zoledronic acid comprises between about 10 g to about 12.5 g of glycine. In another embodiment the unit dose of zoledronic acid comprises between about 12.5 g to about 20 g of glycine. In another embodiment the unit dose of zoledronic acid comprises between about 12.5 g to about 17.5 g of glycine. In another embodiment the unit dose of zoledronic acid comprises between about 15 g to about 20 g of glycine. In another embodiment the unit dose of zoledronic acid comprises between about 17.5 g to about 20 g of glycine. In another embodiment the unit dose of zoledronic acid comprises between about 1 g to about 2 g of glycine.

In one aspect a unit dose of a zoledronic acid pharmaceutical composition comprising zoledronic acid and an amino acid has an oral bioavailability of at least 3%. In another embodiment the composition has an oral bioavailability of at least 5%. In another embodiment the composition has an oral bioavailability of at least 8%. In one embodiment the amino acid is L-lysine and the oral bioavailability is at least 3%. In one embodiment the amino acid is L-lysine and the oral bioavailability is at least 5%. In one embodiment the amino acid is L-lysine and the oral bioavailability is at least 8%. In one embodiment the amino acid is DL-lysine and the oral bioavailability is at least 3%. In one embodiment the amino acid is DL-lysine and the oral bioavailability is at least 5%. In one embodiment the amino acid is DL-lysine and the oral bioavailability is at least 8%. In one embodiment the amino acid is D-lysine and the oral bioavailability is at least 3%. In one embodiment the amino acid is D-lysine and the oral bioavailability is at least 5%. In one embodiment the amino acid is D-lysine and the oral bioavailability is at least 8%. In one embodiment the amino acid is glycine and the oral bioavailability is at least 3%. In one embodiment the amino acid is glycine and the oral bioavailability is at least 5%. In one embodiment the amino acid is glycine and the oral bioavailability is at least 8%.

In one aspect the majority of the increase in oral bioavailability is due to the presence of the coformer, whether as part of a molecular complex or as additional coformer. In one embodiment the coformer is the only component of a pharmaceutical composition comprising a bisphosphonic acid-coformer molecular complex that significantly increases the oral bioavailability of the molecular complex. In one embodiment the amino acid added as an excipient is the only component of a pharmaceutical composition comprising a bisphosphonic acid that increases the oral bioavailability of the molecular complex. In one embodiment the increase in oral bioavailability is achieved without the need of additional excipients, e.g., an intra-granular hydrophilic polymer.

In one aspect a unit oral dose of a zoledronic acid pharmaceutical composition comprising zoledronic acid and an amino acid is no more than 4.1 mg/kg (mass zoledronic acid/mass patient) and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and an amino acid is no more than 2.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and an amino acid is no more than 2.25 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and an amino acid is no more than 2.0 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and an amino acid is no more than 1.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and an amino acid is no more than 1.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and an amino acid is no more than 1.25 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and an amino acid is no more than 1 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and an amino acid is no more than 0.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and an amino acid is no more than 0.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and an amino acid is no more than 0.3 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and lysine is no more than 4.1 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and lysine is no more than 2.25 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and lysine is no more than 2.0 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and lysine is no more than 1.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and lysine is no more than 1.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and lysine is no more than 1.25 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and lysine is no more than 1 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and lysine is no more than 0.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and lysine is no more than 0.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and lysine is no more than 0.3 mg/kg and is at least equivalent in efficacy to a 4 mg unit dose of the marketed form ZOMETA (or its equivalent) administered intravenously. In further particular embodiments the unit dose consists of or consists essentially of zoledronic acid and lysine. In one embodiment a unit oral dose of a zoledronic acid pharmaceutical composition comprising zoledronic acid and L-lysine is no more than 4.1 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and L-lysine is no more than 2.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and L-lysine is no more than 2.25 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and L-lysine is no more than 2.0 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and L-lysine is no more than 1.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and L-lysine is no more than 1.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and L-lysine is no more than 1.25 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and L-lysine is no more than 1 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and L-lysine is no more than 0.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and L-lysine is no more than 0.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and L-lysine is no more than 0.3 mg/kg and is at least equivalent in efficacy to a 4 mg unit dose of the marketed form ZOMETA (or its equivalent) administered intravenously. In further particular embodiments the unit dose consists of or consists essentially of zoledronic acid and L-lysine. In one embodiment a unit oral dose of a zoledronic acid pharmaceutical composition comprising zoledronic acid and DL-lysine is no more than 4.1 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and DL-lysine is no more than 2.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and DL-lysine is no more than 2.25 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and DL-lysine is no more than 2.0 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and DL-lysine is no more than 1.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and DL-lysine is no more than 1.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and DL-lysine is no more than 1.25 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and DL-lysine is no more than 1 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and DL-lysine is no more than 0.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and DL-lysine is no more than 0.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and DL-lysine is no more than 0.3 mg/kg and is at least equivalent in efficacy to a 4 mg unit dose of the marketed form ZOMETA (or its equivalent) administered intravenously. In further particular embodiments the unit dose consists of or consists essentially of zoledronic acid and DL-lysine. In one embodiment a unit oral dose of a zoledronic acid pharmaceutical composition comprising zoledronic acid and D-lysine is no more than 4.1 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and D-lysine is no more than 2.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and D-lysine is no more than 2.25 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and D-lysine is no more than 2.0 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and D-lysine is no more than 1.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and D-lysine is no more than 1.5 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and D-lysine is no more than 1.25 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and D-lysine is no more than 1 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and D-lysine is no more than 0.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and D-lysine is no more than 0.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and D-lysine is no more than 0.3 mg/kg and is at least equivalent in efficacy to a 4 mg unit dose of the marketed form ZOMETA (or its equivalent) administered intravenously. In further particular embodiments the unit dose consists of or consists essentially of zoledronic acid and D-lysine. In one embodiment a unit oral dose of a zoledronic acid pharmaceutical composition comprising zoledronic acid and glycine is no more than 4.1 mg/kg and is at least equivalent in efficacy to a 4 mg unit dose of the marketed form ZOMETA (or its equivalent) administered intravenously. In one embodiment a unit oral dose of a zoledronic acid pharmaceutical composition comprising zoledronic acid and glycine is no more than 2.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and glycine is no more than 1.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and glycine is no more than 1 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and glycine is no more than 0.75 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and glycine is no more than 0.5 mg/kg and is at least equivalent in efficacy to a 4 mg unit dose of the marketed form ZOMETA (or its equivalent) administered intravenously. In another embodiment a unit oral dose of a zoledronic acid pharmaceutical composition comprising zoledronic acid and glycine is no more than 0.3 mg/kg and is at least equivalent in efficacy to a 4 mg unit dose of the marketed form ZOMETA (or its equivalent) administered intravenously. In further particular embodiments the unit dose consists of or consists essentially of zoledronic acid and glycine.

Another aspect of the present invention provides for a method of treating or preventing a disease for which a bisphosphonic acid is indicated, the method comprising the step of administering to a patient in need of the bisphosphonic acid a therapeutically effective amount of a pharmaceutical composition of the present invention. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In one embodiment the disease is selected from osteoporosis, hypercalcemia, cancer induced bone metastasis, Paget's disease, adjuvant cancer therapy or neoadjuvant cancer therapy. In one particular embodiment the method is for treating such a disease. In another particular embodiment the method is for preventing such as disease.

Another aspect of the present invention provides for a medicament comprising a pharmaceutical composition of the present invention for use in treating or preventing a disease for which a bisphosphonic acid is indicated. In one embodiment the bisphosphonic acid is zoledronic acid. In another embodiment the bisphosphonic acid is clodronic acid. In another embodiment the bisphosphonic acid is tiludronic acid. In another embodiment the bisphosphonic acid is pamidronic acid. In another embodiment the bisphosphonic acid is alendronic acid. In another embodiment the bisphosphonic acid is risedronic acid. In another embodiment the bisphosphonic acid is ibandronic acid. In one embodiment the disease is selected from osteoporosis, hypercalcemia, cancer induced bone metastasis, Paget's disease, adjuvant cancer therapy or neoadjuvant cancer therapy. In one embodiment the medicament is for use in treating such a disease. In another embodiment the medicament is for use in preventing such a disease.

In one aspect, the present invention includes complexes of a bisphosphonic acid (e.g., zoledronic acid) with sodium, ammonium, ammonia, L-lysine, DL-lysine, nicotinamide, adenine and glycine which are capable of complexing in the solid-state, for example, through dry or solvent-drop grinding (liquid assisted grinding), heating or solvent evaporation of their solution in single or mixed solvent systems, slurry suspension, supercritical fluids or other techniques known to a person skilled in the art.

In one embodiment the invention provides for a zoledronic and nicotinamide complex to be made by dissolving both compounds in a water:ethylacetate (1:1 v/v) mixture and allowing the solvent to evaporate to form crystalline material.

In another embodiment the invention provides for a zoledronic and glycine solid complex made by dissolving both compounds in water, and allowing the solvent to evaporate to form crystalline material.

In one aspect the invention provides for a molecular complex of zoledronic acid and a coformer selected from sodium, ammonium, ammonia, L-lysine, DL-lysine, nicotinamide, adenine or glycine, suitable for a pharmaceutical formulation than can be delivered orally to the human body. In one aspect of the pharmaceutical composition of the present invention comprises a therapeutically effective amount of at least one of the novel molecular complexes according to the invention and may further include at least one additional coformer and at least one pharmaceutically acceptable excipient. The novel molecular complexes of zoledronic acid are therapeutically useful for the treatment and/or prevention of disease states for which a bisphosphonic acid is indicated, for example, disease states associated with osteoporosis, hypercalcemia (TIH), cancer induced bone metastasis, Paget's disease or adjuvant or neoadjuvant therapies.

Pharmaceutical Compositions

A pharmaceutical composition of the invention may be in any pharmaceutical form, for example, a tablet, capsule, particulate material, e.g., granulated particulate material or a powder, oral liquid suspension, oral liquid solution, an injectable solution, a lyophilized material for reconstitution, suppository, topical, or transdermal.

In one aspect the invention provides for a composition comprising a micronized molecular complex of the present invention. In one embodiment the micronized molecular complex is zoledronic, DL-lysine and water molecular complex. In other embodiment the composition further comprises excess micronized cocrystal former (e.g., DL-lysine).

Another embodiment of the invention provides micronized novel zoledronic acid complex (zoledronic, DL-lysine and water) where the particle mean size diameter is 5 microns by volume.

Another aspect of the invention provides micronized excess coformer (e.g, DL-lysine) where the mean particle size diameter is 5 microns by volume.

Generally, the oral dosage forms of the present invention will contain from about 1 mg to about 500 mg of an API (e.g, bisphosphonic acid) on an anhydrous weight basis, depending on the particular API administered. In one aspect the oral dosage form is a unit dose of bisphosphonic acid. In one embodiment the bisphosphonic acid is zoledronic acid. In one embodiment the unit dose is between about 10 mg to about 500 mg. In one embodiment the unit dose is between about 10 mg to about 400 mg. In one embodiment the unit dose is between about 10 mg to about 300 mg. In one embodiment the unit dose is between about 10 mg to about 200 mg. In another embodiment the unit dose is between about 10 mg to about 100 mg. In another embodiment the unit dose is between about 10 mg to about 90 mg. In another embodiment the unit dose is between about 10 mg to about 80 mg. In another embodiment the unit dose is between about 10 mg to about 70 mg. In another embodiment the unit dose is between about 10 mg to about 60 mg. In another embodiment the unit dose is between about 10 mg to about 50 mg. In another embodiment the unit dose is between about 100 mg to about 500 mg. In another embodiment the unit dose is between about 100 mg to about 400 mg. In another embodiment the unit dose is between about 100 mg to about 300 mg. In another embodiment the unit dose is between about 100 mg to about 200 mg. In another embodiment the unit dose is between about 50 mg to about 250 mg. In another embodiment the unit dose is between about 50 mg to about 150 mg. In another embodiment the unit dose is between about 50 mg to about 100 mg. In another embodiment the unit dose is between about 40 mg to about 120 mg. In another embodiment the unit dose is between about 50 mg to about 100 mg. In another embodiment the unit dose is between about 40 mg to about 50 mg. In another embodiment the unit dose is between about 50 mg to about 60 mg. In another embodiment the unit dose is between about 60 mg to about 70 mg. In another embodiment the unit dose is between about 70 mg to about 80 mg. In another embodiment the unit dose is between about 80 mg to about 90 mg. In another embodiment the unit dose is between about 90 mg to about 100 mg. In another embodiment the unit dose is between about 100 mg to about 110 mg. In another embodiment the unit dose is between about 110 mg to about 120 mg. In another embodiment the unit dose is between about 100 mg to about 200 mg. In another embodiment the unit dose is between about 150 mg to about 250 mg. In another embodiment the unit dose is between about 200 mg to about 300 mg. In another embodiment the unit dose is between about 250 mg to about 350 mg. In another embodiment the unit dose is between about 300 mg to about 400 mg. In another embodiment the unit dose is between about 350 mg to about 450 mg. In another embodiment the unit dose is between about 400 mg to about 500 mg. In another embodiment the unit dose is about 40 mg. In another embodiment the unit dose is about 50 mg. In another embodiment the unit dose is about 60 mg. In another embodiment the unit dose is about 70 mg. In another embodiment the unit dose is about 80 mg. In another embodiment the unit dose is about 90 mg. In another embodiment the unit dose is about 100 mg. In another embodiment the unit dose is about 110 mg. In another embodiment the unit dose is about 120 mg. In another embodiment the unit dose is about 130 mg. In another embodiment the unit dose is about 140 mg. In another embodiment the unit dose is about 150 mg. In another embodiment the unit dose is about 160 mg. In another embodiment the unit dose is about 170 mg. In another embodiment the unit dose is about 180 mg. In another embodiment the unit dose is about 190 mg. In another embodiment the unit dose is about 200 mg. In another embodiment the unit dose is between about 1 mg to about 10 mg. In one embodiment the bisphosphonic acid is dosed on a daily basis. In another embodiment the bisphosphonic acid is dosed twice weekly. In one embodiment the bisphosphonic acid is dosed on a weekly basis. In one embodiment the time between doses is ten days. In another embodiment the time between doses is two weeks. In another embodiment the time between doses is three weeks. In another embodiment the time between doses is four weeks. In another embodiment the time between doses is one month. In another embodiment the time between doses is six weeks. In another embodiment the time between doses is eight weeks. In another embodiment the time between doses is two months. In one embodiment the bisphosphonic acid is dosed no more frequent than once in a three month period. In one embodiment the bisphosphonic acid is dosed no more frequent than once in a six month period. In one embodiment the bisphosphonic acid is dosed no more frequent than once in a year. In one embodiment a course of treatment is between one month and one year. In another embodiment a course of treatment is between one month and six months. In one embodiment a course of treatment is between one month and three months. In one embodiment a course of treatment is between three months and six months. In one embodiment a course of treatment is one month. In another embodiment a course of treatment is two months. In another embodiment a course of treatment is three months.

The API (whether in the form of a molecular complex or as a free acid or base) and additional coformer combinations of the present invention (e.g., a zoledronic acid, L-lysine, and water complex and excess lysine) may be administered together or sequentially in single or multiple doses.

In one aspect the API and excess coformer are administered as a fixed dose combination product (e.g., a tablet containing both the molecular complex and excess coformer). In one embodiment the fixed dose combination product is a tablet or a capsule. In another embodiment the fixed dose combination product is a liquid solution or suspension. In another embodiment the fixed dose combination product is a particulate material, e.g., powder. In another embodiment the fixed dose combination product is a particulate material and is enclosed in a sachet. In another embodiment the fixed dose combination product is administered in single doses as part of a therapeutic treatment program or regimen. In another embodiment the fixed dose combination product is administered in multiple doses as part of a therapeutic treatment program or regimen.

In another aspect the API and excess coformer are administered as separate unit doses (e.g., two different tablets) but as part of the same therapeutic treatment program or regimen. In one embodiment, the API and excess coformer are administered simultaneously. In another embodiment the API and excess coformer are administered sequentially. In another embodiment the excess coformer is administered before the API. In another embodiment the API and excess coformer are administered in a single dose as part of the same therapeutic treatment program or regimen. In another embodiment the API and/or excess coformer is administered in multiple doses as part of the same therapeutic treatment program or regimen.

The compositions and dosage forms described herein can be administered via any conventional route of administration. In one embodiment the route of administration is oral.

Examples of suitable oral compositions of the present invention include tablets, capsules, troches, lozenges, suspensions, solutions, dispersible powders or granules, emulsions, syrups and elixirs.

Examples of fillers and diluents of the present invention include, for example, sodium carbonate, lactose, sodium phosphate and plant cellulose (pure plant filler). A range of vegetable fats and oils may be used in soft gelatin capsules. Other examples of fillers of the present invention include sucrose, glucose, mannitol, sorbitol, and magnesium stearate.

Examples of granulating and disintegrants of the present invention include corn starch and alginic acid, crosslinked polyvinyl pyrrolidone, sodium starch glycolate or crosslinked sodium carboxymethyl cellulose (crosscarmellose).

Examples of binding agents of the present invention include starch, gelatin, acacia, cellulose, cellulose derivatives, such as methyl cellulose, microcrystalline cellulose and hydroxypropyl cellulose, polyvinylpyrrolidone, sucrose, polyethylene glycol, lactose, or sugar alcohols like xylitol, sorbitol and maltitol.

Examples of lubricants of the present invention include magnesium stearate, stearic acid and talc.

Tablets or capsules of the present invention and/or the drug containing particles therein may be uncoated or coated by known techniques. Such coatings may delay disintegration and thus, absorption in the gastrointestinal tract and/or may provide a sustained action over a longer period.

Coatings, e.g., enteric coating, may be applied using an appropriate aqueous solvent or organic solvent. Examples of enteric coatings include polymethacrylates, such as methacrylic acid/ethyl acrylate; cellulose esters, such as cellulose acetate phthalate (CAP), cellulose acetate trimellitate (CAT), and hydroxypropylmethylcellulose acetate succinate (HPMCAS); and polyvinyl derivatives, such as polyvinyl acetate phthalate (PVAP). In one embodiment the tablet/capsule or particles/granules comprising a pharmaceutical composition of the present invention is enteric coated using an organic solvent coating.

The pharmaceutical compositions of the present invention comprising an API and excess coformer may be formulated such that the API and excess coformer have the same release profile or different release profiles. In one aspect the API and excess coformer have the same release profile. In one embodiment a pharmaceutical composition comprising zoledronic acid and an amino acid (e.g., lysine) are formulated such that the zoledronic acid and amino acid have the same release profile. In another embodiment the zoledronic acid is released within one hour of the amino acid. In another embodiment the zoledronic acid is released within 30 minutes of the amino acid. In another embodiment the zoledronic acid is released within 15 minutes of the amino acid. In another embodiment the zoledronic acid is released before the amino acid. In another aspect the API is released before the excess coformer. In another aspect the excess coformer is released before the API. In another aspect the amino acid is released before the API.

The pharmaceutical compositions of the present invention may be formulated as a sustained release formulation such that the API or excess coformer is released over a longer period of time that it would be if formulated as an immediate release formulation. In one embodiment the excess coformer is formulated as a sustained release formulation. In another embodiment the API is formulated as a sustained release formulation. In another embodiment both the API and the excess coformer are formulated as a sustained release formulation.

The pharmaceutical compositions of the present invention may also be formulated as an immediate release formulation. In one embodiment the excess coformer is formulated as an immediate release formulation. In another embodiment the API is formulated as an immediate release formulation. In another embodiment both the API and the excess coformer are formulated as an immediate release formulation.

The pharmaceutical compositions of the present invention may further be formulated as a 'delayed+sustained release' formulation, a formulation intended to delay release of a drug until the dosage form has passed through the stomach, followed by sustained release of the drug in the small intestine. Such a release profile can be achieved, e.g., through coating of multiparticulates or hydrophilic matrix tablets with pH-dependent coating polymers, or coating with combinations of pH dependent coating polymers and extended release barrier membrane systems. In one embodiment the excess coformer is formulated as a delayed+sustained release formulation. In another embodiment the API is formulated as a delayed+sustained release formulation.

The pharmaceutical compositions of the present invention may further be formulated as an "enteric release" formulation, a formulation intended to delay release of a drug until the dosage form has passed through the stomach, followed by rapid release of the drug in the proximal small intestine. Such a release profile can be achieved through coating of particles or granules within a tablet or capsule or coating of the tablet, caplet or capsule with a pH-dependent polymeric coating system. In one embodiment the excess coformer is formulated as an enteric release formulation. In another embodiment the API is formulated as an enteric release formulation. In another embodiment the pharmaceutical composition is an enterically coated dosage form. In one embodiment enterically coated dosage form is an enterically coated hard gelatin capsule. In another embodiment enterically coated dosage form is an enterically coated soft or hard gelatin capsule. In another embodiment the enterically coated dosage form is an enterically coated tablet.

The term "modified enteric release" refers to a formulation that allows for a small portion of a drug dose to be released into the stomach, with the remainder of release occurring rapidly upon passage of the dosage form into the small intestine. Such a release profile can be achieved through the use of hydrophilic pore formers in pH dependent enteric coatings. In one embodiment the excess coformer is formulated as a modified enteric release formulation. In another embodiment the API is formulated as a modified enteric release formulation. In another embodiment both the excess coformer and the API are formulated as a modified enteric release formulation.

The term "biphasic release" refers to a formulation whereby a drug is released in a biphasic manner rather than a single phase. It also refers to a formulation where two different components, e.g., the excess coformer and API of the present invention, are released in a biphasic manner rather than a single phase. For example, a first dose may be released as an immediate release dose fraction, while a second dose is released as an extended release phase. Examples of such systems can be found as bilayer tablets, drug layered matrices, or multiparticulate combinations with different release profiles. In one embodiment the excess coformer is formulated as a biphasic release formulation. In another embodiment the molecular complex is formulated as a biphasic release formulation.

In another embodiment the excess coformer and molecular complex are formulated as a biphasic formulation, wherein said excess coformer and said API are formulated to be released in different phases thereby forming a biphasic release profile. In another embodiment the excess coformer and API are formulated as a biphasic release formulation, wherein said excess coformer is formulated to be released as a first phase and said API is formulated to be released as a second phase. In another embodiment the pharmaceutical composition of the present invention is formulated as a bilayer tablet comprising a first layer and a second layer, wherein said first layer comprises an excess coformer and an excipient, and wherein said second layer comprises an API and an excipient.

In another embodiment the pharmaceutical composition of the present invention is formulated as a multiparticulate formulation, i.e., a formulation comprising multiple particles. In one embodiment the API and excess coformer are in the same particle.

In another embodiment the pharmaceutical composition of the present invention is formulated as a tablet or capsule comprising a multiparticulate combination, said multiparticulate combination comprising a first multiparticulate formulation and a second multiparticulate formulation, wherein said first multiparticulate formulation comprises an excess coformer and, optionally, one or more excipient, and wherein said second multiparticulate formulation comprises a API and, optionally, one or more excipient.

In one embodiment the particles comprising the API, excess coformer or both API and excess coformer have a mean size diameter by volume of between about 1 and about 1000 microns. In one embodiment the particles have a mean size of between about 1 and about 100 microns. In one embodiment the particles have a mean size of between about 1 and about 10 microns. In one embodiment the particles have a mean size of between about 1 and about 5 microns. In one embodiment the particles have a mean size of between about 100 and about 1000 microns. In one embodiment the particles have a mean size of between about 100 and about 500 microns. In one embodiment the particles have a mean size of between about 200 and about 400 microns. In one embodiment the particles have a mean size of between about 300 and about 500 microns.

The term "$C_{max}$" refers to the maximum plasma concentration of a drug after administration.

In one embodiment, the excess coformer and API are formulated as a biphasic release formulation, wherein said excess coformer is formulated to be released as a first phase and said API is formulated to be released as a second phase, and wherein a $C_{max}$ of said excess coformer occurs less than 60 minutes before a $C_{max}$ of said API. In another embodiment, the $C_{max}$ for said excess coformer occurs less than 45 minutes before the $C_{max}$ of said API. In another embodiment, the $C_{max}$ for said excess coformer occurs less than 30 minutes before the $C_{max}$ of said API. In another embodiment, the $C_{max}$ for said excess coformer occurs before the $C_{max}$ of said API. In another embodiment, the $C_{max}$ for said API occurs before the $C_{max}$ of said excess coformer. In a particular embodiment wherein the pharmaceutical composition comprises a bisphosphonic acid, e.g., zoledronic acid and an amino acid, e.g., lysine, the $C_{max}$ for said amino acid occurs less than 60 minutes before the $C_{max}$ of said bisphosphonic acid. In another embodiment, the $C_{max}$ for the amino acid occurs less than 45 minutes before the $C_{max}$ of the bisphosphonic acid. In another embodiment, the $C_{max}$ for the amino acid occurs less than 30 minutes before the $C_{max}$ of the bisphosphonic acid. In another embodiment, the $C_{max}$ for the bisphosphonic acid occurs before the $C_{max}$ of the amino acid. In one embodiment, the excess coformer and API are formulated as a biphasic release formulation, wherein said excess coformer is formulated to be released as a first phase and said API is formulated to be released as a second phase, and wherein a $T_{max}$ of said excess coformer occurs less than 60 minutes before a $T_{max}$ of said API. In another embodiment, the $T_{max}$ for said excess coformer occurs less than 45 minutes before the $T_{max}$ of said API. In another embodiment, the $T_{max}$ for said excess coformer occurs less than 30 minutes before the $T_{max}$ of said API. In another embodiment, the $T_{max}$ for said excess coformer occurs before the $T_{max}$ of said API. In another embodiment, the $T_{max}$ for said API occurs before the $T_{max}$ of said excess coformer. In a particular embodiment wherein the pharmaceutical composition comprises a bisphosphonic acid, e.g., zoledronic acid and an amino acid, e.g., lysine, the $T_{max}$ for said amino acid occurs less than 60 minutes before the $T_{max}$ of said bisphosphonic acid. In another embodiment, the $T_{max}$ for the amino acid occurs less than 45 minutes before the $T_{max}$ of the bisphosphonic acid. In another embodiment, the $T_{max}$ for the amino acid occurs less than 30 minutes before the $T_{max}$ of the bisphosphonic acid. In another embodiment, the $T_{max}$ for the bisphosphonic acid occurs before the $T_{max}$ of the amino acid.

In one embodiment, the excess coformer and API are formulated as a biphasic release formulation, wherein said excess coformer is formulated to be released as a first phase and said API is formulated to be released as a second phase, and wherein a $C_{max}$ and $T_{max}$ of said excess coformer occurs less than 60 minutes before a $C_{max}$ and $T_{max}$ of said API. In another embodiment, the $C_{max}$ and $T_{max}$ for said excess coformer occurs less than 45 minutes before the $C_{max}$ and $T_{max}$ of said API. In another embodiment, the $C_{max}$ and $T_{max}$ for said excess coformer occurs less than 30 minutes before the $C_{max}$ and $T_{max}$ of said API. In another embodiment, the $C_{max}$ and $T_{max}$ for said excess coformer occurs before the $C_{max}$ and $T_{max}$ of said API. In another embodiment, the $C_{max}$ and $T_{max}$ for said API occurs before the $C_{max}$ and $T_{max}$ of said excess coformer. In a particular embodiment wherein the pharmaceutical composition comprises a bisphosphonic acid, e.g., zoledronic acid and an amino acid, e.g., lysine, the $C_{max}$ and $T_{max}$ for said amino acid occurs less than 60 minutes before the $C_{max}$ and $T_{max}$ of said bisphosphonic acid. In another embodiment, the $C_{max}$ and $T_{max}$ for the amino acid occur less than 45 minutes before the $C_{max}$ and $T_{max}$ of the bisphosphonic acid. In another embodiment, the $C_{max}$ and $T_{max}$ for the amino acid occur less than 30 minutes before the $C_{max}$ and $T_{max}$ of the bisphosphonic acid. In another embodiment, the $C_{max}$ and $T_{max}$ for the bisphosphonic acid occur before the $C_{max}$ and $T_{max}$ of the amino acid.

In one embodiment the excess coformer and API are formulated as a biphasic release formulation in a fixed dose combination product (e.g., in a single tablet). In one embodiment the excess coformer and API are each formulated as a multi-particulate formulation and combined to form a fixed dose combination product. In one embodiment the dosage form is a capsule comprising a first multiparticulate formulation of said excess coformer and a second multiparticulate formulation of said API as a fixed dose combination product. In another embodiment the fixed dose combination product is a bilayer tablet comprising a first layer and a second layer, wherein said first layer comprises an excess coformer and said second layer comprises an API.

In another embodiment, the API and excess coformer are formulated into a bilayer, whereby the API and matrix-forming material are combined and compressed to form a sustained release layer, and the excess coformer is blended with one or more agents and forms a second layer. In one embodiment the excess coformer layer is an immediate release formulation. In another embodiment the bilayer dosage form is enteric coated. In another embodiment the excess coformer layer and/or the API layer, is an enteric release formulation The term "first-order release" refers to where the rate of elimination of drug from plasma is proportional to the plasma concentration of the drug. In one embodiment the excess coformer is released from the pharmaceutical composition as a first-order release. In one embodiment the API is released from the pharmaceutical composition as a first-order release. In one embodiment both the excess coformer and API are released from the pharmaceutical composition as a first-order release.

The term "zero order release" refers to the ability to deliver a drug at a rate which is independent of time and concentration of the drug within a pharmaceutical dosage form. Zero order mechanism ensures that a steady amount of drug is released over time, minimizing potential peak/trough fluctuations and side effects, while maximizing the amount of time the drug concentrations remain within the therapeutic window (efficacy). Osmotic tablet formulations, coated tablet matrices, and the use of polymer combinations in hydrophilic matrices, for example, can be utilized to provide zero order drug release profiles. In one embodiment the excess coformer is released from the pharmaceutical composition as a zero-order release. In one embodiment the API is released from the pharmaceutical composition as a zero-order release. In one embodiment both the excess coformer and API are released from the pharmaceutical composition as a zero-order release.

Compounds useful for modifying a release profile of a drug are well known in the art. For example, a time delay material such as glyceryl monostearate or glyceryl distearate may be employed. The dosage form may also be coated by the techniques (e.g., those described in the U.S. Pat. Nos. 4,256,108; 4,166,452 and 4,265,874, each incorporated by reference in their entireties) to form osmotic therapeutic tablets for controlled release. Other controlled release technologies are also available and are included herein. Typical ingredients that are useful to slow the release of the drug in sustained release tablets include various cellulosic compounds, such as methylcellulose, ethylcellulose, propylcellulose, hydroxypropylcellulose, hydroxyethylcellulose, hydroxypropylmethylcellulose, microcrystalline cellulose, starch and the like. Various natural and synthetic materials are also of use in sustained release formulations. Examples include alginic acid and various alginates, polyvinyl pyrrolidone, tragacanth, locust bean gum, guar gum, gelatin, various long chain alcohols, such as cetyl alcohol and beeswax.

One embodiment of the invention includes a sustained release tablet that comprises the API in combination with one or more of the cellulosic compounds noted above, compressed into a sustained release tablet to form a polymer matrix. In another embodiment, the API and matrix-forming material are combined and compressed to form a sustained release core, and the excess coformer is blended with one or more coating agents and coated onto the outer surface of the core.

In one embodiment, the excess coformer is provided as a combined first immediate release dose and a second sustained release dose. The sustained release dose can be, for example, zero-order or first order. In certain embodiments the second dose has a lag time wherein the drug is released from the second dose at about 30 minutes, in another embodiment 1 hour, in another embodiment 1.5 hours, in another embodiment 2 hours, in another embodiment 2.5 hours, in another embodiment 3 hours, in another embodiment 3.5 hours and in another embodiment 4 hours after administration. The initial dose may be the same or different amount from the second dose.

In one aspect, the API is provided as a combined first immediate release dose and a second sustained release dose. The sustained release dose can be, for example, zero-order or first order. In certain embodiments the second dose has a lag time where drug is released from the second dose at about 30 minutes, in another embodiment 1 hour, in another embodiment 1.5 hours, in another embodiment 2 hours, in another embodiment 2.5 hours, in another embodiment 3 hours, in another embodiment 3.5 hours and in another embodiment 4 hours after administration. The initial dose may be the same or different from the second dose.

In one aspect, the excess coformer and API is provided in a combined single unit dose whereby the excess coformer is provided as an immediate release dose and API as a sustained release dose. The API sustained release dose can be, for example, zero-order or first order. In one embodiment the API second dose has a lag time where drug is released at about 30 minutes, in another embodiment 1 hour, in another embodiment 1.5 hours, in another embodiment 2 hours, in another embodiment 2.5 hours, in another embodiment 3 hours, in another embodiment 3.5 hours and in another embodiment 4 hours after administration.

Typical release time frames for sustained release tablets in accordance with the present invention range from about 1 to as long as about 48 hours, preferably about 4 to about 24 hours, and more preferably about 8 to about 16 hours.

Hard gelatin capsules constitute another solid dosage form for oral use. Such capsules similarly include the active ingredients mixed with carrier materials as described above. Soft gelatin capsules include the active ingredients mixed with water-miscible solvents such as propylene glycol, PEG and ethanol, or an oil such as peanut oil, liquid paraffin or olive oil. Aqueous suspensions are also contemplated as containing the active material in admixture with excipients suitable for the manufacture of aqueous suspensions. Such excipients include suspending agents, for example sodium carboxymethylcellulose, methylcellulose, hydroxypropylmethylcellulose, sodium alginate, polyvinylpyrrolidone, tragacanth and acacia; dispersing or wetting agents, e.g., lecithin; preservatives, e.g., ethyl, or n-propyl para-hydroxybenzoate, colorants, flavors, sweeteners and the like.

Dispersible powders and granules suitable for preparation of an aqueous suspension by the addition of water provide the active ingredients in admixture with a dispersing or wetting agent, suspending agent and one or more preservatives. Suitable dispersing or wetting agents and suspending agents are exemplified by those already mentioned above. Aqueous solutions, suspensions, syrups and elixirs may also be formulated.

The techniques and approaches set forth in the present disclosure can further be used by the person of ordinary skill in the art to prepare variants thereof, said variants are considered to be part of the inventive disclosure.

EXAMPLES

The following examples illustrate the invention without intending to limit the scope of the invention.

Molecular complexes of zoledronic acid and sodium, ammonium, ammonia, L-lysine, DL-lysine, nicotinamide, adenine, and glycine have been made and are characterized by their PXRD patterns and FTIR spectra disclosed herein. Further, in vivo data in rats concerning the oral bioavailability of zoledronic acid delivered orally, intravenously, and intraduodenally have been generated as well as PK profiles of the parent compound.

Zoledronic acid as a starting material used in all experiments in this disclosure was supplied by Farmkemi Limited (Wuhan Pharma Chemical Co.), China with purity of ca. 98% and was purified further via recrystallization from water. All other pure chemicals (Analytical Grade) were supplied by Sigma-Aldrich and used without further purification.

Enteric coating of gelatin capsules was contracted out to AzoPharma, Hollywood, Fla., USA. A 10% w/w coating solution of Eudragit L100-55, and triethyl citrate, 9.09 and 0.91 w/w % respectively, in purified water and acetone was used in the Vector LDCS pan coater to achieve a uniform coating layer on the capsules. The coating uniformity and functionality for duodenal delivery was tested by 2 hr dissolution in simulated gastric fluid stirred at 75 rpm and 37° C. All capsules remained closed for the duration of this test.

Micronization was carried out at the Jet Pulverizer Company (NJ, USA) using a three inch diameter mill.

Solid Phase Characterization

Analytical techniques used to observe the crystalline forms include powder X-ray diffraction (PXRD) and Fourier transform infrared spectroscopy (FTIR). The particular methodology used in such analytical techniques should be viewed as illustrative, and not limiting in the context of data collection. For example, the particular instrumentation used to collect data may vary; routine operator error or calibration standards may vary; sample preparation method may vary (for example, the use of the KBr disk or Nujol mull technique for FTIR analysis).

Fourier Transform FTIR Spectroscopy (FTIR): FTIR analysis was performed on a Perkin Elmer Spectrum 100 FTIR spectrometer equipped with a solid-state ATR accessory. Powder X-Ray Diffraction (PXRD): All zoledronic acid molecular complex products were observed by a D-8 Bruker X-ray Powder Diffractometer using Cu Kα ($\lambda$=1.540562 Å), 40 kV, 40 mA. The data were collected over an angular range of 3° to 40° 2θ in continuous scan mode at room temperature using a step size of 0.05° 2θ and a scan speed of 6.17°/min.

Laser scattering particle size analysis: All micronized samples were tested using the Horiba LA950 laser scattering particle size analyzer, dry method using air at pressure of 0.3 MPA to fluidize the micronized samples before flowing in the path of a laser beam. The micronized samples were further tested using light microscopy to verify the Horiba results.

Example 1

Figure 2:
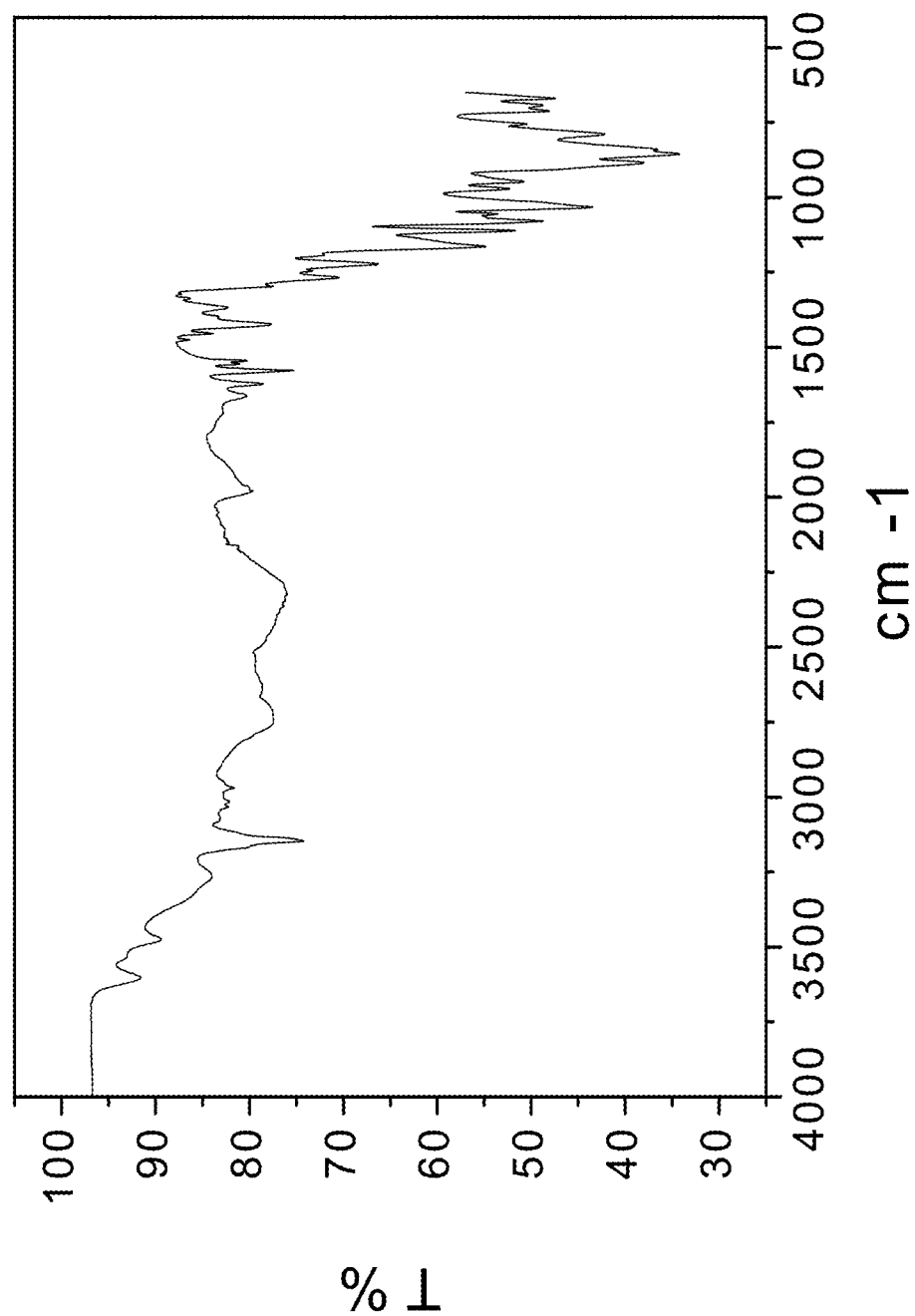
FIG. 2 is an FTIR spectrum of a complex comprising zoledronic acid, sodium zoledronic salt, and water.

Preparation of Zoledronic Acid, Sodium Zoledronic Salt, and Water Complex 200 mg of zoledronic acid was slurried with 180 mg of sodium chloride in 1 mL of 1:1 ethanol:water overnight. The material was filtered and rinsed. The particulate material was gathered and stored in a screw cap vial for subsequent analysis. The material was characterized by PXRD and FTIR corresponding to FIG. 1 and FIG. 2, respectively.

Example 2

Figure 3:
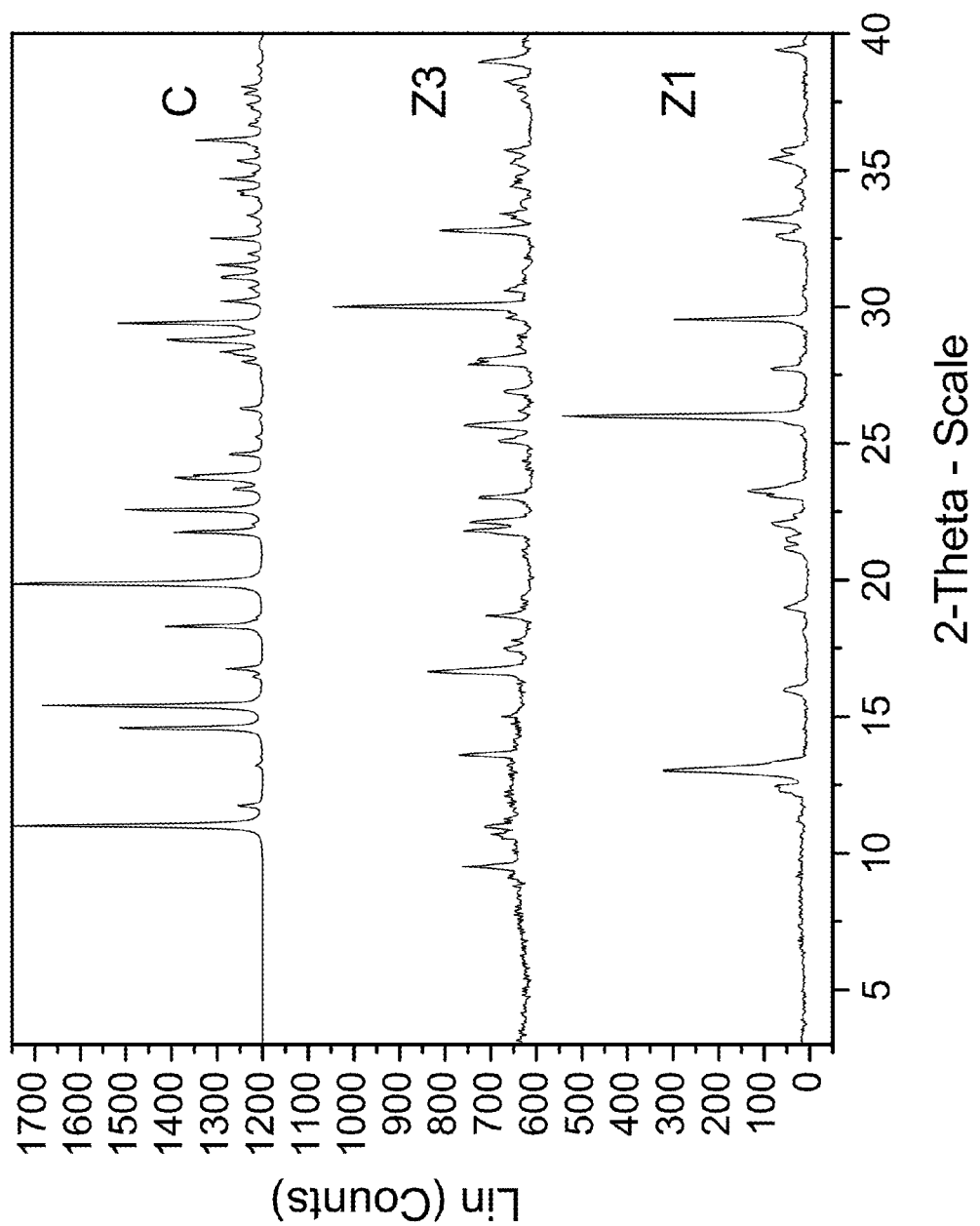
FIG. 3 shows PXRD diffractograms of: (C=ammonium zoledronic salt and water complex), (Z1=Zoledronic acid monohydrate), and (Z3=Zoledronic acid trihydrate).
Figure 4:
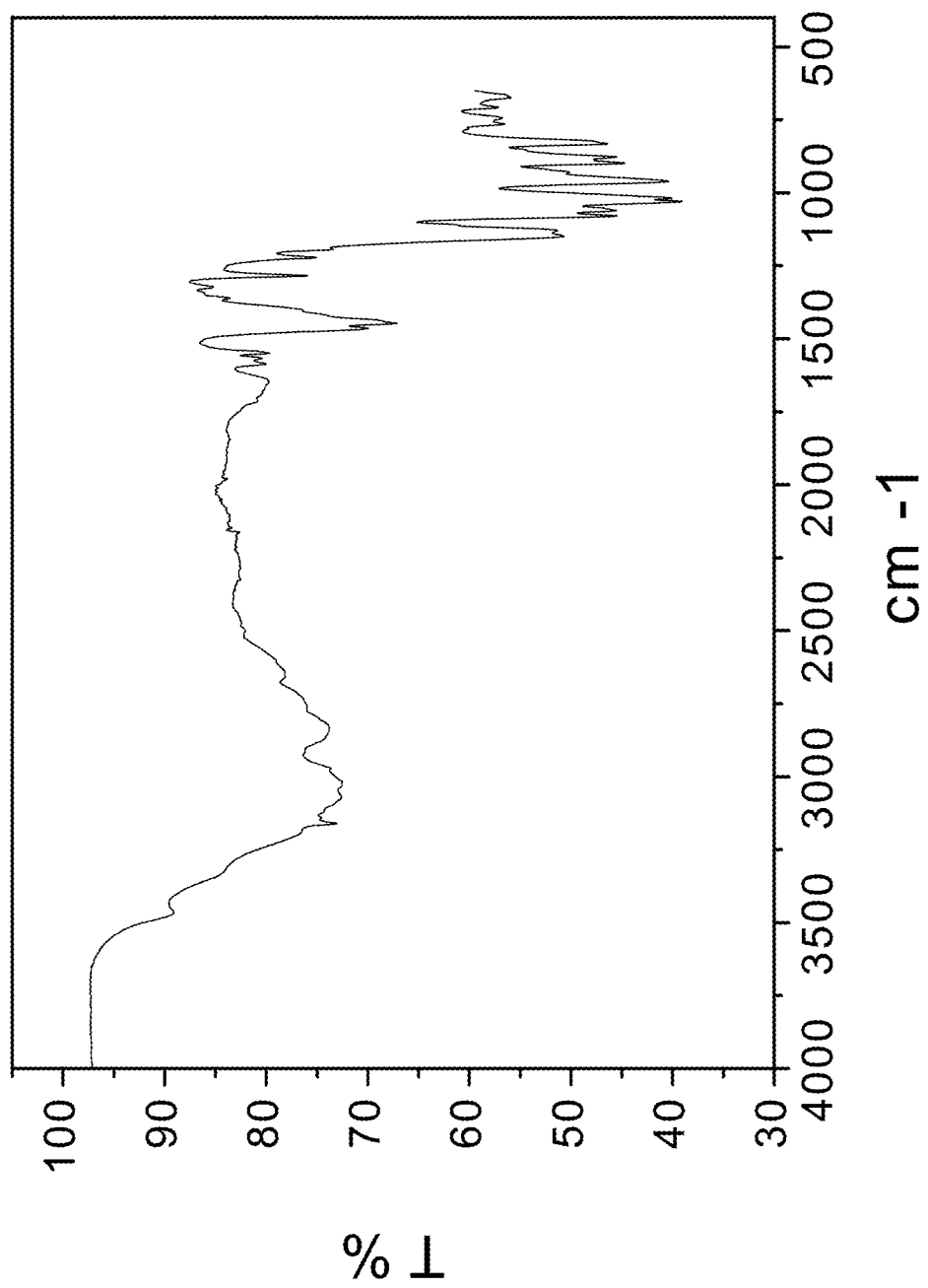
FIG. 4 is an FTIR spectrum of ammonium zoledronic salt and water complex.

Preparation of Ammonium Zoledronic Salt and Water Complex 300 mg of zoledronic acid was slurried in 7N ammonia in methanol overnight. The material was filtered and rinsed. The particulate material was dissolved in water and left to evaporate at ambient conditions to obtain colorless plates after 1 week. The material was characterized by PXRD and FTIR corresponding to FIG. 3 and FIG. 4, respectively.

Example 3

Figure 5:
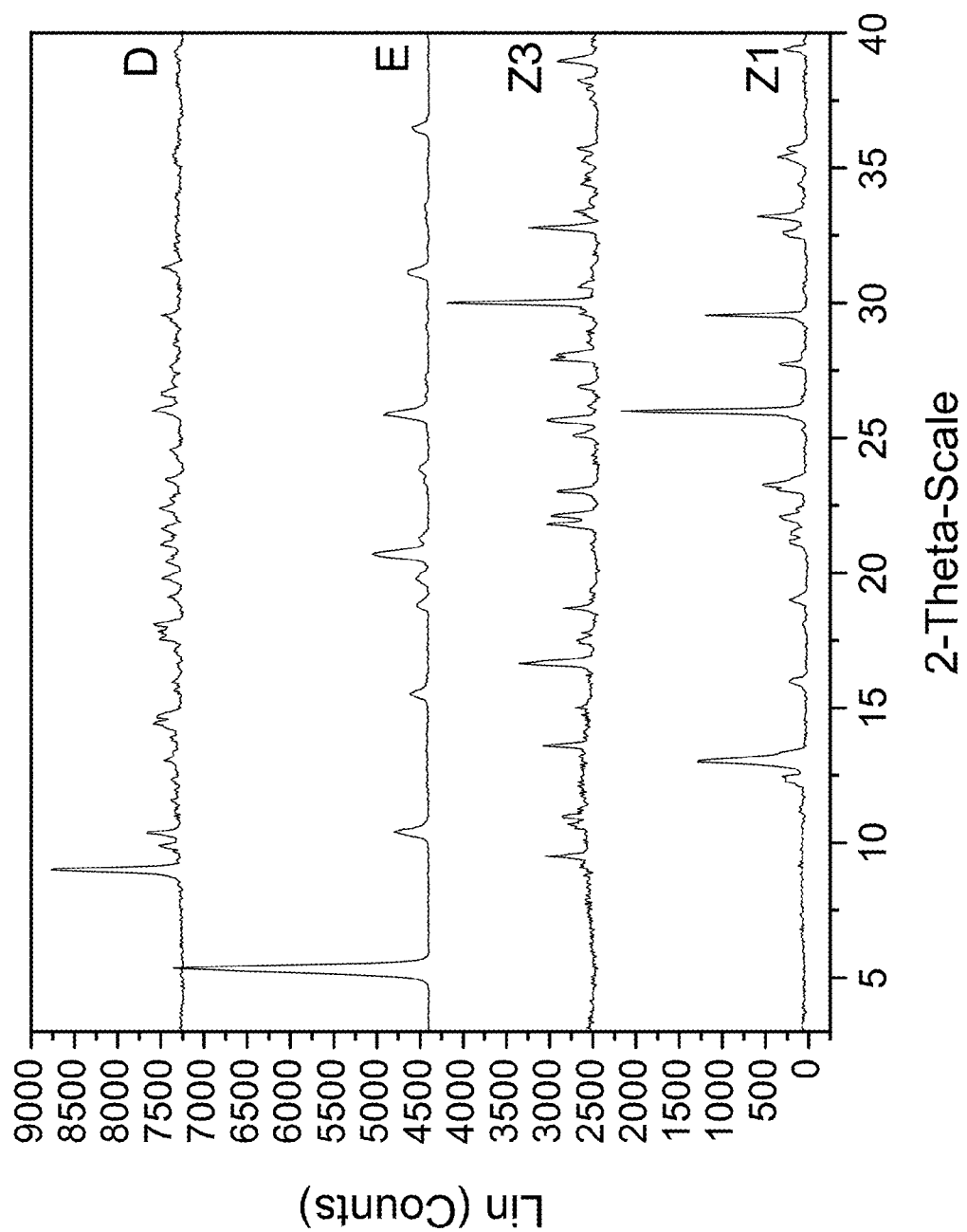
FIG. 5 shows PXRD diffractograms of: (D=zoledronic, L-lysine, and water complex), (E=L-lysine), (Z1=Zoledronic acid monohydrate), and (Z3=Zoledronic acid trihydrate).
Figure 6:
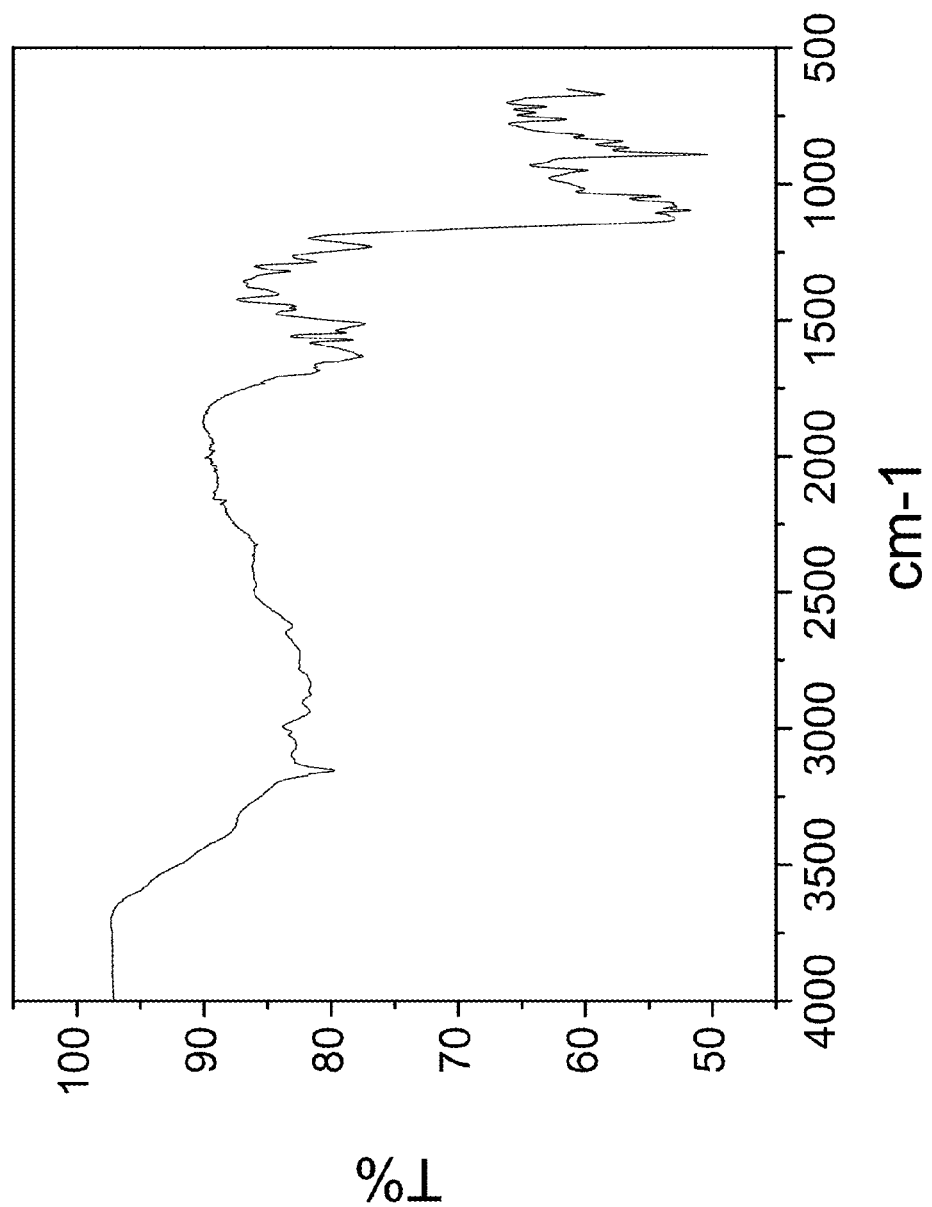
FIG. 6 is an FTIR spectrum of zoledronic, L-lysine, and water complex.

Preparation of Zoledronic, L-Lysine, and Water Complex 200 mg of zoledronic acid and 54 mg of L-lysine were slurried in 2 mL of tetrahydrofuran and 200 µl of water overnight. The solids gathered after filtration were dried and stored in a screw cap vials for subsequent analysis. The material was characterized by PXRD and FTIR corresponding to FIG. 5 and FIG. 6, respectively.

Example 4

Figure 7:
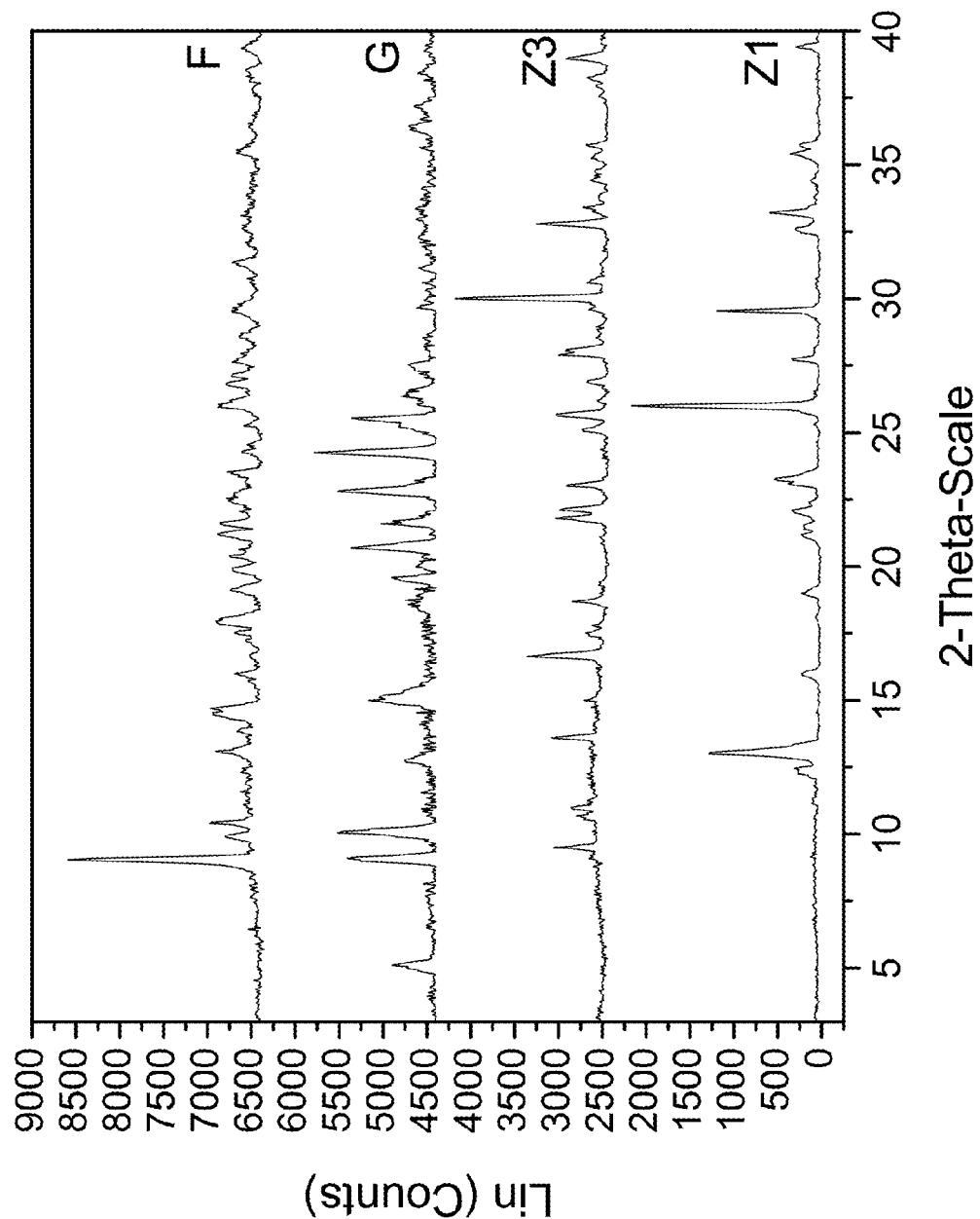
FIG. 7 shows PXRD diffractograms of: (F=zoledronic, DL-lysine, and water complex), (G=DL-lysine), (Z1=Zoledronic acid monohydrate), and (Z3=Zoledronic acid trihydrate).
Figure 8:
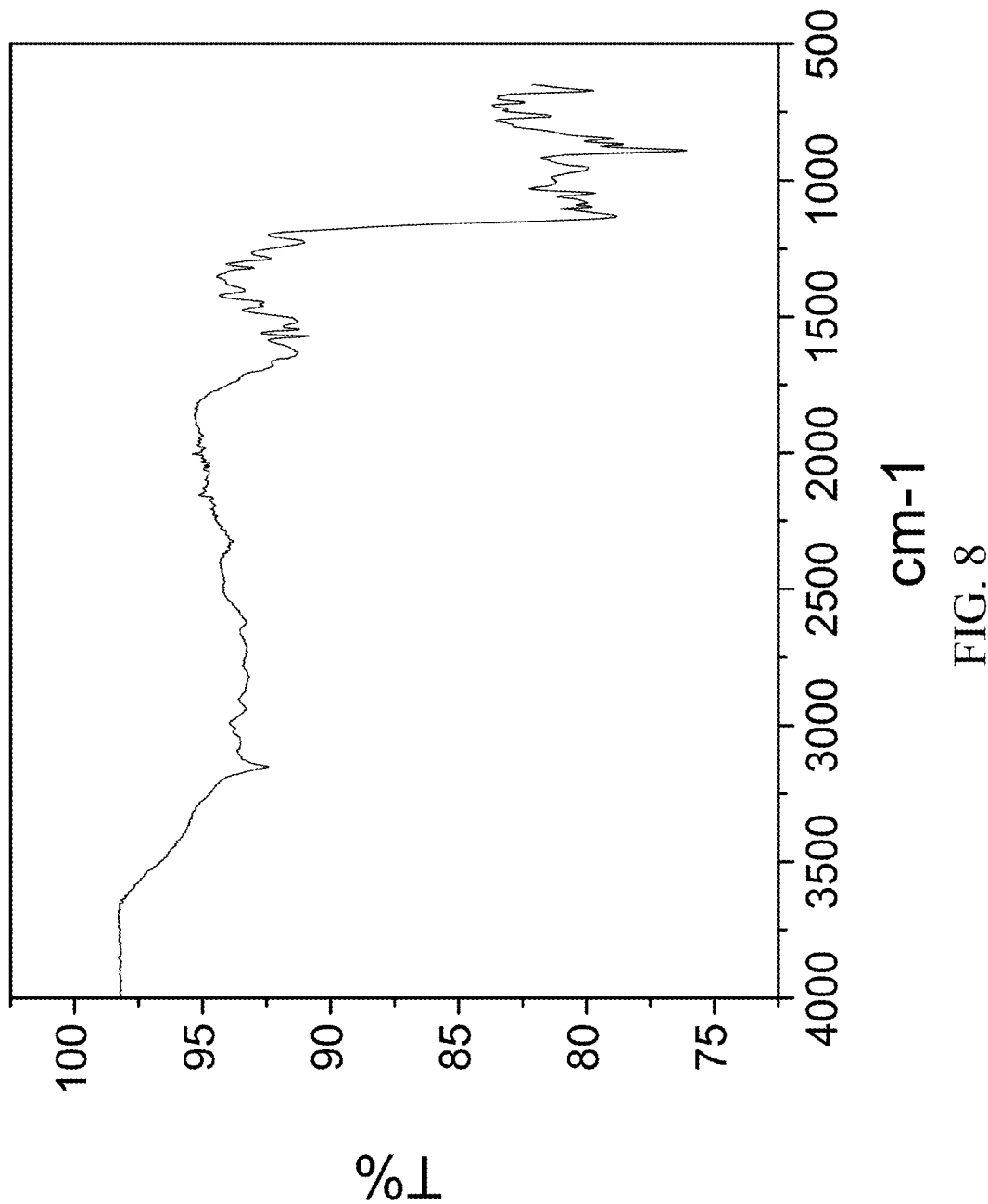
FIG. 8 is an FTIR spectrum of zoledronic, DL-lysine, and water complex.

Preparation of Zoledronic, DL-Lysine, and Water Complex 204 mg of zoledronic acid and 59 mg of DL-lysine were slurried in 2 mL of tetrahydrofuran and 200 µl of water overnight. The solids gathered after filtration were dried and stored in a screw cap vials for subsequent analysis. The material was characterized by PXRD and FTIR corresponding to FIG. 7 and FIG. 8 respectively.

Example 5

Figure 9:
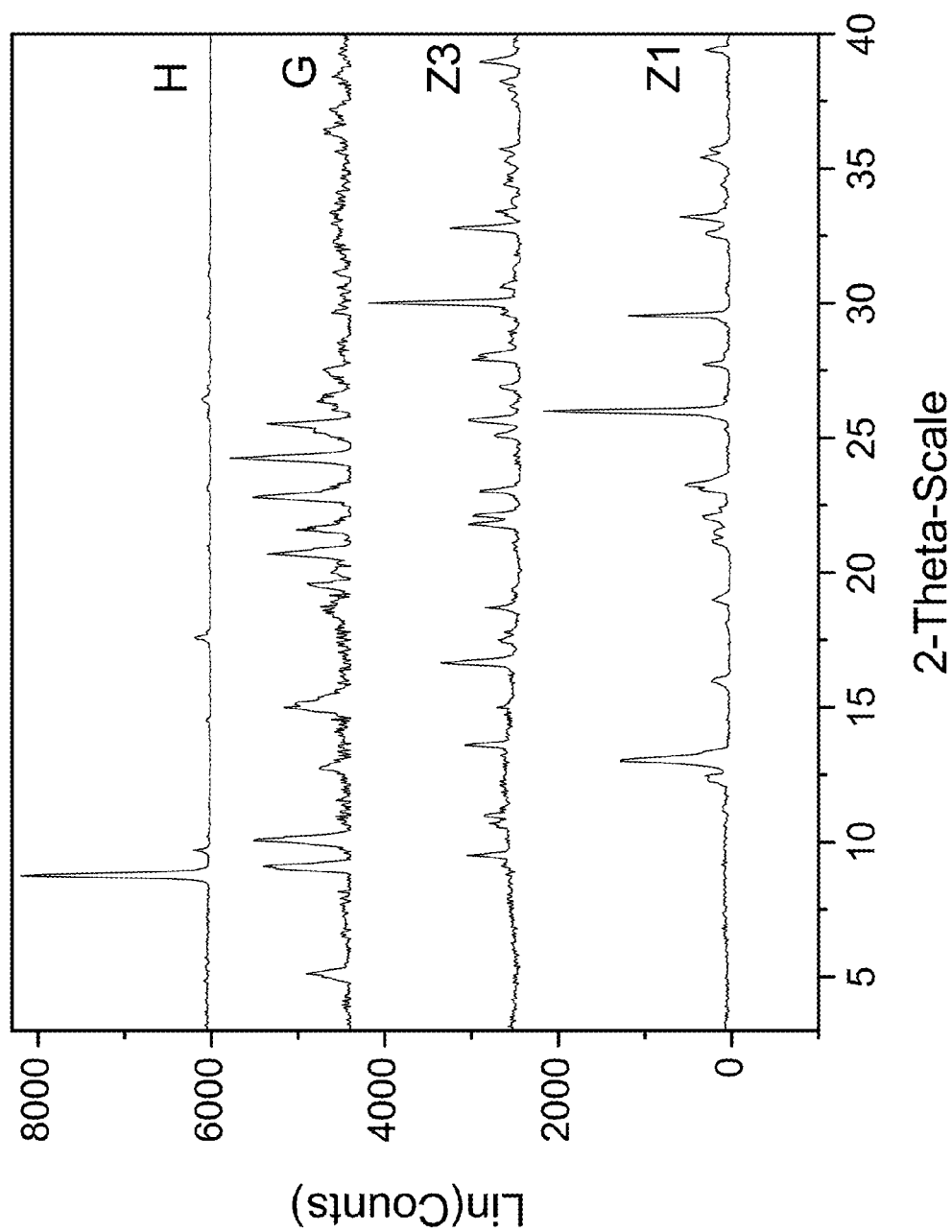
FIG. 9 shows PXRD diffractograms of: (H=zoledronic acid, zoledronic, DL-lysine, ethanol, and water complex), (G=DL-lysine), (Z1=Zoledronic acid monohydrate), (Z3=Zoledronic acid trihydrate).
Figure 10:
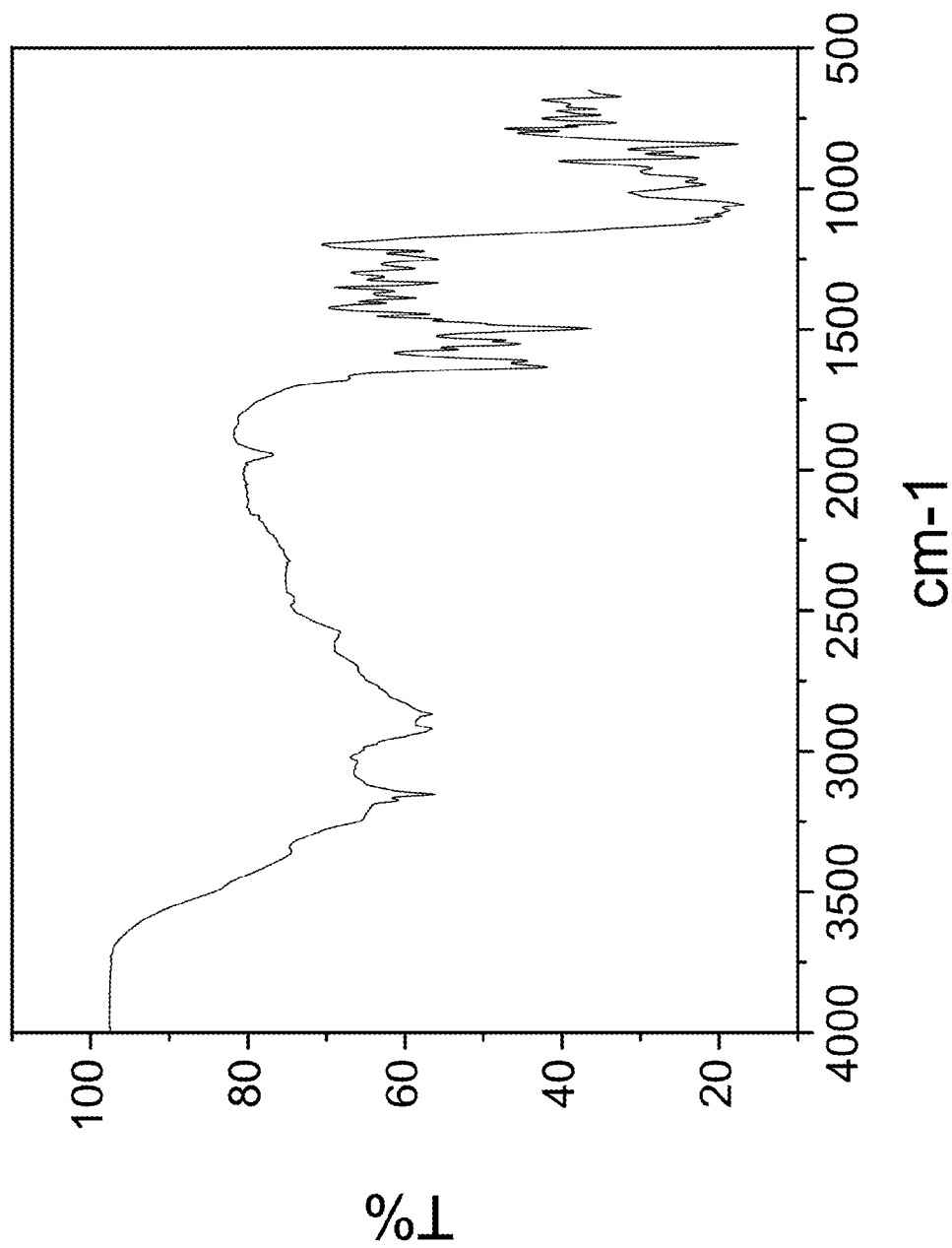
FIG. 10 is an FTIR spectrum of zoledronic acid, zoledronic, DL-lysine, ethanol, and water complex.

Preparation of Zoledronic Acid, Zoledronic, DL-Lysine, Ethanol, and Water Complex 103 mg of zoledronic acid and 54 mg of DL-lysine were dissolved in 400 µl of water, capped and stirred overnight. The next day 0.25 mL of ethanol was added drop wise. The vial was capped with a screw cap vial and after 1 day crystals appeared and were filtered off. The material was stored for subsequent analysis. The material was characterized by PXRD and FTIR corresponding to FIG. 9 and FIG. 10 respectively.

Example 6

Figure 11:
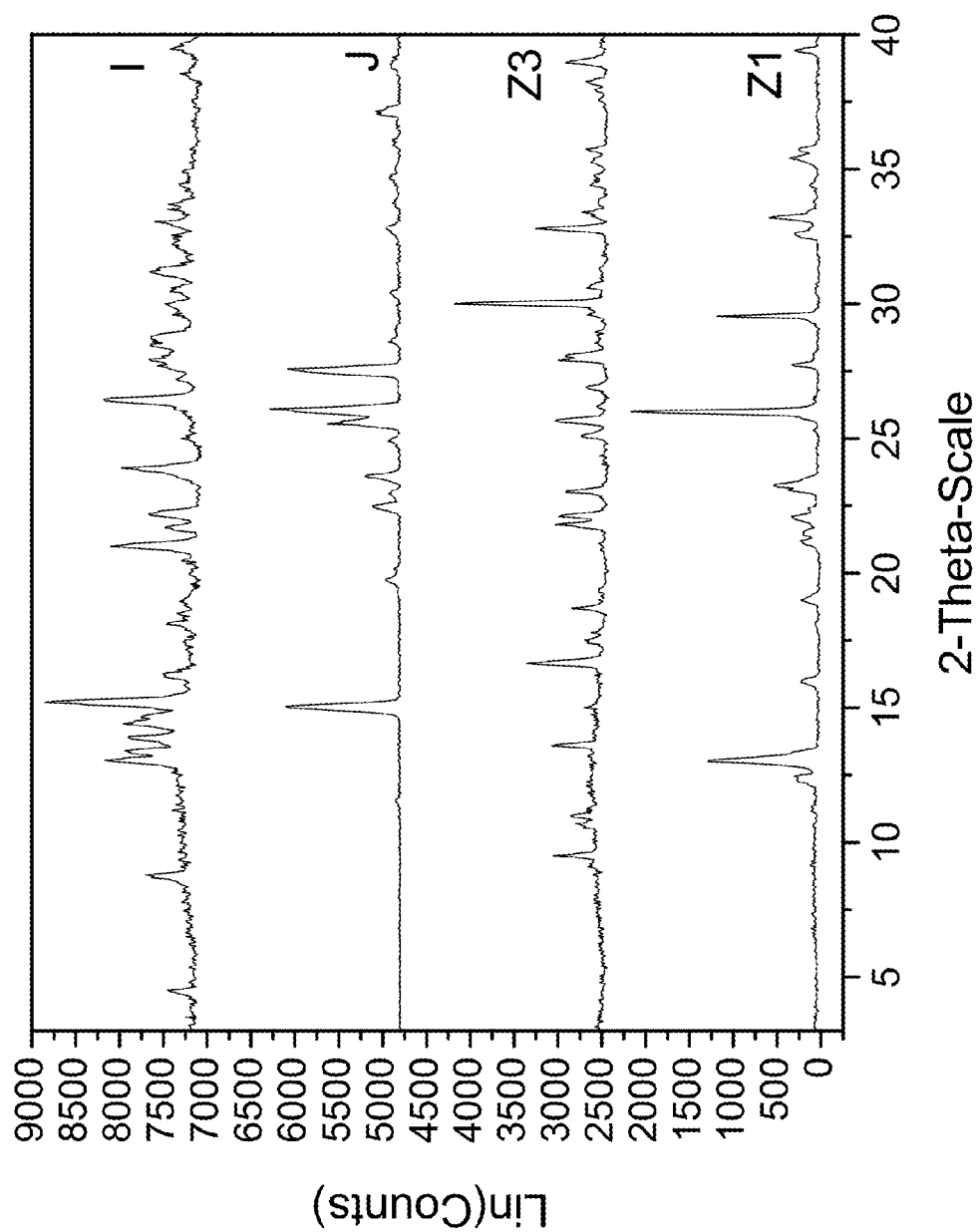
FIG. 11 shows PXRD diffractograms of: (I=zoledronic, nicotinamide, and water complex), (J=nicotinamide), (Z1=Zoledronic acid monohydrate), and (Z3=Zoledronic acid trihydrate).
Figure 12:
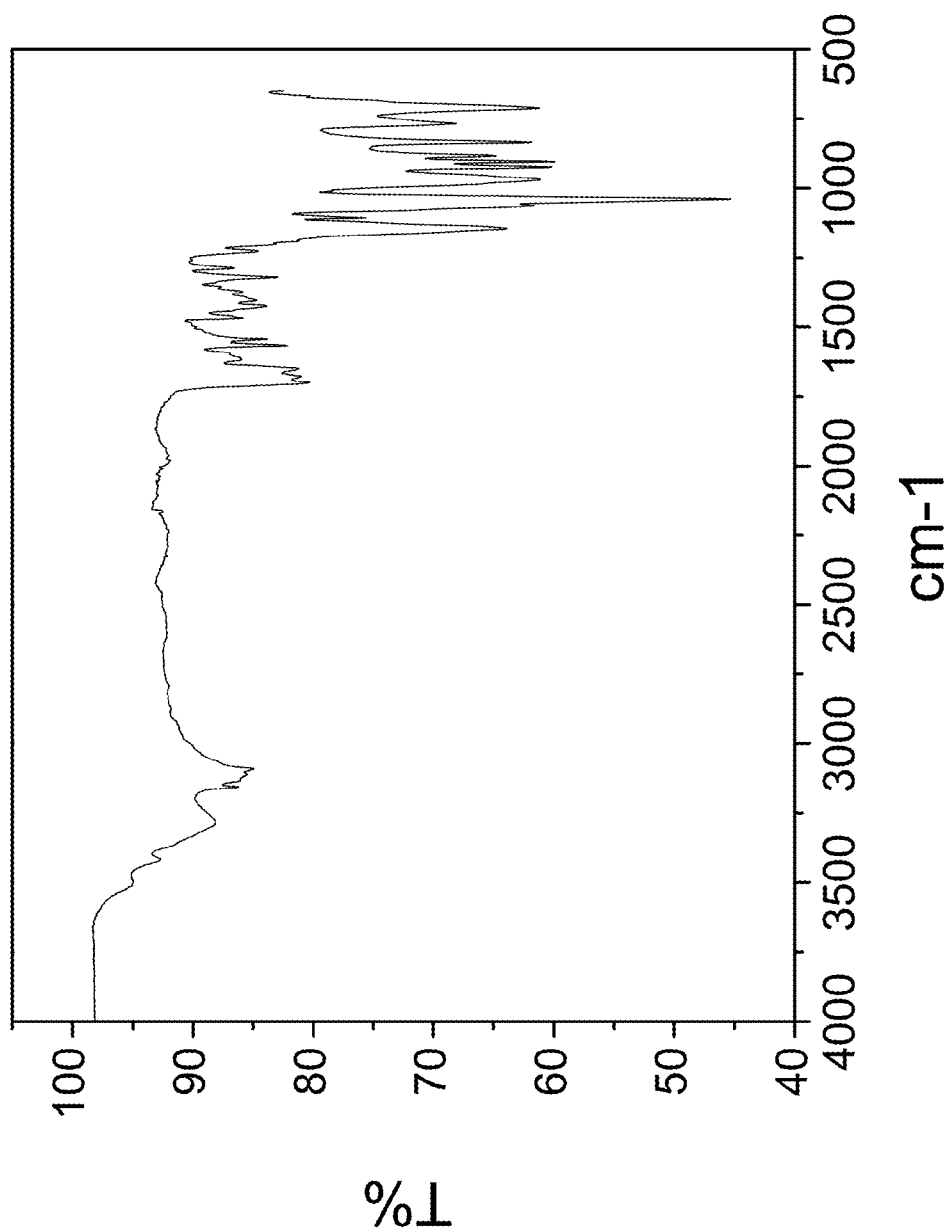
FIG. 12 is an FTIR spectrum of zoledronic, nicotinamide, and water complex.

Preparation of Zoledronic, Nicotinamide, And Water Complex by Solvent-Drop Grinding 99 mg of zoledronic acid was ground with 44 mg of nicotinamide and 40 µl of water was added to the solid mixture. The solids gathered after grinding were stored in screw cap vials for subsequent analysis. The material was characterized by PXRD and FTIR corresponding to FIG. 11 and FIG. 12, respectively.

Example 7

Preparation of Zoledronic, Nicotinamide, and Water Complex from Solution Crystallization 25 mg of zoledronic acid and 138 mg of nicotinamide were dissolved in 2 mL of a water:ethylacetate mix (1:1 v/v). The solution was then allowed to stand for several hours to effect the slow evaporation of solvent. The solids gathered were characterized and produced very similar PXRD and FTIR patterns to that of Example 6 product.

Example 8

Figure 13:
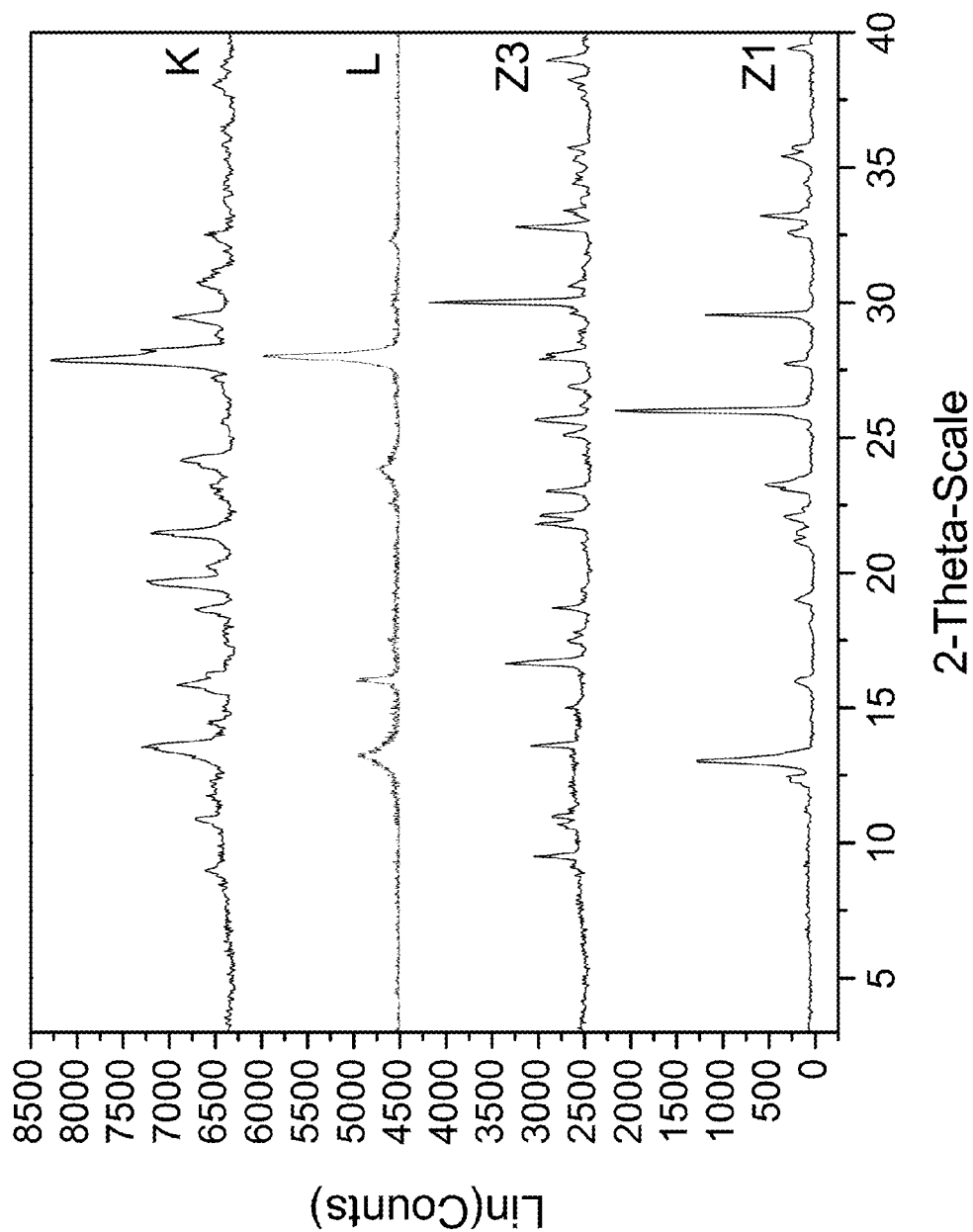
FIG. 13 shows PXRD diffractograms of: (K=zoledronic, adenine, and water complex), (L=adenine), (Z1=Zoledronic acid monohydrate), (Z3=Zoledronic acid trihydrate).
Figure 14:
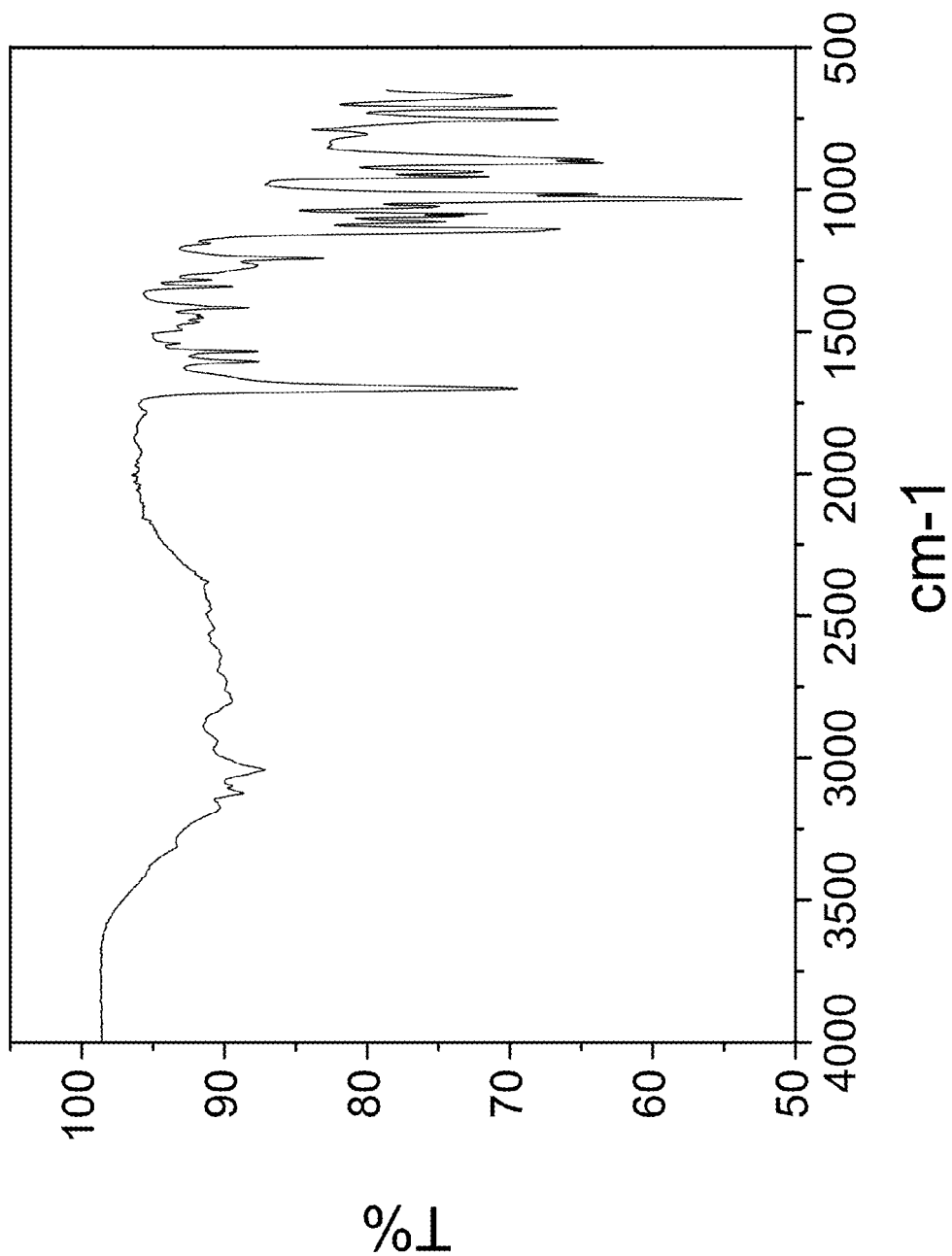
FIG. 14 is an FTIR spectrum of zoledronic, adenine, and water complex.

Preparation of Zoledronic, Adenine, and Water Complex by Solvent-Drop Grinding 96 mg of zoledronic acid was ground with 65 mg of adenine and 60 µL of water was added to the solid mixture. The solids gathered after grinding were stored in screw cap vials for subsequent analysis. The material was characterized by PXRD and FTIR corresponding to FIG. 13 and FIG. 14, respectively.

Example 9

Preparation of Zoledronic, Adenine, and Water Complex from Solution Slurry 99 mg of zoledronic acid and 54 mg of adenine were slurried in 2 mL of a water:ethanol mix (1:1 v/v) overnight. The solids gathered after filtration were dried, characterized and produced very similar PXRD and FTIR patterns to that of Example 8 product.

Example 10

Figure 15:
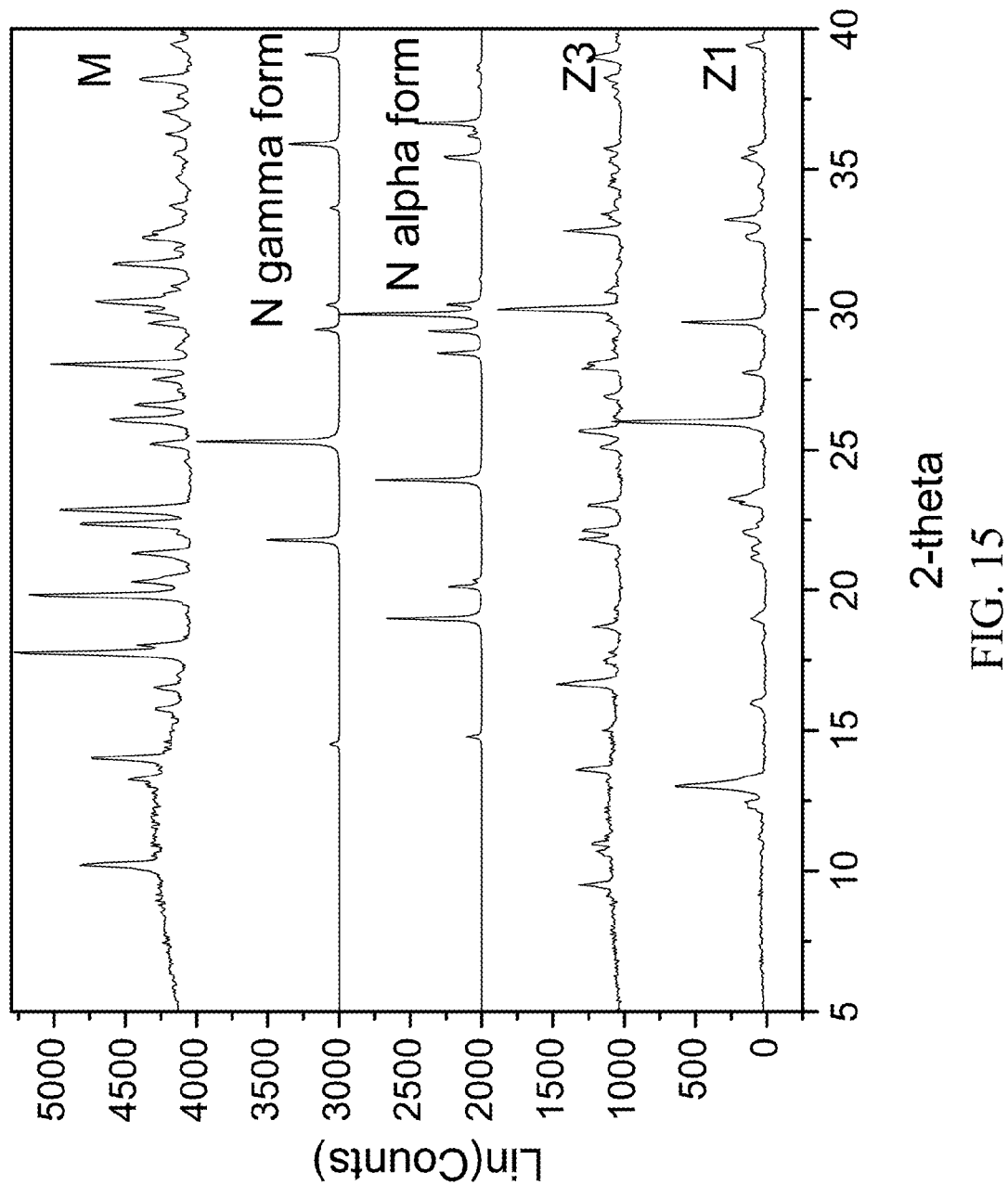
FIG. 15 shows PXRD diffractograms of: (M=zoledronic and glycine complex), (N=glycine), (Z1=Zoledronic acid monohydrate), and (Z3=Zoledronic acid trihydrate).
Figure 16:
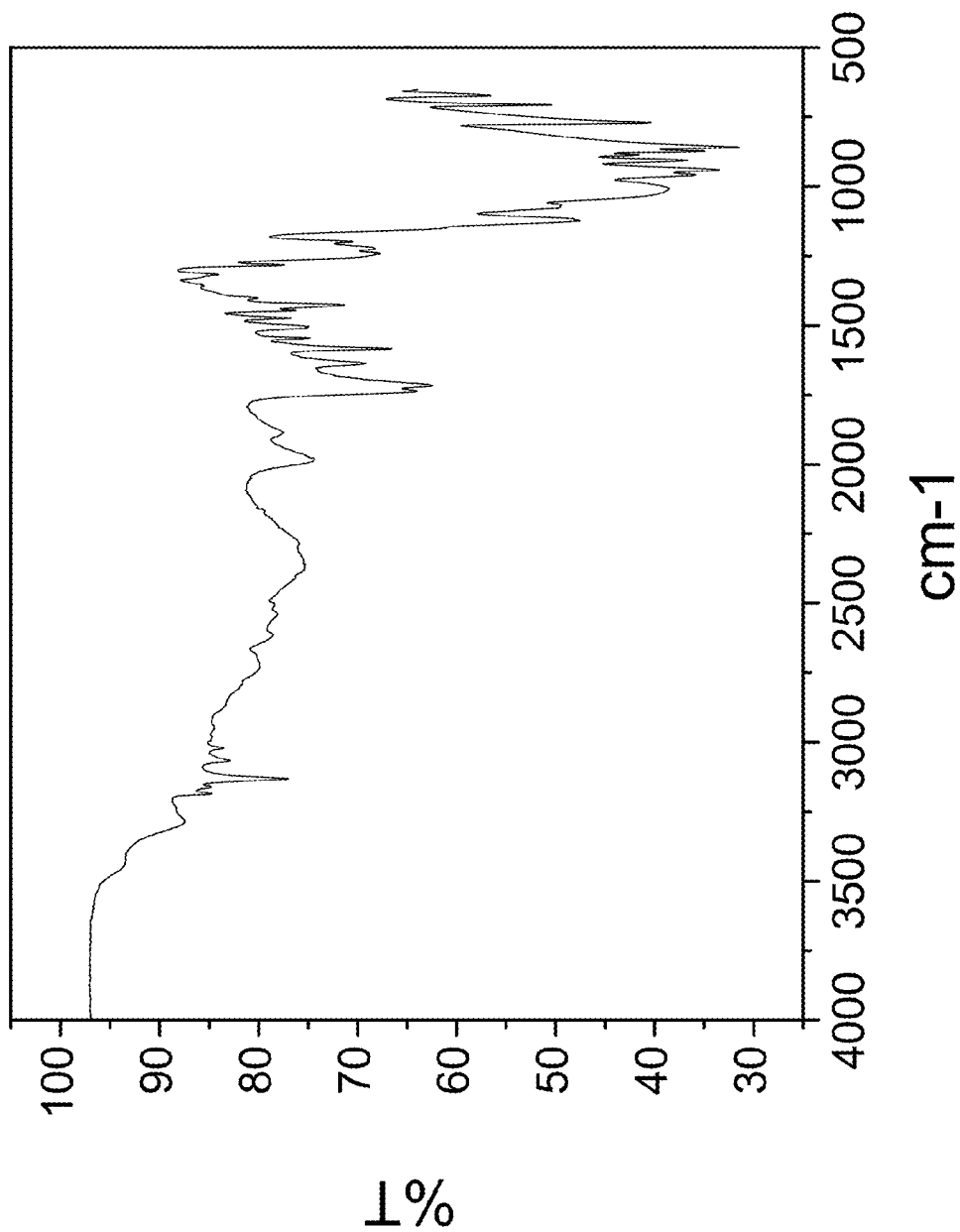
FIG. 16 is an FTIR spectrum of zoledronic and glycine complex.

Preparation of Zoledronic and Glycine Complex 178 mg of zoledronic acid and 45 mg of glycine were slurried in 2 mL of water overnight. The solids gathered after filtration were dried and stored in a screw cap vials for subsequent analysis. The material was characterized by PXRD and FTIR corresponding to FIG. 15 and FIG. 16, respectively.

Example 11

Figure 17:
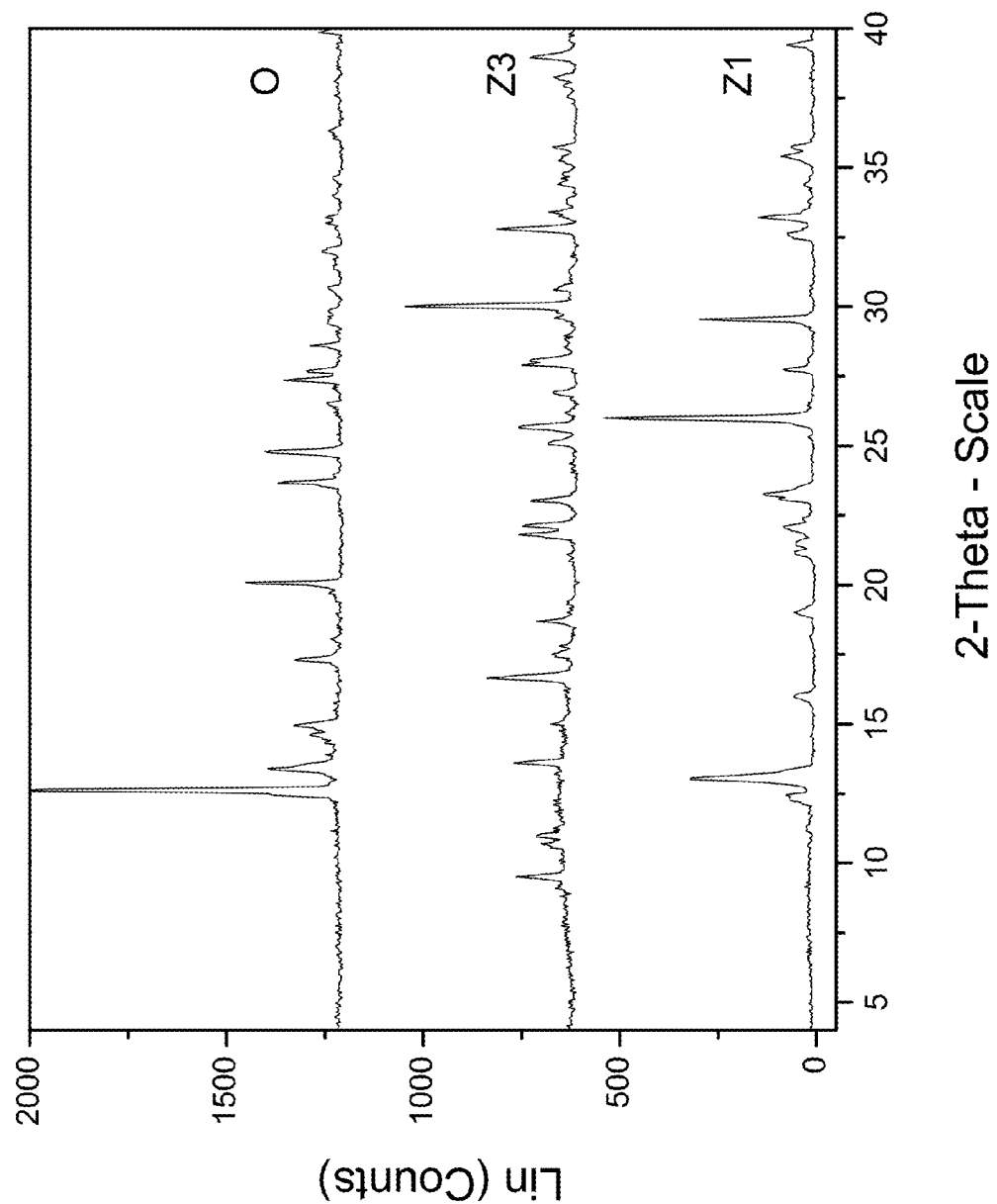
FIG. 17 shows PXRD diffractograms of: (0=zoledronic diammonia water complex), (Z1=Zoledronic acid monohydrate), and (Z3=Zoledronic acid trihydrate).
Figure 18:
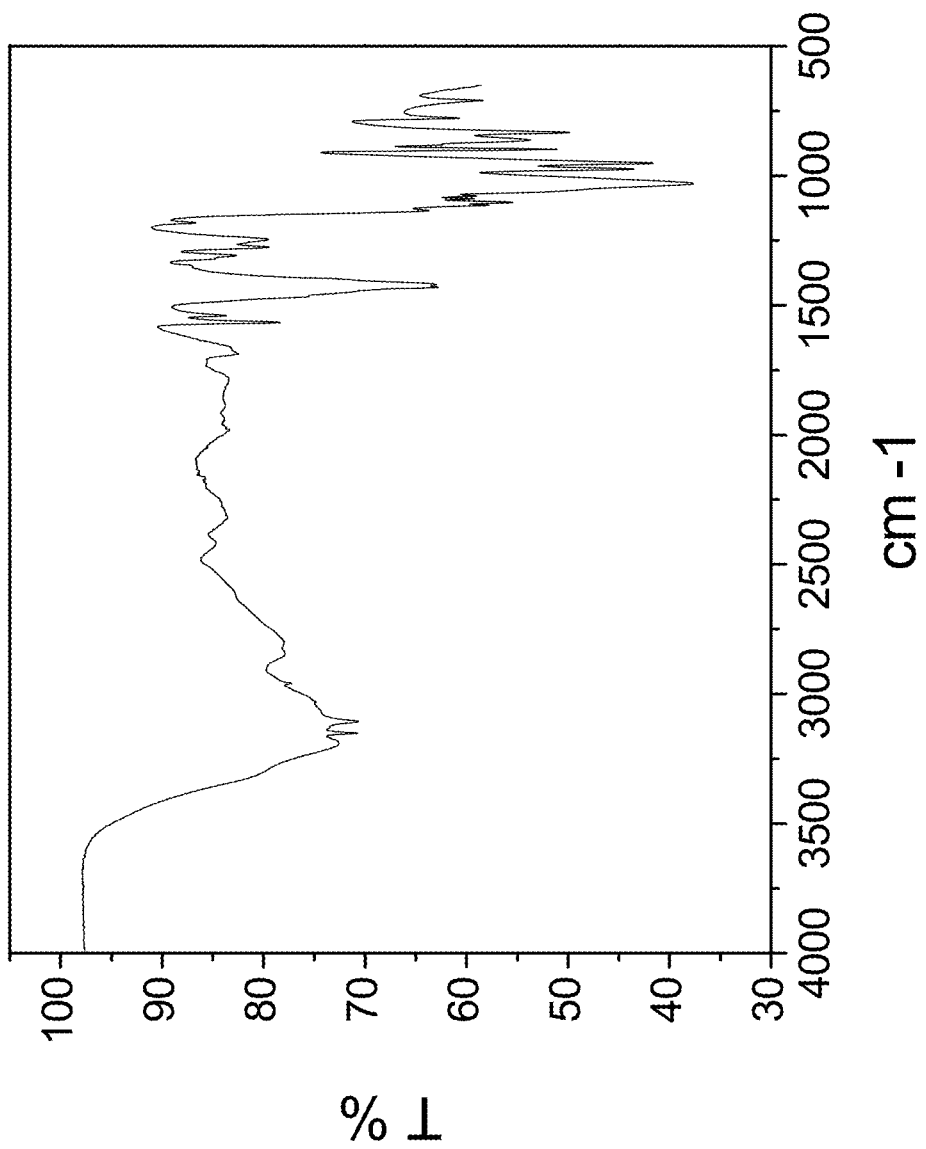
FIG. 18 is an FTIR spectrum of zoledronic diammonia water complex.

Preparation of Zoledronic Diammonia Water Complex 1.5 g of zoledronic acid was slurried in 7N ammonia in methanol overnight. The material was filtered and rinsed. The particulate material was dissolved in water with medium heat and left to evaporate at ambient conditions to obtain colorless blocks after 1 day. The material was characterized by PXRD and FTIR corresponding to FIG. 17 and FIG. 18, respectively.

Example 12

Figure 19:
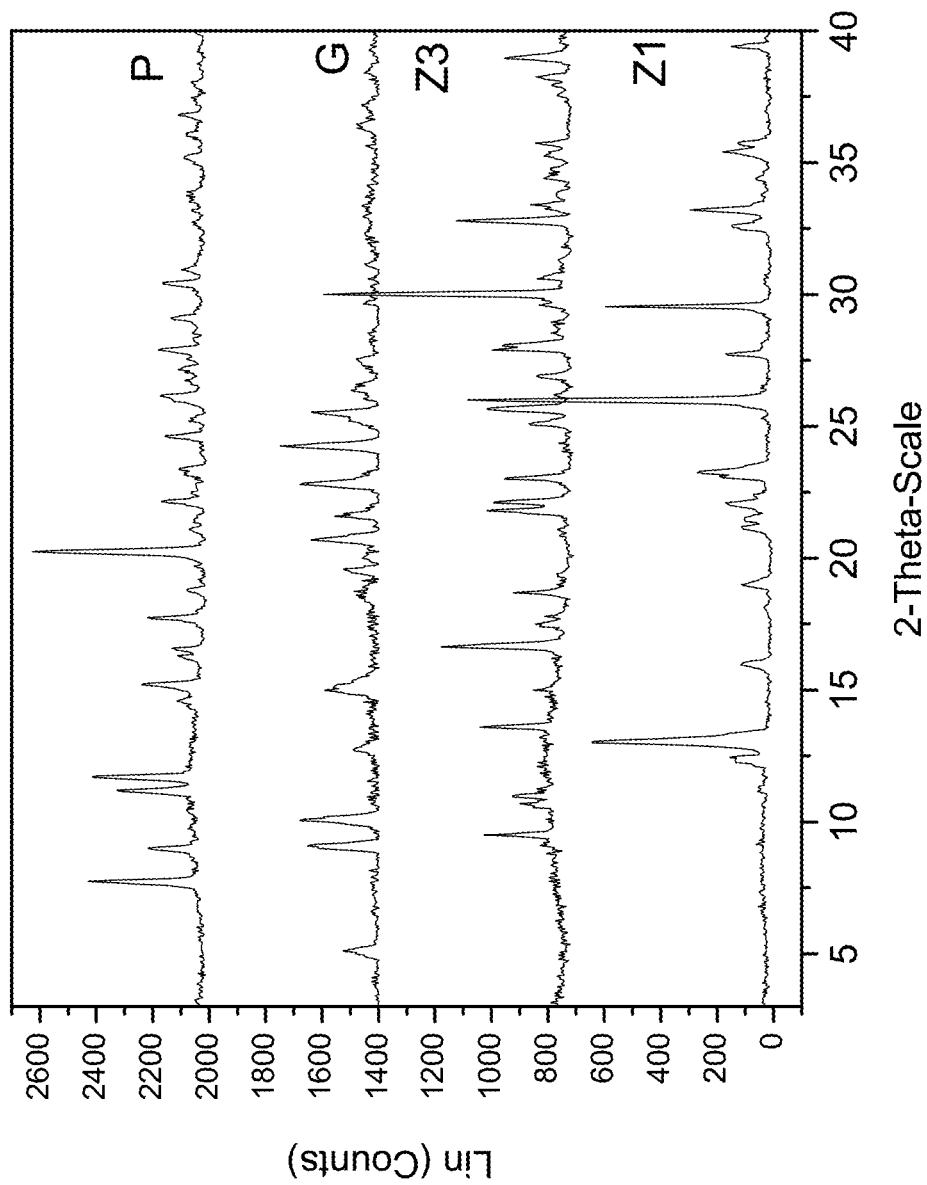
FIG. 19 shows PXRD diffractograms of: (P=zoledronic, DL-lysine, and water complex), (G=DL-lysine), (Z1=Zoledronic acid monohydrate), and (Z3=Zoledronic acid trihydrate).
Figure 20:
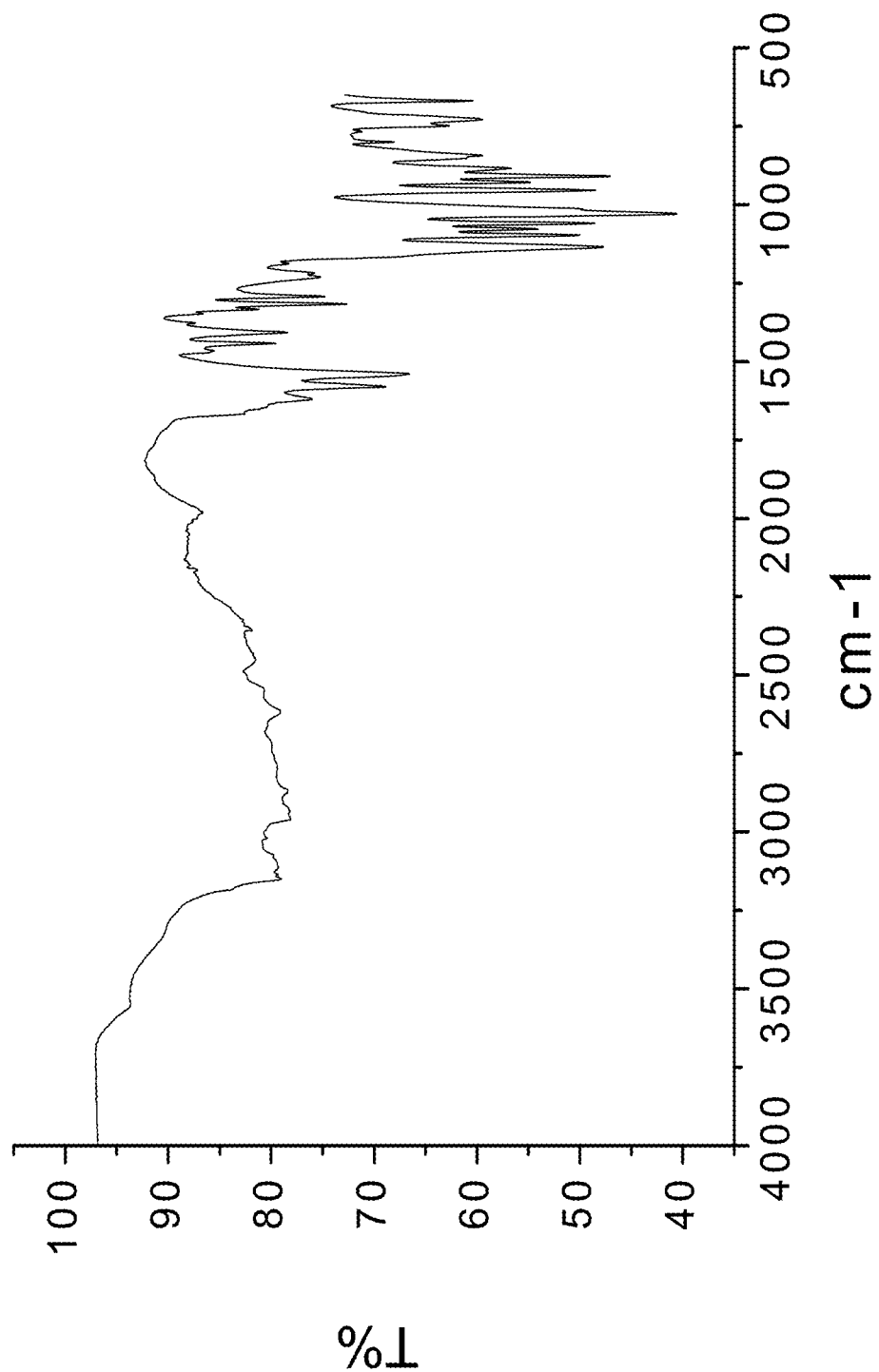
FIG. 20 is an FTIR spectrum of zoledronic, DL-lysine, and water complex.

Preparation of Zoledronic, DL-Lysine, and Water Complex 200 mg of zoledronic acid and 102 mg of DL-lysine were slurried in 2 mL of tetrahydrofuran and 400 μl of water overnight. The solids gathered after filtration were dried and stored in a screw cap vials for subsequent analysis. The material was characterized by PXRD and FTIR corresponding to FIG. 19 and FIG. 20 respectively.

Example 13

Figure 21:
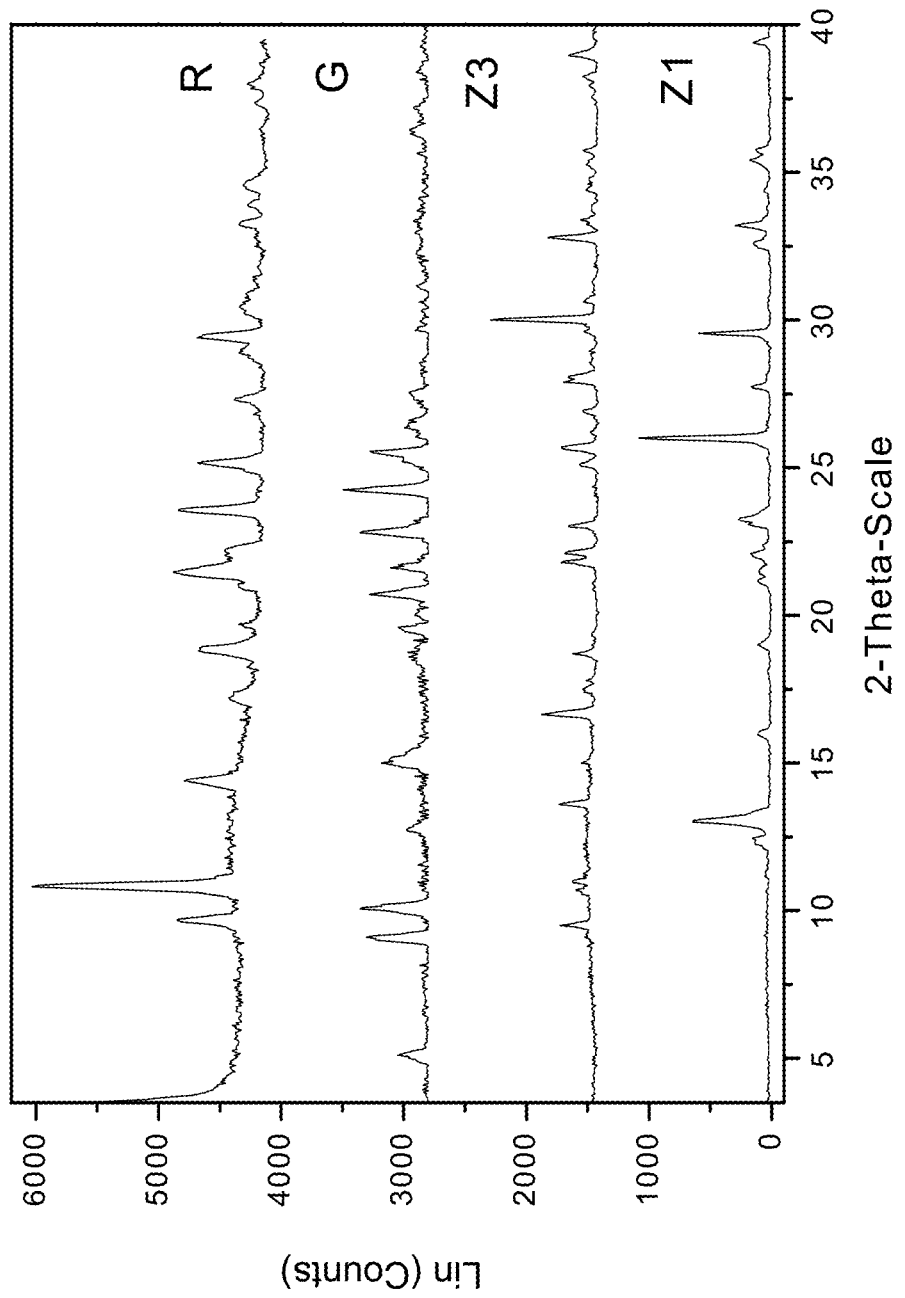
FIG. 21 shows PXRD diffractograms of: (R=zoledronic, DL-lysine, and water complex), (G=DL-lysine), (Z1=Zoledronic acid monohydrate), and (Z3=Zoledronic acid trihydrate).
Figure 22:
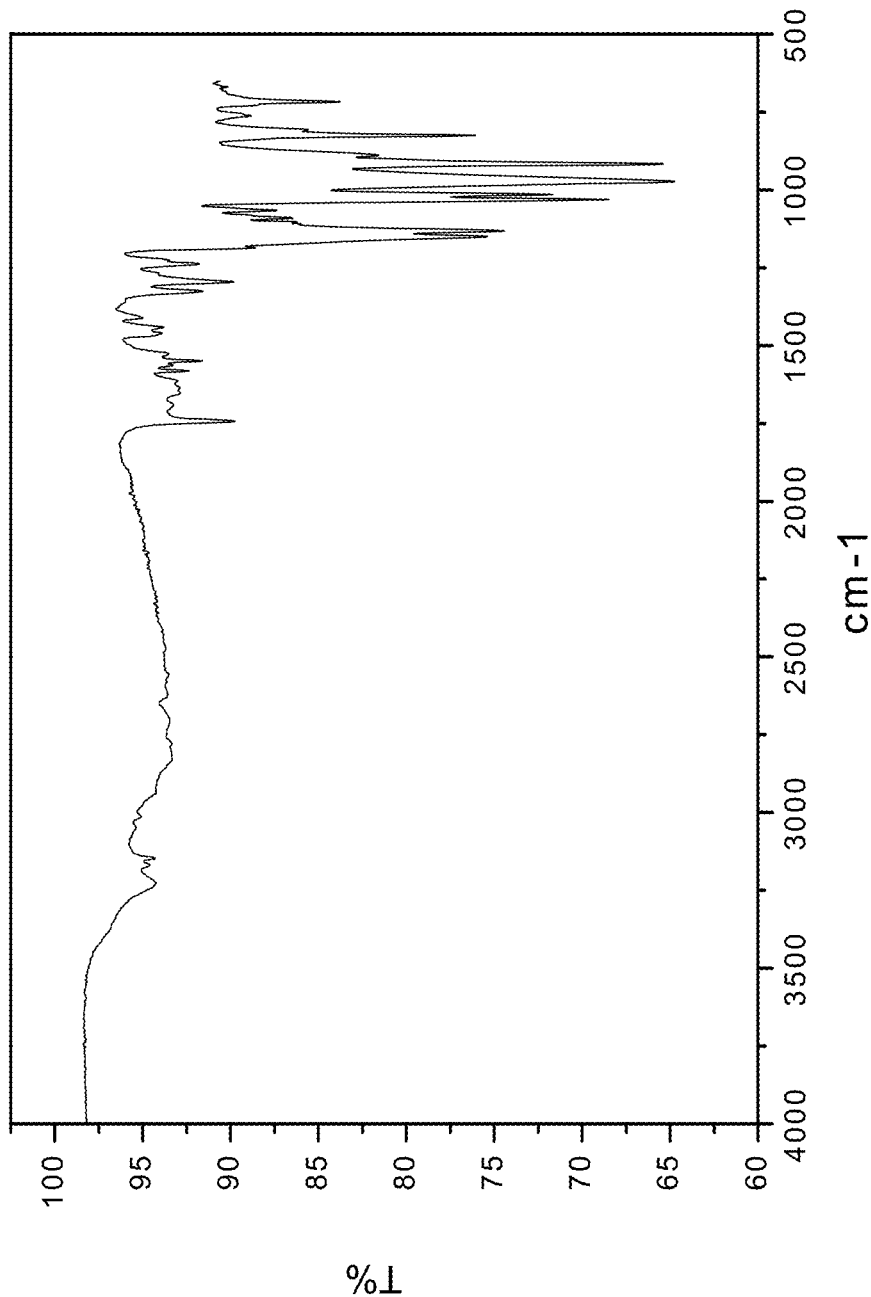
FIG. 22 is an FTIR spectrum of zoledronic, DL-lysine, and water complex.

Preparation of Zoledronic, DL-Lysine, and Water Complex 1 g of zoledronic acid and 283 mg of DL-lysine were slurried in 80 mL of tetrahydrofuran and 8 mL of water overnight. The solids gathered after filtration were dried and stored in a screw cap vials for subsequent analysis. The material was characterized by PXRD and FTIR corresponding to FIG. 21 and FIG. 22 respectively.

Example 14

Preparation of Zoledronic, DL-Lysine, and Water Complex by Antisolvent Method

Figure 23:
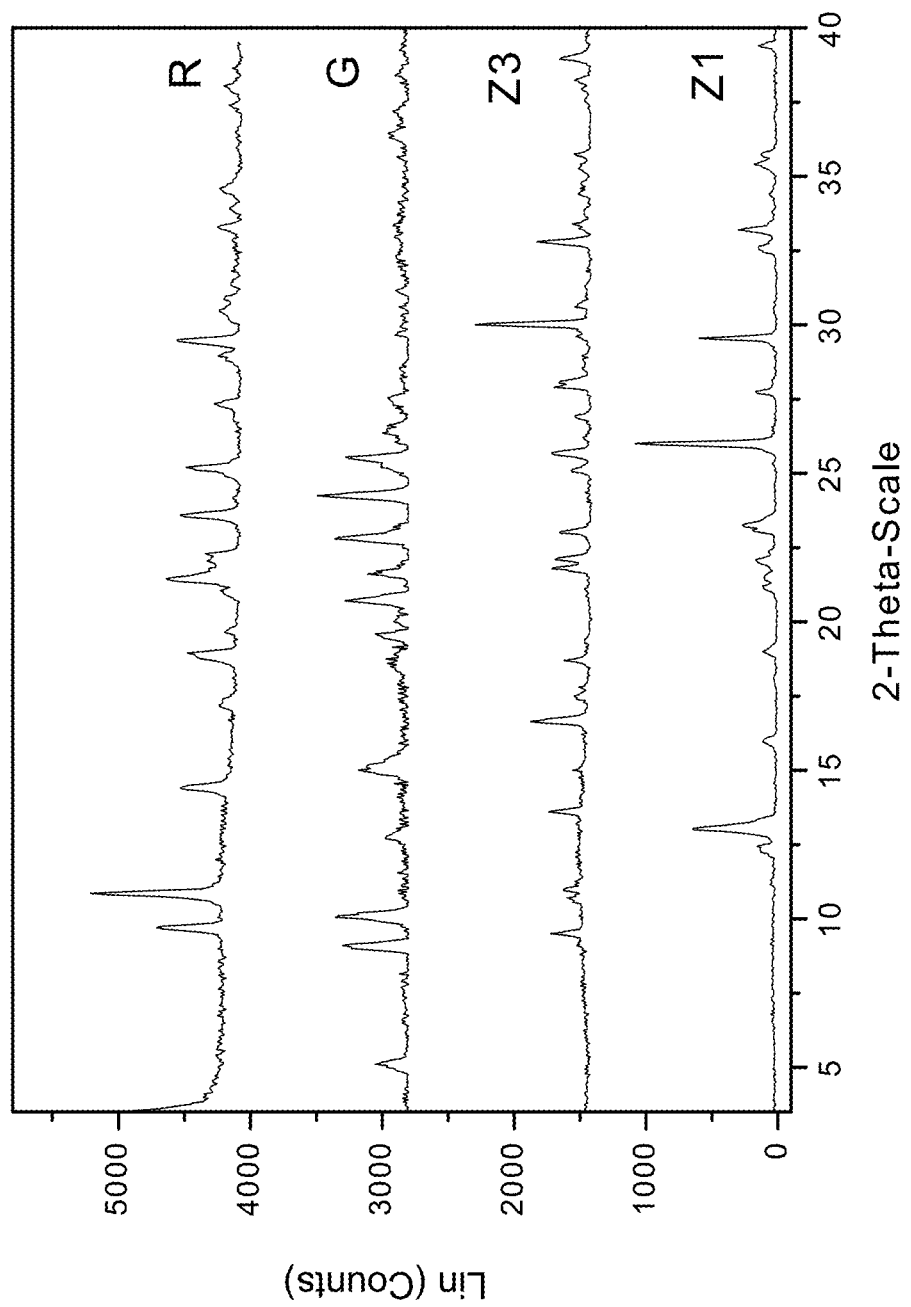
FIG. 23 shows PXRD diffractograms of: (R=zoledronic, DL-lysine, and water complex), (G=DL-lysine), (Z1=Zoledronic acid monohydrate), and (Z3=Zoledronic acid trihydrate).
Figure 24:
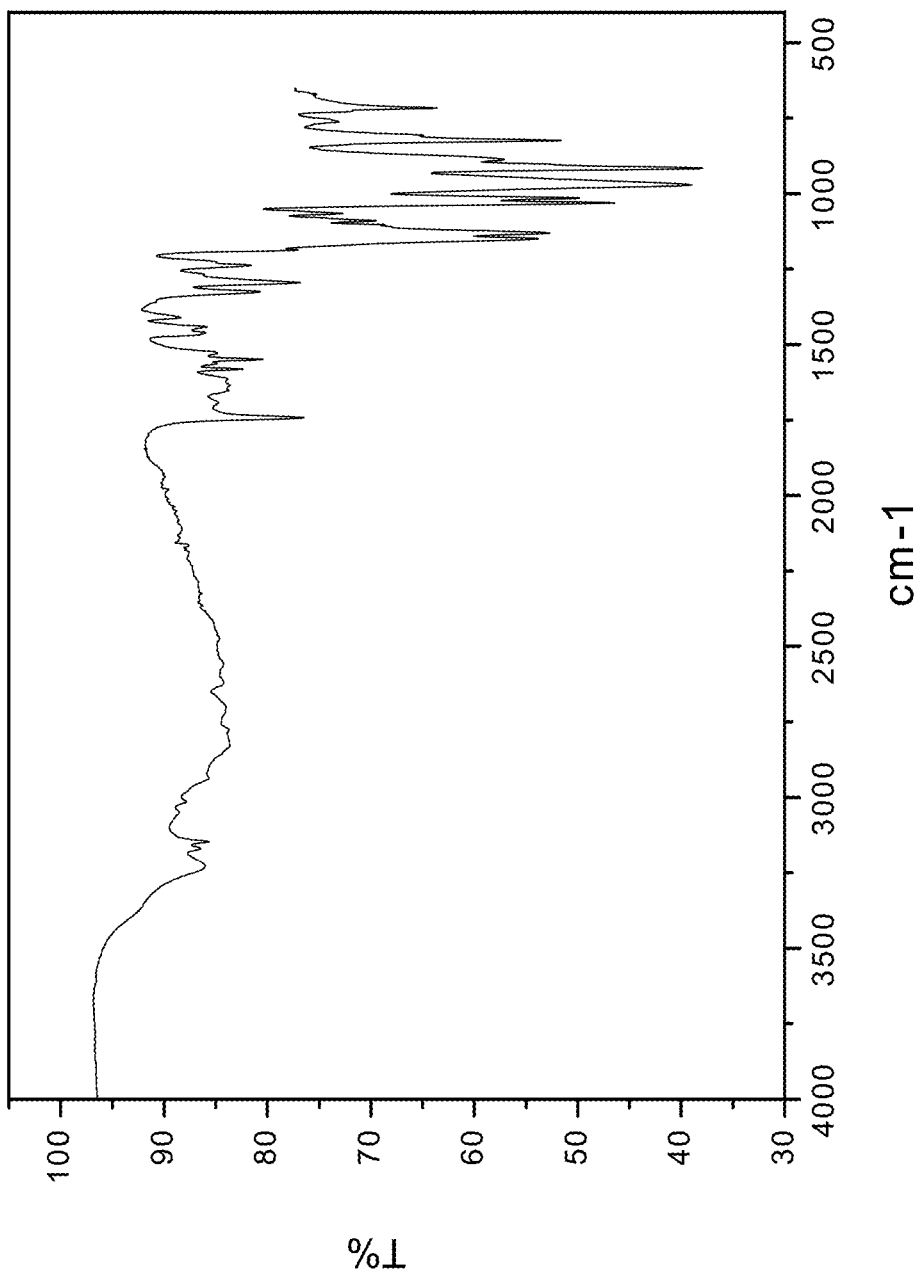
FIG. 24 is an FTIR spectrum of zoledronic, DL-lysine, and water complex.

This complex can also be prepared by the antisolvent method by dissolving 1 g of zoledronic acid and 283 mg of DL-lysine in 5 mL of hot water and adding 40 mL of ethanol as an antisolvent stirred overnight. Similar PXRD and FTIR profiles were obtained as shown in FIG. 23 and FIG. 24 respectively.

Example 15

Figure 25:
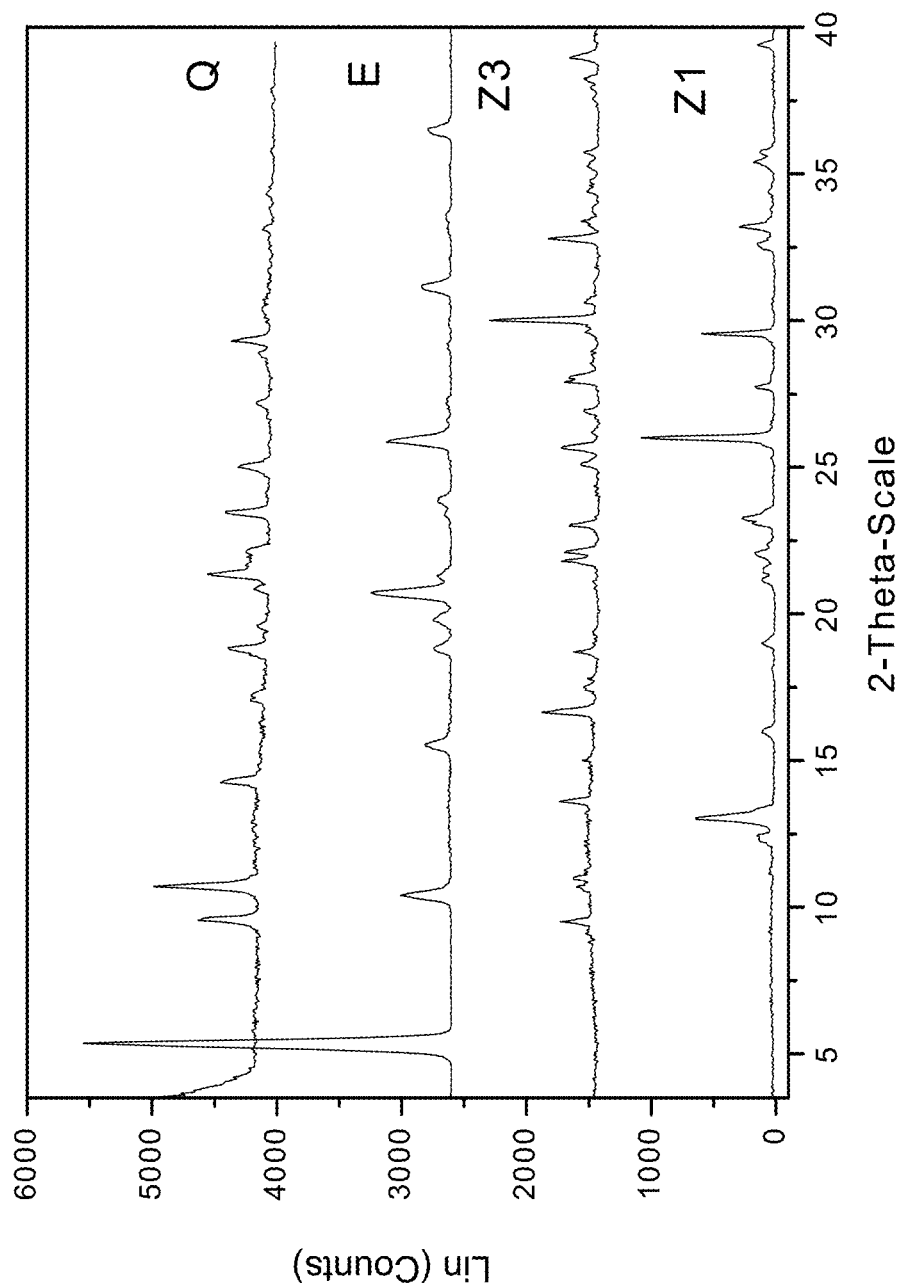
FIG. 25 shows PXRD diffractograms of: (Q=zoledronic, L-lysine, and water complex), (E=L-lysine), (Z1=Zoledronic acid monohydrate), and (Z3=Zoledronic acid trihydrate).
Figure 26:
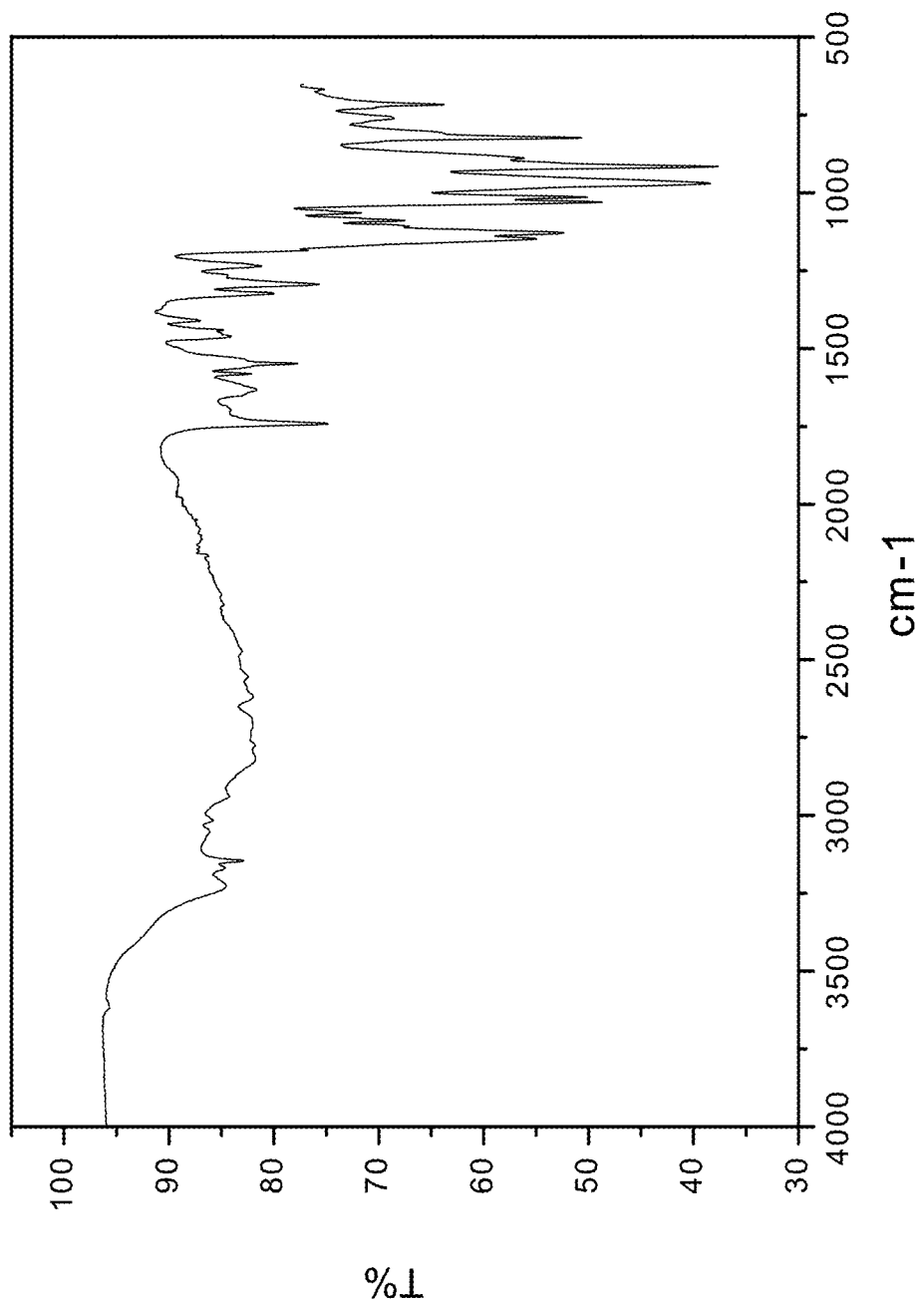
FIG. 26 is an FTIR spectrum of zoledronic, L-lysine, and water complex.

Preparation of Zoledronic, L-Lysine, and Water Complex 1 g of zoledronic acid and 255 mg of L-lysine were dissolved in 60 mL of hot water. 100 mL of ethanol was then added as an antisolvent. The solids gathered after filtration were dried and stored in a screw cap vials for subsequent analysis. The material was characterized by PXRD and FTIR corresponding to FIG. 25 and FIG. 26 respectively.

Example 16

The Animal PK Studies

These studies were conducted on rats and dogs as they are suitable animal models for zoledronic acid. This can be attributed to the fact that both animals have historically been used in the safety evaluation and PK screening studies and are recommended by appropriate regulatory agencies. In addition, rats and dogs have also been established as appropriate species for assessing the absorption of bisphosphonate drugs including zoledronic acid. Pure zoledronic acid and zoledronic acid complexes prepared by the methods in this invention were delivered to the rats and dogs through IV or oral routes. Additional tests included ID administration in rats and administration of enteric coated capsules in dogs. All compounds delivered were well tolerated by the animals with no adverse events or physical abnormalities noticed.

Test Subjects:

8-week male Sprague-Dawley Rats (217-259 grams) were obtained from Hilltop Lab Animals, Scottdale, Pa. USA. Some animals have surgical catheters (jugular vein and intraduodenum) were implanted to the animals prior to the studies. Beagle dogs from Marshall Farms, N.Y., USA, weighing from (9-12 kg) were used in the studies presented herein. Surgical catheters (jugular vein) were implanted prior to the studies.

Housing:

Rats were individually housed in stainless steel cages to prevent catheter exteriorization. Acclimation (Pre-dose Phase) was for 1 day. Dogs were already in the test facility (Absorption Systems Inc., USA) and did not need acclimation.

Environment:

Environmental controls for the animal room were set to maintain 18 to 26° C., a relative humidity of 30 to 70%, a minimum of 10 air changes/hour, and a 12-hour light/12-hour dark cycle. The light/dark cycle could be interrupted for study-related activities.

Diet:

For rats, water and certified Rodent Diet #8728C (Harlan Teklad) were provided. For dogs, water and the standard dog chow diet were given twice daily (every 12 hours).

Fasting:

All test animals were fasted overnight before IV, oral, or ID administration of zoledronic acid or zoledronic acid complexes.

Routes of Rat Dosing:

Zoledronic acid and its complex formulations were administered through IV, oral and ID. The doses administered to all rats in these studies were measured as zoledronic acid, not as the complex form contained in the suspension:

i. IV Administration: the dose of zoledronic acid for IV administration was 0.5 mg/kg. The dose of each rat was calculated on a per rat basis (not on an average weight of all the rats in the lot).

ii. Oral gavage administration: solid suspensions were administered. The dose of each rat was calculated on a per rat basis (not on an average weight of all the rats in the lot). For solid suspensions, animals were administered 5 mg/kg of zoledronic acid or 5 mg/kg of zoledronic acid in zoledronic acid complexes contained in a suspension of PEG 400.

iii. Duodenal cannula administration: solid suspensions were administered. The dose of each rat was calculated on a per rat basis (not on an average weight of all the rats in the lot). For solid suspensions, animals were administered 5 mg/kg of zoledronic acid or 5 mg/kg of zoledronic acid in zoledronic acid complexes contained in a suspension of PEG 400.

Routes of Dog Dosing:

Zoledronic acid and its complex formulations were administered IV and orally. The doses administered to all dogs in these studies were measured as zoledronic acid in each complex, not as the complex form contained in the powder in the gelatin capsule or in solution for IV:

i. IV Administration:

The dose volume of each dog was adjusted based upon the average weight of the dog.

ii. Oral administration: zoledronic acid and its equivalent of zoledronic acid complex formulations were administered through size 0 or 00 gelatin capsules based on the average weight of the dogs.

iii. Oral administration with enteric coated capsules: zoledronic acid and its equivalent of zoledronic acid complex formulations were administered through size 0 enteric coated gelatin capsules based on the average weight of the dogs.

iv. Oral administration of the molecular complexes with additional coformers: physical mixtures of zoledronic acid complexes with additional coformers were administered through size 0 or 00 or 000 or 13 gelatin capsules based on the average weight of the dogs.

Groups:

Two major groups of animals were selected for the study.

Group 1 consists of rat studies. The rat studies were divided into four subgroups (I-IV) where the results of each data point on the PK profile was the average drug concentration in the plasma of 3 rats.

Group 2 consists of dog studies. The dog studies were divided into five groups with subgroups (A, B, C, D, E, F, G, H, J, K, L, M) where the results of each data point on the PK profile was the average drug concentration in the serum of mainly 5 dogs. The PK profile for subgroup N was the average profile of 4 dogs.

Details of Group 1 Rat Dosing

Group I (IV Administration). Group Members, Designated IV Doses are Listed Below

| Group # I | Designation | # of rats | Dose* | Dose volume |
|---|---|---|---|---|
| G1 | Zoledronic Acid | 3 | 0.5 mg/kg | 1 mL |

IV comparator group, was conducted to calculate MAT (mean absorption time) and ka (absorption rate constant) for the oral groups.

Group II (Oral Gavage): Group Designations and Oral Doses are Listed Below:

| Group # II | Designation | # of Rats | Dose* | Dose volume mL/kg | Compound |
|---|---|---|---|---|---|
| G2 | Zoledronic Acid in PEG400 | 3 | 5 mg/kg | 1 mL | Zoledronic acid |
| G3 | Solid suspension in PEG400 | 3 | 5 mg/kg equivalent | 1 mL | Zoledronic and glycine complex |
| G4 | Solid suspension in PEG400 | 3 | 5 mg/kg equivalent | 1 mL | Zoledronic, nicotinamide, and water complex |
| G5 | Solid suspension in PEG400 | 3 | 5 mg/kg equivalent | 1 mL | Zoledronic acid, sodium zoledronic salt, and water complex |
| G6 | Solid suspension in PEG400 | 3 | 5 mg/kg equivalent | 1 mL | Zoledronic, L-lysine, and water complex |
| G7 | Solid suspension in PEG400 | 3 | 5 mg/kg equivalent | 1 mL | Zoledronic, DL-lysine, and water complex |

Group III (ID Administration): Group Designations and Oral Doses are Listed Below:

| Group # III | Designation | # of rats | Dose* | Dose volume mL/kg | Compound |
|---|---|---|---|---|---|
| G8 | Zoledronic Acid in PEG400 | 3 | 5 mg/kg | 1 mL | Zoledronic acid |
| G9 | Solid suspension in PEG400 | 3 | 5 mg/kg equivalent | 1 mL | Zoledronic and glycine complex |
| G10 | Solid suspension in PEG400 | 3 | 5 mg/kg equivalent | 1 mL | Zoledronic, nicotinamide, and water complex |
| G11 | Solid suspension in PEG400 | 3 | 5 mg/kg equivalent | 1 mL | Zoledronic acid, sodium zoledronic salt, and water complex |
| G12 | Solid suspension in PEG400 | 3 | 5 mg/kg equivalent | 1 mL | Zoledronic, L-lysine, and water complex |
| G13 | Solid suspension in PEG400 | 3 | 5 mg/kg equivalent | 1 mL | Zoledronic, DL-lysine, and water complex |

Group IV (Oral Gavage): Group Designations and Oral Doses are Listed Below:

| Group # IV | Compound | # of rats | Dose | Dose volume/kg | Excess coformer | Excess coformer amount mg/kg |
|---|---|---|---|---|---|---|
| G14 | Zoledronic and glycine complex, solid suspension in PEG400 | 3 | 5 mg/kg equivalent | 1 mL | Glycine | 45 |
| G15 | Zoledronic and glycine complex, solid suspension in PEG400 | 3 | 5 mg/kg equivalent | 1 mL | Glycine | 25 |
| G16 | Zoledronic and glycine complex, solid suspension in PEG400 | 3 | 5 mg/kg equivalent | 1 mL | Glycine | 5 |
| G17 | Zoledronic, DL-lysine, and water complex, solid suspension in PEG400 | 3 | 5 mg/kg equivalent | 1 mL | DL-lysine monohydrate | 39.32 |

-continued

| Group # IV | Compound | # of rats | Dose | Dose volume/kg | Excess coformer | Excess coformer amount mg/kg |
|---|---|---|---|---|---|---|
| G18 | Zoledronic, DL-lysine, and water complex, solid suspension in PEG400 | 3 | 5 mg/kg equivalent | 1 mL | DL-lysine monohydrate | 28.08 |
| G19 | Zoledronic, DL-lysine, and water complex, solid suspension in PEG400 | 3 | 5 mg/kg equivalent | 1 mL | DL-lysine monohydrate | 5.62 |
| G20 | Zoledronic, DL-lysine, and water complex, solid suspension in PEG400 | 3 | 5 mg/kg equivalent | 1 mL | n/a | n/a |

Rat Blood Sample Collection, Handling and Analysis:

Blood (approx. 300 μL per sample) samples were withdrawn from each of 3 animals in Group I (IV administration) at eight (8) time points: 5 min, 15 min, 30 min, 1 hr, 2 hr, 4 hr, 8 hr, and 24 hrs, after initial administration of zoledronic acid or its complexes, into EDTA plasma tubes. Plasma was collected after centrifugation at 13,000 rpm for 5 min at 4° C. and immediately frozen and stored at −60 to −80° C. until analysis.

Samples were thawed on the day of analysis and the amount of zoledronic acid in the samples was quantified by analyzed by LC/MS/MS method.

Details of Group 2 Dog Dosing:

Prior to dosing, all dogs received a 20 mL dose of citric acid (24 mg/mL in water) to lower the pH of their stomach. After dosing capsules or IV, all dogs received additional 6.25 mL citric acid solution (24 mg/mL in water) as a rinse.

Group A, (IV Administration). Group Members, Designated IV Doses are Listed Below:

| Group # A | Designation | # of fasted Dogs | Dose* | Dose volume |
|---|---|---|---|---|
| Leg 1 | Zoledronic Acid | 5 | 0.05 mg/kg | 1 mL/kg |

IV comparator group, was conducted to calculate MAT (mean absorption time) and ka (absorption rate constant) for the oral groups.

Group B (Oral Administration): Group Designations and Oral Doses are Listed Below:

| Group # B | Compound | Dosing Route | Dose of compound in the gelatin capsules | # of fasted Dogs (9-12 kg) | Dosing Solution Conc. mg/mL |
|---|---|---|---|---|---|
| Leg 2 | Zoledronic acid | oral | 5 mg/kg equivalent | 5 | n/a |
| Leg 3 | Zoledronic and glycine complex | oral | 5 mg/kg equivalent | 5 | n/a |
| Leg 4 | Zoledronic, DL-lysine, and water complex | oral | 5 mg/kg equivalent | 5 | n/a |
| Leg 5 | Zoledronic, L-lysine, and water complex | oral | 5 mg/kg equivalent | 5 | n/a |
| Leg 6 | Zoledronic, DL-lysine, and water complex | oral | 5 mg/kg equivalent | 5 | n/a |

Group C (Oral Administration): Group Designations and Oral Doses are Listed Below:

| Group # C | Compound | # of fasted Dogs (9-12 kg) | Dosing Route | Dose of compound in the gelatin capsules | Excess coformer | Excess coformer amount |
|---|---|---|---|---|---|---|
| Leg 7 | Zoledronic acid monohydrate | 5 | oral | 56.0 mg; enterically coated capsules | n/a | n/a |
| Leg 8 | Zoledronic and glycine complex | 5 | oral | 67.0 mg; enterically coated capsules | n/a | n/a |
| Leg 9 | Zoledronic, DL-lysine, and water complex | 5 | oral | 87.7 mg | DL-lysine monohydrate | 294.8 mg |
| Leg 10 | Zoledronic, DL-lysine, and water complex | 5 | oral | 87.7 mg; enterically coated capsules | DL-lysine monohydrate | 294.8 mg |

-continued

| Group # C | Compound | # of fasted Dogs (9-12 kg) | Dosing Route | Dose of compound in the gelatin capsules | Excess coformer | Excess coformer amount |
|---|---|---|---|---|---|---|
| Leg 11 | Zoledronic, DL-lysine, and water complex | 5 | oral | 84.2 mg | DL-lysine monohydrate | 294.8 mg |
| Leg 12 | Zoledronic, DL-lysine, and water complex | 5 | oral | 87.7 mg; enterically coated capsules | n/a | n/a |

Group D, (15 Min IV Infusion): Group Members, Designated IV Doses are Listed Below:

| Group # D | Designation | # of fasted Dogs (9-12 kg) | Dose* | Dosing solution concentration |
|---|---|---|---|---|
| Leg 13 | Zoledronic Acid | 5 | 0.183 mg/kg IV | 0.1 mg/mL |

Group E, (Oral Administration): Group Members, Designated IV Doses are Listed Below:

| Group # E | Compound | # of fasted Dogs (9-12 kg) | Dosing Route | Dose of compound in the gelatin capsules | Excess coformer | Excess coformer amount |
|---|---|---|---|---|---|---|
| Leg 14 | Zoledronic, DL-lysine, and water complex | 5 | oral | 35.4 mg | DL-lysine monohydrate | 123.8 mg |
| Leg 15 | Zoledronic and glycine complex | 5 | oral | 67.0 mg | DL-lysine monohydrate | 294.8 mg |
| Leg 16 | Zoledronic, L-lysine, and water complex | 5 | oral | 87.7 mg | DL-lysine monohydrate | 294.8 mg |
| Leg 17 | Zoledronic, DL-lysine, and water complex | 5 | oral | 35.4 mg | DL-lysine monohydrate | 294.8 mg |

Group F, (15 Min IV Infusion): Group Members, Designated IV Doses are Listed Below:

| Group # F | Designation | # of fasted Dogs (9-12 kg) | Dose* | Dosing solution concentration |
|---|---|---|---|---|
| Leg 18 | Zoledronic Acid | 5 | 0.12 mg/kg IV infusion | 0.1 mg/mL |

Group G (Oral Administration): Group Designations and Oral Doses are Listed Below:

| Group # G | Compound | # of fasted Dogs (10-13 kg) | Dosing Route | Dose of compound in the gelatin capsules | Excess coformer | Excess coformer amount |
|---|---|---|---|---|---|---|
| Leg 19 | Zoledronic acid | 5 | PO | 61.3 mg | DL-lysine monohydrate | 322.9 mg |
| Leg 20 | Zoledronic, L-lysine, and water complex | 5 | PO | 76.8 mg | L-lysine HCl | 359.2 mg |

Group H (Oral Administration): Group Designations and Oral Doses are Listed Below:

| Group # H | Compound | # of fasted Dogs (9-12 kg) | Dosing Route | Dose of compound in the gelatin capsules | Excess coformer | Excess coformer amount |
|---|---|---|---|---|---|---|
| Leg 21 | Zoledronic, DL-lysine, and water complex | 5 | PO | 84.2 mg | L-lysine HCl | 328.0 mg |
| Leg 22 | Zoledronic, DL-lysine, and water complex | 5 | PO | 69.0 mg | DL-lysine monohydrate | 241.8 mg |
| Leg 23 | Zoledronic, L-lysine, and water complex | 5 | PO | 70.1 mg | DL-lysine monohydrate | 294.9 mg |

Group J (Oral Administration): Group Designations and Oral Doses are Listed Below:

| Group # J | Compound | # of fasted Dogs (10.5-13.5 kg) | Dosing Route | Dose of compound in the gelatin capsules | Excess coformer | Excess coformer amount |
|---|---|---|---|---|---|---|
| Leg 24 | Zoledronic acid | 5 | PO | 64.0 mg | L-lysine HCl | 374.8 mg |
| Leg 25 | Zoledronic, L-lysine, and water complex | 5 | PO | 80.1 mg | N/A | N/A |
| Leg 26 | Zoledronic and glycine complex | 5 | PO | 76.5 mg | L-lysine HCl | 374.8 mg |

Group K (Oral Administration): Group Designations and Oral Doses are Listed Below:

| Group # K | Compound | # of fasted Dogs (8-11 kg) | Dosing Route | Dose of compound in the gelatin capsules | Excess coformer | Excess coformer amount |
|---|---|---|---|---|---|---|
| Leg 27 | Zoledronic, DL-lysine, and water complex | 5 | PO | 32.0 mg | DL-lysine monohydrate | 266.8 mg |
| Leg 28 | Zoledronic, DL-lysine, and water complex | 5 | PO | 76.2 mg | DL-lysine monohydrate | 266.8 mg |

Group L (Oral Administration): Group Designations and Oral Doses are Listed Below:

| Group # L | Compound | # of fasted Dogs (8.3-11.3 kg) | Dosing Route | Dose of compound in the gelatin capsules | Excess coformer | Excess coformer amount |
|---|---|---|---|---|---|---|
| Leg 29 | Zoledronic, DL-lysine, and water complex | 5 | PO | 64.4 mg | DL-lysine monohydrate | 275.2 mg |
| Leg 30 | Micronized Zoledronic, DL-lysine, and water complex | 5 | PO | 64.4 mg | Micronized DL-lysine monohydrate | 275.2 mg |

Group M (Oral Administration): Group Designations and Oral Doses are Listed Below:

| Group # M | Compound | # of fasted Dogs (8.4-11.4 kg) | Dosing Route | Dose of compound in the gelatin capsules | Excess coformer | Excess coformer amount |
|---|---|---|---|---|---|---|
| Leg 31 | Zoledronic, DL-lysine, and water complex | 4 | PO | 50.8 mg | DL-lysine monohydrate | 278.0 mg |
| Leg 32 | Micronized Zoledronic, DL-lysine, and water complex | 5 | PO | 50.8 mg | Micronized DL-lysine monohydrate | 278.0 mg |

Group N (Oral Administration): Group Designations and Oral Doses are Listed Below:

| Group # N | Compound | # of fasted Dogs | Dosing Route | Dose of compound | Excess coformer | Excess coformer amount |
|---|---|---|---|---|---|---|
| Leg 33 | Zoledronic, DL-lysine, and water complex | 4 (7.5-10.5 kg) | PO | 59.2 mg in the gelatin capsules | DL-lysine monohydrate | 112.3 mg |
| Leg 34 | Zoledronic, DL-lysine, and water complex | 4 (8.1-11.1 kg) | PO | 63.1 mg in the gelatin capsules | DL-lysine monohydrate | 280.8 mg |
| Leg 35 | Zoledronic, DL-lysine, and water complex | 4 (10.1-13.1 kg) | PO | 76.3 mg in the gelatin capsules | DL-lysine monohydrate | 561.6 mg |
| Leg 36 | Zoledronic, DL-lysine, and water complex | 4 (7.5-10.5 kg) | PO | 59.2 mg in the gelatin capsules | DL-lysine monohydrate | 1123.3 mg |
| Leg 37 | Zoledronic, DL-lysine, and water complex | 4 (8.1-11.1 kg) | PO | 63.1 mg in the gelatin capsules | DL-lysine monohydrate | 1965.7 mg |
| Leg 38 | Zoledronic acid | 4 (10.1-13.1 kg) | IV | 0.12 mg/kg, 15 min IV infusion | N/A | N/A |

After initial administration of zoledronic acid or its complexes, blood (approx. 2.5 mL per sample) was withdrawn from each of 5 animals in Group A (IV administration) at 15 time points: Pre-dose (0), 2, 5, 10, 15, 30, 45 min, 1, 1.5, 2, 4, 6, 8, 24 and 48 hrs and at 13 time points for Group B (oral administration): Pre-dose (0), 5, 10, 15, 30, 45 min, 1, 1.5, 2, 4, 6, 8, and 24 hrs. Blood samples were placed without the use of an anticoagulant and allowed to sit at room temperature for approximately 30 minutes. Samples were then centrifuged at a temperature of 4° C., at a speed of 13,000 rpm, for 5 minutes. Serum was collected and split into two aliquots and stored frozen (−80° C.) until analysis. Samples were thawed on the day of analysis and processed using analytical procedures for zoledronic acid containing an LC/MS/MS analysis method.

Animal PK Studies Results

Figure 27:
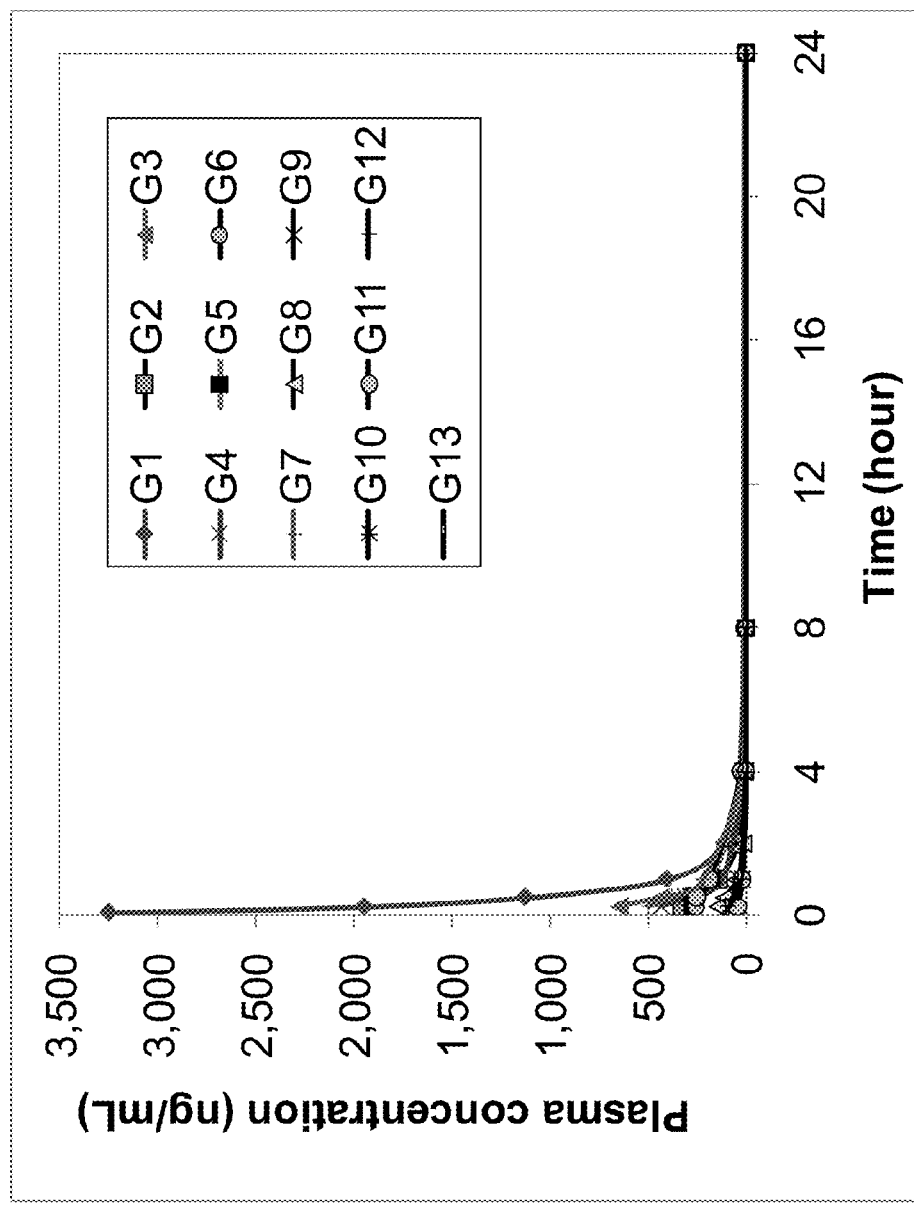
FIG. 27 shows the 24 hr rat plasma PK profile of parent zoledronic acid and zoledronic acid complexes delivered via IV, oral, and intraduodenal (ID) routes.
Figure 28:
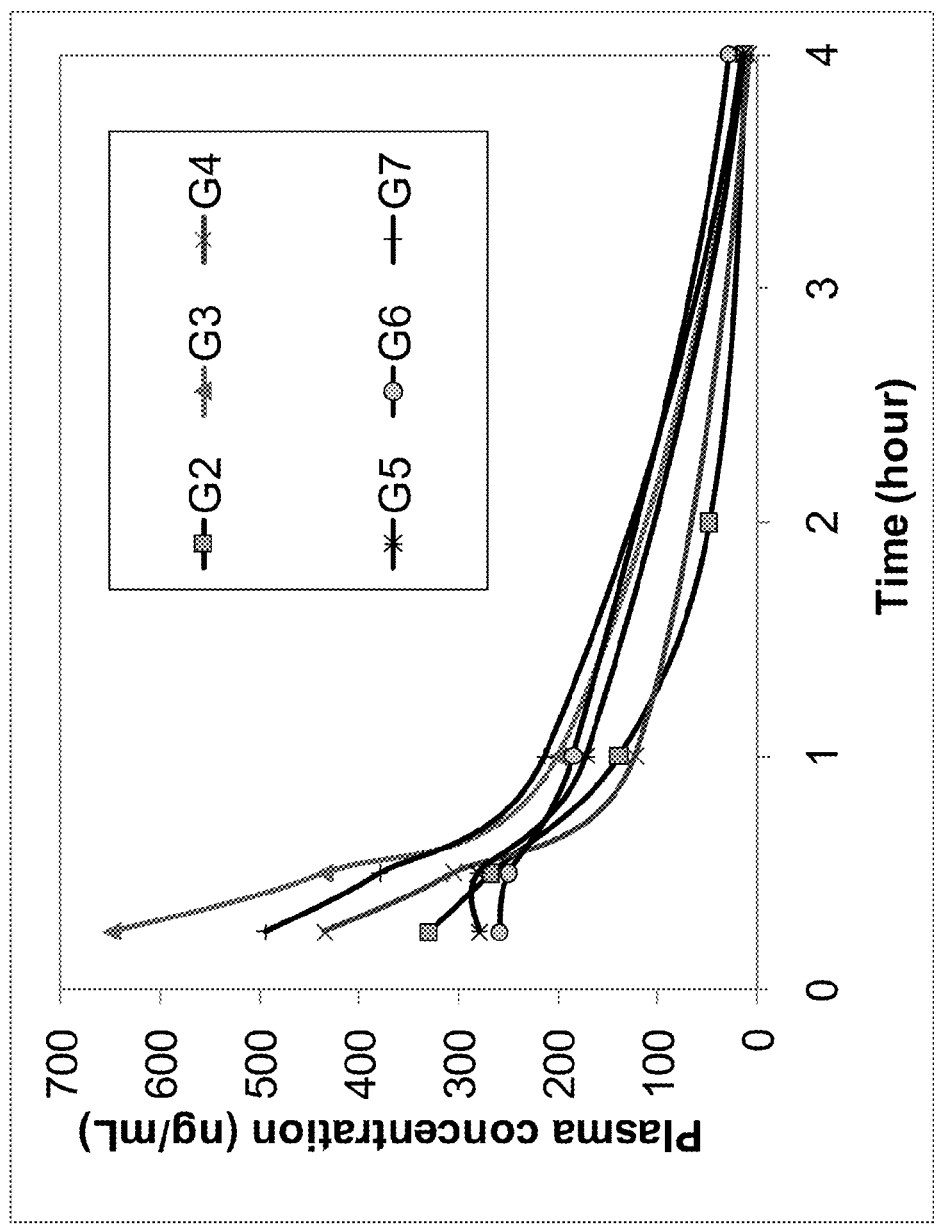
FIG. 28 shows the 4 hr rat plasma PK profile of parent zoledronic acid and zoledronic acid complexes delivered orally.
Figure 29:
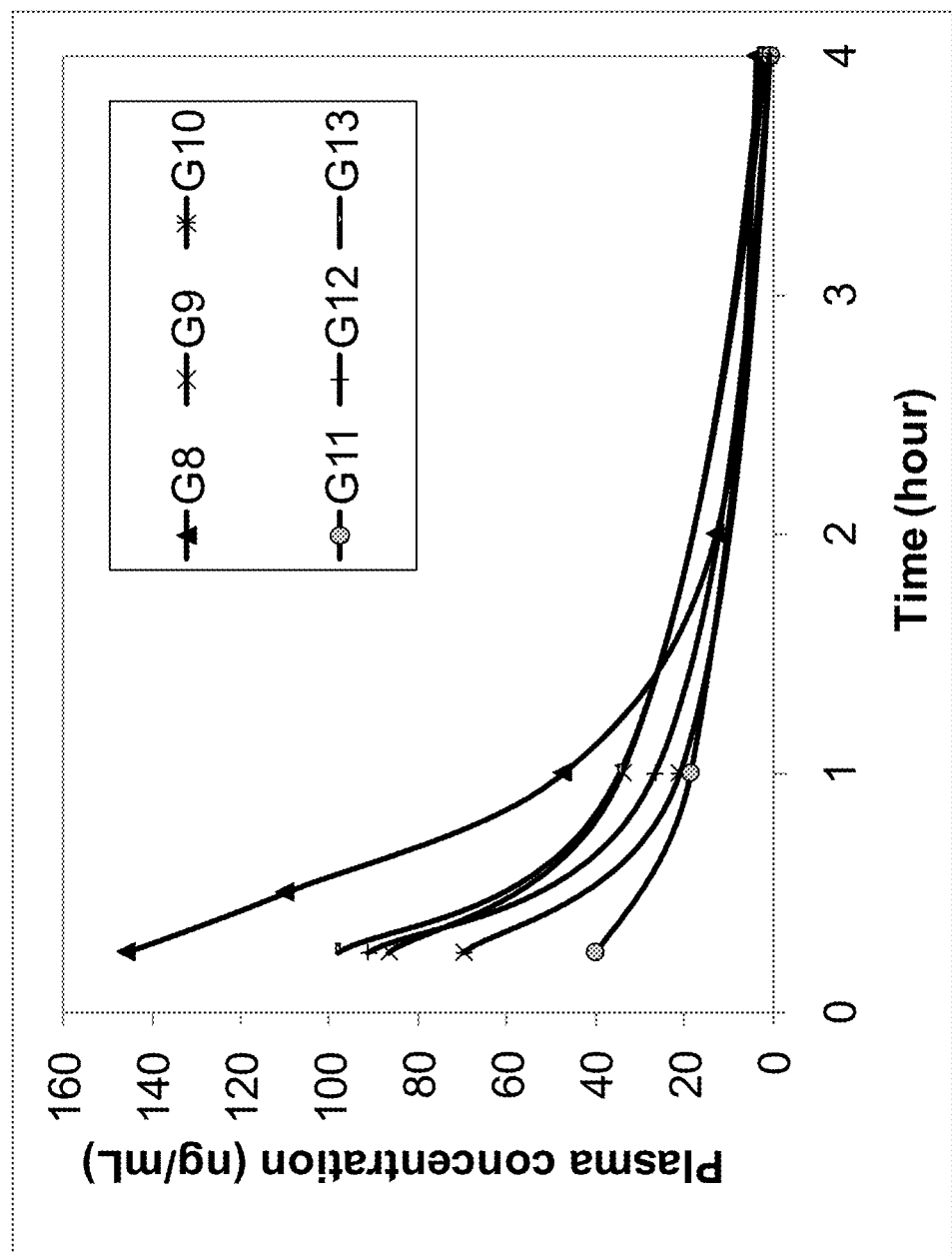
FIG. 29 shows the 4 hr rat plasma PK profile of parent zoledronic acid and zoledronic acid complexes delivered ID.
Figure 30:
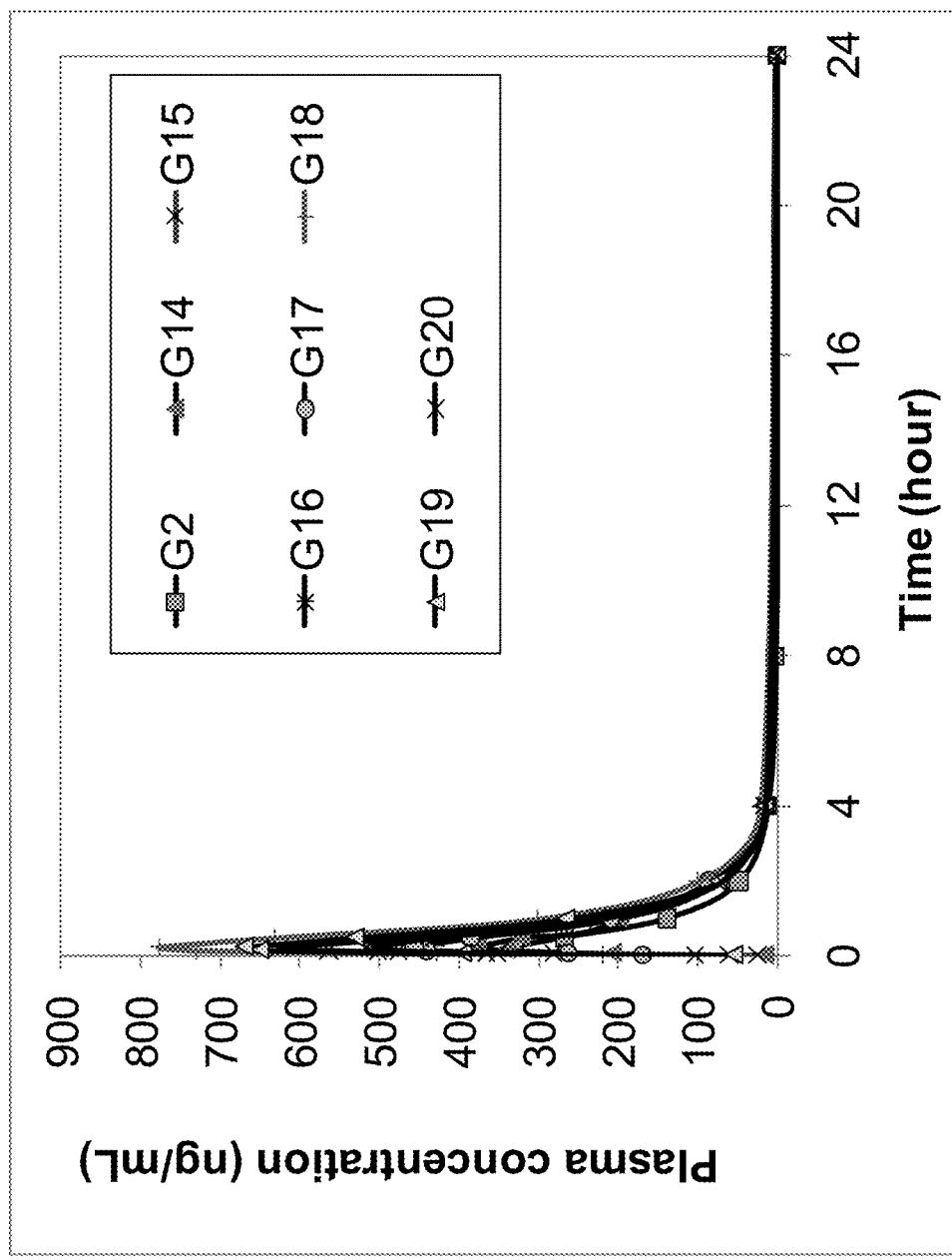
FIG. 30 shows the 24 hr rat plasma PK profile of parent zoledronic acid and zoledronic acid complexes delivered by oral gavage.
Figure 31:
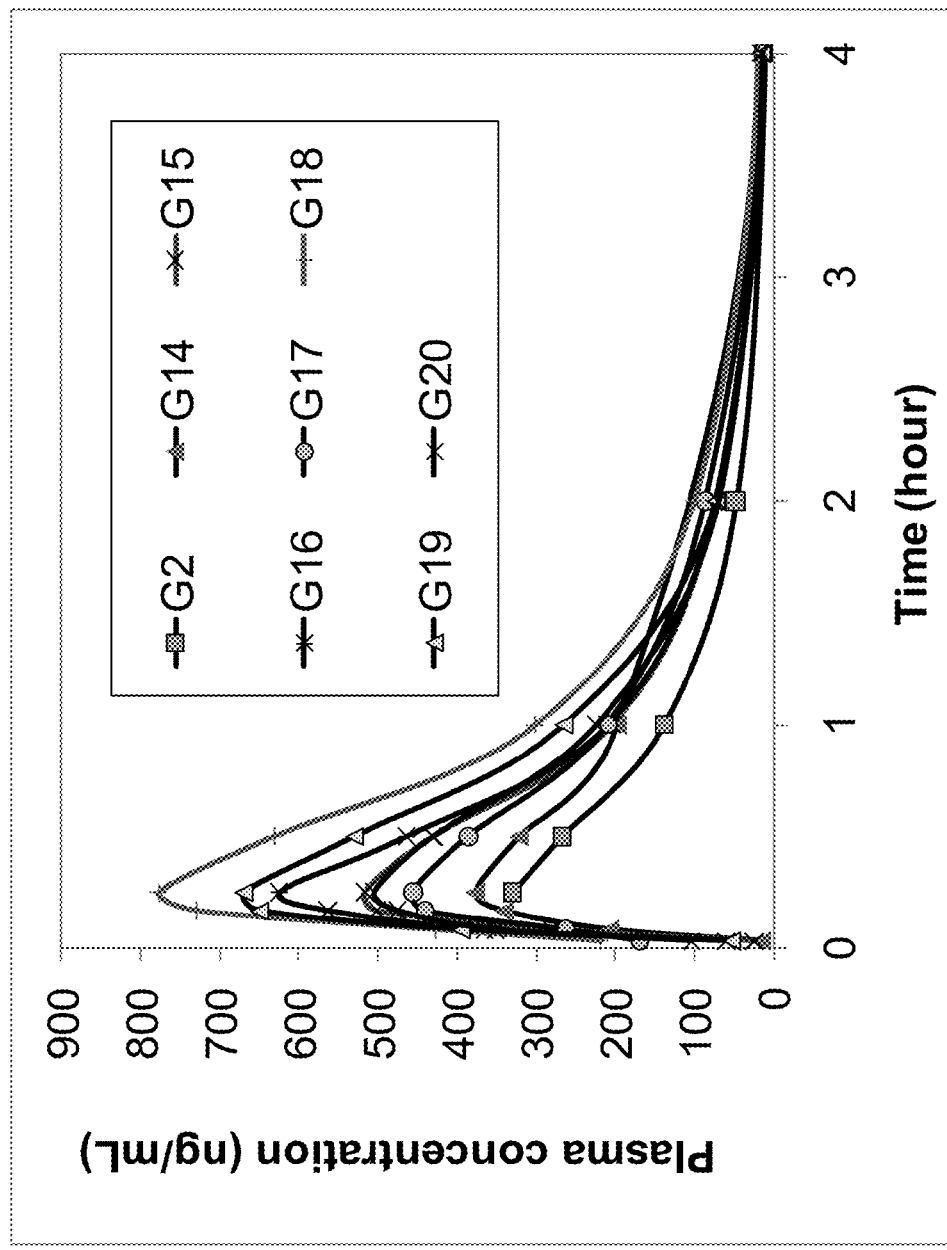
FIG. 31 shows the 4 hr rat plasma PK profile of parent zoledronic acid and zoledronic acid complexes delivered orally.
Figure 32:
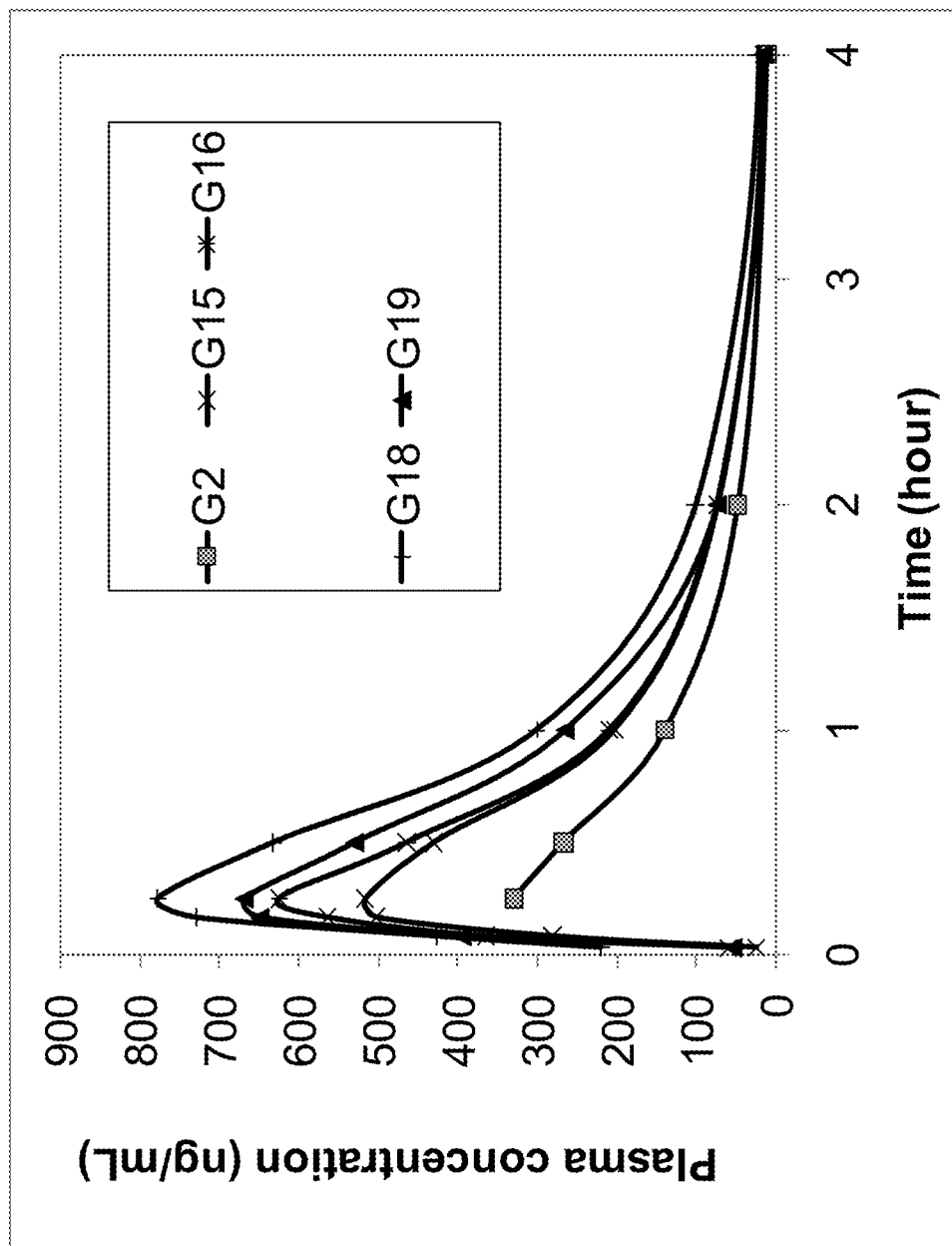
FIG. 32 shows the 4 hr rat plasma PK profile of parent zoledronic acid and selected zoledronic acid complexes delivered orally.

Rat Study:

The results of the first rat study are summarized in Table 1; the concentrations (ng/mL) of zoledronic acid in the plasma samples are the average values of the analytical results of 3 rats. In addition, the PK profiles of the IV, oral and ID groups are shown in FIG. 27. The profiles of oral and ID groups are shown in FIGS. 28 and 29. It suggests that some zoledronic acid complexes have improved oral bioavailability compared with that of the parent zoledronic acid. The complexes with improved bioavailability were further tested in a second rat PK study in which excess coformers were added to the zoledronic acid complexes and then administered to rats by oral gavage. The results of this second study are summarized in Table 2 and their PK profiles are shown in FIGS. 30, 31 and 32. These figures show improved bioavailabilities of several zoledronic acid complexes with excess coformers. The effect of excess coformers with zoledronic acid complexes in improving bioavailability is not fully understood.

Figure 33:
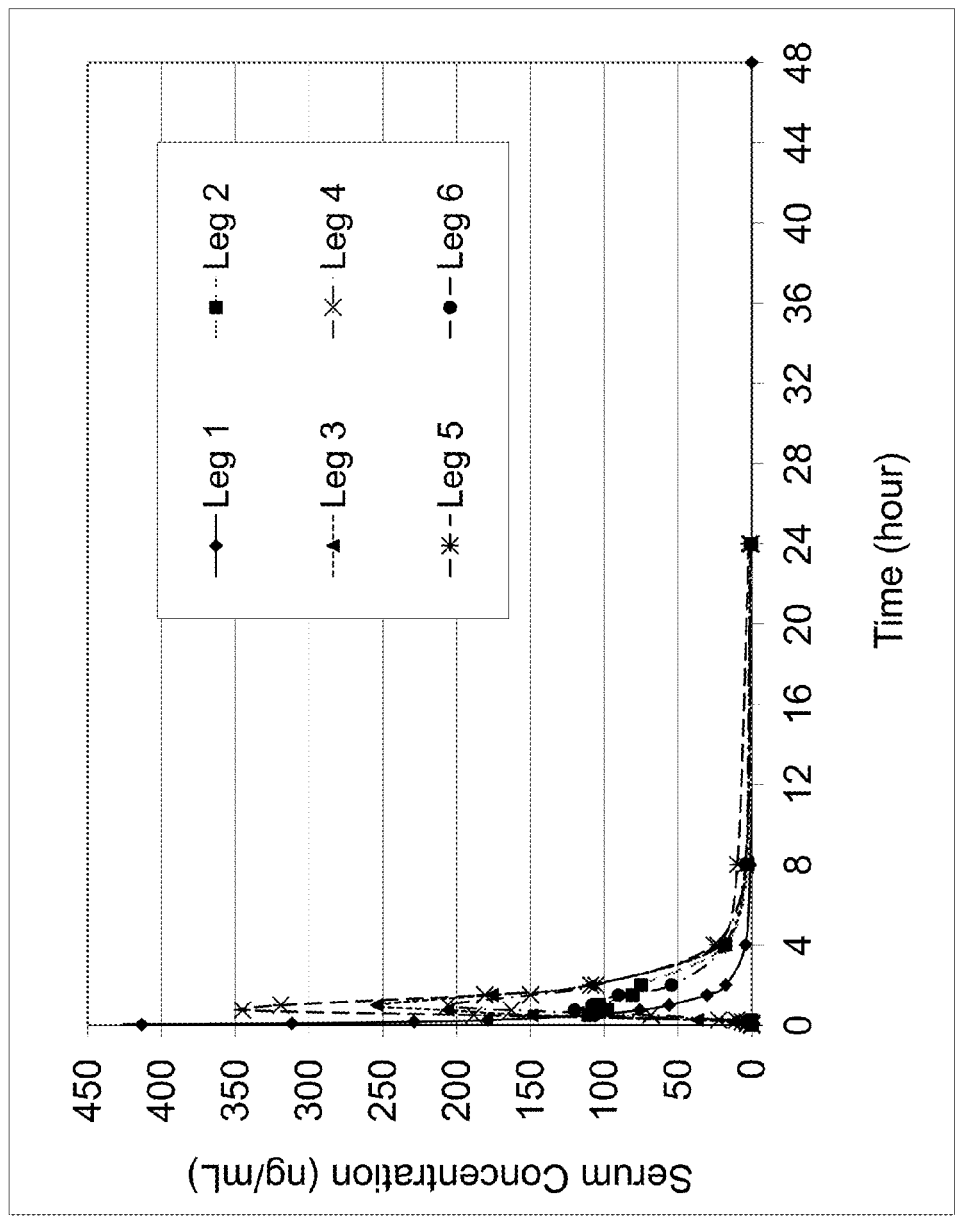
FIG. 33 shows the dog serum PK profile of parent zoledronic acid and zoledronic acid complexes delivered IV and orally.
Figure 34:
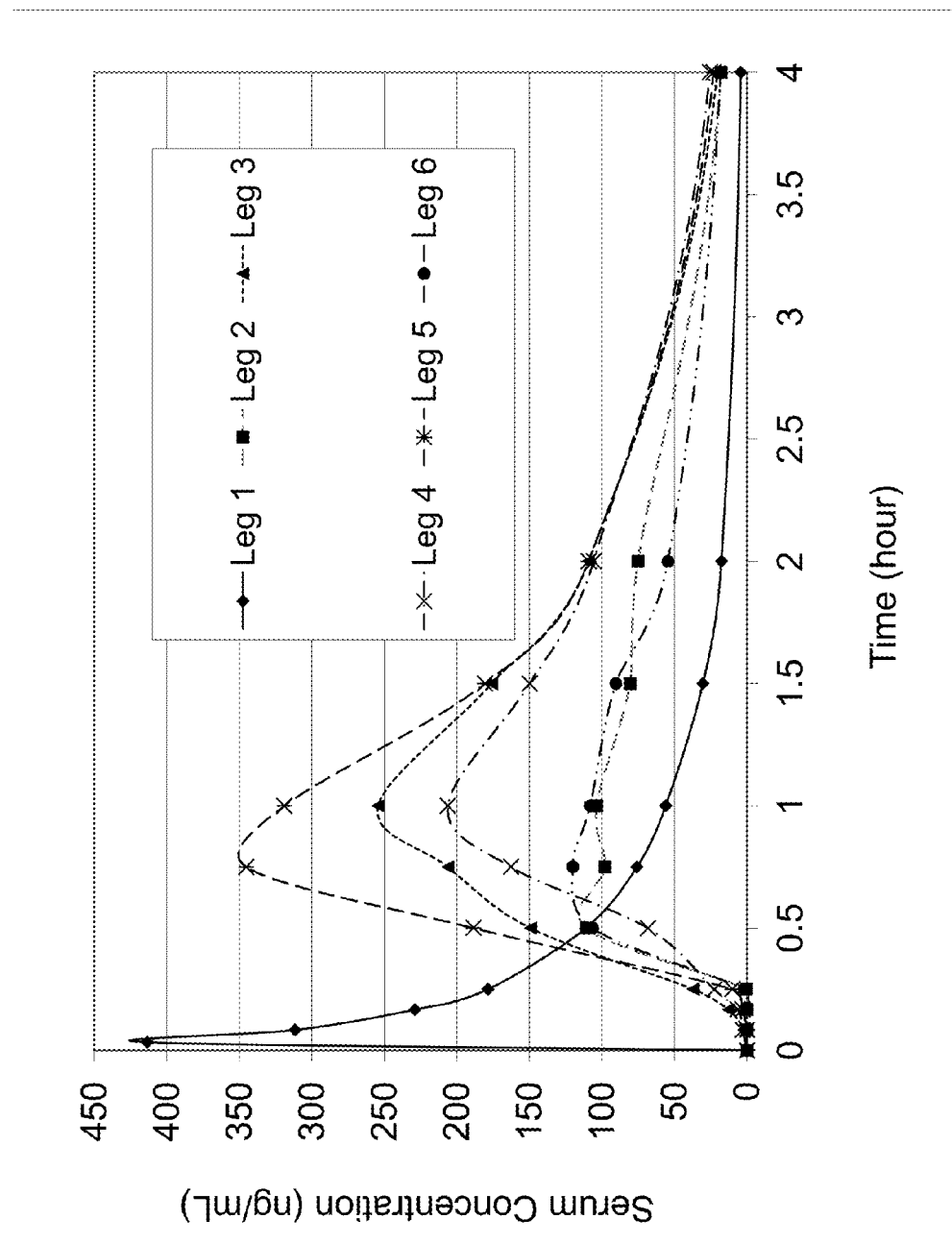
FIG. 34 shows the 4 hr dog serum PK profile of parent zoledronic acid and zoledronic acid complexes delivered IV and orally.

Dog study: The results of the first dog study (Legs 1-6) are summarized in Table 3. The concentrations (ng/mL) of zoledronic acid are the average values of the analytical results of 5 dogs. The PK profiles of the IV and oral groups are shown in FIGS. 33 and 34 which represent the first four hours of the 48 hr PK profile. These results and FIG. 34 suggest that most if not all zoledronic acid complexes have achieved improved oral bioavailability compared to that of the parent zoledronic acid delivered orally.

Figure 35:
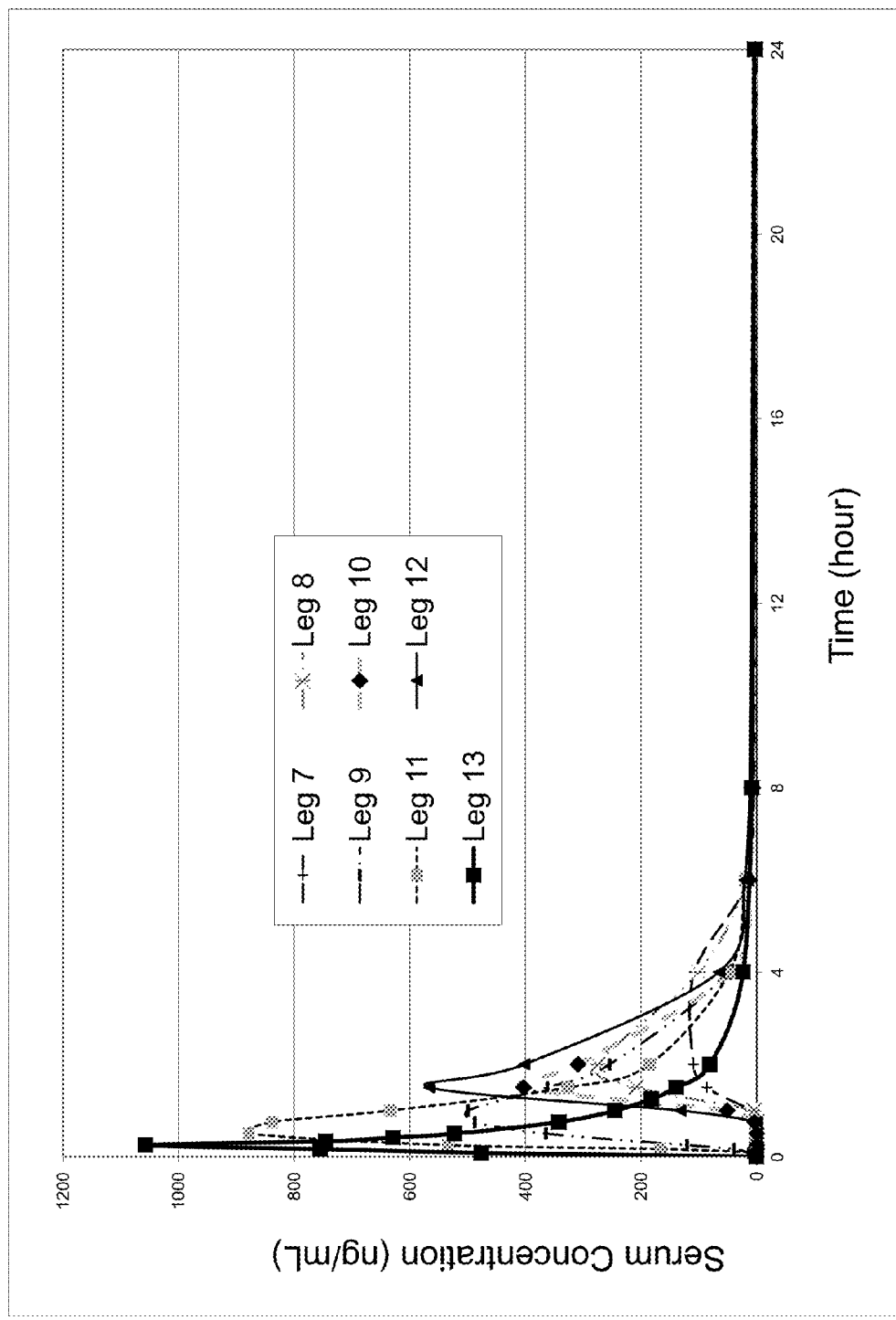
FIG. 35 shows the dog serum PK profile of parent zoledronic acid and zoledronic acid complexes delivered IV and orally, using enteric and non-enteric coated capsules.
Figure 36:
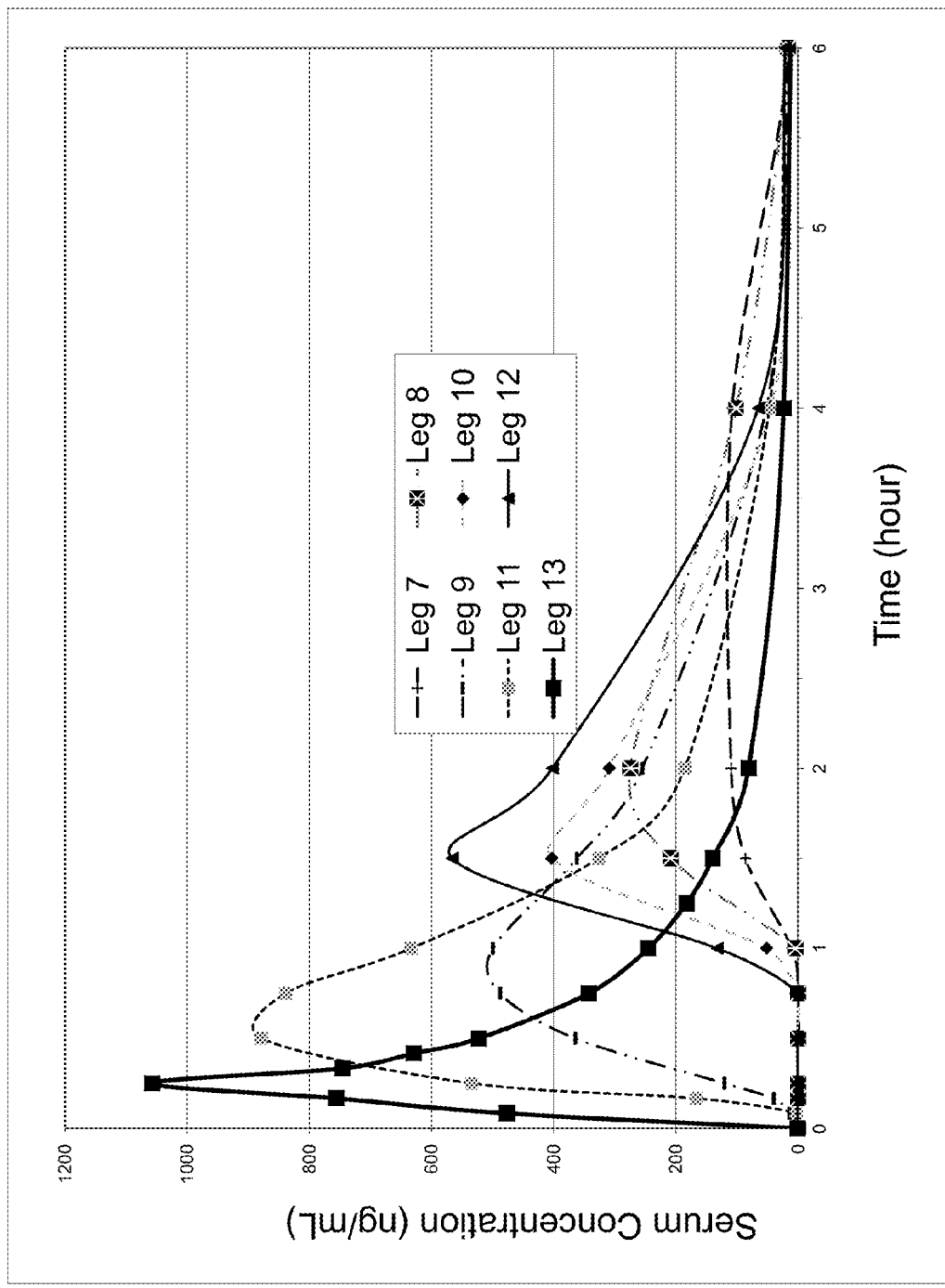
FIG. 36 shows the 6 hr dog serum PK profile of parent zoledronic acid and zoledronic acid complexes delivered IV and orally, using enteric and non-enteric coated capsules.
Figure 37:
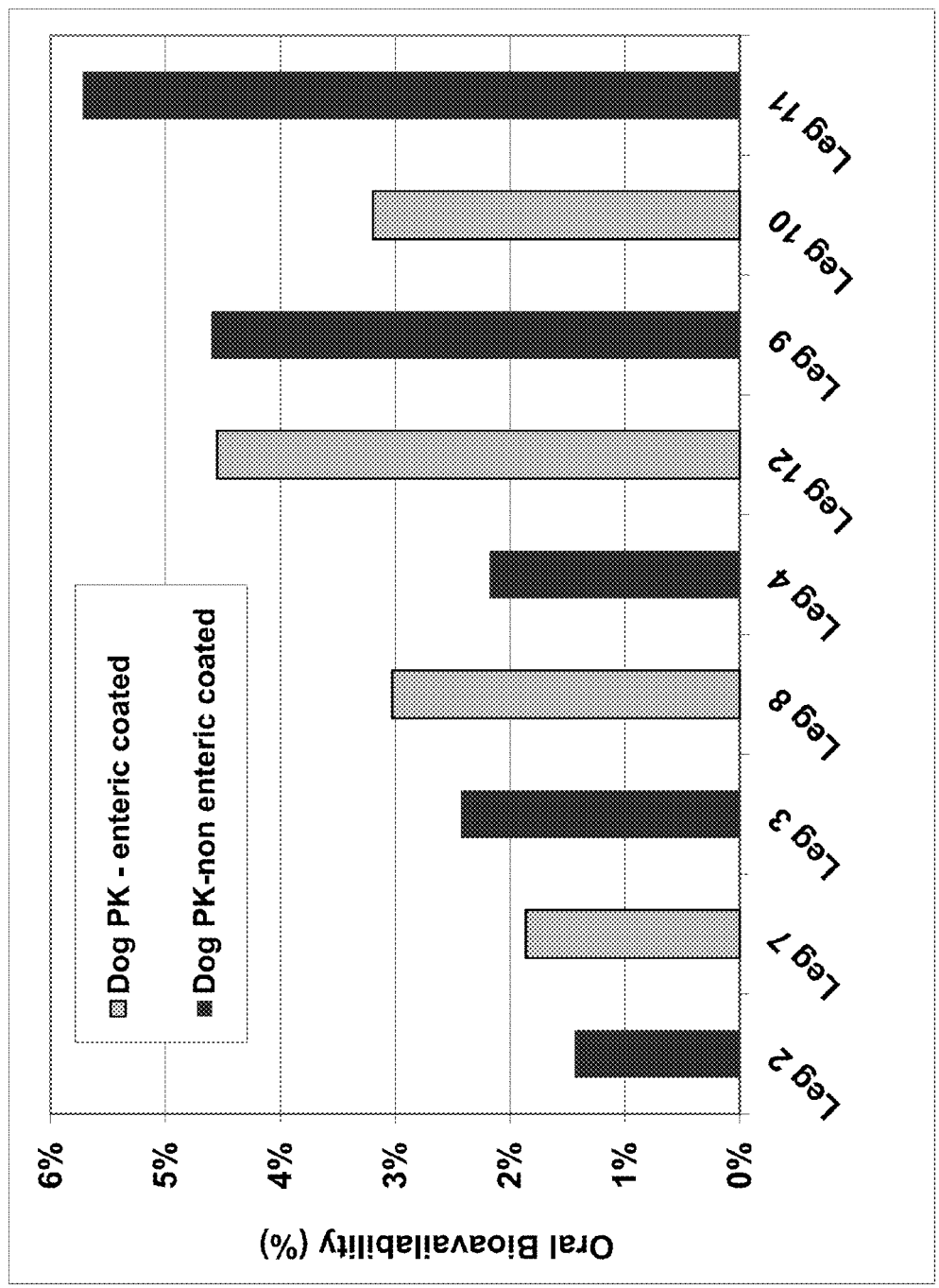
FIG. 37 shows the dog serum PK data for the enteric and non-enteric coated hard gelatin capsules.

The results of another dog study (Legs 7-13) are summarized in Table 4; the concentrations (ng/mL) of zoledronic acid shown are the average values of the analytical results of 5 dogs. The PK profiles of the IV and oral groups are shown in FIGS. 35 and 36. FIG. 36 represents the first 6 hours of the 24 hour PK profile. These results and FIG. 35 suggest that most if not all zoledronic acid complexes have achieved improved oral bioavailability compared with that of the parent zoledronic acid delivered orally. Specifically, there was a significant improvement in zoledronic acid bioavailability for the novel zoledronic acid complexes with excess amino acid coformer (Leg 11, FIG. 37) compared to that of the parent drug. The results have also shown that there was improvement in the bioavailability of the enterically coated capsules compared with the non-enterically coated capsules (FIG. 37, Legs 7 and 2, Legs 8 and 3, Legs 12 and 4), but surprisingly the bioavailability was significantly altered when excess amino acid coformer was added to form a physical mixture inside the enterically coated capsules (FIG. 37, Legs 9 and 10). The reason behind it is not fully understood.

The results have shown that there is a slight increase in the oral bioavailability of zoledronic acid from the enteric coated capsules filled with neat (i.e. with no excess coformer) zoledronic acid amino acid complex. Therefore, it is expected that the excess coformer with the novel zoledronic acid complexes would also lead to increased bioavailability when delivered in enterically coated capsules. Surprisingly, when excess coformer was added to the zoledronic acid, the bioavailability of the enterically coated capsules was lower than that of the non-enterically coated capsules. This suggests that a physical powder mixture of the molecular complex and excess coformer might decrease the bioavailability when delivered to the duodenum. The mechanism behind this surprising finding is not yet understood.

Figure 38:
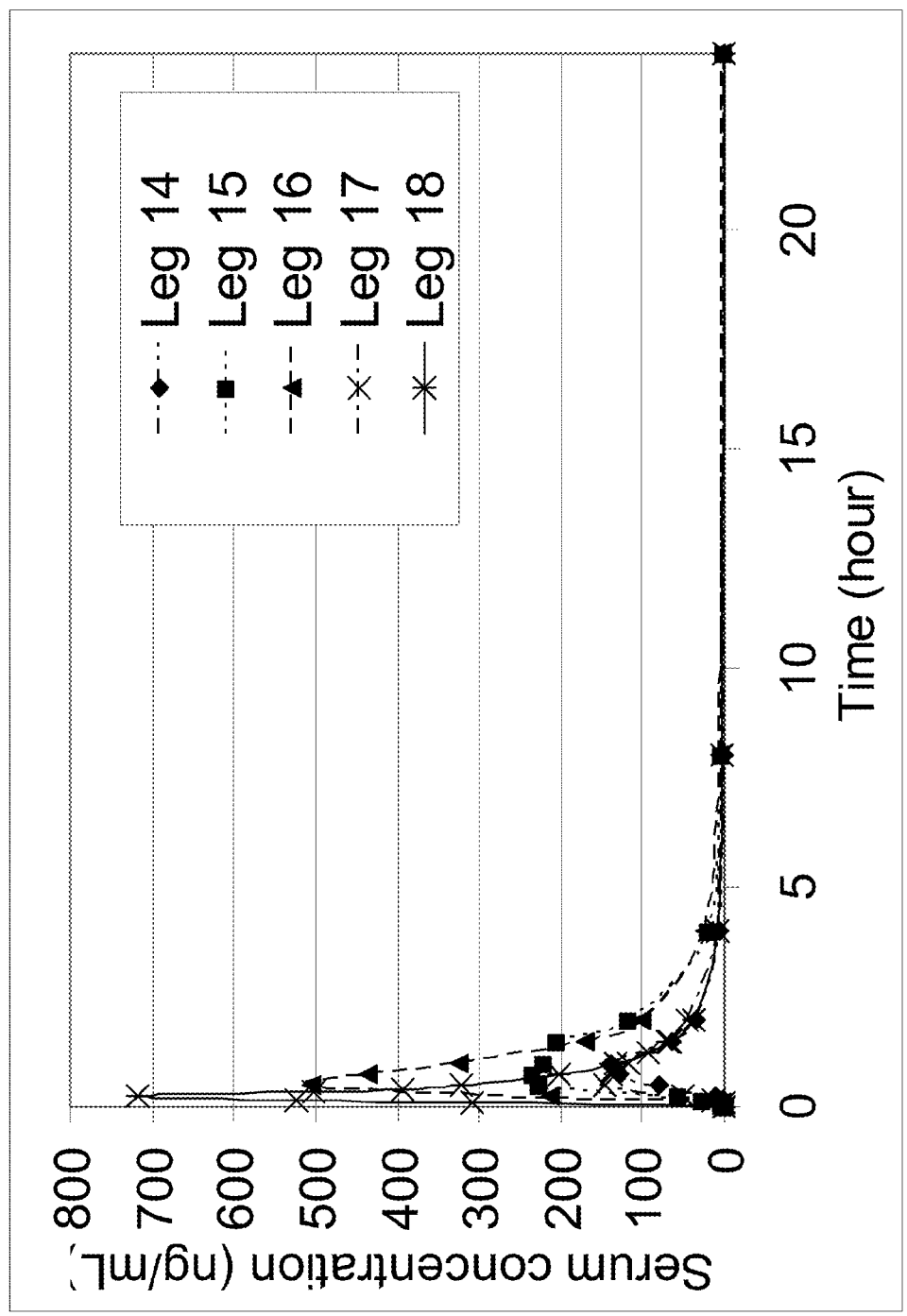
FIG. 38 shows the 24 hr dog serum PK profile of zoledronic acid complexes delivered IV and orally.
Figure 39:
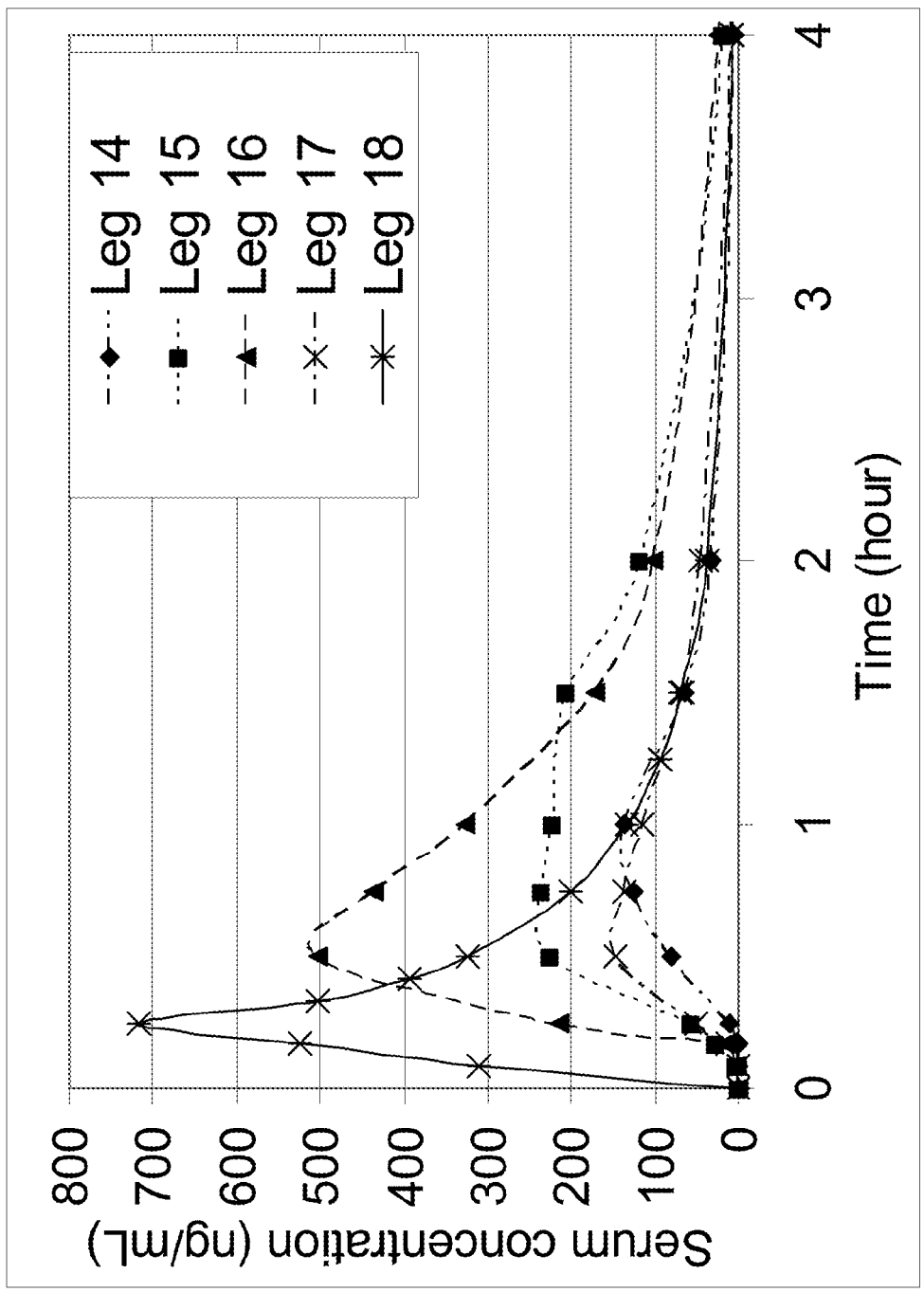
FIG. 39 shows the 4 hr dog serum PK profile of zoledronic acid complexes delivered IV and orally.

The analytical results of yet another dog study (Legs 14-18) are shown in Table 5, which contains averaged data from five dogs. The PK profiles of the IV and oral groups are shown in FIGS. 38 and 39. FIG. 39 represents the first 4 hours of the 24 hour PK profile.

Figure 40:
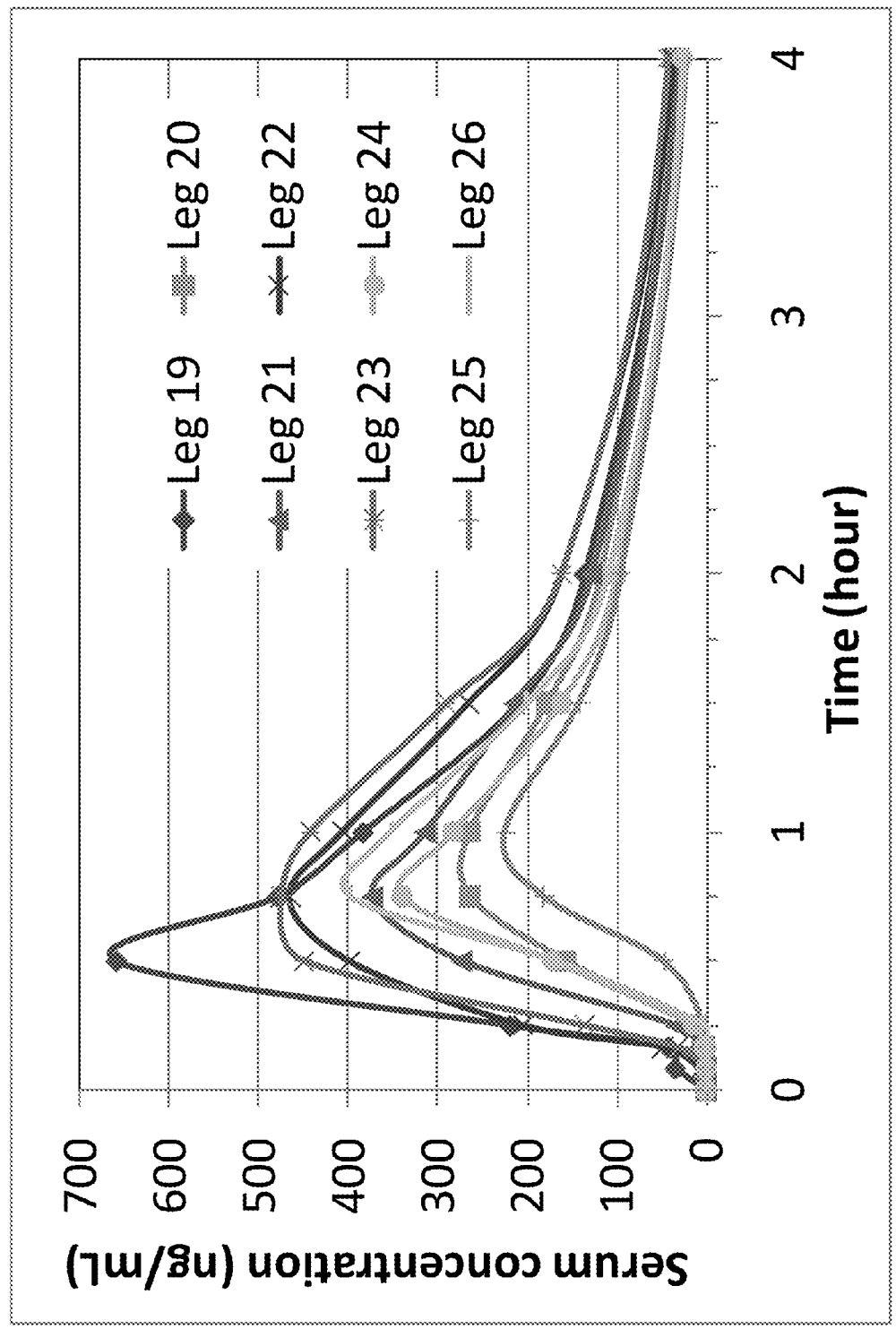
FIG. 40 shows the 4 hr dog serum PK profile of zoledronic acid complexes delivered orally.
Figure 41:
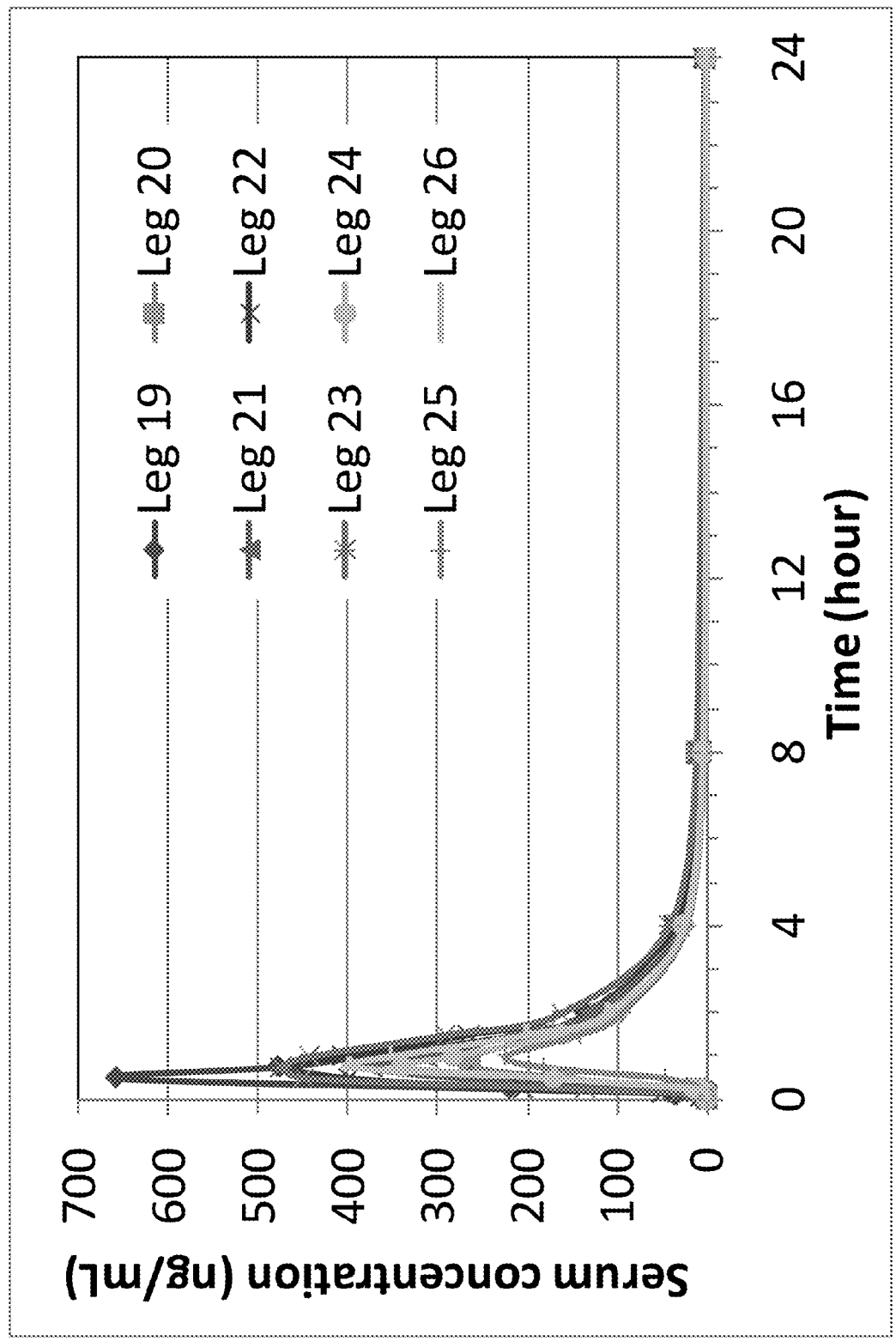
FIG. 41 shows the 24 hr dog serum PK profile of zoledronic acid complexes delivered orally.

The analytical results of another dog study (Legs 19-26) are shown in Table 6, which contains averaged data from five dogs. The PK profiles of the IV and oral groups are shown in FIGS. 40 and 41. FIG. 40 represents the first 4 hours of the 24 hour PK profile.

Figure 42:
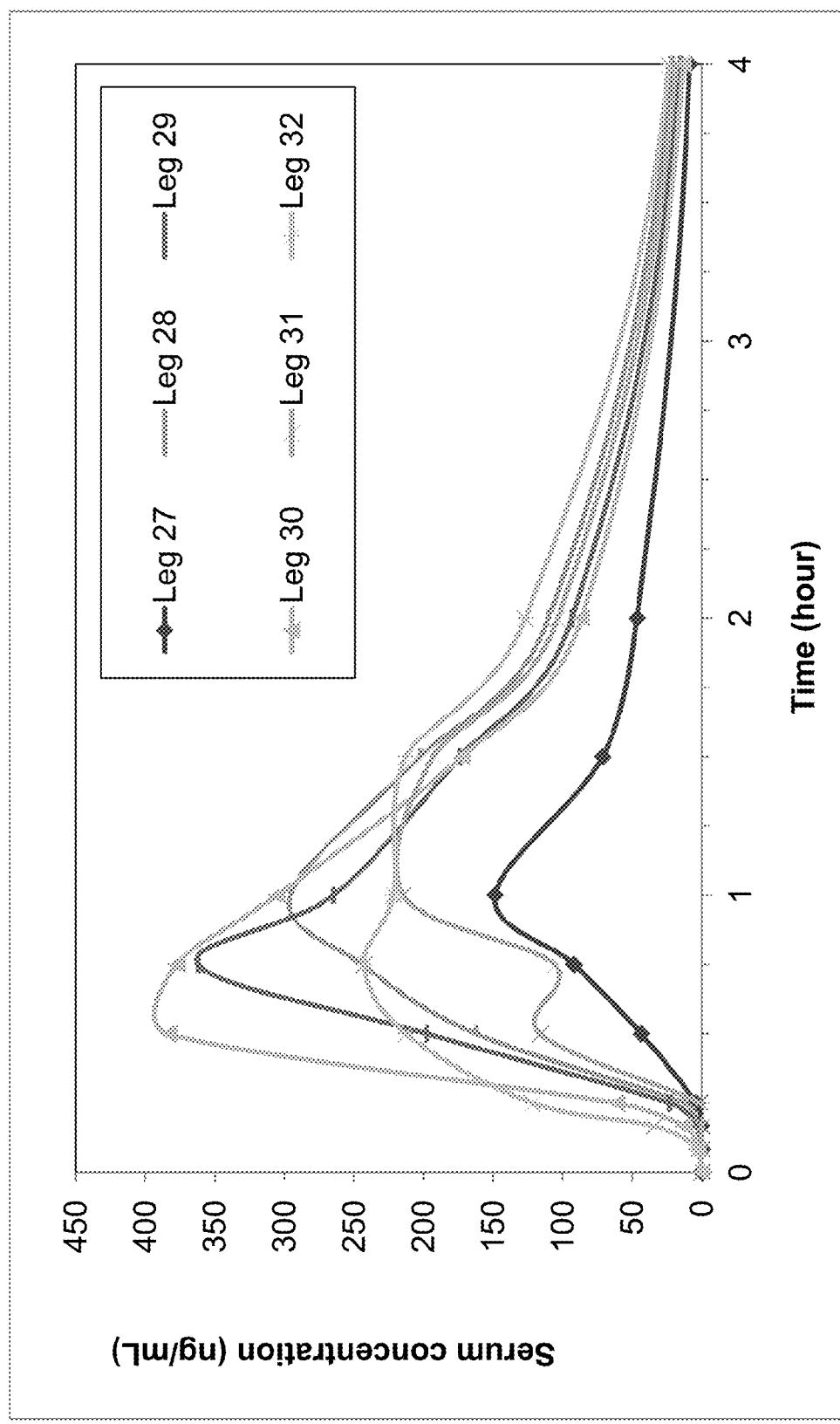
FIG. 42 shows the 4 hr dog serum PK profile of zoledronic acid complex delivered orally.
Figure 43:
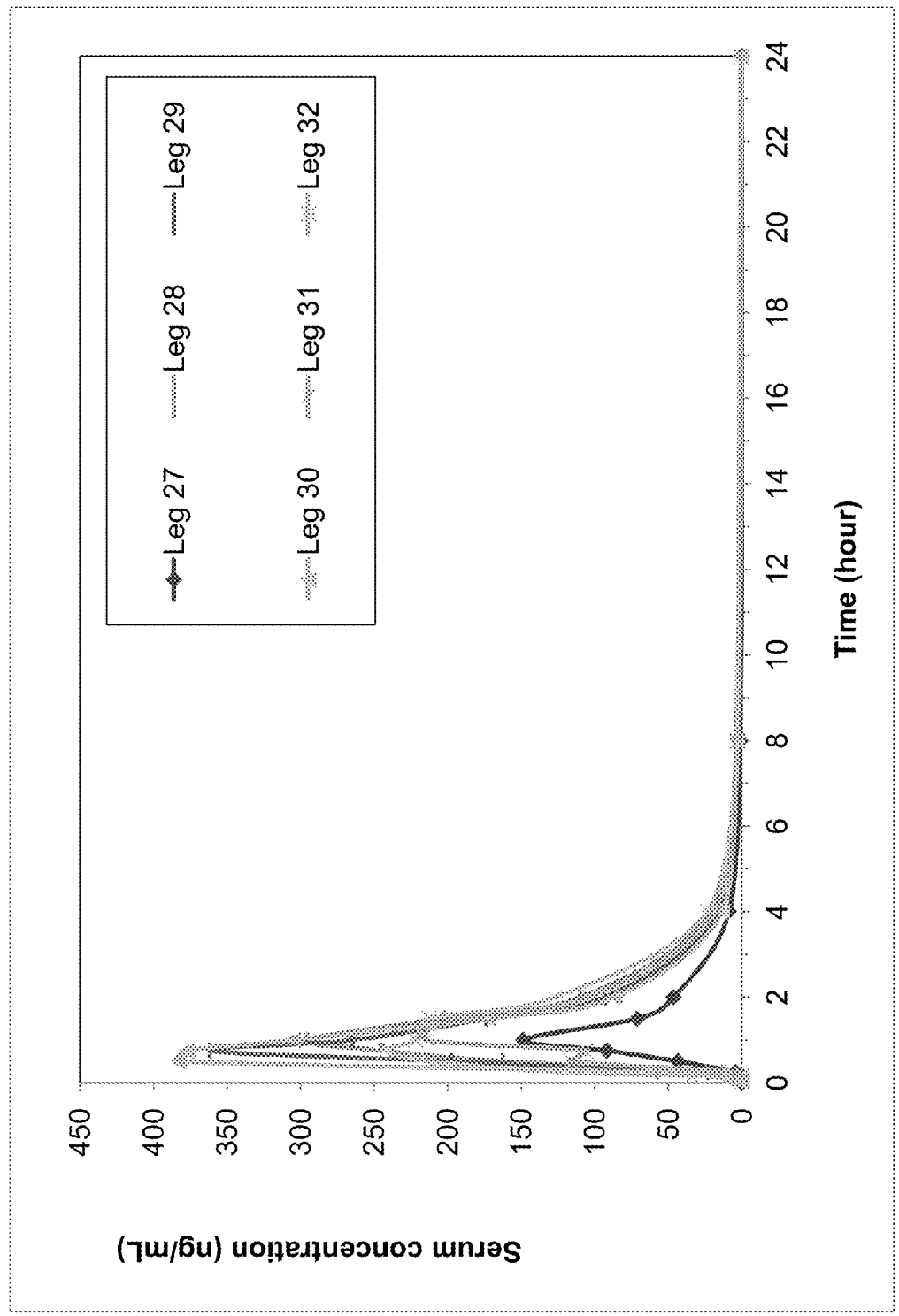
FIG. 43 shows the 24 hr dog serum PK profile of zoledronic acid complex delivered orally.

The analytical results of another dog study (Legs 27-32) are shown in Table 7, which contains the average data from 5 dogs with the exception of Leg 31 which is the average of 4 dogs. In this study, micronized materials (zoledronic:DL-lysine:water complex and pure DL-lysine) with size mean diameter of 5 micron by volume were used in some legs. Micronized materials were employed in our study to examine the possibility of increasing the $C_{max}$ of the drug through increasing the surface area and subsequently improving its rate of dissolution that should lead to higher concentration of the drug available for absorption through the GI tract. The results are summarized in Leg 30 and 32 in Table 7. The results of the micronized materials in both legs have shown a slight increase in the bioavailability of the drug. The PK profiles of the oral groups are shown in FIGS. 42 and 43. FIG. 42 represents the first 4 hours of the 24 hour PK profile.

The analytical results of yet another dog study (Legs 33-38) are shown in Tables 8 and 9 which contains the average data from 4 dogs. In this study, capsules of particulate materials (zoledronic:DL-lysine:water complex and excess pure DL-lysine). Prior to dosing, all dogs received a 20 ml dose of citric acid (24 mg/mL in water) to lower the pH of the stomach. After dosing capsules or IV, all dogs received additional 6.25 mL citric acid solution (24 mg/mL in water) as a rinse.

During the study, both serum and urine samples were collected from the animals. Urine samples were collected (N=4) over five intervals, 0-4 hours, 4-8 hours, 8-12 hours, 12-24 hours and 24-96 hours. Bioanalysis for urine excretion samples after dosing was performed. Samples were assayed for zoledronic acid using a validated LC/MS/MS method.

Figure 44:
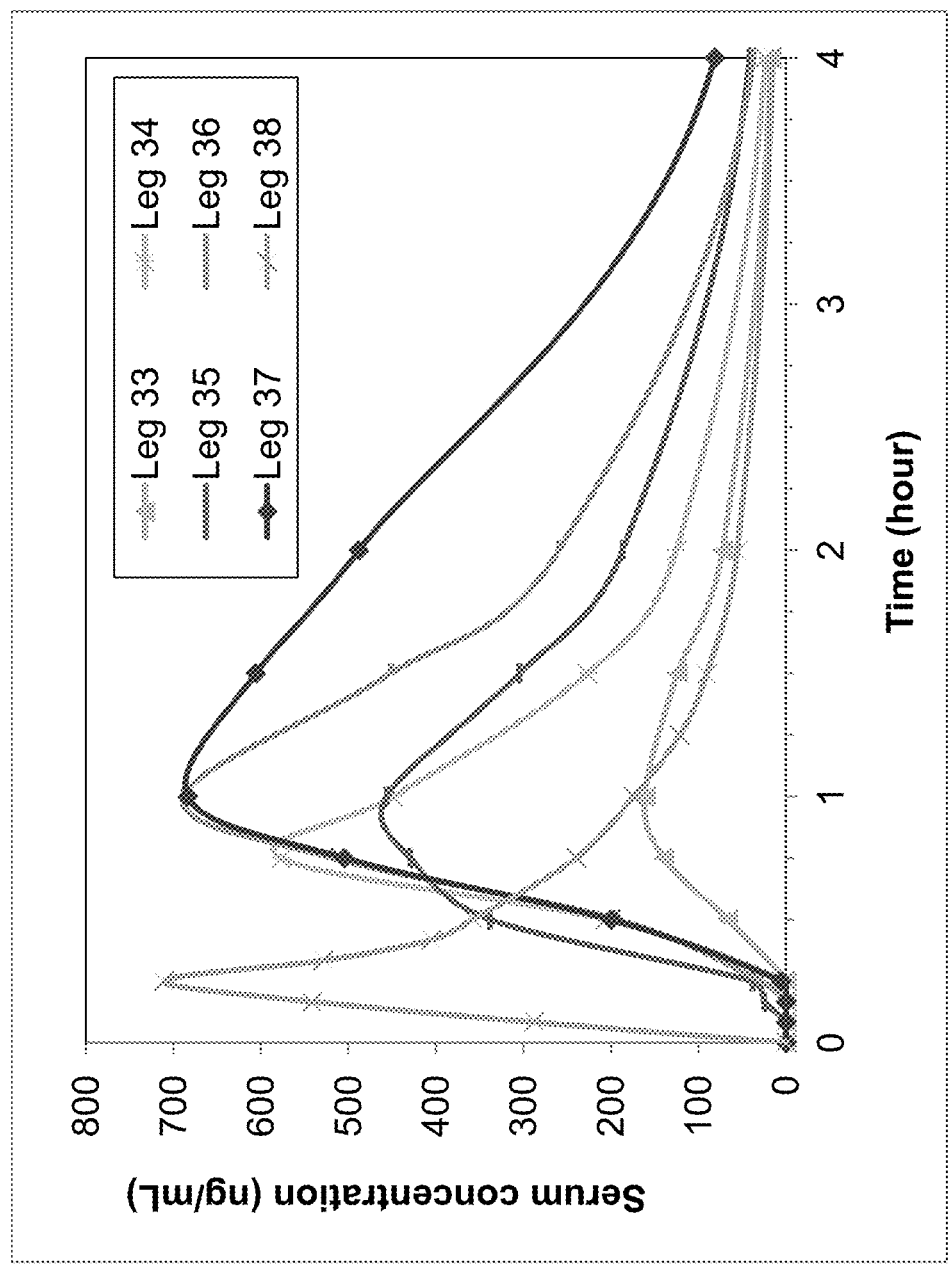
FIG. 44 shows the 4 hr dog serum PK profile of zoledronic acid complex with excess coformer delivered orally.
Figure 45:
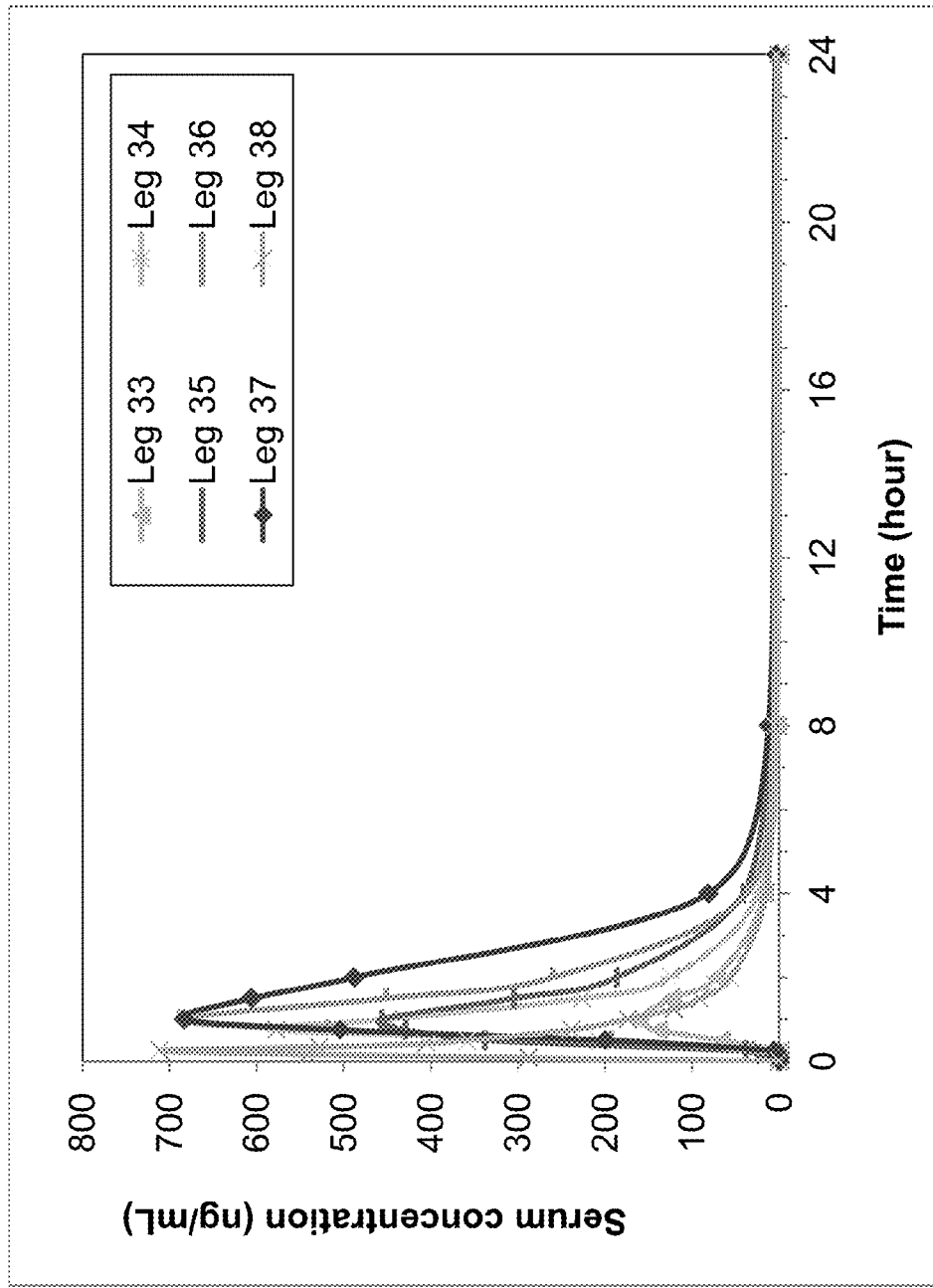
FIG. 45 shows the 24 hr dog serum PK profile of zoledronic acid complex with excess coformer delivered orally.

The results of Legs 33-38 are summarized in Table 8 (serum) and Table 9 (urine). The results show a significant increase in bioavailability of the bisphosphonic acid, particularly with high levels of lysine. The PK profiles are shown in FIGS. 44 and 45. FIG. 44 represents the first 4 hours of the 24 hour PK profile.

Example 17

Preparation of Zoledronic, DL-Lysine, and Water Complex

Figure 46:
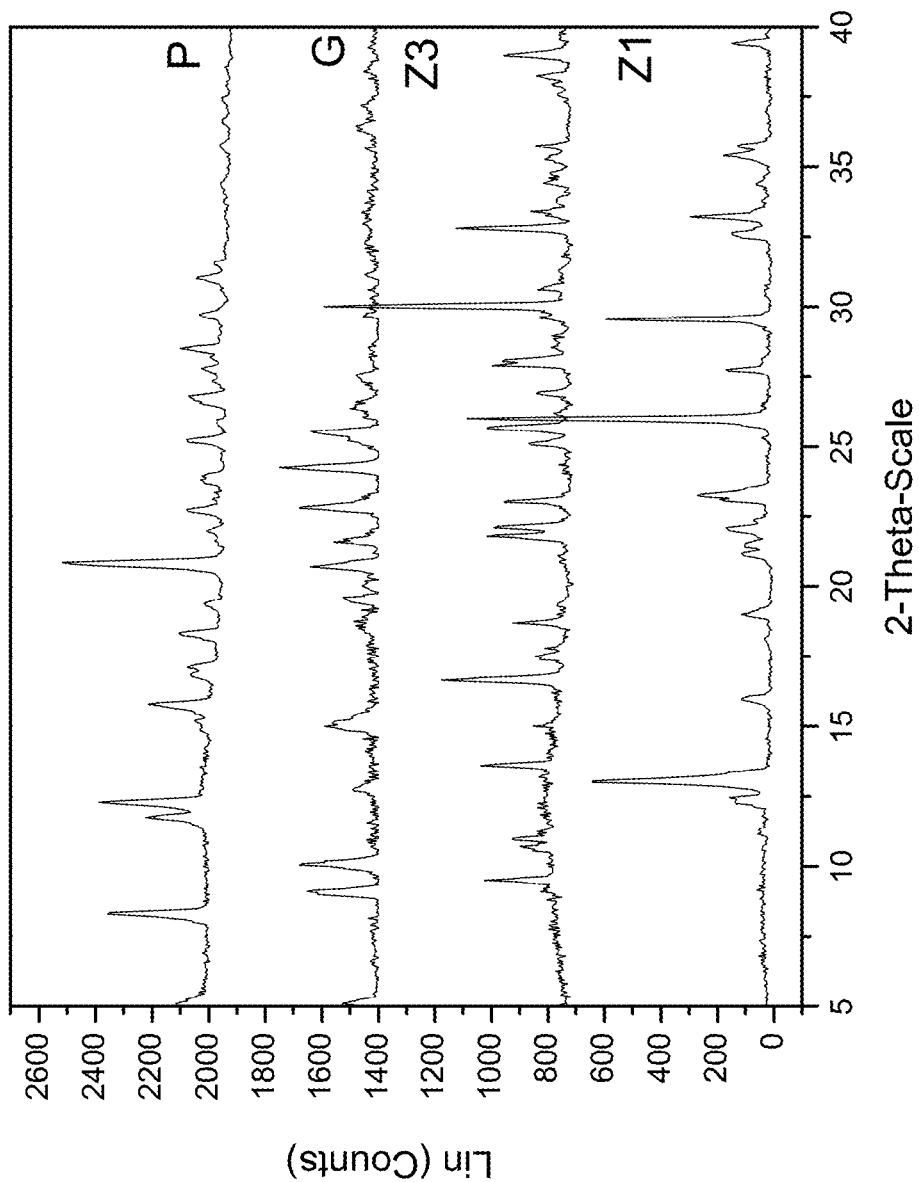
FIG. 46 shows PXRD diffractograms of: (P=zoledronic, DL-lysine, and water complex), (G=DL-lysine), (Z1=Zoledronic acid monohydrate), and (Z3=Zoledronic acid trihydrate).
Figure 47:
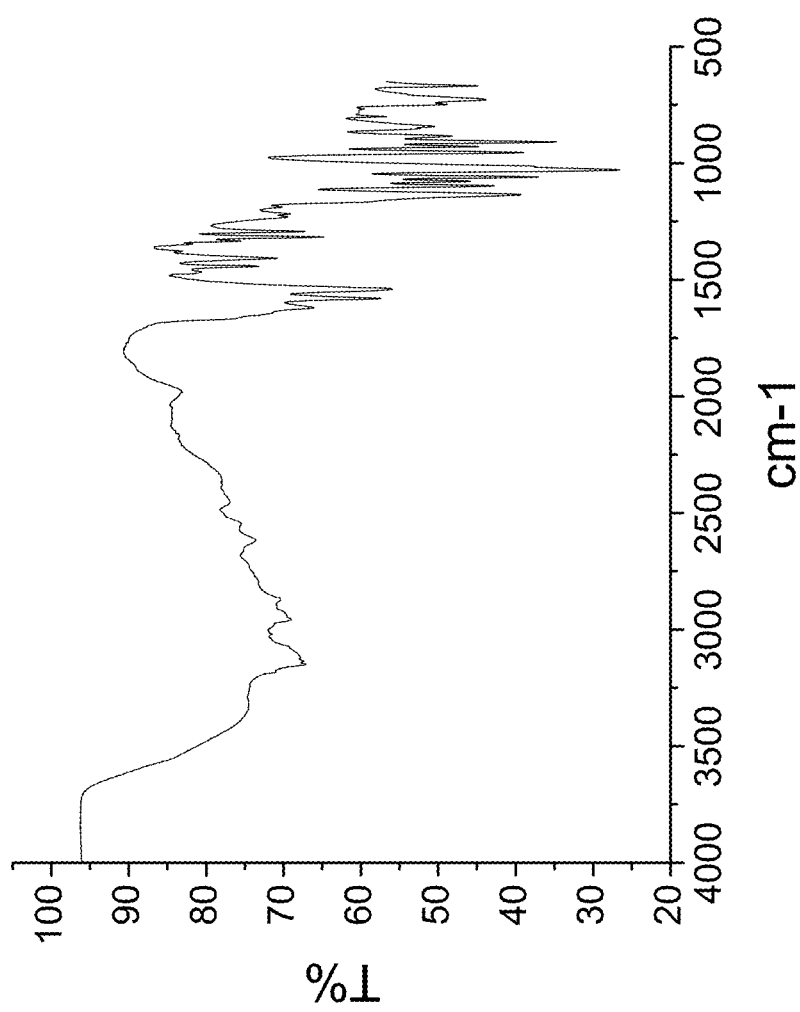
FIG. 47 is an FTIR spectrum of zoledronic, DL-lysine, and water complex.

In a scaled-up version of Example 12, 1.0 g of zoledronic acid and 0.56 g of DL-Lysine were slurried in 20 mL of tetrahydrofuran. 2 mL of water was then added drop wise. The solution was covered and left to stir overnight. The resulting precipitates were collected by filtration, dried, and stored in a screw cap vial for subsequent analysis. The solids gathered were characterized by PXRD and FTIR corresponding to FIG. 46 and FIG. 47 respectively.

TABLE 1

Rat plasma concentrations of zoledronic acid from pure zoledronic acid and zoledronic acid complexes delivered via different routes.

| Group # | Complex | Dosing Route | Vehicle | Time (hour) | Average plasma concentration of 3 rats (ng/mL) |
|---|---|---|---|---|---|
| G1 | Zoledronic acid | IV | Water | 0.083333 | 3254.05 |
|  |  |  |  | 0.25 | 1950.62 |
|  |  |  |  | 0.5 | 1128.75 |
|  |  |  |  | 1 | 404.28 |
|  |  |  |  | 2 | 112.68 |
|  |  |  |  | 4 | 30.46 |
|  |  |  |  | 8 | 10.66 |
|  |  |  |  | 24 | 2.98 |
| G2 | Zoledronic acid | PO | PEG 400 | 0.25 | 330.06 |
|  |  |  |  | 0.5 | 267.45 |
|  |  |  |  | 1 | 138.91 |
|  |  |  |  | 2 | 47.72 |
|  |  |  |  | 4 | 11.78 |
|  |  |  |  | 8 | 2.00 |
|  |  |  |  | 24 | 0.00 |
| G3 | Zoledronic and glycine complex | PO | PEG 400 | 0.25 | 648.01 |
|  |  |  |  | 0.5 | 435.38 |
|  |  |  |  | 1 | 200.88 |
|  |  |  |  | 4 | 12.78 |
|  |  |  |  | 8 | 1.46 |
|  |  |  |  | 24 | 0.00 |

TABLE 1-continued

Rat plasma concentrations of zoledronic acid from pure zoledronic acid and zoledronic acid complexes delivered via different routes.

| Group # | Complex | Dosing Route | Vehicle | Time (hour) | Average plasma concentration of 3 rats (ng/mL) |
|---|---|---|---|---|---|
| G4 | Zoledronic, nicotinamide, and water complex | PO | PEG 400 | 0.25 | 434.61 |
| | | | | 0.5 | 304.94 |
| | | | | 1 | 122.35 |
| | | | | 4 | 7.68 |
| | | | | 8 | 1.82 |
| | | | | 24 | 0.00 |
| G5 | Zoledronic acid, sodium zoledronic salt, and water complex | PO | PEG 400 | 0.25 | 278.47 |
| | | | | 0.5 | 280.20 |
| | | | | 1 | 171.59 |
| | | | | 4 | 13.42 |
| | | | | 8 | 1.78 |
| | | | | 24 | 0.00 |
| G6 | Zoledronic, L-lysine, and water complex | PO | PEG 400 | 0.25 | 258.43 |
| | | | | 0.5 | 249.82 |
| | | | | 1 | 184.95 |
| | | | | 4 | 28.70 |
| | | | | 8 | 3.27 |
| | | | | 24 | 0.00 |
| G7 | Zoledronic, DL-lysine, and water complex | PO | PEG 400 | 0.25 | 494.31 |
| | | | | 0.5 | 379.27 |
| | | | | 1 | 213.48 |
| | | | | 4 | 14.57 |
| | | | | 8 | 3.42 |
| | | | | 24 | 0.00 |
| G8 | Zoledronic acid | ID | PEG 400 | 0.25 | 145.67 |
| | | | | 0.5 | 109.92 |
| | | | | 1 | 47.36 |
| | | | | 2 | 12.94 |
| | | | | 4 | 3.85 |
| | | | | 8 | 0.97 |
| | | | | 24 | 0.00 |
| G9 | Zoledronic and glycine complex | ID | PEG 400 | 0.25 | 86.51 |
| | | | | 1 | 33.93 |
| | | | | 4 | 1.75 |
| | | | | 8 | 1.55 |
| | | | | 24 | 0.00 |
| G10 | Zoledronic, nicotinamide, and water complex | ID | PEG 400 | 0.25 | 69.71 |
| | | | | 1 | 21.03 |
| | | | | 4 | 0.86 |
| | | | | 8 | 0.00 |
| | | | | 24 | 0.00 |
| G11 | Zoledronic acid, sodium zoledronic salt, and water complex | ID | PEG 400 | 0.25 | 39.99 |
| | | | | 1 | 18.50 |
| | | | | 4 | 0.71 |
| | | | | 8 | 0.00 |
| | | | | 24 | 0.00 |
| G12 | Zoledronic, L-lysine, and water complex | ID | PEG 400 | 0.25 | 91.21 |
| | | | | 1 | 26.53 |
| | | | | 4 | 0.74 |
| | | | | 8 | 0.00 |
| | | | | 24 | 0.00 |
| G13 | Zoledronic, DL-lysine, and water complex | ID | PEG 400 | 0.25 | 98.25 |
| | | | | 1 | 34.61 |
| | | | | 4 | 2.65 |
| | | | | 8 | 1.02 |
| | | | | 24 | 0.80 |

TABLE 2

Rat plasma concentrations of zoledronic acid from zoledronic acid complexes with excess coformers, delivered by oral gavage

| Group # | Complex | Dosing Route | Vehicle | Time (hour) | Average plasma concentration of 3 rats (ng/mL) |
|---|---|---|---|---|---|
| G14 | Zoledronic and glycine complex and 45 mg/kg glycine | PO | PEG 400 | 0.0333333 | 14.61 |
| | | | | 0.0833333 | 206.26 |
| | | | | 0.1666667 | 340.19 |
| | | | | 0.25 | 375.99 |
| | | | | 0.5 | 321.36 |
| | | | | 1 | 197.01 |
| | | | | 4 | 17.35 |
| | | | | 24 | 0.00 |
| G15 | Zoledronic and glycine complex and 25 mg/kg glycine | PO | PEG 400 | 0.0333333 | 24.48 |
| | | | | 0.0833333 | 281.08 |
| | | | | 0.1666667 | 502.20 |
| | | | | 0.25 | 516.58 |
| | | | | 0.5 | 430.10 |
| | | | | 1 | 203.48 |
| | | | | 2 | 73.27 |
| | | | | 4 | 14.70 |
| | | | | 24 | 0.00 |
| G16 | Zoledronic and glycine complex and 5 mg/kg glycine | PO | PEG 400 | 0.0333333 | 60.03 |
| | | | | 0.0833333 | 365.23 |
| | | | | 0.1666667 | 563.83 |
| | | | | 0.25 | 625.05 |
| | | | | 0.5 | 464.34 |
| | | | | 1 | 209.65 |
| | | | | 2 | 74.28 |
| | | | | 4 | 12.17 |
| | | | | 24 | 0.00 |
| G17 | Zoledronic, DL-lysine, and water complex and 39.32 mg/kg DL-lysine monohydrate | PO | PEG 400 | 0.0333333 | 168.19 |
| | | | | 0.0833333 | 263.28 |
| | | | | 0.1666667 | 440.26 |
| | | | | 0.25 | 456.18 |
| | | | | 0.5 | 385.57 |
| | | | | 1 | 209.26 |
| | | | | 2 | 85.65 |
| | | | | 4 | 14.58 |
| | | | | 24 | 0.71 |
| G18 | Zoledronic, DL-lysine, and water complex and 28.08 mg/kg DL-lysine monohydrate | PO | PEG 400 | 0.0333333 | 219.95 |
| | | | | 0.0833333 | 427.02 |
| | | | | 0.1666667 | 729.65 |
| | | | | 0.25 | 777.54 |
| | | | | 0.5 | 632.07 |
| | | | | 1 | 300.86 |
| | | | | 2 | 100.59 |
| | | | | 4 | 21.14 |
| | | | | 24 | 0.00 |
| G19 | Zoledronic, DL-lysine, and water complex and 5.62 mg/kg DL-lysine monohydrate | PO | PEG 400 | 0.0333333 | 53.78 |
| | | | | 0.0833333 | 394.73 |
| | | | | 0.1666667 | 649.52 |
| | | | | 0.25 | 669.20 |
| | | | | 0.5 | 530.00 |
| | | | | 1 | 265.20 |
| | | | | 2 | 73.31 |
| | | | | 4 | 15.41 |
| | | | | 24 | 0.00 |
| G20 | Zoledronic, DL-lysine, and water complex | PO | PEG 400 | 0.0333333 | 103.13 |
| | | | | 0.0833333 | 352.18 |
| | | | | 0.1666667 | 475.33 |
| | | | | 0.25 | 505.48 |
| | | | | 0.5 | 431.41 |
| | | | | 1 | 224.56 |
| | | | | 2 | 69.95 |
| | | | | 4 | 14.96 |
| | | | | 24 | 0.00 |

TABLE 3

Dog serum concentrations of zoledronic acid from pure zoledronic acid and zoledronic acid complexes delivered via different routes.

| Leg # | Complex | Dosing Route | Vehicle | Time (hour) | Average serum concentration of 5 dogs (ng/mL) |
|---|---|---|---|---|---|
| 1 | 0.05 mg/kg Zoledronic acid | IV | Saline solution | 0 | 0.00 |
| | | | | 0.0333 | 413.44 |
| | | | | 0.0833 | 311.68 |
| | | | | 0.1667 | 228.97 |
| | | | | 0.25 | 178.63 |
| | | | | 0.5 | 111.11 |
| | | | | 0.75 | 75.91 |
| | | | | 1 | 56.07 |
| | | | | 1.5 | 30.35 |
| | | | | 2 | 17.61 |
| | | | | 4 | 4.29 |
| | | | | 8 | 1.13 |
| | | | | 24 | 0.00 |
| | | | | 48 | 0.00 |
| 2 | 56.0 mg Zoledronic acid monohydrate capsule | PO | n/a | 0 | 0.00 |
| | | | | 0.0833 | 0.00 |
| | | | | 0.1667 | 0.00 |
| | | | | 0.25 | 0.31 |
| | | | | 0.5 | 110.73 |
| | | | | 0.75 | 97.98 |
| | | | | 1 | 103.60 |
| | | | | 1.5 | 80.57 |
| | | | | 2 | 75.16 |
| | | | | 4 | 17.86 |
| | | | | 8 | 2.71 |
| | | | | 24 | 0.56 |
| 3 | 67.0 mg Zoledronic and glycine complex capsule | PO | n/a | 0 | 0.00 |
| | | | | 0.0833 | 2.45 |
| | | | | 0.1667 | 12.75 |
| | | | | 0.25 | 37.07 |
| | | | | 0.5 | 149.20 |
| | | | | 0.75 | 206.14 |
| | | | | 1 | 254.20 |
| | | | | 1.5 | 176.11 |
| | | | | 2 | 109.25 |
| | | | | 4 | 20.43 |
| | | | | 8 | 3.96 |
| | | | | 24 | 0.97 |
| 4 | 87.7 mg Zoledronic, DL-lysine, and water complex capsule | PO | n/a | 0 | 0.00 |
| | | | | 0.0833 | 3.11 |
| | | | | 0.1667 | 6.49 |
| | | | | 0.25 | 22.55 |
| | | | | 0.5 | 68.28 |
| | | | | 0.75 | 162.72 |
| | | | | 1 | 206.14 |
| | | | | 1.5 | 149.92 |
| | | | | 2 | 105.81 |
| | | | | 4 | 25.51 |
| | | | | 8 | 4.22 |
| | | | | 24 | 0.56 |
| 5 | 87.7 mg Zoledronic, L-lysine, and water complex capsule | PO | n/a | 0 | 0.00 |
| | | | | 0.0833 | 0.00 |
| | | | | 0.1667 | 3.13 |
| | | | | 0.25 | 10.06 |
| | | | | 0.5 | 188.52 |
| | | | | 0.75 | 345.28 |
| | | | | 1 | 318.97 |
| | | | | 1.5 | 180.77 |
| | | | | 2 | 109.23 |
| | | | | 4 | 23.11 |
| | | | | 8 | 9.73 |
| | | | | 24 | 1.93 |
| 6 | 84.2 mg Zoledronic, DL-lysine, and water complex capsule | PO | n/a | 0 | 0.00 |
| | | | | 0.0833 | 0.00 |
| | | | | 0.1667 | 0.20 |
| | | | | 0.25 | 1.92 |
| | | | | 0.5 | 106.47 |
| | | | | 0.75 | 120.13 |
| | | | | 1 | 108.13 |
| | | | | 1.5 | 90.45 |
| | | | | 2 | 54.48 |

TABLE 3-continued

Dog serum concentrations of zoledronic acid from pure zoledronic acid and zoledronic acid complexes delivered via different routes.

| Leg # | Complex | Dosing Route | Vehicle | Time (hour) | Average serum concentration of 5 dogs (ng/mL) |
|---|---|---|---|---|---|
| | | | | 4 | 18.14 |
| | | | | 8 | 4.35 |
| | | | | 24 | 1.06 |

TABLE 4

Dog serum concentrations of zoledronic acid from pure zoledronic acid and zoledronic acid complexes delivered via different routes, using enteric or non-enteric coated gelatin capsules.

| Leg # | Complex | Dosing Route | Vehicle | Time (hour) | Average serum concentration of 5 dogs (ng/mL) |
|---|---|---|---|---|---|
| 7 | 56.0 mg Zoledronic acid monohydrate enteric coated capsule | PO | n/a | 0 | 0.00 |
| | | | | 0.1667 | 0.00 |
| | | | | 0.25 | 0.00 |
| | | | | 0.5 | 0.00 |
| | | | | 0.75 | 0.00 |
| | | | | 1 | 9.84 |
| | | | | 1.5 | 86.13 |
| | | | | 2 | 109.37 |
| | | | | 4 | 107.64 |
| | | | | 6 | 14.15 |
| | | | | 8 | 4.57 |
| | | | | 24 | 0.50 |
| 8 | 67.0 mg Zoledronic and glycine complex enteric coated capsule | PO | n/a | 0 | 0.00 |
| | | | | 0.1667 | 0.00 |
| | | | | 0.25 | 0.00 |
| | | | | 0.5 | 0.00 |
| | | | | 0.75 | 0.00 |
| | | | | 1 | 4.42 |
| | | | | 1.5 | 208.97 |
| | | | | 2 | 274.53 |
| | | | | 4 | 101.20 |
| | | | | 6 | 16.71 |
| | | | | 8 | 7.14 |
| | | | | 24 | 2.17 |
| 9 | 87.7 mg Zoledronic, DL-lysine, and water complex with 294.8 mg DL-lysine monohydrate capsule | PO | n/a | 0 | 0.00 |
| | | | | 0.0833 | 13.31 |
| | | | | 0.1667 | 39.76 |
| | | | | 0.25 | 120.41 |
| | | | | 0.5 | 364.68 |
| | | | | 0.75 | 487.59 |
| | | | | 1 | 499.60 |
| | | | | 1.5 | 362.16 |
| | | | | 2 | 254.72 |
| | | | | 4 | 52.22 |
| | | | | 6 | 16.61 |
| | | | | 8 | 8.93 |
| | | | | 24 | 2.92 |
| 10 | 87.7 mg Zoledronic, DL-lysine, and water complex with 294.8 mg DL-lysine monohydrate enteric coated capsule | PO | n/a | 0 | 0.00 |
| | | | | 0.1667 | 0.00 |
| | | | | 0.25 | 0.00 |
| | | | | 0.5 | 0.00 |
| | | | | 0.75 | 3.71 |
| | | | | 1 | 51.32 |
| | | | | 1.5 | 403.15 |
| | | | | 2 | 309.08 |
| | | | | 4 | 44.83 |
| | | | | 6 | 13.15 |
| | | | | 8 | 7.09 |
| | | | | 24 | 2.66 |
| 11 | 84.2 mg Zoledronic, DL-lysine, and water complex with 294.8 mg DL-lysine | PO | n/a | 0 | 0.22 |
| | | | | 0.1667 | 167.03 |
| | | | | 0.25 | 533.96 |

TABLE 4-continued

Dog serum concentrations of zoledronic acid from pure zoledronic acid and zoledronic acid complexes delivered via different routes, using enteric or non-enteric coated gelatin capsules.

| Leg # | Complex | Dosing Route | Vehicle | Time (hour) | Average serum concentration of 5 dogs (ng/mL) |
|---|---|---|---|---|---|
|  | monohydrate capsule |  |  | 0.5 | 878.63 |
|  |  |  |  | 0.75 | 838.82 |
|  |  |  |  | 1 | 633.50 |
|  |  |  |  | 1.5 | 326.63 |
|  |  |  |  | 2 | 185.44 |
|  |  |  |  | 4 | 46.86 |
|  |  |  |  | 6 | 20.26 |
|  |  |  |  | 8 | 11.49 |
|  |  |  |  | 24 | 5.95 |
| 12 | 87.7 mg Zoledronic, DL-lysine, and water complex enteric coated capsule | PO | n/a | 0 | 0.57 |
|  |  |  |  | 0.1667 | 0.60 |
|  |  |  |  | 0.25 | 0.59 |
|  |  |  |  | 0.5 | 0.61 |
|  |  |  |  | 0.75 | 0.40 |
|  |  |  |  | 1 | 132.15 |
|  |  |  |  | 1.5 | 566.18 |
|  |  |  |  | 2 | 402.12 |
|  |  |  |  | 4 | 65.35 |
|  |  |  |  | 6 | 21.02 |
|  |  |  |  | 8 | 12.18 |
|  |  |  |  | 24 | 4.33 |
| 13 | 0.183 mg/kg Zoledronic acid | IV | Saline solution | 0 | 0.64 |
|  |  |  |  | 0.0833 | 476.79 |
|  |  |  |  | 0.1667 | 755.68 |
|  |  |  |  | 0.25 | 1057.75 |
|  |  |  |  | 0.3333 | 745.67 |
|  |  |  |  | 0.4167 | 629.22 |
|  |  |  |  | 0.5 | 522.78 |
|  |  |  |  | 0.75 | 342.58 |
|  |  |  |  | 1 | 245.36 |
|  |  |  |  | 1.25 | 182.59 |
|  |  |  |  | 1.5 | 139.77 |
|  |  |  |  | 2 | 80.87 |
|  |  |  |  | 4 | 23.40 |
|  |  |  |  | 8 | 8.78 |
|  |  |  |  | 24 | 3.84 |

TABLE 5

Dog serum concentrations of zoledronic acid from pure zoledronic acid and zoledronic acid complexes delivered via different routes.

| Leg # | Complex | Dosing Route | Vehicle | Time (hour) | Average serum concentration of 5 dogs (ng/mL) |
|---|---|---|---|---|---|
| 14 | 35.4 mg Zoledronic, DL-lysine, and water complex, with 123.8 mg DL-lysine monohydrate gelatin capsule | PO | n/a | 0 | 0.00 |
|  |  |  |  | 0.0833 | 0.00 |
|  |  |  |  | 0.1667 | 0.72 |
|  |  |  |  | 0.25 | 11.40 |
|  |  |  |  | 0.5 | 78.95 |
|  |  |  |  | 0.75 | 126.46 |
|  |  |  |  | 1 | 137.38 |
|  |  |  |  | 1.5 | 64.73 |
|  |  |  |  | 2 | 33.38 |
|  |  |  |  | 4 | 6.14 |
|  |  |  |  | 8 | 0.89 |
|  |  |  |  | 24 | 0.00 |
| 15 | 67.0 mg Zoledronic and glycine complex, with 294.8 mg DL-lysine monohydrate gelatin capsule | PO | n/a | 0 | 0.00 |
|  |  |  |  | 0.0833 | 2.58 |
|  |  |  |  | 0.1667 | 26.13 |
|  |  |  |  | 0.25 | 55.58 |
|  |  |  |  | 0.5 | 225.41 |
|  |  |  |  | 0.75 | 234.95 |
|  |  |  |  | 1 | 221.91 |

TABLE 5-continued

Dog serum concentrations of zoledronic acid from pure zoledronic acid and zoledronic acid complexes delivered via different routes.

| Leg # | Complex | Dosing Route | Vehicle | Time (hour) | Average serum concentration of 5 dogs (ng/mL) |
|---|---|---|---|---|---|
| | | | | 1.5 | 204.90 |
| | | | | 2 | 117.22 |
| | | | | 4 | 17.79 |
| | | | | 8 | 3.34 |
| | | | | 24 | 0.77 |
| 16 | 87.7 mg Zoledronic, L-lysine, and water complex, with 294.8 mg DL-lysine monohydrate gelatin capsule | PO | n/a | 0 | 0.00 |
| | | | | 0.0833 | 3.26 |
| | | | | 0.1667 | 17.21 |
| | | | | 0.25 | 213.77 |
| | | | | 0.5 | 504.17 |
| | | | | 0.75 | 436.00 |
| | | | | 1 | 325.21 |
| | | | | 1.5 | 171.42 |
| | | | | 2 | 100.81 |
| | | | | 4 | 23.38 |
| | | | | 8 | 4.65 |
| | | | | 24 | 1.48 |
| 17 | 35.4 mg Zoledronic, DL-lysine, and water complex, with 294.8 mg DL-lysine monohydrate gelatin capsule | PO | n/a | 0 | 0.00 |
| | | | | 0.0833 | 0.00 |
| | | | | 0.1667 | 13.47 |
| | | | | 0.25 | 50.04 |
| | | | | 0.5 | 146.68 |
| | | | | 0.75 | 137.24 |
| | | | | 1 | 116.38 |
| | | | | 1.5 | 66.70 |
| | | | | 2 | 44.94 |
| | | | | 4 | 8.87 |
| | | | | 8 | 1.58 |
| | | | | 24 | 0.21 |
| 18 | 0.12 mg/kg Zoledronic acid | IV | Saline solution | 0 | 0.00 |
| | | | | 0.0833 | 309.13 |
| | | | | 0.1667 | 524.58 |
| | | | | 0.25 | 717.15 |
| | | | | 0.3333 | 501.70 |
| | | | | 0.4167 | 392.35 |
| | | | | 0.5 | 322.84 |
| | | | | 0.75 | 201.78 |
| | | | | 1 | 132.86 |
| | | | | 1.25 | 93.22 |
| | | | | 1.5 | 69.06 |
| | | | | 2 | 38.38 |
| | | | | 4 | 9.14 |
| | | | | 8 | 3.24 |
| | | | | 24 | 1.21 |

TABLE 6

Dog serum concentrations of zoledronic acid from pure zoledronic acid and zoledronic acid complexes delivered orally.

| Leg # | Complex | Dosing Route | Vehicle | Time (hour) | Average serum concentration of 5 dogs (ng/mL) |
|---|---|---|---|---|---|
| 19 | 61.3 mg Zoledronic acid, with 322.9 mg DL-lysine monohydrate gelatin capsule | PO | n/a | 0 | 0.00 |
| | | | | 0.0833 | 34.10 |
| | | | | 0.1667 | 42.74 |
| | | | | 0.25 | 219.76 |
| | | | | 0.5 | 659.25 |
| | | | | 0.75 | 478.77 |
| | | | | 1 | 383.80 |
| | | | | 1.5 | 209.87 |
| | | | | 2 | 135.97 |
| | | | | 4 | 34.22 |
| | | | | 8 | 8.53 |
| | | | | 24 | 2.07 |

TABLE 6-continued

Dog serum concentrations of zoledronic acid from pure zoledronic acid and zoledronic acid complexes delivered orally.

| Leg # | Complex | Dosing Route | Vehicle | Time (hour) | Average serum concentration of 5 dogs (ng/mL) |
|---|---|---|---|---|---|
| 20 | 76.8 mg Zoledronic, L-lysine, and water complex, with 359.2 mg L-lysine HCl gelatin capsule | PO | n/a | 0 | 0.20 |
| | | | | 0.0833 | 0.21 |
| | | | | 0.1667 | 4.10 |
| | | | | 0.25 | 12.03 |
| | | | | 0.5 | 156.89 |
| | | | | 0.75 | 263.80 |
| | | | | 1 | 265.48 |
| | | | | 1.5 | 178.89 |
| | | | | 2 | 118.73 |
| | | | | 4 | 36.12 |
| | | | | 8 | 12.32 |
| | | | | 24 | 2.56 |
| 21 | 84.2 mg Zoledronic, DL-lysine, and water complex, with 328.0 mg L-lysine HCl gelatin capsule | PO | n/a | 0 | 0.00 |
| | | | | 0.0833 | 0.20 |
| | | | | 0.1667 | 5.77 |
| | | | | 0.25 | 32.62 |
| | | | | 0.5 | 273.09 |
| | | | | 0.75 | 373.00 |
| | | | | 1 | 314.46 |
| | | | | 1.5 | 214.18 |
| | | | | 2 | 128.08 |
| | | | | 4 | 30.87 |
| | | | | 8 | 6.80 |
| | | | | 24 | 2.12 |
| 22 | 69.0 mg Zoledronic, DL-lysine, and water complex, with 241.8 mg DL-lysine monohydrate gelatin capsule | PO | n/a | 0 | 0.00 |
| | | | | 0.0833 | 7.35 |
| | | | | 0.1667 | 48.84 |
| | | | | 0.25 | 204.61 |
| | | | | 0.5 | 398.98 |
| | | | | 0.75 | 465.56 |
| | | | | 1 | 406.10 |
| | | | | 1.5 | 265.75 |
| | | | | 2 | 161.63 |
| | | | | 4 | 36.68 |
| | | | | 8 | 9.66 |
| | | | | 24 | 3.45 |
| 23 | 70.1 mg Zoledronic, L-lysine, and water complex, with 294.9 mg DL-lysine monohydrate gelatin capsule | PO | n/a | 0 | 0.52 |
| | | | | 0.0833 | 1.99 |
| | | | | 0.1667 | 31.45 |
| | | | | 0.25 | 135.92 |
| | | | | 0.5 | 449.28 |
| | | | | 0.75 | 474.97 |
| | | | | 1 | 442.86 |
| | | | | 1.5 | 290.01 |
| | | | | 2 | 162.59 |
| | | | | 4 | 42.25 |
| | | | | 8 | 10.77 |
| | | | | 24 | 3.28 |
| 24 | 64.0 mg Zoledronic acid, with 374.8 mg L-lysine HCl gelatin capsule | PO | n/a | 0 | 0.00 |
| | | | | 0.0833 | 0.00 |
| | | | | 0.1667 | 1.20 |
| | | | | 0.25 | 14.11 |
| | | | | 0.5 | 171.59 |
| | | | | 0.75 | 340.09 |
| | | | | 1 | 283.01 |
| | | | | 1.5 | 162.59 |
| | | | | 2 | 99.96 |
| | | | | 4 | 26.27 |
| | | | | 8 | 4.56 |
| | | | | 24 | 0.89 |

TABLE 6-continued

Dog serum concentrations of zoledronic acid from pure zoledronic acid and zoledronic acid complexes delivered orally.

| Leg # | Complex | Dosing Route | Vehicle | Time (hour) | Average serum concentration of 5 dogs (ng/mL) |
|---|---|---|---|---|---|
| 25 | 80.1 mg Zoledronic, L-lysine, and water complex gelatin capsule | PO | n/a | 0 | 0.00 |
| | | | | 0.0833 | 0.00 |
| | | | | 0.1667 | 0.32 |
| | | | | 0.25 | 2.16 |
| | | | | 0.5 | 47.70 |
| | | | | 0.75 | 181.00 |
| | | | | 1 | 224.61 |
| | | | | 1.5 | 142.02 |
| | | | | 2 | 95.10 |
| | | | | 4 | 23.06 |
| | | | | 8 | 3.97 |
| | | | | 24 | 1.20 |
| 26 | 76.5 mg Zoledronic and glycine complex, with 374.8 mg L-lysine HCl gelatin capsule | PO | n/a | 0 | 0.00 |
| | | | | 0.0833 | 0.00 |
| | | | | 0.1667 | 0.85 |
| | | | | 0.25 | 3.18 |
| | | | | 0.5 | 169.29 |
| | | | | 0.75 | 397.95 |
| | | | | 1 | 352.39 |
| | | | | 1.5 | 200.22 |
| | | | | 2 | 109.96 |
| | | | | 4 | 25.15 |
| | | | | 8 | 4.34 |
| | | | | 24 | 1.66 |

TABLE 7

Dog serum concentrations of zoledronic acid from pure zoledronic acid and zoledronic acid complexes delivered orally.

| Leg # | Complex | Dosing Route | Vehicle | Time (hour) | Average serum concentration of 5 dogs (ng/mL) |
|---|---|---|---|---|---|
| 27 | 32.0 mg Zoledronic, DL-lysine, and water complex, with 266.8 mg DL-lysine monohydrate gelatin capsule | PO | n/a | 0 | 0.00 |
| | | | | 0.0833 | 0.00 |
| | | | | 0.1667 | 0.52 |
| | | | | 0.25 | 4.25 |
| | | | | 0.5 | 43.64 |
| | | | | 0.75 | 91.85 |
| | | | | 1 | 148.71 |
| | | | | 1.5 | 71.25 |
| | | | | 2 | 46.68 |
| | | | | 4 | 8.83 |
| | | | | 8 | 1.02 |
| | | | | 24 | 0.00 |
| 28 | 76.2 mg Zoledronic, DL-lysine, and water complex, with 266.8 mg DL-lysine monohydrate gelatin capsule | PO | n/a | 0 | 0.00 |
| | | | | 0.0833 | 0.37 |
| | | | | 0.1667 | 3.48 |
| | | | | 0.25 | 12.59 |
| | | | | 0.5 | 162.37 |
| | | | | 0.75 | 244.28 |
| | | | | 1 | 295.79 |
| | | | | 1.5 | 202.36 |
| | | | | 2 | 110.16 |
| | | | | 4 | 21.43 |
| | | | | 8 | 3.16 |
| | | | | 24 | 0.81 |

TABLE 7-continued

Dog serum concentrations of zoledronic acid from pure zoledronic acid and zoledronic acid complexes delivered orally.

| Leg # | Complex | Dosing Route | Vehicle | Time (hour) | Average serum concentration of 5 dogs (ng/mL) |
|---|---|---|---|---|---|
| 29 | 64.4 mg Zoledronic, DL-lysine, and water complex, with 275.2 mg DL-lysine monohydrate gelatin capsule | PO | n/a | 0 | 0.00 |
| | | | | 0.0833 | 0.00 |
| | | | | 0.1667 | 2.10 |
| | | | | 0.25 | 23.08 |
| | | | | 0.5 | 197.71 |
| | | | | 0.75 | 361.80 |
| | | | | 1 | 264.70 |
| | | | | 1.5 | 173.72 |
| | | | | 2 | 93.35 |
| | | | | 4 | 15.54 |
| | | | | 8 | 2.97 |
| | | | | 24 | 0.71 |
| 30 | 64.4 mg micronized Zoledronic, DL-lysine, and water complex, with 275.2 mg micronized DL-lysine monohydrate gelatin capsule | PO | n/a | 0 | 0.00 |
| | | | | 0.0833 | 2.95 |
| | | | | 0.1667 | 13.08 |
| | | | | 0.25 | 61.19 |
| | | | | 0.5 | 383.13 |
| | | | | 0.75 | 377.27 |
| | | | | 1 | 305.30 |
| | | | | 1.5 | 172.67 |
| | | | | 2 | 86.54 |
| | | | | 4 | 13.56 |
| | | | | 8 | 3.52 |
| | | | | 24 | 0.87 |
| 31 | 50.8 mg Zoledronic, DL-lysine, and water complex, with 278.0 mg DL-lysine monohydrate gelatin capsule | PO | n/a | 0 | 0.00 |
| | | | | 0.0833 | 0.00 |
| | | | | 0.1667 | 0.00 |
| | | | | 0.25 | 1.50 |
| | | | | 0.5 | 116.12 |
| | | | | 0.75 | 105.85 |
| | | | | 1 | 214.29 |
| | | | | 1.5 | 193.10 |
| | | | | 2 | 103.50 |
| | | | | 4 | 18.42 |
| | | | | 8 | 2.57 |
| | | | | 24 | 0.31 |
| 32 | 50.8 mg micronized Zoledronic, DL-lysine, and water complex, with 278.0 mg micronized DL-lysine monohydrate gelatin capsule | PO | n/a | 0 | 0.00 |
| | | | | 0.0833 | 2.42 |
| | | | | 0.1667 | 33.98 |
| | | | | 0.25 | 121.95 |
| | | | | 0.5 | 212.75 |
| | | | | 0.75 | 242.80 |
| | | | | 1 | 221.71 |
| | | | | 1.5 | 212.75 |
| | | | | 2 | 126.93 |
| | | | | 4 | 23.77 |
| | | | | 8 | 3.64 |
| | | | | 24 | 0.80 |

TABLE 8

Dog serum concentrations of zoledronic acid from pure zoledronic acid and zoledronic acid complexes delivered via different routes.

| Leg # | Complex | Dosing Route | Vehicle | Time (hour) | Average serum concentration of 4 dogs (ng/mL) |
|---|---|---|---|---|---|
| 33 | 59.2 mg Zoledronic, DL-lysine, and water complex, with 112.3 mg DL-lysine monohydrate gelatin capsule | PO | n/a | 0 | 0.00 |
| | | | | 0.0833 | 0.00 |
| | | | | 0.1667 | 0.00 |
| | | | | 0.25 | 0.00 |
| | | | | 0.5 | 66.80 |
| | | | | 0.75 | 139.37 |
| | | | | 1 | 161.23 |
| | | | | 1.5 | 124.08 |

TABLE 8-continued

Dog serum concentrations of zoledronic acid from pure zoledronic acid and zoledronic acid complexes delivered via different routes.

| Leg # | Complex | Dosing Route | Vehicle | Time (hour) | Average serum concentration of 4 dogs (ng/mL) |
|---|---|---|---|---|---|
| | | | | 2 | 72.53 |
| | | | | 4 | 16.99 |
| | | | | 8 | 2.30 |
| | | | | 24 | 0.00 |
| 34 | 63.1 mg Zoledronic, DL-lysine, and water complex, with 280.8 mg DL-lysine monohydrate gelatin capsule | PO | n/a | 0 | 0.00 |
| | | | | 0.0833 | 0.00 |
| | | | | 0.1667 | 0.00 |
| | | | | 0.25 | 0.00 |
| | | | | 0.5 | 206.30 |
| | | | | 0.75 | 577.25 |
| | | | | 1 | 449.00 |
| | | | | 1.5 | 226.50 |
| | | | | 2 | 125.33 |
| | | | | 4 | 23.45 |
| | | | | 8 | 6.00 |
| | | | | 24 | 1.37 |
| 35 | 76.3 mg Zoledronic, DL-lysine, and water complex, with 561.6 mg DL-lysine monohydrate gelatin capsule | PO | n/a | 0 | 0.00 |
| | | | | 0.0833 | 0.00 |
| | | | | 0.1667 | 24.88 |
| | | | | 0.25 | 38.21 |
| | | | | 0.5 | 338.33 |
| | | | | 0.75 | 429.38 |
| | | | | 1 | 456.23 |
| | | | | 1.5 | 304.78 |
| | | | | 2 | 186.70 |
| | | | | 4 | 41.48 |
| | | | | 8 | 11.11 |
| | | | | 24 | 2.35 |
| 36 | 59.2 mg Zoledronic, DL-lysine, and water complex, with 1123.3 mg DL-lysine monohydrate gelatin capsule | PO | n/a | 0 | 0.00 |
| | | | | 0.0833 | 0.00 |
| | | | | 0.1667 | 0.31 |
| | | | | 0.25 | 29.50 |
| | | | | 0.5 | 192.57 |
| | | | | 0.75 | 517.75 |
| | | | | 1 | 688.50 |
| | | | | 1.5 | 451.50 |
| | | | | 2 | 259.75 |
| | | | | 4 | 37.05 |
| | | | | 8 | 6.95 |
| | | | | 24 | 2.62 |
| 37 | 63.1 mg Zoledronic, DL-lysine, and water complex, with 1965.7 mg DL-lysine monohydrate gelatin capsule | PO | n/a | 0 | 0.00 |
| | | | | 0.0833 | 0.00 |
| | | | | 0.1667 | 0.00 |
| | | | | 0.25 | 5.55 |
| | | | | 0.5 | 200.00 |
| | | | | 0.75 | 504.73 |
| | | | | 1 | 683.50 |
| | | | | 1.5 | 606.00 |
| | | | | 2 | 488.03 |
| | | | | 4 | 81.28 |
| | | | | 8 | 12.34 |
| | | | | 24 | 4.07 |
| 38 | 0.12 mg/kg Zoledronic acid | IV | Saline solution | 0 | 0.00 |
| | | | | 0.0833 | 287.75 |
| | | | | 0.1667 | 541.50 |
| | | | | 0.25 | 710.75 |
| | | | | 0.3333 | 528.75 |
| | | | | 0.4167 | 405.50 |
| | | | | 0.5 | 358.25 |
| | | | | 0.75 | 239.50 |
| | | | | 1 | 174.00 |
| | | | | 1.25 | 121.38 |
| | | | | 1.5 | 90.58 |
| | | | | 2 | 55.68 |
| | | | | 4 | 15.13 |
| | | | | 8 | 5.74 |
| | | | | 24 | 2.49 |

TABLE 9

Quantity of zoledronic acid in dog urine from zoledronic acid, DL-lysine and water complex and excess coformer delivered via different routes at different doses. During the study, urine samples were collected from the animals (N = 4) over five intervals, 0-4 hours, 4-8 hours, 8-12 hours, 12-24 hours and 24-96 hours. Bioanalysis for urine excretion samples after dosing has been performed. Samples were assayed for zoledronic acid using a validated LC/MS/MS method.

| Leg # | Complex | Dosing Route | Vehicle | Time interval (hour) | Average quantity of zoledronic acid in urine excretion of 4 dogs (ng) |
|---|---|---|---|---|---|
| 33 | 59.2 mg Zoledronic, DL-lysine, and water complex, with 112.3 mg DL-lysine monohydrate gelatin capsule | PO | n/a | 0-4<br>4-8<br>8-12<br>12-24<br>24-96 | 43251<br>548<br>102750<br>147710<br>20571 |
| 34 | 63.1 mg Zoledronic, DL-lysine, and water complex, with 280.8 mg DL-lysine monohydrate gelatin capsule | PO | n/a | 0-4<br>4-8<br>8-12<br>12-24<br>24-96 | 121045<br>1393<br>228375<br>204485<br>98205 |
| 35 | 76.3 mg Zoledronic, DL-lysine, and water complex, with 561.6 mg DL-lysine monohydrate gelatin capsule | PO | n/a | 0-4<br>4-8<br>8-12<br>12-24<br>24-96 | 440062<br>16970<br>285490<br>287863<br>97306 |
| 36 | 59.2 mg Zoledronic, DL-lysine, and water complex, with 1123.3 mg DL-lysine monohydrate gelatin capsule | PO | n/a | 0-4<br>4-8<br>8-12<br>12-24<br>24-96 | 311764<br>24<br>385625<br>456538<br>105767 |
| 37 | 63.1 mg Zoledronic, DL-lysine, and water complex, with 1965.7 mg DL-lysine monohydrate gelatin capsule | PO | n/a | 0-4<br>4-8<br>8-12<br>12-24<br>24-96 | 234333<br>178950<br>888750<br>117100<br>186090 |
| 38 | 0.12 mg/kg Zoledronic acid | IV | Saline solution | 0-4<br>4-8<br>8-12<br>12-24<br>24-96 | 242050<br>21165<br>10925<br>43700<br>263151 |

TABLE 10

Aqueous solubility of zoledronic acid (ZA) and novel zoledronic acid complexes at room temperature.

| Compound | Conc. mg/mL | mMol/L (complex) |
|---|---|---|
| ZA monohydrate | 1.57 | 5.41 |
| ZA: Glycine | 11.89 | 34.25 |
| ZA: L-Lysine dihydrate | 8.22 | 18.09 |
| ZA: DL-Lysine dihydrate | 6.85 | 15.08 |
| ZA: DL-Lysine monohydrate | 13.9 | 31.86 |

TABLE 11

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| abacavir | lysine | ≥100 mg | abacavir | lysine | ≥3 g |
| acarbose | lysine | ≥100 mg | acarbose | lysine | ≥3 g |
| acetazolamide | lysine | ≥100 mg | acetazolamide | lysine | ≥3 g |
| acyclovir | lysine | ≥100 mg | acyclovir | lysine | ≥3 g |
| albuterol (salbutamol) | lysine | ≥100 mg | albuterol (salbutamol) | lysine | ≥3 g |
| allopurinol | lysine | ≥100 mg | allopurinol | lysine | ≥3 g |
| amiloride | lysine | ≥100 mg | amiloride | lysine | ≥3 g |
| amisulpride | lysine | ≥100 mg | amisulpride | lysine | ≥3 g |
| amlodipine | lysine | ≥100 mg | amlodipine | lysine | ≥3 g |
| amoxicillin | lysine | ≥100 mg | amoxicillin | lysine | ≥3 g |
| amphetamine | lysine | ≥100 mg | amphetamine | lysine | ≥3 g |
| atenolol | lysine | ≥100 mg | atenolol | lysine | ≥3 g |
| atropine | lysine | ≥100 mg | atropine | lysine | ≥3 g |
| azathioprine | lysine | ≥100 mg | azathioprine | lysine | ≥3 g |
| benserazide | lysine | ≥100 mg | benserazide | lysine | ≥3 g |
| benznidazole | lysine | ≥100 mg | benznidazole | lysine | ≥3 g |
| camostat | lysine | ≥100 mg | camostat | lysine | ≥3 g |
| captopril | lysine | ≥100 mg | captopril | lysine | ≥3 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| cefdinir | lysine | ≥100 mg | cefdinir | lysine | ≥3 g |
| cefotiam hexetil hydrochloride | lysine | ≥100 mg | cefotiam hexetil hydrochloride | lysine | ≥3 g |
| cefprozil | lysine | ≥100 mg | cefprozil | lysine | ≥3 g |
| cefuroxime axetil | lysine | ≥100 mg | cefuroxime axetil | lysine | ≥3 g |
| chloramphenicol | lysine | ≥100 mg | chloramphenicol | lysine | ≥3 g |
| cimetidine | lysine | ≥100 mg | cimetidine | lysine | ≥3 g |
| ciprofloxacin | lysine | ≥100 mg | ciprofloxacin | lysine | ≥3 g |
| codeine | lysine | ≥100 mg | codeine | lysine | ≥3 g |
| colchicine | lysine | ≥100 mg | colchicine | lysine | ≥3 g |
| cyclophosphamide | lysine | ≥100 mg | cyclophosphamide | lysine | ≥3 g |
| dapsone | lysine | ≥100 mg | dapsone | lysine | ≥3 g |
| dexamethasone | lysine | ≥100 mg | dexamethasone | lysine | ≥3 g |
| didanosine | lysine | ≥100 mg | didanosine | lysine | ≥3 g |
| diethylcarbamazine | lysine | ≥100 mg | diethylcarbamazine | lysine | ≥3 g |
| methionine | lysine | ≥100 mg | methionine | lysine | ≥3 g |
| dolasetron | lysine | ≥100 mg | dolasetron | lysine | ≥3 g |
| doxifluridine | lysine | ≥100 mg | doxifluridine | lysine | ≥3 g |
| doxycycline | lysine | ≥100 mg | doxycycline | lysine | ≥3 g |
| ergonovine | lysine | ≥100 mg | ergonovine | lysine | ≥3 g |
| erythromycin ethylsuccinate | lysine | ≥100 mg | erythromycin ethylsuccinate | lysine | ≥3 g |
| ethambutol | lysine | ≥100 mg | ethambutol | lysine | ≥3 g |
| ethosuximide | lysine | ≥100 mg | ethosuximide | lysine | ≥3 g |
| famotidine | lysine | ≥100 mg | famotidine | lysine | ≥3 g |
| fluconazole | lysine | ≥100 mg | fluconazole | lysine | ≥3 g |
| folic acid | lysine | ≥100 mg | folic acid | lysine | ≥3 g |
| furosemide | lysine | ≥100 mg | furosemide | lysine | ≥3 g |
| fursultiamine | lysine | ≥100 mg | fursultiamine | lysine | ≥3 g |
| gabapentin | lysine | ≥100 mg | gabapentin | lysine | ≥3 g |
| glipizide | lysine | ≥100 mg | glipizide | lysine | ≥3 g |
| granisetron | lysine | ≥100 mg | granisetron | lysine | ≥3 g |
| griseofulvin | lysine | ≥100 mg | griseofulvin | lysine | ≥3 g |
| hydralazine | lysine | ≥100 mg | hydralazine | lysine | ≥3 g |
| hydrochlorothiazide | lysine | ≥100 mg | hydrochlorothiazide | lysine | ≥3 g |
| imidapril | lysine | ≥100 mg | imidapril | lysine | ≥3 g |
| isoniazid | lysine | ≥100 mg | isoniazid | lysine | ≥3 g |
| lamivudine | lysine | ≥100 mg | lamivudine | lysine | ≥3 g |
| l-carbocysteine | lysine | ≥100 mg | l-carbocysteine | lysine | ≥3 g |
| levetiracetam | lysine | ≥100 mg | levetiracetam | lysine | ≥3 g |
| levofloxacin | lysine | ≥100 mg | levofloxacin | lysine | ≥3 g |
| linezolid | lysine | ≥100 mg | linezolid | lysine | ≥3 g |
| lisinopril | lysine | ≥100 mg | lisinopril | lysine | ≥3 g |
| losartan | lysine | ≥100 mg | losartan | lysine | ≥3 g |
| methotrexate | lysine | ≥100 mg | methotrexate | lysine | ≥3 g |
| methyldopa | lysine | ≥100 mg | methyldopa | lysine | ≥3 g |
| s-methylmethionine | lysine | ≥100 mg | s-methylmethionine | lysine | ≥3 g |
| metoclopramide | lysine | ≥100 mg | metoclopramide | lysine | ≥3 g |
| metronidazole | lysine | ≥100 mg | metronidazole | lysine | ≥3 g |
| moxifloxacin | lysine | ≥100 mg | moxifloxacin | lysine | ≥3 g |
| nalidixic acid | lysine | ≥100 mg | nalidixic acid | lysine | ≥3 g |
| nicorandil | lysine | ≥100 mg | nicorandil | lysine | ≥3 g |
| nifurtimox | lysine | ≥100 mg | nifurtimox | lysine | ≥3 g |
| nitrofurantoin | lysine | ≥100 mg | nitrofurantoin | lysine | ≥3 g |
| nizatidine | lysine | ≥100 mg | nizatidine | lysine | ≥3 g |
| nystatin | lysine | ≥100 mg | nystatin | lysine | ≥3 g |
| ondansetron | lysine | ≥100 mg | ondansetron | lysine | ≥3 g |
| oseltamivir | lysine | ≥100 mg | oseltamivir | lysine | ≥3 g |
| oxcarbazepine | lysine | ≥100 mg | oxcarbazepine | lysine | ≥3 g |
| penicillamine | lysine | ≥100 mg | penicillamine | lysine | ≥3 g |
| perindopril | lysine | ≥100 mg | perindopril | lysine | ≥3 g |
| phenobarbital | lysine | ≥100 mg | phenobarbital | lysine | ≥3 g |
| phenoxymethylpenicillin | lysine | ≥100 mg | phenoxymethylpenicillin | lysine | ≥3 g |
| pravastatin sodium | lysine | ≥100 mg | pravastatin sodium | lysine | ≥3 g |
| prednisolone | lysine | ≥100 mg | prednisolone | lysine | ≥3 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| primaquine | lysine | ≥100 mg | primaquine | lysine | ≥3 g |
| procaterol | lysine | ≥100 mg | procaterol | lysine | ≥3 g |
| propylthiouracil | lysine | ≥100 mg | propylthiouracil | lysine | ≥3 g |
| pseudoephedrine | lysine | ≥100 mg | pseudoephedrine | lysine | ≥3 g |
| pyrazinamide | lysine | ≥100 mg | pyrazinamide | lysine | ≥3 g |
| pyridostigmine bromide | lysine | ≥100 mg | pyridostigmine bromide | lysine | ≥3 g |
| pyridoxine hydrochloride | lysine | ≥100 mg | pyridoxine hydrochloride | lysine | ≥3 g |
| ranitidine | lysine | ≥100 mg | ranitidine | lysine | ≥3 g |
| ribavirin | lysine | ≥100 mg | ribavirin | lysine | ≥3 g |
| riboflavin | lysine | ≥100 mg | riboflavin | lysine | ≥3 g |
| rizatriptan | lysine | ≥100 mg | rizatriptan | lysine | ≥3 g |
| stavudine | lysine | ≥100 mg | stavudine | lysine | ≥3 g |
| sulfadiazine | lysine | ≥100 mg | sulfadiazine | lysine | ≥3 g |
| sulfamethoxazole | lysine | ≥100 mg | sulfamethoxazole | lysine | ≥3 g |
| sultamicillin | lysine | ≥100 mg | sultamicillin | lysine | ≥3 g |
| sumatriptan | lysine | ≥100 mg | sumatriptan | lysine | ≥3 g |
| taltirelin | lysine | ≥100 mg | taltirelin | lysine | ≥3 g |
| tegafur | lysine | ≥100 mg | tegafur | lysine | ≥3 g |
| tenofovir disoproxil | lysine | ≥100 mg | tenofovir disoproxil | lysine | ≥3 g |
| theophylline | lysine | ≥100 mg | theophylline | lysine | ≥3 g |
| thiamine | lysine | ≥100 mg | thiamine | lysine | ≥3 g |
| trimetazidine | lysine | ≥100 mg | trimetazidine | lysine | ≥3 g |
| trimethoprim | lysine | ≥100 mg | trimethoprim | lysine | ≥3 g |
| voglibose | lysine | ≥100 mg | voglibose | lysine | ≥3 g |
| zidovudine | lysine | ≥100 mg | zidovudine | lysine | ≥3 g |
| zolmitriptan | lysine | ≥100 mg | zolmitriptan | lysine | ≥3 g |
| acetylcarnitine | lysine | ≥100 mg | acetylcarnitine | lysine | ≥3 g |
| capecitabine | lysine | ≥100 mg | capecitabine | lysine | ≥3 g |
| cefaclor | lysine | ≥100 mg | cefaclor | lysine | ≥3 g |
| cefixime | lysine | ≥100 mg | cefixime | lysine | ≥3 g |
| cefmetazole | lysine | ≥100 mg | cefmetazole | lysine | ≥3 g |
| cefpodoxime proxetil | lysine | ≥100 mg | cefpodoxime proxetil | lysine | ≥3 g |
| cefroxadine | lysine | ≥100 mg | cefroxadine | lysine | ≥3 g |
| alfoscerate | lysine | ≥100 mg | alfoscerate | lysine | ≥3 g |
| cilazapril | lysine | ≥100 mg | cilazapril | lysine | ≥3 g |
| cimetropium bromide | lysine | ≥100 mg | cimetropium bromide | lysine | ≥3 g |
| diacerein | lysine | ≥100 mg | diacerein | lysine | ≥3 g |
| erdosteine | lysine | ≥100 mg | erdosteine | lysine | ≥3 g |
| famciclovir | lysine | ≥100 mg | famciclovir | lysine | ≥3 g |
| gemifloxacin | lysine | ≥100 mg | gemifloxacin | lysine | ≥3 g |
| levosulpiride | lysine | ≥100 mg | levosulpiride | lysine | ≥3 g |
| nabumetone | lysine | ≥100 mg | nabumetone | lysine | ≥3 g |
| oxiracetam | lysine | ≥100 mg | oxiracetam | lysine | ≥3 g |
| phendimetrazine | lysine | ≥100 mg | phendimetrazine | lysine | ≥3 g |
| rabeprazole | lysine | ≥100 mg | rabeprazole | lysine | ≥3 g |
| roxatidine acetate | lysine | ≥100 mg | roxatidine acetate | lysine | ≥3 g |
| tamsulosin | lysine | ≥100 mg | tamsulosin | lysine | ≥3 g |
| terazosin | lysine | ≥100 mg | terazosin | lysine | ≥3 g |
| thioctic | lysine | ≥100 mg | Thioctic | lysine | ≥3 g |
| tosufloxacin | lysine | ≥100 mg | tosufloxacin | lysine | ≥3 g |
| triflusal | lysine | ≥100 mg | Triflusal | lysine | ≥3 g |
| zaltoprofen | lysine | ≥100 mg | zaltoprofen | lysine | ≥3 g |
| etidronic acid | lysine | ≥100 mg | etidronic acid | lysine | ≥3 g |
| zoledronic acid | lysine | ≥100 mg | zoledronic acid | lysine | ≥3 g |
| clodronic acid | lysine | ≥100 mg | clodronic acid | lysine | ≥3 g |
| tiludronic acid | lysine | ≥100 mg | tiludronic acid | lysine | ≥3 g |
| pamidronic acid | lysine | ≥100 mg | pamidronic acid | lysine | ≥3 g |
| alendronic acid | lysine | ≥100 mg | alendronic acid | lysine | ≥3 g |
| risedronic acid | lysine | ≥100 mg | risedronic acid | lysine | ≥3 g |
| ibandronic acid | lysine | ≥100 mg | ibandronic acid | lysine | ≥3 g |
| abacavir | glycine | ≥100 mg | abacavir | glycine | ≥3 g |
| acarbose | glycine | ≥100 mg | acarbose | glycine | ≥3 g |
| acetazolamide | glycine | ≥100 mg | acetazolamide | glycine | ≥3 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| acyclovir | glycine | ≥100 mg | acyclovir | glycine | ≥3 g |
| albuterol (salbutamol) | glycine | ≥100 mg | albuterol (salbutamol) | glycine | ≥3 g |
| allopurinol | glycine | ≥100 mg | allopurinol | glycine | ≥3 g |
| amiloride | glycine | ≥100 mg | amiloride | glycine | ≥3 g |
| amisulpride | glycine | ≥100 mg | amisulpride | glycine | ≥3 g |
| amlodipine | glycine | ≥100 mg | amlodipine | glycine | ≥3 g |
| amoxicillin | glycine | ≥100 mg | amoxicillin | glycine | ≥3 g |
| amphetamine | glycine | ≥100 mg | amphetamine | glycine | ≥3 g |
| atenolol | glycine | ≥100 mg | atenolol | glycine | ≥3 g |
| atropine | glycine | ≥100 mg | Atropine | glycine | ≥3 g |
| azathioprine | glycine | ≥100 mg | azathioprine | glycine | ≥3 g |
| benserazide | glycine | ≥100 mg | benserazide | glycine | ≥3 g |
| benznidazole | glycine | ≥100 mg | benznidazole | glycine | ≥3 g |
| camostat | glycine | ≥100 mg | camostat | glycine | ≥3 g |
| captopril | glycine | ≥100 mg | captopril | glycine | ≥3 g |
| cefdinir | glycine | ≥100 mg | Cefdinir | glycine | ≥3 g |
| cefotiam hexetil hydrochloride | glycine | ≥100 mg | cefotiam hexetil hydrochloride | glycine | ≥3 g |
| cefprozil | glycine | ≥100 mg | cefprozil | glycine | ≥3 g |
| cefuroxime axetil | glycine | ≥100 mg | cefuroxime axetil | glycine | ≥3 g |
| chloramphenicol | glycine | ≥100 mg | chloramphenicol | glycine | ≥3 g |
| cimetidine | glycine | ≥100 mg | cimetidine | glycine | ≥3 g |
| ciprofloxacin | glycine | ≥100 mg | ciprofloxacin | glycine | ≥3 g |
| codeine | glycine | ≥100 mg | Codeine | glycine | ≥3 g |
| colchicine | glycine | ≥100 mg | colchicine | glycine | ≥3 g |
| cyclophosphamide | glycine | ≥100 mg | cyclophosphamide | glycine | ≥3 g |
| dapsone | glycine | ≥100 mg | Dapsone | glycine | ≥3 g |
| dexamethasone | glycine | ≥100 mg | dexamethasone | glycine | ≥3 g |
| didanosine | glycine | ≥100 mg | didanosine | glycine | ≥3 g |
| diethylcarbamazine | glycine | ≥100 mg | diethylcarbamazine | glycine | ≥3 g |
| methionine | glycine | ≥100 mg | methionine | glycine | ≥3 g |
| dolasetron | glycine | ≥100 mg | dolasetron | glycine | ≥3 g |
| doxifluridine | glycine | ≥100 mg | doxifluridine | glycine | ≥3 g |
| doxycycline | glycine | ≥100 mg | doxycycline | glycine | ≥3 g |
| ergonovine | glycine | ≥100 mg | ergonovine | glycine | ≥3 g |
| erythromycin ethylsuccinate | glycine | ≥100 mg | erythromycin ethylsuccinate | glycine | ≥3 g |
| ethambutol | glycine | ≥100 mg | ethambutol | glycine | ≥3 g |
| ethosuximide | glycine | ≥100 mg | ethosuximide | glycine | ≥3 g |
| famotidine | glycine | ≥100 mg | famotidine | glycine | ≥3 g |
| fluconazole | glycine | ≥100 mg | fluconazole | glycine | ≥3 g |
| folic acid | glycine | ≥100 mg | folic acid | glycine | ≥3 g |
| furosemide | glycine | ≥100 mg | furosemide | glycine | ≥3 g |
| fursultiamine | glycine | ≥100 mg | fursultiamine | glycine | ≥3 g |
| gabapentin | glycine | ≥100 mg | gabapentin | glycine | ≥3 g |
| glipizide | glycine | ≥100 mg | Glipizide | glycine | ≥3 g |
| granisetron | glycine | ≥100 mg | granisetron | glycine | ≥3 g |
| griseofulvin | glycine | ≥100 mg | griseofulvin | glycine | ≥3 g |
| hydralazine | glycine | ≥100 mg | hydralazine | glycine | ≥3 g |
| hydrochlorothiazide | glycine | ≥100 mg | hydrochlorothiazide | glycine | ≥3 g |
| imidapril | glycine | ≥100 mg | imidapril | glycine | ≥3 g |
| isoniazid | glycine | ≥100 mg | isoniazid | glycine | ≥3 g |
| lamivudine | glycine | ≥100 mg | lamivudine | glycine | ≥3 g |
| l-carbocysteine | glycine | ≥100 mg | l-carbocysteine | glycine | ≥3 g |
| levetiracetam | glycine | ≥100 mg | levetiracetam | glycine | ≥3 g |
| levofloxacin | glycine | ≥100 mg | levofloxacin | glycine | ≥3 g |
| linezolid | glycine | ≥100 mg | Linezolid | glycine | ≥3 g |
| lisinopril | glycine | ≥100 mg | lisinopril | glycine | ≥3 g |
| losartan | glycine | ≥100 mg | Losartan | glycine | ≥3 g |
| methotrexate | glycine | ≥100 mg | methotrexate | glycine | ≥3 g |
| methyldopa | glycine | ≥100 mg | methyldopa | glycine | ≥3 g |
| s-methylmethionine | glycine | ≥100 mg | s-methylmethionine | glycine | ≥3 g |
| metoclopramide | glycine | ≥100 mg | metoclopramide | glycine | ≥3 g |
| metronidazole | glycine | ≥100 mg | metronidazole | glycine | ≥3 g |
| moxifloxacin | glycine | ≥100 mg | moxifloxacin | glycine | ≥3 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| nalidixic acid | glycine | ≥100 mg | nalidixic acid | glycine | ≥3 g |
| nicorandil | glycine | ≥100 mg | nicorandil | glycine | ≥3 g |
| nifurtimox | glycine | ≥100 mg | nifurtimox | glycine | ≥3 g |
| nitrofurantoin | glycine | ≥100 mg | nitrofurantoin | glycine | ≥3 g |
| nizatidine | glycine | ≥100 mg | nizatidine | glycine | ≥3 g |
| nystatin | glycine | ≥100 mg | Nystatin | glycine | ≥3 g |
| ondansetron | glycine | ≥100 mg | ondansetron | glycine | ≥3 g |
| oseltamivir | glycine | ≥100 mg | oseltamivir | glycine | ≥3 g |
| oxcarbazepine | glycine | ≥100 mg | oxcarbazepine | glycine | ≥3 g |
| penicillamine | glycine | ≥100 mg | penicillamine | glycine | ≥3 g |
| perindopril | glycine | ≥100 mg | perindopril | glycine | ≥3 g |
| phenobarbital | glycine | ≥100 mg | phenobarbital | glycine | ≥3 g |
| phenoxymethylpenicillin | glycine | ≥100 mg | Phenoxymethylpenicillin | glycine | ≥3 g |
| pravastatin sodium | glycine | ≥100 mg | pravastatin sodium | glycine | ≥3 g |
| prednisolone | glycine | ≥100 mg | prednisolone | glycine | ≥3 g |
| primaquine | glycine | ≥100 mg | primaquine | glycine | ≥3 g |
| procaterol | glycine | ≥100 mg | procaterol | glycine | ≥3 g |
| propylthiouracil | glycine | ≥100 mg | propylthiouracil | glycine | ≥3 g |
| pseudoephedrine | glycine | ≥100 mg | pseudoephedrine | glycine | ≥3 g |
| pyrazinamide | glycine | ≥100 mg | pyrazinamide | glycine | ≥3 g |
| pyridostigmine bromide | glycine | ≥100 mg | pyridostigmine bromide | glycine | ≥3 g |
| pyridoxine hydrochloride | glycine | ≥100 mg | pyridoxine hydrochloride | glycine | ≥3 g |
| ranitidine | glycine | ≥100 mg | ranitidine | glycine | ≥3 g |
| ribavirin | glycine | ≥100 mg | Ribavirin | glycine | ≥3 g |
| riboflavin | glycine | ≥100 mg | riboflavin | glycine | ≥3 g |
| rizatriptan | glycine | ≥100 mg | rizatriptan | glycine | ≥3 g |
| stavudine | glycine | ≥100 mg | stavudine | glycine | ≥3 g |
| sulfadiazine | glycine | ≥100 mg | sulfadiazine | glycine | ≥3 g |
| sulfamethoxazole | glycine | ≥100 mg | sulfamethoxazole | glycine | ≥3 g |
| sultamicillin | glycine | ≥100 mg | sultamicillin | glycine | ≥3 g |
| sumatriptan | glycine | ≥100 mg | sumatriptan | glycine | ≥3 g |
| taltirelin | glycine | ≥100 mg | Taltirelin | glycine | ≥3 g |
| tegafur | glycine | ≥100 mg | Tegafur | glycine | ≥3 g |
| tenofovir disoproxil | glycine | ≥100 mg | tenofovir disoproxil | glycine | ≥3 g |
| theophylline | glycine | ≥100 mg | theophylline | glycine | ≥3 g |
| thiamine | glycine | ≥100 mg | thiamine | glycine | ≥3 g |
| trimetazidine | glycine | ≥100 mg | trimetazidine | glycine | ≥3 g |
| trimethoprim | glycine | ≥100 mg | trimethoprim | glycine | ≥3 g |
| voglibose | glycine | ≥100 mg | voglibose | glycine | ≥3 g |
| zidovudine | glycine | ≥100 mg | zidovudine | glycine | ≥3 g |
| zolmitriptan | glycine | ≥100 mg | zolmitriptan | glycine | ≥3 g |
| acetylcarnitine | glycine | ≥100 mg | acetylcarnitine | glycine | ≥3 g |
| capecitabine | glycine | ≥100 mg | capecitabine | glycine | ≥3 g |
| cefaclor | glycine | ≥100 mg | Cefaclor | glycine | ≥3 g |
| cefixime | glycine | ≥100 mg | cefixime | glycine | ≥3 g |
| cefmetazole | glycine | ≥100 mg | cefmetazole | glycine | ≥3 g |
| cefpodoxime proxetil | glycine | ≥100 mg | cefpodoxime proxetil | glycine | ≥3 g |
| cefroxadine | glycine | ≥100 mg | cefroxadine | glycine | ≥3 g |
| alfoscerate | glycine | ≥100 mg | alfoscerate | glycine | ≥3 g |
| cilazapril | glycine | ≥100 mg | cilazapril | glycine | ≥3 g |
| cimetropium bromide | glycine | ≥100 mg | cimetropium bromide | glycine | ≥3 g |
| diacerein | glycine | ≥100 mg | diacerein | glycine | ≥3 g |
| erdosteine | glycine | ≥100 mg | erdosteine | glycine | ≥3 g |
| famciclovir | glycine | ≥100 mg | famciclovir | glycine | ≥3 g |
| gemifloxacin | glycine | ≥100 mg | gemifloxacin | glycine | ≥3 g |
| levosulpiride | glycine | ≥100 mg | levosulpiride | glycine | ≥3 g |
| nabumetone | glycine | ≥100 mg | nabumetone | glycine | ≥3 g |
| oxiracetam | glycine | ≥100 mg | oxiracetam | glycine | ≥3 g |
| phendimetrazine | glycine | ≥100 mg | phendimetrazine | glycine | ≥3 g |
| rabeprazole | glycine | ≥100 mg | rabeprazole | glycine | ≥3 g |
| roxatidine acetate | glycine | ≥100 mg | roxatidine acetate | glycine | ≥3 g |
| tamsulosin | glycine | ≥100 mg | tamsulosin | glycine | ≥3 g |
| terazosin | glycine | ≥100 mg | terazosin | glycine | ≥3 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| thioctic | glycine | ≥100 mg | Thioctic | glycine | ≥3 g |
| tosufloxacin | glycine | ≥100 mg | tosufloxacin | glycine | ≥3 g |
| triflusal | glycine | ≥100 mg | Triflusal | glycine | ≥3 g |
| zaltoprofen | glycine | ≥100 mg | zaltoprofen | glycine | ≥3 g |
| etidronic acid | glycine | ≥100 mg | etidronic acid | glycine | ≥3 g |
| zoledronic acid | glycine | ≥100 mg | zoledronic acid | glycine | ≥3 g |
| clodronic acid | glycine | ≥100 mg | clodronic acid | glycine | ≥3 g |
| tiludronic acid | glycine | ≥100 mg | tiludronic acid | glycine | ≥3 g |
| pamidronic acid | glycine | ≥100 mg | pamidronic acid | glycine | ≥3 g |
| alendronic acid | glycine | ≥100 mg | alendronic acid | glycine | ≥3 g |
| risedronic acid | glycine | ≥100 mg | risedronic acid | glycine | ≥3 g |
| ibandronic acid | glycine | ≥100 mg | ibandronic acid | glycine | ≥3 g |
| ibandronic acid | glycine | ≥100 mg | abacavir | lysine | ≥5 g |
| abacavir | lysine | ≥500 mg | acarbose | lysine | ≥5 g |
| acarbose | lysine | ≥500 mg | acetazolamide | lysine | ≥5 g |
| acetazolamide | lysine | ≥500 mg | acyclovir | lysine | ≥5 g |
| acyclovir | lysine | ≥500 mg | albuterol (salbutamol) | lysine | ≥5 g |
| albuterol (salbutamol) | lysine | ≥500 mg | allopurinol | lysine | ≥5 g |
| allopurinol | lysine | ≥500 mg | amiloride | lysine | ≥5 g |
| amiloride | lysine | ≥500 mg | amisulpride | lysine | ≥5 g |
| amisulpride | lysine | ≥500 mg | amlodipine | lysine | ≥5 g |
| amlodipine | lysine | ≥500 mg | amoxicillin | lysine | ≥5 g |
| amoxicillin | lysine | ≥500 mg | amphetamine | lysine | ≥5 g |
| amphetamine | lysine | ≥500 mg | atenolol | lysine | ≥5 g |
| atenolol | lysine | ≥500 mg | Atropine | lysine | ≥5 g |
| atropine | lysine | ≥500 mg | azathioprine | lysine | ≥5 g |
| azathioprine | lysine | ≥500 mg | benserazide | lysine | ≥5 g |
| benserazide | lysine | ≥500 mg | benznidazole | lysine | ≥5 g |
| benznidazole | lysine | ≥500 mg | camostat | lysine | ≥5 g |
| camostat | lysine | ≥500 mg | captopril | lysine | ≥5 g |
| captopril | lysine | ≥500 mg | Cefdinir | lysine | ≥5 g |
| cefdinir | lysine | ≥500 mg | cefotiam hexetil hydrochloride | lysine | ≥5 g |
| cefotiam hexetil hydrochloride | lysine | ≥500 mg | cefprozil | lysine | ≥5 g |
| cefprozil | lysine | ≥500 mg | cefuroxime axetil | lysine | ≥5 g |
| cefuroxime axetil | lysine | ≥500 mg | chloramphenicol | lysine | ≥5 g |
| chloramphenicol | lysine | ≥500 mg | cimetidine | lysine | ≥5 g |
| cimetidine | lysine | ≥500 mg | ciprofloxacin | lysine | ≥5 g |
| ciprofloxacin | lysine | ≥500 mg | Codeine | lysine | ≥5 g |
| codeine | lysine | ≥500 mg | colchicine | lysine | ≥5 g |
| colchicines | lysine | ≥500 mg | cyclophosphamide | lysine | ≥5 g |
| cyclophosphamide | lysine | ≥500 mg | Dapsone | lysine | ≥5 g |
| dapsone | lysine | ≥500 mg | dexamethasone | lysine | ≥5 g |
| dexamethasone | lysine | ≥500 mg | didanosine | lysine | ≥5 g |
| didanosine | lysine | ≥500 mg | diethylcarbamazine | lysine | ≥5 g |
| diethylcarbamazine | lysine | ≥500 mg | methionine | lysine | ≥5 g |
| methionine | lysine | ≥500 mg | dolasetron | lysine | ≥5 g |
| dolasetron | lysine | ≥500 mg | doxifluridine | lysine | ≥5 g |
| doxifluridine | lysine | ≥500 mg | doxycycline | lysine | ≥5 g |
| doxycycline | lysine | ≥500 mg | ergonovine | lysine | ≥5 g |
| ergonovine | lysine | ≥500 mg | erythromycin ethylsuccinate | lysine | ≥5 g |
| erythromycin ethylsuccinate | lysine | ≥500 mg | ethambutol | lysine | ≥5 g |
| ethambutol | lysine | ≥500 mg | ethosuximide | lysine | ≥5 g |
| ethosuximide | lysine | ≥500 mg | famotidine | lysine | ≥5 g |
| famotidine | lysine | ≥500 mg | fluconazole | lysine | ≥5 g |
| fluconazole | lysine | ≥500 mg | folic acid | lysine | ≥5 g |
| folic acid | lysine | ≥500 mg | furosemide | lysine | ≥5 g |
| furosemide | lysine | ≥500 mg | fursultiamine | lysine | ≥5 g |
| fursultiamine | lysine | ≥500 mg | gabapentin | lysine | ≥5 g |
| gabapentin | lysine | ≥500 mg | Glipizide | lysine | ≥5 g |
| glipizide | lysine | ≥500 mg | granisetron | lysine | ≥5 g |
| granisetron | lysine | ≥500 mg | griseofulvin | lysine | ≥5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
| --- | --- | --- | --- | --- | --- |
| griseofulvin | lysine | ≥500 mg | hydralazine | lysine | ≥5 g |
| hydralazine | lysine | ≥500 mg | hydrochlorothiazide | lysine | ≥5 g |
| hydrochlorothiazide | lysine | ≥500 mg | imidapril | lysine | ≥5 g |
| imidapril | lysine | ≥500 mg | isoniazid | lysine | ≥5 g |
| isoniazid | lysine | ≥500 mg | lamivudine | lysine | ≥5 g |
| lamivudine | lysine | ≥500 mg | l-carbocysteine | lysine | ≥5 g |
| l-carbocysteine | lysine | ≥500 mg | levetiracetam | lysine | ≥5 g |
| levetiracetam | lysine | ≥500 mg | levofloxacin | lysine | ≥5 g |
| levofloxacin | lysine | ≥500 mg | Linezolid | lysine | ≥5 g |
| linezolid | lysine | ≥500 mg | lisinopril | lysine | ≥5 g |
| lisinopril | lysine | ≥500 mg | Losartan | lysine | ≥5 g |
| losartan | lysine | ≥500 mg | methotrexate | lysine | ≥5 g |
| methotrexate | lysine | ≥500 mg | methyldopa | lysine | ≥5 g |
| methyldopa | lysine | ≥500 mg | s-methylmethionine | lysine | ≥5 g |
| s-methylmethionine | lysine | ≥500 mg | metoclopramide | lysine | ≥5 g |
| metoclopramide | lysine | ≥500 mg | metronidazole | lysine | ≥5 g |
| metronidazole | lysine | ≥500 mg | moxifloxacin | lysine | ≥5 g |
| moxifloxacin | lysine | ≥500 mg | nalidixic acid | lysine | ≥5 g |
| nalidixic acid | lysine | ≥500 mg | nicorandil | lysine | ≥5 g |
| nicorandil | lysine | ≥500 mg | nifurtimox | lysine | ≥5 g |
| nifurtimox | lysine | ≥500 mg | nitrofurantoin | lysine | ≥5 g |
| nitrofurantoin | lysine | ≥500 mg | nizatidine | lysine | ≥5 g |
| nizatidine | lysine | ≥500 mg | Nystatin | lysine | ≥5 g |
| nystatin | lysine | ≥500 mg | ondansetron | lysine | ≥5 g |
| ondansetron | lysine | ≥500 mg | oseltamivir | lysine | ≥5 g |
| oseltamivir | lysine | ≥500 mg | oxcarbazepine | lysine | ≥5 g |
| oxcarbazepine | lysine | ≥500 mg | penicillamine | lysine | ≥5 g |
| penicillamine | lysine | ≥500 mg | perindopril | lysine | ≥5 g |
| perindopril | lysine | ≥500 mg | phenobarbital | lysine | ≥5 g |
| phenobarbital | lysine | ≥500 mg | Phenoxymethylpenicillin | lysine | ≥5 g |
| phenoxymethylpenicillin | lysine | ≥500 mg | pravastatin sodium | lysine | ≥5 g |
| pravastatin sodium | lysine | ≥500 mg | prednisolone | lysine | ≥5 g |
| prednisolone | lysine | ≥500 mg | primaquine | lysine | ≥5 g |
| primaquine | lysine | ≥500 mg | procaterol | lysine | ≥5 g |
| procaterol | lysine | ≥500 mg | propylthiouracil | lysine | ≥5 g |
| propylthiouracil | lysine | ≥500 mg | pseudoephedrine | lysine | ≥5 g |
| pseudoephedrine | lysine | ≥500 mg | pyrazinamide | lysine | ≥5 g |
| pyrazinamide | lysine | ≥500 mg | pyridostigmine bromide | lysine | ≥5 g |
| pyridostigmine bromide | lysine | ≥500 mg | pyridoxine hydrochloride | lysine | ≥5 g |
| pyridoxine hydrochloride | lysine | ≥500 mg | ranitidine | lysine | ≥5 g |
| ranitidine | lysine | ≥500 mg | Ribavirin | lysine | ≥5 g |
| ribavirin | lysine | ≥500 mg | riboflavin | lysine | ≥5 g |
| riboflavin | lysine | ≥500 mg | rizatriptan | lysine | ≥5 g |
| rizatriptan | lysine | ≥500 mg | stavudine | lysine | ≥5 g |
| stavudine | lysine | ≥500 mg | sulfadiazine | lysine | ≥5 g |
| sulfadiazine | lysine | ≥500 mg | sulfamethoxazole | lysine | ≥5 g |
| sulfamethoxazole | lysine | ≥500 mg | sultamicillin | lysine | ≥5 g |
| sultamicillin | lysine | ≥500 mg | sumatriptan | lysine | ≥5 g |
| sumatriptan | lysine | ≥500 mg | Taltirelin | lysine | ≥5 g |
| taltirelin | lysine | ≥500 mg | Tegafur | lysine | ≥5 g |
| tegafur | lysine | ≥500 mg | tenofovir disoproxil | lysine | ≥5 g |
| tenofovir disoproxil | lysine | ≥500 mg | theophylline | lysine | ≥5 g |
| theophylline | lysine | ≥500 mg | thiamine | lysine | ≥5 g |
| thiamine | lysine | ≥500 mg | trimetazidine | lysine | ≥5 g |
| trimetazidine | lysine | ≥500 mg | trimethoprim | lysine | ≥5 g |
| trimethoprim | lysine | ≥500 mg | voglibose | lysine | ≥5 g |
| voglibose | lysine | ≥500 mg | zidovudine | lysine | ≥5 g |
| zidovudine | lysine | ≥500 mg | zolmitriptan | lysine | ≥5 g |
| zolmitriptan | lysine | ≥500 mg | acetylcarnitine | lysine | ≥5 g |
| acetylcarnitine | lysine | ≥500 mg | capecitabine | lysine | ≥5 g |
| capecitabine | lysine | ≥500 mg | Cefaclor | lysine | ≥5 g |
| cefaclor | lysine | ≥500 mg | cefixime | lysine | ≥5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| cefixime | lysine | ≥500 mg | cefmetazole | lysine | ≥5 g |
| cefmetazole | lysine | ≥500 mg | cefpodoxime proxetil | lysine | ≥5 g |
| cefpodoxime proxetil | lysine | ≥500 mg | cefroxadine | lysine | ≥5 g |
| cefroxadine | lysine | ≥500 mg | alfoscerate | lysine | ≥5 g |
| alfoscerate | lysine | ≥500 mg | cilazapril | lysine | ≥5 g |
| cilazapril | lysine | ≥500 mg | cimetropium bromide | lysine | ≥5 g |
| cimetropium bromide | lysine | ≥500 mg | diacerein | lysine | ≥5 g |
| diacerein | lysine | ≥500 mg | erdosteine | lysine | ≥5 g |
| erdosteine | lysine | ≥500 mg | famciclovir | lysine | ≥5 g |
| famciclovir | lysine | ≥500 mg | gemifloxacin | lysine | ≥5 g |
| gemifloxacin | lysine | ≥500 mg | levosulpiride | lysine | ≥5 g |
| levosulpiride | lysine | ≥500 mg | nabumetone | lysine | ≥5 g |
| nabumetone | lysine | ≥500 mg | oxiracetam | lysine | ≥5 g |
| oxiracetam | lysine | ≥500 mg | phendimetrazine | lysine | ≥5 g |
| phendimetrazine | lysine | ≥500 mg | rabeprazole | lysine | ≥5 g |
| rabeprazole | lysine | ≥500 mg | roxatidine acetate | lysine | ≥5 g |
| roxatidine acetate | lysine | ≥500 mg | tamsulosin | lysine | ≥5 g |
| tamsulosin | lysine | ≥500 mg | terazosin | lysine | ≥5 g |
| terazosin | lysine | ≥500 mg | Thioctic | lysine | ≥5 g |
| thioctic | lysine | ≥500 mg | tosufloxacin | lysine | ≥5 g |
| tosufloxacin | lysine | ≥500 mg | Triflusal | lysine | ≥5 g |
| triflusal | lysine | ≥500 mg | zaltoprofen | lysine | ≥5 g |
| zaltoprofen | lysine | ≥500 mg | etidronic acid | lysine | ≥5 g |
| etidronic acid | lysine | ≥500 mg | zoledronic acid | lysine | ≥5 g |
| zoledronic acid | lysine | ≥500 mg | clodronic acid | lysine | ≥5 g |
| zoledronic acid | lysine | ≥600 mg | zoledronic acid | lysine | ≥900 mg |
| zoledronic acid | lysine | ≥700 mg | zoledronic acid | lysine | ≥1000 mg |
| zoledronic acid | lysine | ≥800 mg | zoledronic acid | lysine | ≥1100 mg |
| clodronic acid | lysine | ≥500 mg | tiludronic acid | lysine | ≥5 g |
| tiludronic acid | lysine | ≥500 mg | pamidronic acid | lysine | ≥5 g |
| pamidronic acid | lysine | ≥500 mg | alendronic acid | lysine | ≥5 g |
| alendronic acid | lysine | ≥500 mg | risedronic acid | lysine | ≥5 g |
| risedronic acid | lysine | ≥500 mg | ibandronic acid | lysine | ≥5 g |
| ibandronic acid | lysine | ≥500 mg | abacavir | glycine | ≥5 g |
| abacavir | glycine | ≥500 mg | acarbose | glycine | ≥5 g |
| acarbose | glycine | ≥500 mg | acetazolamide | glycine | ≥5 g |
| acetazolamide | glycine | ≥500 mg | acyclovir | glycine | ≥5 g |
| acyclovir | glycine | ≥500 mg | albuterol (salbutamol) | glycine | ≥5 g |
| albuterol (salbutamol) | glycine | ≥500 mg | allopurinol | glycine | ≥5 g |
| allopurinol | glycine | ≥500 mg | amiloride | glycine | ≥5 g |
| amiloride | glycine | ≥500 mg | amisulpride | glycine | ≥5 g |
| amisulpride | glycine | ≥500 mg | amlodipine | glycine | ≥5 g |
| amlodipine | glycine | ≥500 mg | amoxicillin | glycine | ≥5 g |
| amoxicillin | glycine | ≥500 mg | amphetamine | glycine | ≥5 g |
| amphetamine | glycine | ≥500 mg | atenolol | glycine | ≥5 g |
| atenolol | glycine | ≥500 mg | Atropine | glycine | ≥5 g |
| atropine | glycine | ≥500 mg | azathioprine | glycine | ≥5 g |
| azathioprine | glycine | ≥500 mg | benserazide | glycine | ≥5 g |
| benserazide | glycine | ≥500 mg | benznidazole | glycine | ≥5 g |
| benznidazole | glycine | ≥500 mg | camostat | glycine | ≥5 g |
| camostat | glycine | ≥500 mg | captopril | glycine | ≥5 g |
| captopril | glycine | ≥500 mg | Cefdinir | glycine | ≥5 g |
| cefdinir | glycine | ≥500 mg | cefotiam hexetil hydrochloride | glycine | ≥5 g |
| cefotiam hexetil hydrochloride | glycine | ≥500 mg | cefprozil | glycine | ≥5 g |
| cefprozil | glycine | ≥500 mg | cefuroxime axetil | glycine | ≥5 g |
| cefuroxime axetil | glycine | ≥500 mg | chloramphenicol | glycine | ≥5 g |
| chloramphenicol | glycine | ≥500 mg | cimetidine | glycine | ≥5 g |
| cimetidine | glycine | ≥500 mg | ciprofloxacin | glycine | ≥5 g |
| ciprofloxacin | glycine | ≥500 mg | Codeine | glycine | ≥5 g |
| codeine | glycine | ≥500 mg | colchicine | glycine | ≥5 g |
| colchicines | glycine | ≥500 mg | cyclophosphamide | glycine | ≥5 g |
| cyclophosphamide | glycine | ≥500 mg | Dapsone | glycine | ≥5 g |
| dapsone | glycine | ≥500 mg | dexamethasone | glycine | ≥5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| dexamethasone | glycine | ≥500 mg | didanosine | glycine | ≥5 g |
| didanosine | glycine | ≥500 mg | diethylcarbamazine | glycine | ≥5 g |
| diethylcarbamazine | glycine | ≥500 mg | methionine | glycine | ≥5 g |
| methionine | glycine | ≥500 mg | dolasetron | glycine | ≥5 g |
| dolasetron | glycine | ≥500 mg | doxifluridine | glycine | ≥5 g |
| doxifluridine | glycine | ≥500 mg | doxycycline | glycine | ≥5 g |
| doxycycline | glycine | ≥500 mg | ergonovine | glycine | ≥5 g |
| ergonovine | glycine | ≥500 mg | erythromycin ethylsuccinate | glycine | ≥5 g |
| erythromycin ethylsuccinate | glycine | ≥500 mg | ethambutol | glycine | ≥5 g |
| ethambutol | glycine | ≥500 mg | ethosuximide | glycine | ≥5 g |
| ethosuximide | glycine | ≥500 mg | famotidine | glycine | ≥5 g |
| famotidine | glycine | ≥500 mg | fluconazole | glycine | ≥5 g |
| fluconazole | glycine | ≥500 mg | folic acid | glycine | ≥5 g |
| folic acid | glycine | ≥500 mg | furosemide | glycine | ≥5 g |
| furosemide | glycine | ≥500 mg | fursultiamine | glycine | ≥5 g |
| fursultiamine | glycine | ≥500 mg | gabapentin | glycine | ≥5 g |
| gabapentin | glycine | ≥500 mg | glipizide | glycine | ≥5 g |
| glipizide | glycine | ≥500 mg | granisetron | glycine | ≥5 g |
| granisetron | glycine | ≥500 mg | griseofulvin | glycine | ≥5 g |
| griseofulvin | glycine | ≥500 mg | hydralazine | glycine | ≥5 g |
| hydralazine | glycine | ≥500 mg | hydrochlorothiazide | glycine | ≥5 g |
| hydrochlorothiazide | glycine | ≥500 mg | imidapril | glycine | ≥5 g |
| imidapril | glycine | ≥500 mg | isoniazid | glycine | ≥5 g |
| isoniazid | glycine | ≥500 mg | lamivudine | glycine | ≥5 g |
| lamivudine | glycine | ≥500 mg | l-carbocysteine | glycine | ≥5 g |
| l-carbocysteine | glycine | ≥500 mg | levetiracetam | glycine | ≥5 g |
| levetiracetam | glycine | ≥500 mg | levofloxacin | glycine | ≥5 g |
| levofloxacin | glycine | ≥500 mg | linezolid | glycine | ≥5 g |
| linezolid | glycine | ≥500 mg | lisinopril | glycine | ≥5 g |
| lisinopril | glycine | ≥500 mg | losartan | glycine | ≥5 g |
| losartan | glycine | ≥500 mg | methotrexate | glycine | ≥5 g |
| methotrexate | glycine | ≥500 mg | methyldopa | glycine | ≥5 g |
| methyldopa | glycine | ≥500 mg | s-methylmethionine | glycine | ≥5 g |
| s-methylmethionine | glycine | ≥500 mg | metoclopramide | glycine | ≥5 g |
| metoclopramide | glycine | ≥500 mg | metronidazole | glycine | ≥5 g |
| metronidazole | glycine | ≥500 mg | moxifloxacin | glycine | ≥5 g |
| moxifloxacin | glycine | ≥500 mg | nalidixic acid | glycine | ≥5 g |
| nalidixic acid | glycine | ≥500 mg | nicorandil | glycine | ≥5 g |
| nicorandil | glycine | ≥500 mg | nifurtimox | glycine | ≥5 g |
| nifurtimox | glycine | ≥500 mg | nitrofurantoin | glycine | ≥5 g |
| nitrofurantoin | glycine | ≥500 mg | nizatidine | glycine | ≥5 g |
| nizatidine | glycine | ≥500 mg | nystatin | glycine | ≥5 g |
| nystatin | glycine | ≥500 mg | ondansetron | glycine | ≥5 g |
| ondansetron | glycine | ≥500 mg | oseltamivir | glycine | ≥5 g |
| oseltamivir | glycine | ≥500 mg | oxcarbazepine | glycine | ≥5 g |
| oxcarbazepine | glycine | ≥500 mg | penicillamine | glycine | ≥5 g |
| penicillamine | glycine | ≥500 mg | perindopril | glycine | ≥5 g |
| perindopril | glycine | ≥500 mg | phenobarbital | glycine | ≥5 g |
| phenobarbital | glycine | ≥500 mg | phenoxymethylpenicillin | glycine | ≥5 g |
| phenoxymethylpenicillin | glycine | ≥500 mg | pravastatin sodium | glycine | ≥5 g |
| pravastatin sodium | glycine | ≥500 mg | prednisolone | glycine | ≥5 g |
| prednisolone | glycine | ≥500 mg | primaquine | glycine | ≥5 g |
| primaquine | glycine | ≥500 mg | procaterol | glycine | ≥5 g |
| procaterol | glycine | ≥500 mg | propylthiouracil | glycine | ≥5 g |
| propylthiouracil | glycine | ≥500 mg | pseudoephedrine | glycine | ≥5 g |
| pseudoephedrine | glycine | ≥500 mg | pyrazinamide | glycine | ≥5 g |
| pyrazinamide | glycine | ≥500 mg | pyridostigmine bromide | glycine | ≥5 g |
| pyridostigmine bromide | glycine | ≥500 mg | pyridoxine hydrochloride | glycine | ≥5 g |
| pyridoxine hydrochloride | glycine | ≥500 mg | ranitidine | glycine | ≥5 g |
| ranitidine | glycine | ≥500 mg | ribavirin | glycine | ≥5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| ribavirin | glycine | ≥500 mg | riboflavin | glycine | ≥5 g |
| riboflavin | glycine | ≥500 mg | rizatriptan | glycine | ≥5 g |
| rizatriptan | glycine | ≥500 mg | stavudine | glycine | ≥5 g |
| stavudine | glycine | ≥500 mg | sulfadiazine | glycine | ≥5 g |
| sulfadiazine | glycine | ≥500 mg | sulfamethoxazole | glycine | ≥5 g |
| sulfamethoxazole | glycine | ≥500 mg | sultamicillin | glycine | ≥5 g |
| sultamicillin | glycine | ≥500 mg | sumatriptan | glycine | ≥5 g |
| sumatriptan | glycine | ≥500 mg | taltirelin | glycine | ≥5 g |
| taltirelin | glycine | ≥500 mg | tegafur | glycine | ≥5 g |
| tegafur | glycine | ≥500 mg | tenofovir disoproxil | glycine | ≥5 g |
| tenofovir disoproxil | glycine | ≥500 mg | theophylline | glycine | ≥5 g |
| theophylline | glycine | ≥500 mg | thiamine | glycine | ≥5 g |
| thiamine | glycine | ≥500 mg | trimetazidine | glycine | ≥5 g |
| trimetazidine | glycine | ≥500 mg | trimethoprim | glycine | ≥5 g |
| trimethoprim | glycine | ≥500 mg | voglibose | glycine | ≥5 g |
| voglibose | glycine | ≥500 mg | zidovudine | glycine | ≥5 g |
| zidovudine | glycine | ≥500 mg | zolmitriptan | glycine | ≥5 g |
| zolmitriptan | glycine | ≥500 mg | acetylcarnitine | glycine | ≥5 g |
| acetylcarnitine | glycine | ≥500 mg | capecitabine | glycine | ≥5 g |
| capecitabine | glycine | ≥500 mg | cefaclor | glycine | ≥5 g |
| cefaclor | glycine | ≥500 mg | cefixime | glycine | ≥5 g |
| cefixime | glycine | ≥500 mg | cefmetazole | glycine | ≥5 g |
| cefmetazole | glycine | ≥500 mg | cefpodoxime proxetil | glycine | ≥5 g |
| cefpodoxime proxetil | glycine | ≥500 mg | cefroxadine | glycine | ≥5 g |
| cefroxadine | glycine | ≥500 mg | alfoscerate | glycine | ≥5 g |
| alfoscerate | glycine | ≥500 mg | cilazapril | glycine | ≥5 g |
| cilazapril | glycine | ≥500 mg | cimetropium bromide | glycine | ≥5 g |
| cimetropium bromide | glycine | ≥500 mg | diacerein | glycine | ≥5 g |
| diacerein | glycine | ≥500 mg | erdosteine | glycine | ≥5 g |
| erdosteine | glycine | ≥500 mg | famciclovir | glycine | ≥5 g |
| famciclovir | glycine | ≥500 mg | gemifloxacin | glycine | ≥5 g |
| gemifloxacin | glycine | ≥500 mg | levosulpiride | glycine | ≥5 g |
| levosulpiride | glycine | ≥500 mg | nabumetone | glycine | ≥5 g |
| nabumetone | glycine | ≥500 mg | oxiracetam | glycine | ≥5 g |
| oxiracetam | glycine | ≥500 mg | phendimetrazine | glycine | ≥5 g |
| phendimetrazine | glycine | ≥500 mg | rabeprazole | glycine | ≥5 g |
| rabeprazole | glycine | ≥500 mg | roxatidine acetate | glycine | ≥5 g |
| roxatidine acetate | glycine | ≥500 mg | tamsulosin | glycine | ≥5 g |
| tamsulosin | glycine | ≥500 mg | terazosin | glycine | ≥5 g |
| terazosin | glycine | ≥500 mg | thioctic | glycine | ≥5 g |
| thioctic | glycine | ≥500 mg | tosufloxacin | glycine | ≥5 g |
| tosufloxacin | glycine | ≥500 mg | triflusal | glycine | ≥5 g |
| triflusal | glycine | ≥500 mg | zaltoprofen | glycine | ≥5 g |
| zaltoprofen | glycine | ≥500 mg | etidronic acid | glycine | ≥5 g |
| etidronic acid | glycine | ≥500 mg | zoledronic acid | glycine | ≥5 g |
| zoledronic acid | glycine | ≥500 mg | clodronic acid | glycine | ≥5 g |
| clodronic acid | glycine | ≥500 mg | tiludronic acid | glycine | ≥5 g |
| tiludronic acid | glycine | ≥500 mg | pamidronic acid | glycine | ≥5 g |
| pamidronic acid | glycine | ≥500 mg | alendronic acid | glycine | ≥5 g |
| alendronic acid | glycine | ≥500 mg | risedronic acid | glycine | ≥5 g |
| risedronic acid | glycine | ≥500 mg | ibandronic acid | glycine | ≥5 g |
| ibandronic acid | glycine | ≥500 mg | abacavir | lysine | ≥7.5 g |
| ibandronic acid | glycine | ≥500 mg | acarbose | lysine | ≥7.5 g |
| abacavir | lysine | ≥1.25 g | acetazolamide | lysine | ≥7.5 g |
| acarbose | lysine | ≥1.25 g | acyclovir | lysine | ≥7.5 g |
| acetazolamide | lysine | ≥1.25 g | albuterol (salbutamol) | lysine | ≥7.5 g |
| acyclovir | lysine | ≥1.25 g | allopurinol | lysine | ≥7.5 g |
| albuterol (salbutamol) | lysine | ≥1.25 g | amiloride | lysine | ≥7.5 g |
| allopurinol | lysine | ≥1.25 g | amisulpride | lysine | ≥7.5 g |
| amiloride | lysine | ≥1.25 g | amlodipine | lysine | ≥7.5 g |
| amisulpride | lysine | ≥1.25 g | amoxicillin | lysine | ≥7.5 g |
| amlodipine | lysine | ≥1.25 g | amphetamine | lysine | ≥7.5 g |
| amoxicillin | lysine | ≥1.25 g | atenolol | lysine | ≥7.5 g |
| amphetamine | lysine | ≥1.25 g | atropine | lysine | ≥7.5 g |
| atenolol | lysine | ≥1.25 g | azathioprine | lysine | ≥7.5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| atropine | lysine | ≥1.25 g | benserazide | lysine | ≥7.5 g |
| azathioprine | lysine | ≥1.25 g | benznidazole | lysine | ≥7.5 g |
| benserazide | lysine | ≥1.25 g | camostat | lysine | ≥7.5 g |
| benznidazole | lysine | ≥1.25 g | captopril | lysine | ≥7.5 g |
| camostat | lysine | ≥1.25 g | cefdinir | lysine | ≥7.5 g |
| captopril | lysine | ≥1.25 g | cefotiam hexetil hydrochloride | lysine | ≥7.5 g |
| cefdinir | lysine | ≥1.25 g | cefprozil | lysine | ≥7.5 g |
| cefotiam hexetil hydrochloride | lysine | ≥1.25 g | cefuroxime axetil | lysine | ≥7.5 g |
| cefprozil | lysine | ≥1.25 g | chloramphenicol | lysine | ≥7.5 g |
| cefuroxime axetil | lysine | ≥1.25 g | cimetidine | lysine | ≥7.5 g |
| chloramphenicol | lysine | ≥1.25 g | ciprofloxacin | lysine | ≥7.5 g |
| cimetidine | lysine | ≥1.25 g | codeine | lysine | ≥7.5 g |
| ciprofloxacin | lysine | ≥1.25 g | colchicine | lysine | ≥7.5 g |
| codeine | lysine | ≥1.25 g | cyclophosphamide | lysine | ≥7.5 g |
| colchicine | lysine | ≥1.25 g | dapsone | lysine | ≥7.5 g |
| cyclophosphamide | lysine | ≥1.25 g | dexamethasone | lysine | ≥7.5 g |
| dapsone | lysine | ≥1.25 g | didanosine | lysine | ≥7.5 g |
| dexamethasone | lysine | ≥1.25 g | diethylcarbamazine | lysine | ≥7.5 g |
| didanosine | lysine | ≥1.25 g | methionine | lysine | ≥7.5 g |
| diethylcarbamazine | lysine | ≥1.25 g | dolasetron | lysine | ≥7.5 g |
| methionine | lysine | ≥1.25 g | doxifluridine | lysine | ≥7.5 g |
| dolasetron | lysine | ≥1.25 g | doxycycline | lysine | ≥7.5 g |
| doxifluridine | lysine | ≥1.25 g | ergonovine | lysine | ≥7.5 g |
| doxycycline | lysine | ≥1.25 g | erythromycin ethylsuccinate | lysine | ≥7.5 g |
| ergonovine | lysine | ≥1.25 g | ethambutol | lysine | ≥7.5 g |
| erythromycin ethylsuccinate | lysine | ≥1.25 g | ethosuximide | lysine | ≥7.5 g |
| ethambutol | lysine | ≥1.25 g | famotidine | lysine | ≥7.5 g |
| ethosuximide | lysine | ≥1.25 g | fluconazole | lysine | ≥7.5 g |
| famotidine | lysine | ≥1.25 g | folic acid | lysine | ≥7.5 g |
| fluconazole | lysine | ≥1.25 g | furosemide | lysine | ≥7.5 g |
| folic acid | lysine | ≥1.25 g | fursultiamine | lysine | ≥7.5 g |
| furosemide | lysine | ≥1.25 g | gabapentin | lysine | ≥7.5 g |
| fursultiamine | lysine | ≥1.25 g | glipizide | lysine | ≥7.5 g |
| gabapentin | lysine | ≥1.25 g | granisetron | lysine | ≥7.5 g |
| glipizide | lysine | ≥1.25 g | griseofulvin | lysine | ≥7.5 g |
| granisetron | lysine | ≥1.25 g | hydralazine | lysine | ≥7.5 g |
| griseofulvin | lysine | ≥1.25 g | hydrochlorothiazide | lysine | ≥7.5 g |
| hydralazine | lysine | ≥1.25 g | imidapril | lysine | ≥7.5 g |
| hydrochlorothiazide | lysine | ≥1.25 g | isoniazid | lysine | ≥7.5 g |
| imidapril | lysine | ≥1.25 g | lamivudine | lysine | ≥7.5 g |
| isoniazid | lysine | ≥1.25 g | l-carbocysteine | lysine | ≥7.5 g |
| lamivudine | lysine | ≥1.25 g | levetiracetam | lysine | ≥7.5 g |
| l-carbocysteine | lysine | ≥1.25 g | levofloxacin | lysine | ≥7.5 g |
| levetiracetam | lysine | ≥1.25 g | linezolid | lysine | ≥7.5 g |
| levofloxacin | lysine | ≥1.25 g | lisinopril | lysine | ≥7.5 g |
| linezolid | lysine | ≥1.25 g | losartan | lysine | ≥7.5 g |
| lisinopril | lysine | ≥1.25 g | methotrexate | lysine | ≥7.5 g |
| losartan | lysine | ≥1.25 g | methyldopa | lysine | ≥7.5 g |
| methotrexate | lysine | ≥1.25 g | s-methylmethionine | lysine | ≥7.5 g |
| methyldopa | lysine | ≥1.25 g | metoclopramide | lysine | ≥7.5 g |
| s-methylmethionine | lysine | ≥1.25 g | metronidazole | lysine | ≥7.5 g |
| metoclopramide | lysine | ≥1.25 g | moxifloxacin | lysine | ≥7.5 g |
| metronidazole | lysine | ≥1.25 g | nalidixic acid | lysine | ≥7.5 g |
| moxifloxacin | lysine | ≥1.25 g | nicorandil | lysine | ≥7.5 g |
| nalidixic acid | lysine | ≥1.25 g | nifurtimox | lysine | ≥7.5 g |
| nicorandil | lysine | ≥1.25 g | nitrofurantoin | lysine | ≥7.5 g |
| nifurtimox | lysine | ≥1.25 g | nizatidine | lysine | ≥7.5 g |
| nitrofurantoin | lysine | ≥1.25 g | nystatin | lysine | ≥7.5 g |
| nizatidine | lysine | ≥1.25 g | ondansetron | lysine | ≥7.5 g |
| nystatin | lysine | ≥1.25 g | oseltamivir | lysine | ≥7.5 g |
| ondansetron | lysine | ≥1.25 g | oxcarbazepine | lysine | ≥7.5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| oseltamivir | lysine | ≥1.25 g | penicillamine | lysine | ≥7.5 g |
| oxcarbazepine | lysine | ≥1.25 g | perindopril | lysine | ≥7.5 g |
| penicillamine | lysine | ≥1.25 g | phenobarbital | lysine | ≥7.5 g |
| perindopril | lysine | ≥1.25 g | phenoxymethylpenicillin | lysine | ≥7.5 g |
| phenobarbital | lysine | ≥1.25 g | pravastatin sodium | lysine | ≥7.5 g |
| phenoxymethylpenicillin | lysine | ≥1.25 g | prednisolone | lysine | ≥7.5 g |
| pravastatin sodium | lysine | ≥1.25 g | primaquine | lysine | ≥7.5 g |
| prednisolone | lysine | ≥1.25 g | procaterol | lysine | ≥7.5 g |
| primaquine | lysine | ≥1.25 g | propylthiouracil | lysine | ≥7.5 g |
| procaterol | lysine | ≥1.25 g | pseudoephedrine | lysine | ≥7.5 g |
| propylthiouracil | lysine | ≥1.25 g | pyrazinamide | lysine | ≥7.5 g |
| pseudoephedrine | lysine | ≥1.25 g | pyridostigmine bromide | lysine | ≥7.5 g |
| pyrazinamide | lysine | ≥1.25 g | pyridoxine hydrochloride | lysine | ≥7.5 g |
| pyridostigmine bromide | lysine | ≥1.25 g | ranitidine | lysine | ≥7.5 g |
| pyridoxine hydrochloride | lysine | ≥1.25 g | ribavirin | lysine | ≥7.5 g |
| ranitidine | lysine | ≥1.25 g | riboflavin | lysine | ≥7.5 g |
| ribavirin | lysine | ≥1.25 g | rizatriptan | lysine | ≥7.5 g |
| riboflavin | lysine | ≥1.25 g | stavudine | lysine | ≥7.5 g |
| rizatriptan | lysine | ≥1.25 g | sulfadiazine | lysine | ≥7.5 g |
| stavudine | lysine | ≥1.25 g | sulfamethoxazole | lysine | ≥7.5 g |
| sulfadiazine | lysine | ≥1.25 g | sultamicillin | lysine | ≥7.5 g |
| sulfamethoxazole | lysine | ≥1.25 g | sumatriptan | lysine | ≥7.5 g |
| sultamicillin | lysine | ≥1.25 g | taltirelin | lysine | ≥7.5 g |
| sumatriptan | lysine | ≥1.25 g | tegafur | lysine | ≥7.5 g |
| taltirelin | lysine | ≥1.25 g | tenofovir disoproxil | lysine | ≥7.5 g |
| tegafur | lysine | ≥1.25 g | theophylline | lysine | ≥7.5 g |
| tenofovir disoproxil | lysine | ≥1.25 g | thiamine | lysine | ≥7.5 g |
| theophylline | lysine | ≥1.25 g | trimetazidine | lysine | ≥7.5 g |
| thiamine | lysine | ≥1.25 g | trimethoprim | lysine | ≥7.5 g |
| trimetazidine | lysine | ≥1.25 g | voglibose | lysine | ≥7.5 g |
| trimethoprim | lysine | ≥1.25 g | zidovudine | lysine | ≥7.5 g |
| voglibose | lysine | ≥1.25 g | zolmitriptan | lysine | ≥7.5 g |
| zidovudine | lysine | ≥1.25 g | acetylcarnitine | lysine | ≥7.5 g |
| zolmitriptan | lysine | ≥1.25 g | capecitabine | lysine | ≥7.5 g |
| acetylcarnitine | lysine | ≥1.25 g | cefaclor | lysine | ≥7.5 g |
| capecitabine | lysine | ≥1.25 g | cefixime | lysine | ≥7.5 g |
| cefaclor | lysine | ≥1.25 g | cefmetazole | lysine | ≥7.5 g |
| cefixime | lysine | ≥1.25 g | cefpodoxime proxetil | lysine | ≥7.5 g |
| cefmetazole | lysine | ≥1.25 g | cefroxadine | lysine | ≥7.5 g |
| cefpodoxime proxetil | lysine | ≥1.25 g | alfoscerate | lysine | ≥7.5 g |
| cefroxadine | lysine | ≥1.25 g | cilazapril | lysine | ≥7.5 g |
| alfoscerate | lysine | ≥1.25 g | cimetropium bromide | lysine | ≥7.5 g |
| cilazapril | lysine | ≥1.25 g | diacerein | lysine | ≥7.5 g |
| cimetropium bromide | lysine | ≥1.25 g | erdosteine | lysine | ≥7.5 g |
| diacerein | lysine | ≥1.25 g | famciclovir | lysine | ≥7.5 g |
| erdosteine | lysine | ≥1.25 g | gemifloxacin | lysine | ≥7.5 g |
| famciclovir | lysine | ≥1.25 g | levosulpiride | lysine | ≥7.5 g |
| gemifloxacin | lysine | ≥1.25 g | nabumetone | lysine | ≥7.5 g |
| levosulpiride | lysine | ≥1.25 g | oxiracetam | lysine | ≥7.5 g |
| nabumetone | lysine | ≥1.25 g | phendimetrazine | lysine | ≥7.5 g |
| oxiracetam | lysine | ≥1.25 g | rabeprazole | lysine | ≥7.5 g |
| phendimetrazine | lysine | ≥1.25 g | roxatidine acetate | lysine | ≥7.5 g |
| rabeprazole | lysine | ≥1.25 g | tamsulosin | lysine | ≥7.5 g |
| roxatidine acetate | lysine | ≥1.25 g | terazosin | lysine | ≥7.5 g |
| tamsulosin | lysine | ≥1.25 g | thioctic | lysine | ≥7.5 g |
| terazosin | lysine | ≥1.25 g | tosufloxacin | lysine | ≥7.5 g |
| thioctic | lysine | ≥1.25 g | triflusal | lysine | ≥7.5 g |
| tosufloxacin | lysine | ≥1.25 g | zaltoprofen | lysine | ≥7.5 g |
| triflusal | lysine | ≥1.25 g | etidronic acid | lysine | ≥7.5 g |
| zaltoprofen | lysine | ≥1.25 g | zoledronic acid | lysine | ≥7.5 g |
| etidronic acid | lysine | ≥1.25 g | clodronic acid | lysine | ≥7.5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| zoledronic acid | lysine | ≥1.25 g | tiludronic acid | lysine | ≥7.5 g |
| zoledronic acid | lysine | ≥1.3 g | zoledronic acid | lysine | ≥1.6 g |
| zoledronic acid | lysine | ≥1.4 g | zoledronic acid | lysine | ≥1.7 g |
| zoledronic acid | lysine | ≥1.8 g | zoledronic acid | lysine | ≥1.9 g |
| clodronic acid | lysine | ≥1.25 g | pamidronic acid | lysine | ≥7.5 g |
| tiludronic acid | lysine | ≥1.25 g | alendronic acid | lysine | ≥7.5 g |
| pamidronic acid | lysine | ≥1.25 g | risedronic acid | lysine | ≥7.5 g |
| alendronic acid | lysine | ≥1.25 g | ibandronic acid | lysine | ≥7.5 g |
| risedronic acid | lysine | ≥1.25 g | abacavir | glycine | ≥7.5 g |
| ibandronic acid | lysine | ≥1.25 g | acarbose | glycine | ≥7.5 g |
| abacavir | glycine | ≥1.25 g | acetazolamide | glycine | ≥7.5 g |
| acarbose | glycine | ≥1.25 g | acyclovir | glycine | ≥7.5 g |
| acetazolamide | glycine | ≥1.25 g | albuterol (salbutamol) | glycine | ≥7.5 g |
| acyclovir | glycine | ≥1.25 g | allopurinol | glycine | ≥7.5 g |
| albuterol (salbutamol) | glycine | ≥1.25 g | amiloride | glycine | ≥7.5 g |
| allopurinol | glycine | ≥1.25 g | amisulpride | glycine | ≥7.5 g |
| amiloride | glycine | ≥1.25 g | amlodipine | glycine | ≥7.5 g |
| amisulpride | glycine | ≥1.25 g | amoxicillin | glycine | ≥7.5 g |
| amlodipine | glycine | ≥1.25 g | amphetamine | glycine | ≥7.5 g |
| amoxicillin | glycine | ≥1.25 g | atenolol | glycine | ≥7.5 g |
| amphetamine | glycine | ≥1.25 g | atropine | glycine | ≥7.5 g |
| atenolol | glycine | ≥1.25 g | azathioprine | glycine | ≥7.5 g |
| atropine | glycine | ≥1.25 g | benserazide | glycine | ≥7.5 g |
| azathioprine | glycine | ≥1.25 g | benznidazole | glycine | ≥7.5 g |
| benserazide | glycine | ≥1.25 g | camostat | glycine | ≥7.5 g |
| benznidazole | glycine | ≥1.25 g | captopril | glycine | ≥7.5 g |
| camostat | glycine | ≥1.25 g | cefdinir | glycine | ≥7.5 g |
| captopril | glycine | ≥1.25 g | cefotiam hexetil hydrochloride | glycine | ≥7.5 g |
| cefdinir | glycine | ≥1.25 g | cefprozil | glycine | ≥7.5 g |
| cefotiam hexetil hydrochloride | glycine | ≥1.25 g | cefuroxime axetil | glycine | ≥7.5 g |
| cefprozil | glycine | ≥1.25 g | chloramphenicol | glycine | ≥7.5 g |
| cefuroxime axetil | glycine | ≥1.25 g | cimetidine | glycine | ≥7.5 g |
| chloramphenicol | glycine | ≥1.25 g | ciprofloxacin | glycine | ≥7.5 g |
| cimetidine | glycine | ≥1.25 g | codeine | glycine | ≥7.5 g |
| ciprofloxacin | glycine | ≥1.25 g | colchicine | glycine | ≥7.5 g |
| codeine | glycine | ≥1.25 g | cyclophosphamide | glycine | ≥7.5 g |
| colchicine | glycine | ≥1.25 g | dapsone | glycine | ≥7.5 g |
| cyclophosphamide | glycine | ≥1.25 g | dexamethasone | glycine | ≥7.5 g |
| dapsone | glycine | ≥1.25 g | didanosine | glycine | ≥7.5 g |
| dexamethasone | glycine | ≥1.25 g | diethylcarbamazine | glycine | ≥7.5 g |
| didanosine | glycine | ≥1.25 g | methionine | glycine | ≥7.5 g |
| diethylcarbamazine | glycine | ≥1.25 g | dolasetron | glycine | ≥7.5 g |
| methionine | glycine | ≥1.25 g | doxifluridine | glycine | ≥7.5 g |
| dolasetron | glycine | ≥1.25 g | doxycycline | glycine | ≥7.5 g |
| doxifluridine | glycine | ≥1.25 g | ergonovine | glycine | ≥7.5 g |
| doxycycline | glycine | ≥1.25 g | erythromycin ethylsuccinate | glycine | ≥7.5 g |
| ergonovine | glycine | ≥1.25 g | ethambutol | glycine | ≥7.5 g |
| erythromycin ethylsuccinate | glycine | ≥1.25 g | ethosuximide | glycine | ≥7.5 g |
| ethambutol | glycine | ≥1.25 g | famotidine | glycine | ≥7.5 g |
| ethosuximide | glycine | ≥1.25 g | fluconazole | glycine | ≥7.5 g |
| famotidine | glycine | ≥1.25 g | folic acid | glycine | ≥7.5 g |
| fluconazole | glycine | ≥1.25 g | furosemide | glycine | ≥7.5 g |
| folic acid | glycine | ≥1.25 g | fursultiamine | glycine | ≥7.5 g |
| furosemide | glycine | ≥1.25 g | gabapentin | glycine | ≥7.5 g |
| fursultiamine | glycine | ≥1.25 g | glipizide | glycine | ≥7.5 g |
| gabapentin | glycine | ≥1.25 g | granisetron | glycine | ≥7.5 g |
| glipizide | glycine | ≥1.25 g | griseofulvin | glycine | ≥7.5 g |
| granisetron | glycine | ≥1.25 g | hydralazine | glycine | ≥7.5 g |
| griseofulvin | glycine | ≥1.25 g | hydrochlorothiazide | glycine | ≥7.5 g |
| hydralazine | glycine | ≥1.25 g | imidapril | glycine | ≥7.5 g |
| hydrochlorothiazide | glycine | ≥1.25 g | isoniazid | glycine | ≥7.5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| imidapril | glycine | ≥1.25 g | lamivudine | glycine | ≥7.5 g |
| isoniazid | glycine | ≥1.25 g | l-carbocysteine | glycine | ≥7.5 g |
| lamivudine | glycine | ≥1.25 g | levetiracetam | glycine | ≥7.5 g |
| l-carbocysteine | glycine | ≥1.25 g | levofloxacin | glycine | ≥7.5 g |
| levetiracetam | glycine | ≥1.25 g | linezolid | glycine | ≥7.5 g |
| levofloxacin | glycine | ≥1.25 g | lisinopril | glycine | ≥7.5 g |
| linezolid | glycine | ≥1.25 g | losartan | glycine | ≥7.5 g |
| lisinopril | glycine | ≥1.25 g | methotrexate | glycine | ≥7.5 g |
| losartan | glycine | ≥1.25 g | methyldopa | glycine | ≥7.5 g |
| methotrexate | glycine | ≥1.25 g | s-methylmethionine | glycine | ≥7.5 g |
| methyldopa | glycine | ≥1.25 g | metoclopramide | glycine | ≥7.5 g |
| s-methylmethionine | glycine | ≥1.25 g | metronidazole | glycine | ≥7.5 g |
| metoclopramide | glycine | ≥1.25 g | moxifloxacin | glycine | ≥7.5 g |
| metronidazole | glycine | ≥1.25 g | nalidixic acid | glycine | ≥7.5 g |
| moxifloxacin | glycine | ≥1.25 g | nicorandil | glycine | ≥7.5 g |
| nalidixic acid | glycine | ≥1.25 g | nifurtimox | glycine | ≥7.5 g |
| nicorandil | glycine | ≥1.25 g | nitrofurantoin | glycine | ≥7.5 g |
| nifurtimox | glycine | ≥1.25 g | nizatidine | glycine | ≥7.5 g |
| nitrofurantoin | glycine | ≥1.25 g | nystatin | glycine | ≥7.5 g |
| nizatidine | glycine | ≥1.25 g | ondansetron | glycine | ≥7.5 g |
| nystatin | glycine | ≥1.25 g | oseltamivir | glycine | ≥7.5 g |
| ondansetron | glycine | ≥1.25 g | oxcarbazepine | glycine | ≥7.5 g |
| oseltamivir | glycine | ≥1.25 g | penicillamine | glycine | ≥7.5 g |
| oxcarbazepine | glycine | ≥1.25 g | perindopril | glycine | ≥7.5 g |
| penicillamine | glycine | ≥1.25 g | phenobarbital | glycine | ≥7.5 g |
| perindopril | glycine | ≥1.25 g | phenoxymethylpenicillin | glycine | ≥7.5 g |
| phenobarbital | glycine | ≥1.25 g | pravastatin sodium | glycine | ≥7.5 g |
| phenoxymethylpenicillin | glycine | ≥1.25 g | prednisolone | glycine | ≥7.5 g |
| pravastatin sodium | glycine | ≥1.25 g | primaquine | glycine | ≥7.5 g |
| prednisolone | glycine | ≥1.25 g | procaterol | glycine | ≥7.5 g |
| primaquine | glycine | ≥1.25 g | propylthiouracil | glycine | ≥7.5 g |
| procaterol | glycine | ≥1.25 g | pseudoephedrine | glycine | ≥7.5 g |
| propylthiouracil | glycine | ≥1.25 g | pyrazinamide | glycine | ≥7.5 g |
| pseudoephedrine | glycine | ≥1.25 g | pyridostigmine bromide | glycine | ≥7.5 g |
| pyrazinamide | glycine | ≥1.25 g | pyridoxine hydrochloride | glycine | ≥7.5 g |
| pyridostigmine bromide | glycine | ≥1.25 g | ranitidine | glycine | ≥7.5 g |
| pyridoxine hydrochloride | glycine | ≥1.25 g | ribavirin | glycine | ≥7.5 g |
| ranitidine | glycine | ≥1.25 g | riboflavin | glycine | ≥7.5 g |
| ribavirin | glycine | ≥1.25 g | rizatriptan | glycine | ≥7.5 g |
| riboflavin | glycine | ≥1.25 g | stavudine | glycine | ≥7.5 g |
| rizatriptan | glycine | ≥1.25 g | sulfadiazine | glycine | ≥7.5 g |
| stavudine | glycine | ≥1.25 g | sulfamethoxazole | glycine | ≥7.5 g |
| sulfadiazine | glycine | ≥1.25 g | sultamicillin | glycine | ≥7.5 g |
| sulfamethoxazole | glycine | ≥1.25 g | sumatriptan | glycine | ≥7.5 g |
| sultamicillin | glycine | ≥1.25 g | taltirelin | glycine | ≥7.5 g |
| sumatriptan | glycine | ≥1.25 g | tegafur | glycine | ≥7.5 g |
| taltirelin | glycine | ≥1.25 g | tenofovir disoproxil | glycine | ≥7.5 g |
| tegafur | glycine | ≥1.25 g | theophylline | glycine | ≥7.5 g |
| tenofovir disoproxil | glycine | ≥1.25 g | thiamine | glycine | ≥7.5 g |
| theophylline | glycine | ≥1.25 g | trimetazidine | glycine | ≥7.5 g |
| thiamine | glycine | ≥1.25 g | trimethoprim | glycine | ≥7.5 g |
| trimetazidine | glycine | ≥1.25 g | voglibose | glycine | ≥7.5 g |
| trimethoprim | glycine | ≥1.25 g | zidovudine | glycine | ≥7.5 g |
| voglibose | glycine | ≥1.25 g | zolmitriptan | glycine | ≥7.5 g |
| zidovudine | glycine | ≥1.25 g | acetylcarnitine | glycine | ≥7.5 g |
| zolmitriptan | glycine | ≥1.25 g | capecitabine | glycine | ≥7.5 g |
| acetylcarnitine | glycine | ≥1.25 g | cefaclor | glycine | ≥7.5 g |
| capecitabine | glycine | ≥1.25 g | cefixime | glycine | ≥7.5 g |
| cefaclor | glycine | ≥1.25 g | cefmetazole | glycine | ≥7.5 g |
| cefixime | glycine | ≥1.25 g | cefpodoxime proxetil | glycine | ≥7.5 g |
| cefmetazole | glycine | ≥1.25 g | cefroxadine | glycine | ≥7.5 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| cefpodoxime proxetil | glycine | ≥1.25 g | alfoscerate | glycine | ≥7.5 g |
| cefroxadine | glycine | ≥1.25 g | cilazapril | glycine | ≥7.5 g |
| alfoscerate | glycine | ≥1.25 g | cimetropium bromide | glycine | ≥7.5 g |
| cilazapril | glycine | ≥1.25 g | diacerein | glycine | ≥7.5 g |
| cimetropium bromide | glycine | ≥1.25 g | erdosteine | glycine | ≥7.5 g |
| diacerein | glycine | ≥1.25 g | famciclovir | glycine | ≥7.5 g |
| erdosteine | glycine | ≥1.25 g | gemifloxacin | glycine | ≥7.5 g |
| famciclovir | glycine | ≥1.25 g | levosulpiride | glycine | ≥7.5 g |
| gemifloxacin | glycine | ≥1.25 g | nabumetone | glycine | ≥7.5 g |
| levosulpiride | glycine | ≥1.25 g | oxiracetam | glycine | ≥7.5 g |
| nabumetone | glycine | ≥1.25 g | phendimetrazine | glycine | ≥7.5 g |
| oxiracetam | glycine | ≥1.25 g | rabeprazole | glycine | ≥7.5 g |
| phendimetrazine | glycine | ≥1.25 g | roxatidine acetate | glycine | ≥7.5 g |
| rabeprazole | glycine | ≥1.25 g | tamsulosin | glycine | ≥7.5 g |
| roxatidine acetate | glycine | ≥1.25 g | terazosin | glycine | ≥7.5 g |
| tamsulosin | glycine | ≥1.25 g | thioctic | glycine | ≥7.5 g |
| terazosin | glycine | ≥1.25 g | tosufloxacin | glycine | ≥7.5 g |
| thioctic | glycine | ≥1.25 g | triflusal | glycine | ≥7.5 g |
| tosufloxacin | glycine | ≥1.25 g | zaltoprofen | glycine | ≥7.5 g |
| triflusal | glycine | ≥1.25 g | etidronic acid | glycine | ≥7.5 g |
| zaltoprofen | glycine | ≥1.25 g | zoledronic acid | glycine | ≥7.5 g |
| etidronic acid | glycine | ≥1.25 g | clodronic acid | glycine | ≥7.5 g |
| zoledronic acid | glycine | ≥1.25 g | tiludronic acid | glycine | ≥7.5 g |
| clodronic acid | glycine | ≥1.25 g | pamidronic acid | glycine | ≥7.5 g |
| tiludronic acid | glycine | ≥1.25 g | alendronic acid | glycine | ≥7.5 g |
| pamidronic acid | glycine | ≥1.25 g | risedronic acid | glycine | ≥7.5 g |
| alendronic acid | glycine | ≥1.25 g | ibandronic acid | glycine | ≥7.5 g |
| risedronic acid | glycine | ≥1.25 g | abacavir | lysine | ≥10 g |
| ibandronic acid | glycine | ≥1.25 g | acarbose | lysine | ≥10 g |
| abacavir | lysine | ≥1.5 g | acetazolamide | lysine | ≥10 g |
| acarbose | lysine | ≥1.5 g | acyclovir | lysine | ≥10 g |
| acetazolamide | lysine | ≥1.5 g | albuterol (salbutamol) | lysine | ≥10 g |
| acyclovir | lysine | ≥1.5 g | allopurinol | lysine | ≥10 g |
| albuterol (salbutamol) | lysine | ≥1.5 g | amiloride | lysine | ≥10 g |
| allopurinol | lysine | ≥1.5 g | amisulpride | lysine | ≥10 g |
| amiloride | lysine | ≥1.5 g | amlodipine | lysine | ≥10 g |
| amisulpride | lysine | ≥1.5 g | amoxicillin | lysine | ≥10 g |
| amlodipine | lysine | ≥1.5 g | amphetamine | lysine | ≥10 g |
| amoxicillin | lysine | ≥1.5 g | atenolol | lysine | ≥10 g |
| amphetamine | lysine | ≥1.5 g | atropine | lysine | ≥10 g |
| atenolol | lysine | ≥1.5 g | azathioprine | lysine | ≥10 g |
| atropine | lysine | ≥1.5 g | benserazide | lysine | ≥10 g |
| azathioprine | lysine | ≥1.5 g | benznidazole | lysine | ≥10 g |
| benserazide | lysine | ≥1.5 g | camostat | lysine | ≥10 g |
| benznidazole | lysine | ≥1.5 g | captopril | lysine | ≥10 g |
| camostat | lysine | ≥1.5 g | cefdinir | lysine | ≥10 g |
| captopril | lysine | ≥1.5 g | cefotiam hexetil hydrochloride | lysine | ≥10 g |
| cefdinir | lysine | ≥1.5 g | cefprozil | lysine | ≥10 g |
| cefotiam hexetil hydrochloride | lysine | ≥1.5 g | cefuroxime axetil | lysine | ≥10 g |
| cefprozil | lysine | ≥1.5 g | chloramphenicol | lysine | ≥10 g |
| cefuroxime axetil | lysine | ≥1.5 g | cimetidine | lysine | ≥10 g |
| chloramphenicol | lysine | ≥1.5 g | ciprofloxacin | lysine | ≥10 g |
| cimetidine | lysine | ≥1.5 g | codeine | lysine | ≥10 g |
| ciprofloxacin | lysine | ≥1.5 g | colchicine | lysine | ≥10 g |
| codeine | lysine | ≥1.5 g | cyclophosphamide | lysine | ≥10 g |
| colchicine | lysine | ≥1.5 g | dapsone | lysine | ≥10 g |
| cyclophosphamide | lysine | ≥1.5 g | dexamethasone | lysine | ≥10 g |
| dapsone | lysine | ≥1.5 g | didanosine | lysine | ≥10 g |
| dexamethasone | lysine | ≥1.5 g | diethylcarbamazine | lysine | ≥10 g |
| didanosine | lysine | ≥1.5 g | methionine | lysine | ≥10 g |
| diethylcarbamazine | lysine | ≥1.5 g | dolasetron | lysine | ≥10 g |
| methionine | lysine | ≥1.5 g | doxifluridine | lysine | ≥10 g |
| dolasetron | lysine | ≥1.5 g | doxycycline | lysine | ≥10 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| doxifluridine | lysine | ≥1.5 g | ergonovine | lysine | ≥10 g |
| doxycycline | lysine | ≥1.5 g | erythromycin ethylsuccinate | lysine | ≥10 g |
| ergonovine | lysine | ≥1.5 g | ethambutol | lysine | ≥10 g |
| erythromycin ethylsuccinate | lysine | ≥1.5 g | ethosuximide | lysine | ≥10 g |
| ethambutol | lysine | ≥1.5 g | famotidine | lysine | ≥10 g |
| ethosuximide | lysine | ≥1.5 g | fluconazole | lysine | ≥10 g |
| famotidine | lysine | ≥1.5 g | folic acid | lysine | ≥10 g |
| fluconazole | lysine | ≥1.5 g | furosemide | lysine | ≥10 g |
| folic acid | lysine | ≥1.5 g | fursultiamine | lysine | ≥10 g |
| furosemide | lysine | ≥1.5 g | gabapentin | lysine | ≥10 g |
| fursultiamine | lysine | ≥1.5 g | glipizide | lysine | ≥10 g |
| gabapentin | lysine | ≥1.5 g | granisetron | lysine | ≥10 g |
| glipizide | lysine | ≥1.5 g | griseofulvin | lysine | ≥10 g |
| granisetron | lysine | ≥1.5 g | hydralazine | lysine | ≥10 g |
| griseofulvin | lysine | ≥1.5 g | hydrochlorothiazide | lysine | ≥10 g |
| hydralazine | lysine | ≥1.5 g | imidapril | lysine | ≥10 g |
| hydrochlorothiazide | lysine | ≥1.5 g | isoniazid | lysine | ≥10 g |
| imidapril | lysine | ≥1.5 g | lamivudine | lysine | ≥10 g |
| isoniazid | lysine | ≥1.5 g | l-carbocysteine | lysine | ≥10 g |
| lamivudine | lysine | ≥1.5 g | levetiracetam | lysine | ≥10 g |
| l-carbocysteine | lysine | ≥1.5 g | levofloxacin | lysine | ≥10 g |
| levetiracetam | lysine | ≥1.5 g | linezolid | lysine | ≥10 g |
| levofloxacin | lysine | ≥1.5 g | lisinopril | lysine | ≥10 g |
| linezolid | lysine | ≥1.5 g | losartan | lysine | ≥10 g |
| lisinopril | lysine | ≥1.5 g | methotrexate | lysine | ≥10 g |
| losartan | lysine | ≥1.5 g | methyldopa | lysine | ≥10 g |
| methotrexate | lysine | ≥1.5 g | s-methylmethionine | lysine | ≥10 g |
| methyldopa | lysine | ≥1.5 g | metoclopramide | lysine | ≥10 g |
| s-methylmethionine | lysine | ≥1.5 g | metronidazole | lysine | ≥10 g |
| metoclopramide | lysine | ≥1.5 g | moxifloxacin | lysine | ≥10 g |
| metronidazole | lysine | ≥1.5 g | nalidixic acid | lysine | ≥10 g |
| moxifloxacin | lysine | ≥1.5 g | nicorandil | lysine | ≥10 g |
| nalidixic acid | lysine | ≥1.5 g | nifurtimox | lysine | ≥10 g |
| nicorandil | lysine | ≥1.5 g | nitrofurantoin | lysine | ≥10 g |
| nifurtimox | lysine | ≥1.5 g | nizatidine | lysine | ≥10 g |
| nitrofurantoin | lysine | ≥1.5 g | nystatin | lysine | ≥10 g |
| nizatidine | lysine | ≥1.5 g | ondansetron | lysine | ≥10 g |
| nystatin | lysine | ≥1.5 g | oseltamivir | lysine | ≥10 g |
| ondansetron | lysine | ≥1.5 g | oxcarbazepine | lysine | ≥10 g |
| oseltamivir | lysine | ≥1.5 g | penicillamine | lysine | ≥10 g |
| oxcarbazepine | lysine | ≥1.5 g | perindopril | lysine | ≥10 g |
| penicillamine | lysine | ≥1.5 g | phenobarbital | lysine | ≥10 g |
| perindopril | lysine | ≥1.5 g | phenoxymethylpenicillin | lysine | ≥10 g |
| phenobarbital | lysine | ≥1.5 g | pravastatin sodium | lysine | ≥10 g |
| phenoxymethylpenicillin | lysine | ≥1.5 g | prednisolone | lysine | ≥10 g |
| pravastatin sodium | lysine | ≥1.5 g | primaquine | lysine | ≥10 g |
| prednisolone | lysine | ≥1.5 g | procaterol | lysine | ≥10 g |
| primaquine | lysine | ≥1.5 g | propylthiouracil | lysine | ≥10 g |
| procaterol | lysine | ≥1.5 g | pseudoephedrine | lysine | ≥10 g |
| propylthiouracil | lysine | ≥1.5 g | pyrazinamide | lysine | ≥10 g |
| pseudoephedrine | lysine | ≥1.5 g | pyridostigmine bromide | lysine | ≥10 g |
| pyrazinamide | lysine | ≥1.5 g | pyridoxine hydrochloride | lysine | ≥10 g |
| pyridostigmine bromide | lysine | ≥1.5 g | ranitidine | lysine | ≥10 g |
| pyridoxine hydrochloride | lysine | ≥1.5 g | ribavirin | lysine | ≥10 g |
| ranitidine | lysine | ≥1.5 g | riboflavin | lysine | ≥10 g |
| ribavirin | lysine | ≥1.5 g | rizatriptan | lysine | ≥10 g |
| riboflavin | lysine | ≥1.5 g | stavudine | lysine | ≥10 g |
| rizatriptan | lysine | ≥1.5 g | sulfadiazine | lysine | ≥10 g |
| stavudine | lysine | ≥1.5 g | sulfamethoxazole | lysine | ≥10 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| sulfadiazine | lysine | ≥1.5 g | sultamicillin | lysine | ≥10 g |
| sulfamethoxazole | lysine | ≥1.5 g | sumatriptan | lysine | ≥10 g |
| sultamicillin | lysine | ≥1.5 g | taltirelin | lysine | ≥10 g |
| sumatriptan | lysine | ≥1.5 g | tegafur | lysine | ≥10 g |
| taltirelin | lysine | ≥1.5 g | tenofovir disoproxil | lysine | ≥10 g |
| tegafur | lysine | ≥1.5 g | theophylline | lysine | ≥10 g |
| tenofovir disoproxil | lysine | ≥1.5 g | thiamine | lysine | ≥10 g |
| theophylline | lysine | ≥1.5 g | trimetazidine | lysine | ≥10 g |
| thiamine | lysine | ≥1.5 g | trimethoprim | lysine | ≥10 g |
| trimetazidine | lysine | ≥1.5 g | voglibose | lysine | ≥10 g |
| trimethoprim | lysine | ≥1.5 g | zidovudine | lysine | ≥10 g |
| voglibose | lysine | ≥1.5 g | zolmitriptan | lysine | ≥10 g |
| zidovudine | lysine | ≥1.5 g | acetylcarnitine | lysine | ≥10 g |
| zolmitriptan | lysine | ≥1.5 g | capecitabine | lysine | ≥10 g |
| acetylcarnitine | lysine | ≥1.5 g | cefaclor | lysine | ≥10 g |
| capecitabine | lysine | ≥1.5 g | cefixime | lysine | ≥10 g |
| cefaclor | lysine | ≥1.5 g | cefmetazole | lysine | ≥10 g |
| cefixime | lysine | ≥1.5 g | cefpodoxime proxetil | lysine | ≥10 g |
| cefmetazole | lysine | ≥1.5 g | cefroxadine | lysine | ≥10 g |
| cefpodoxime proxetil | lysine | ≥1.5 g | alfoscerate | lysine | ≥10 g |
| cefroxadine | lysine | ≥1.5 g | cilazapril | lysine | ≥10 g |
| alfoscerate | lysine | ≥1.5 g | cimetropium bromide | lysine | ≥10 g |
| cilazapril | lysine | ≥1.5 g | diacerein | lysine | ≥10 g |
| cimetropium bromide | lysine | ≥1.5 g | erdosteine | lysine | ≥10 g |
| diacerein | lysine | ≥1.5 g | famciclovir | lysine | ≥10 g |
| erdosteine | lysine | ≥1.5 g | gemifloxacin | lysine | ≥10 g |
| famciclovir | lysine | ≥1.5 g | levosulpiride | lysine | ≥10 g |
| gemifloxacin | lysine | ≥1.5 g | nabumetone | lysine | ≥10 g |
| levosulpiride | lysine | ≥1.5 g | oxiracetam | lysine | ≥10 g |
| nabumetone | lysine | ≥1.5 g | phendimetrazine | lysine | ≥10 g |
| oxiracetam | lysine | ≥1.5 g | rabeprazole | lysine | ≥10 g |
| phendimetrazine | lysine | ≥1.5 g | roxatidine acetate | lysine | ≥10 g |
| rabeprazole | lysine | ≥1.5 g | tamsulosin | lysine | ≥10 g |
| roxatidine acetate | lysine | ≥1.5 g | terazosin | lysine | ≥10 g |
| tamsulosin | lysine | ≥1.5 g | thioctic | lysine | ≥10 g |
| terazosin | lysine | ≥1.5 g | tosufloxacin | lysine | ≥10 g |
| thioctic | lysine | ≥1.5 g | triflusal | lysine | ≥10 g |
| tosufloxacin | lysine | ≥1.5 g | zaltoprofen | lysine | ≥10 g |
| triflusal | lysine | ≥1.5 g | etidronic acid | lysine | ≥10 g |
| zaltoprofen | lysine | ≥1.5 g | zoledronic acid | lysine | ≥10 g |
| etidronic acid | lysine | ≥1.5 g | clodronic acid | lysine | ≥10 g |
| zoledronic acid | lysine | ≥1.5 g | tiludronic acid | lysine | ≥10 g |
| clodronic acid | lysine | ≥1.5 g | pamidronic acid | lysine | ≥10 g |
| tiludronic acid | lysine | ≥1.5 g | alendronic acid | lysine | ≥10 g |
| pamidronic acid | lysine | ≥1.5 g | risedronic acid | lysine | ≥10 g |
| alendronic acid | lysine | ≥1.5 g | ibandronic acid | lysine | ≥10 g |
| risedronic acid | lysine | ≥1.5 g | abacavir | glycine | ≥10 g |
| ibandronic acid | lysine | ≥1.5 g | acarbose | glycine | ≥10 g |
| abacavir | glycine | ≥1.5 g | acetazolamide | glycine | ≥10 g |
| acarbose | glycine | ≥1.5 g | acyclovir | glycine | ≥10 g |
| acetazolamide | glycine | ≥1.5 g | albuterol (salbutamol) | glycine | ≥10 g |
| acyclovir | glycine | ≥1.5 g | allopurinol | glycine | ≥10 g |
| albuterol (salbutamol) | glycine | ≥1.5 g | amiloride | glycine | ≥10 g |
| allopurinol | glycine | ≥1.5 g | amisulpride | glycine | ≥10 g |
| amiloride | glycine | ≥1.5 g | amlodipine | glycine | ≥10 g |
| amisulpride | glycine | ≥1.5 g | amoxicillin | glycine | ≥10 g |
| amlodipine | glycine | ≥1.5 g | amphetamine | glycine | ≥10 g |
| amoxicillin | glycine | ≥1.5 g | atenolol | glycine | ≥10 g |
| amphetamine | glycine | ≥1.5 g | atropine | glycine | ≥10 g |
| atenolol | glycine | ≥1.5 g | azathioprine | glycine | ≥10 g |
| atropine | glycine | ≥1.5 g | benserazide | glycine | ≥10 g |
| azathioprine | glycine | ≥1.5 g | benznidazole | glycine | ≥10 g |
| benserazide | glycine | ≥1.5 g | camostat | glycine | ≥10 g |
| benznidazole | glycine | ≥1.5 g | captopril | glycine | ≥10 g |
| camostat | glycine | ≥1.5 g | cefdinir | glycine | ≥10 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| captopril | glycine | ≥1.5 g | cefotiam hexetil hydrochloride | glycine | ≥10 g |
| cefdinir | glycine | ≥1.5 g | cefprozil | glycine | ≥10 g |
| cefotiam hexetil hydrochloride | glycine | ≥1.5 g | cefuroxime axetil | glycine | ≥10 g |
| cefprozil | glycine | ≥1.5 g | chloramphenicol | glycine | ≥10 g |
| cefuroxime axetil | glycine | ≥1.5 g | cimetidine | glycine | ≥10 g |
| chloramphenicol | glycine | ≥1.5 g | ciprofloxacin | glycine | ≥10 g |
| cimetidine | glycine | ≥1.5 g | codeine | glycine | ≥10 g |
| ciprofloxacin | glycine | ≥1.5 g | colchicine | glycine | ≥10 g |
| codeine | glycine | ≥1.5 g | cyclophosphamide | glycine | ≥10 g |
| colchicine | glycine | ≥1.5 g | dapsone | glycine | ≥10 g |
| cyclophosphamide | glycine | ≥1.5 g | dexamethasone | glycine | ≥10 g |
| dapsone | glycine | ≥1.5 g | didanosine | glycine | ≥10 g |
| dexamethasone | glycine | ≥1.5 g | diethylcarbamazine | glycine | ≥10 g |
| didanosine | glycine | ≥1.5 g | methionine | glycine | ≥10 g |
| diethylcarbamazine | glycine | ≥1.5 g | dolasetron | glycine | ≥10 g |
| methionine | glycine | ≥1.5 g | doxifluridine | glycine | ≥10 g |
| dolasetron | glycine | ≥1.5 g | doxycycline | glycine | ≥10 g |
| doxifluridine | glycine | ≥1.5 g | ergonovine | glycine | ≥10 g |
| doxycycline | glycine | ≥1.5 g | erythromycin ethylsuccinate | glycine | ≥10 g |
| ergonovine | glycine | ≥1.5 g | ethambutol | glycine | ≥10 g |
| erythromycin ethylsuccinate | glycine | ≥1.5 g | ethosuximide | glycine | ≥10 g |
| ethambutol | glycine | ≥1.5 g | famotidine | glycine | ≥10 g |
| ethosuximide | glycine | ≥1.5 g | fluconazole | glycine | ≥10 g |
| famotidine | glycine | ≥1.5 g | folic acid | glycine | ≥10 g |
| fluconazole | glycine | ≥1.5 g | furosemide | glycine | ≥10 g |
| folic acid | glycine | ≥1.5 g | fursultiamine | glycine | ≥10 g |
| furosemide | glycine | ≥1.5 g | gabapentin | glycine | ≥10 g |
| fursultiamine | glycine | ≥1.5 g | glipizide | glycine | ≥10 g |
| gabapentin | glycine | ≥1.5 g | granisetron | glycine | ≥10 g |
| glipizide | glycine | ≥1.5 g | griseofulvin | glycine | ≥10 g |
| granisetron | glycine | ≥1.5 g | hydralazine | glycine | ≥10 g |
| griseofulvin | glycine | ≥1.5 g | hydrochlorothiazide | glycine | ≥10 g |
| hydralazine | glycine | ≥1.5 g | imidapril | glycine | ≥10 g |
| hydrochlorothiazide | glycine | ≥1.5 g | isoniazid | glycine | ≥10 g |
| imidapril | glycine | ≥1.5 g | lamivudine | glycine | ≥10 g |
| isoniazid | glycine | ≥1.5 g | l-carbocysteine | glycine | ≥10 g |
| lamivudine | glycine | ≥1.5 g | levetiracetam | glycine | ≥10 g |
| l-carbocysteine | glycine | ≥1.5 g | levofloxacin | glycine | ≥10 g |
| levetiracetam | glycine | ≥1.5 g | linezolid | glycine | ≥10 g |
| levofloxacin | glycine | ≥1.5 g | lisinopril | glycine | ≥10 g |
| linezolid | glycine | ≥1.5 g | losartan | glycine | ≥10 g |
| lisinopril | glycine | ≥1.5 g | methotrexate | glycine | ≥10 g |
| losartan | glycine | ≥1.5 g | methyldopa | glycine | ≥10 g |
| methotrexate | glycine | ≥1.5 g | s-methylmethionine | glycine | ≥10 g |
| methyldopa | glycine | ≥1.5 g | metoclopramide | glycine | ≥10 g |
| s-methylmethionine | glycine | ≥1.5 g | metronidazole | glycine | ≥10 g |
| metoclopramide | glycine | ≥1.5 g | moxifloxacin | glycine | ≥10 g |
| metronidazole | glycine | ≥1.5 g | nalidixic acid | glycine | ≥10 g |
| moxifloxacin | glycine | ≥1.5 g | nicorandil | glycine | ≥10 g |
| nalidixic acid | glycine | ≥1.5 g | nifurtimox | glycine | ≥10 g |
| nicorandil | glycine | ≥1.5 g | nitrofurantoin | glycine | ≥10 g |
| nifurtimox | glycine | ≥1.5 g | nizatidine | glycine | ≥10 g |
| nitrofurantoin | glycine | ≥1.5 g | nystatin | glycine | ≥10 g |
| nizatidine | glycine | ≥1.5 g | ondansetron | glycine | ≥10 g |
| nystatin | glycine | ≥1.5 g | oseltamivir | glycine | ≥10 g |
| ondansetron | glycine | ≥1.5 g | oxcarbazepine | glycine | ≥10 g |
| oseltamivir | glycine | ≥1.5 g | penicillamine | glycine | ≥10 g |
| oxcarbazepine | glycine | ≥1.5 g | perindopril | glycine | ≥10 g |
| penicillamine | glycine | ≥1.5 g | phenobarbital | glycine | ≥10 g |
| perindopril | glycine | ≥1.5 g | phenoxymethylpenicillin | glycine | ≥10 g |
| phenobarbital | glycine | ≥1.5 g | pravastatin sodium | glycine | ≥10 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| phenoxymethylpenicillin | glycine | ≥1.5 g | prednisolone | glycine | ≥10 g |
| pravastatin sodium | glycine | ≥1.5 g | primaquine | glycine | ≥10 g |
| prednisolone | glycine | ≥1.5 g | procaterol | glycine | ≥10 g |
| primaquine | glycine | ≥1.5 g | propylthiouracil | glycine | ≥10 g |
| procaterol | glycine | ≥1.5 g | pseudoephedrine | glycine | ≥10 g |
| propylthiouracil | glycine | ≥1.5 g | pyrazinamide | glycine | ≥10 g |
| pseudoephedrine | glycine | ≥1.5 g | pyridostigmine bromide | glycine | ≥10 g |
| pyrazinamide | glycine | ≥1.5 g | pyridoxine hydrochloride | glycine | ≥10 g |
| pyridostigmine bromide | glycine | ≥1.5 g | ranitidine | glycine | ≥10 g |
| pyridoxine hydrochloride | glycine | ≥1.5 g | ribavirin | glycine | ≥10 g |
| ranitidine | glycine | ≥1.5 g | riboflavin | glycine | ≥10 g |
| ribavirin | glycine | ≥1.5 g | rizatriptan | glycine | ≥10 g |
| riboflavin | glycine | ≥1.5 g | stavudine | glycine | ≥10 g |
| rizatriptan | glycine | ≥1.5 g | sulfadiazine | glycine | ≥10 g |
| stavudine | glycine | ≥1.5 g | sulfamethoxazole | glycine | ≥10 g |
| sulfadiazine | glycine | ≥1.5 g | sultamicillin | glycine | ≥10 g |
| sulfamethoxazole | glycine | ≥1.5 g | sumatriptan | glycine | ≥10 g |
| sultamicillin | glycine | ≥1.5 g | taltirelin | glycine | ≥10 g |
| sumatriptan | glycine | ≥1.5 g | tegafur | glycine | ≥10 g |
| taltirelin | glycine | ≥1.5 g | tenofovir disoproxil | glycine | ≥10 g |
| tegafur | glycine | ≥1.5 g | theophylline | glycine | ≥10 g |
| tenofovir disoproxil | glycine | ≥1.5 g | thiamine | glycine | ≥10 g |
| theophylline | glycine | ≥1.5 g | trimetazidine | glycine | ≥10 g |
| thiamine | glycine | ≥1.5 g | trimethoprim | glycine | ≥10 g |
| trimetazidine | glycine | ≥1.5 g | voglibose | glycine | ≥10 g |
| trimethoprim | glycine | ≥1.5 g | zidovudine | glycine | ≥10 g |
| voglibose | glycine | ≥1.5 g | zolmitriptan | glycine | ≥10 g |
| zidovudine | glycine | ≥1.5 g | acetylcarnitine | glycine | ≥10 g |
| zolmitriptan | glycine | ≥1.5 g | capecitabine | glycine | ≥10 g |
| acetylcarnitine | glycine | ≥1.5 g | cefaclor | glycine | ≥10 g |
| capecitabine | glycine | ≥1.5 g | cefixime | glycine | ≥10 g |
| cefaclor | glycine | ≥1.5 g | cefmetazole | glycine | ≥10 g |
| cefixime | glycine | ≥1.5 g | cefpodoxime proxetil | glycine | ≥10 g |
| cefmetazole | glycine | ≥1.5 g | cefroxadine | glycine | ≥10 g |
| cefpodoxime proxetil | glycine | ≥1.5 g | alfoscerate | glycine | ≥10 g |
| cefroxadine | glycine | ≥1.5 g | cilazapril | glycine | ≥10 g |
| alfoscerate | glycine | ≥1.5 g | cimetropium bromide | glycine | ≥10 g |
| cilazapril | glycine | ≥1.5 g | diacerein | glycine | ≥10 g |
| cimetropium bromide | glycine | ≥1.5 g | erdosteine | glycine | ≥10 g |
| diacerein | glycine | ≥1.5 g | famciclovir | glycine | ≥10 g |
| erdosteine | glycine | ≥1.5 g | gemifloxacin | glycine | ≥10 g |
| famciclovir | glycine | ≥1.5 g | levosulpiride | glycine | ≥10 g |
| gemifloxacin | glycine | ≥1.5 g | nabumetone | glycine | ≥10 g |
| levosulpiride | glycine | ≥1.5 g | oxiracetam | glycine | ≥10 g |
| nabumetone | glycine | ≥1.5 g | phendimetrazine | glycine | ≥10 g |
| oxiracetam | glycine | ≥1.5 g | rabeprazole | glycine | ≥10 g |
| phendimetrazine | glycine | ≥1.5 g | roxatidine acetate | glycine | ≥10 g |
| rabeprazole | glycine | ≥1.5 g | tamsulosin | glycine | ≥10 g |
| roxatidine acetate | glycine | ≥1.5 g | terazosin | glycine | ≥10 g |
| tamsulosin | glycine | ≥1.5 g | thioctic | glycine | ≥10 g |
| terazosin | glycine | ≥1.5 g | tosufloxacin | glycine | ≥10 g |
| thioctic | glycine | ≥1.5 g | triflusal | glycine | ≥10 g |
| tosufloxacin | glycine | ≥1.5 g | zaltoprofen | glycine | ≥10 g |
| triflusal | glycine | ≥1.5 g | etidronic acid | glycine | ≥10 g |
| zaltoprofen | glycine | ≥1.5 g | zoledronic acid | glycine | ≥10 g |
| etidronic acid | glycine | ≥1.5 g | clodronic acid | glycine | ≥10 g |
| zoledronic acid | glycine | ≥1.5 g | tiludronic acid | glycine | ≥10 g |
| clodronic acid | glycine | ≥1.5 g | pamidronic acid | glycine | ≥10 g |
| tiludronic acid | glycine | ≥1.5 g | alendronic acid | glycine | ≥10 g |
| pamidronic acid | glycine | ≥1.5 g | risedronic acid | glycine | ≥10 g |
| alendronic acid | glycine | ≥1.5 g | ibandronic acid | glycine | ≥10 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| risedronic acid | glycine | ≥1.5 g | abacavir | lysine | ≥15 g |
| ibandronic acid | glycine | ≥1.5 g | acarbose | lysine | ≥15 g |
| abacavir | lysine | ≥1.75 g | acetazolamide | lysine | ≥15 g |
| acarbose | lysine | ≥1.75 g | acyclovir | lysine | ≥15 g |
| acetazolamide | lysine | ≥1.75 g | albuterol (salbutamol) | lysine | ≥15 g |
| acyclovir | lysine | ≥1.75 g | allopurinol | lysine | ≥15 g |
| albuterol (salbutamol) | lysine | ≥1.75 g | amiloride | lysine | ≥15 g |
| allopurinol | lysine | ≥1.75 g | amisulpride | lysine | ≥15 g |
| amiloride | lysine | ≥1.75 g | amlodipine | lysine | ≥15 g |
| amisulpride | lysine | ≥1.75 g | amoxicillin | lysine | ≥15 g |
| amlodipine | lysine | ≥1.75 g | amphetamine | lysine | ≥15 g |
| amoxicillin | lysine | ≥1.75 g | atenolol | lysine | ≥15 g |
| amphetamine | lysine | ≥1.75 g | atropine | lysine | ≥15 g |
| atenolol | lysine | ≥1.75 g | azathioprine | lysine | ≥15 g |
| atropine | lysine | ≥1.75 g | benserazide | lysine | ≥15 g |
| azathioprine | lysine | ≥1.75 g | benznidazole | lysine | ≥15 g |
| benserazide | lysine | ≥1.75 g | camostat | lysine | ≥15 g |
| benznidazole | lysine | ≥1.75 g | captopril | lysine | ≥15 g |
| camostat | lysine | ≥1.75 g | cefdinir | lysine | ≥15 g |
| captopril | lysine | ≥1.75 g | cefotiam hexetil hydrochloride | lysine | ≥15 g |
| cefdinir | lysine | ≥1.75 g | cefprozil | lysine | ≥15 g |
| cefotiam hexetil hydrochloride | lysine | ≥1.75 g | cefuroxime axetil | lysine | ≥15 g |
| cefprozil | lysine | ≥1.75 g | chloramphenicol | lysine | ≥15 g |
| cefuroxime axetil | lysine | ≥1.75 g | cimetidine | lysine | ≥15 g |
| chloramphenicol | lysine | ≥1.75 g | ciprofloxacin | lysine | ≥15 g |
| cimetidine | lysine | ≥1.75 g | codeine | lysine | ≥15 g |
| ciprofloxacin | lysine | ≥1.75 g | colchicine | lysine | ≥15 g |
| codeine | lysine | ≥1.75 g | cyclophosphamide | lysine | ≥15 g |
| colchicine | lysine | ≥1.75 g | dapsone | lysine | ≥15 g |
| cyclophosphamide | lysine | ≥1.75 g | dexamethasone | lysine | ≥15 g |
| dapsone | lysine | ≥1.75 g | didanosine | lysine | ≥15 g |
| dexamethasone | lysine | ≥1.75 g | diethylcarbamazine | lysine | ≥15 g |
| didanosine | lysine | ≥1.75 g | methionine | lysine | ≥15 g |
| diethylcarbamazine | lysine | ≥1.75 g | dolasetron | lysine | ≥15 g |
| methionine | lysine | ≥1.75 g | doxifluridine | lysine | ≥15 g |
| dolasetron | lysine | ≥1.75 g | doxycycline | lysine | ≥15 g |
| doxifluridine | lysine | ≥1.75 g | ergonovine | lysine | ≥15 g |
| doxycycline | lysine | ≥1.75 g | erythromycin ethylsuccinate | lysine | ≥15 g |
| ergonovine | lysine | ≥1.75 g | ethambutol | lysine | ≥15 g |
| erythromycin ethylsuccinate | lysine | ≥1.75 g | ethosuximide | lysine | ≥15 g |
| ethambutol | lysine | ≥1.75 g | famotidine | lysine | ≥15 g |
| ethosuximide | lysine | ≥1.75 g | fluconazole | lysine | ≥15 g |
| famotidine | lysine | ≥1.75 g | folic acid | lysine | ≥15 g |
| fluconazole | lysine | ≥1.75 g | furosemide | lysine | ≥15 g |
| folic acid | lysine | ≥1.75 g | fursultiamine | lysine | ≥15 g |
| furosemide | lysine | ≥1.75 g | gabapentin | lysine | ≥15 g |
| fursultiamine | lysine | ≥1.75 g | glipizide | lysine | ≥15 g |
| gabapentin | lysine | ≥1.75 g | granisetron | lysine | ≥15 g |
| glipizide | lysine | ≥1.75 g | griseofulvin | lysine | ≥15 g |
| granisetron | lysine | ≥1.75 g | hydralazine | lysine | ≥15 g |
| griseofulvin | lysine | ≥1.75 g | hydrochlorothiazide | lysine | ≥15 g |
| hydralazine | lysine | ≥1.75 g | imidapril | lysine | ≥15 g |
| hydrochlorothiazide | lysine | ≥1.75 g | isoniazid | lysine | ≥15 g |
| imidapril | lysine | ≥1.75 g | lamivudine | lysine | ≥15 g |
| isoniazid | lysine | ≥1.75 g | l-carbocysteine | lysine | ≥15 g |
| lamivudine | lysine | ≥1.75 g | levetiracetam | lysine | ≥15 g |
| l-carbocysteine | lysine | ≥1.75 g | levofloxacin | lysine | ≥15 g |
| levetiracetam | lysine | ≥1.75 g | linezolid | lysine | ≥15 g |
| levofloxacin | lysine | ≥1.75 g | lisinopril | lysine | ≥15 g |
| linezolid | lysine | ≥1.75 g | losartan | lysine | ≥15 g |
| lisinopril | lysine | ≥1.75 g | methotrexate | lysine | ≥15 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| losartan | lysine | ≥1.75 g | methyldopa | lysine | ≥15 g |
| methotrexate | lysine | ≥1.75 g | s-methylmethionine | lysine | ≥15 g |
| methyldopa | lysine | ≥1.75 g | metoclopramide | lysine | ≥15 g |
| s-methylmethionine | lysine | ≥1.75 g | metronidazole | lysine | ≥15 g |
| metoclopramide | lysine | ≥1.75 g | moxifloxacin | lysine | ≥15 g |
| metronidazole | lysine | ≥1.75 g | nalidixic acid | lysine | ≥15 g |
| moxifloxacin | lysine | ≥1.75 g | nicorandil | lysine | ≥15 g |
| nalidixic acid | lysine | ≥1.75 g | nifurtimox | lysine | ≥15 g |
| nicorandil | lysine | ≥1.75 g | nitrofurantoin | lysine | ≥15 g |
| nifurtimox | lysine | ≥1.75 g | nizatidine | lysine | ≥15 g |
| nitrofurantoin | lysine | ≥1.75 g | nystatin | lysine | ≥15 g |
| nizatidine | lysine | ≥1.75 g | ondansetron | lysine | ≥15 g |
| nystatin | lysine | ≥1.75 g | oseltamivir | lysine | ≥15 g |
| ondansetron | lysine | ≥1.75 g | oxcarbazepine | lysine | ≥15 g |
| oseltamivir | lysine | ≥1.75 g | penicillamine | lysine | ≥15 g |
| oxcarbazepine | lysine | ≥1.75 g | perindopril | lysine | ≥15 g |
| penicillamine | lysine | ≥1.75 g | phenobarbital | lysine | ≥15 g |
| perindopril | lysine | ≥1.75 g | phenoxymethylpenicillin | lysine | ≥15 g |
| phenobarbital | lysine | ≥1.75 g | pravastatin sodium | lysine | ≥15 g |
| phenoxymethylpenicillin | lysine | ≥1.75 g | prednisolone | lysine | ≥15 g |
| pravastatin sodium | lysine | ≥1.75 g | primaquine | lysine | ≥15 g |
| prednisolone | lysine | ≥1.75 g | procaterol | lysine | ≥15 g |
| primaquine | lysine | ≥1.75 g | propylthiouracil | lysine | ≥15 g |
| procaterol | lysine | ≥1.75 g | pseudoephedrine | lysine | ≥15 g |
| propylthiouracil | lysine | ≥1.75 g | pyrazinamide | lysine | ≥15 g |
| pseudoephedrine | lysine | ≥1.75 g | pyridostigmine bromide | lysine | ≥15 g |
| pyrazinamide | lysine | ≥1.75 g | pyridoxine hydrochloride | lysine | ≥15 g |
| pyridostigmine bromide | lysine | ≥1.75 g | ranitidine | lysine | ≥15 g |
| pyridoxine hydrochloride | lysine | ≥1.75 g | ribavirin | lysine | ≥15 g |
| ranitidine | lysine | ≥1.75 g | riboflavin | lysine | ≥15 g |
| ribavirin | lysine | ≥1.75 g | rizatriptan | lysine | ≥15 g |
| riboflavin | lysine | ≥1.75 g | stavudine | lysine | ≥15 g |
| rizatriptan | lysine | ≥1.75 g | sulfadiazine | lysine | ≥15 g |
| stavudine | lysine | ≥1.75 g | sulfamethoxazole | lysine | ≥15 g |
| sulfadiazine | lysine | ≥1.75 g | sultamicillin | lysine | ≥15 g |
| sulfamethoxazole | lysine | ≥1.75 g | sumatriptan | lysine | ≥15 g |
| sultamicillin | lysine | ≥1.75 g | taltirelin | lysine | ≥15 g |
| sumatriptan | lysine | ≥1.75 g | tegafur | lysine | ≥15 g |
| taltirelin | lysine | ≥1.75 g | tenofovir disoproxil | lysine | ≥15 g |
| tegafur | lysine | ≥1.75 g | theophylline | lysine | ≥15 g |
| tenofovir disoproxil | lysine | ≥1.75 g | thiamine | lysine | ≥15 g |
| theophylline | lysine | ≥1.75 g | trimetazidine | lysine | ≥15 g |
| thiamine | lysine | ≥1.75 g | trimethoprim | lysine | ≥15 g |
| trimetazidine | lysine | ≥1.75 g | voglibose | lysine | ≥15 g |
| trimethoprim | lysine | ≥1.75 g | zidovudine | lysine | ≥15 g |
| voglibose | lysine | ≥1.75 g | zolmitriptan | lysine | ≥15 g |
| zidovudine | lysine | ≥1.75 g | acetylcarnitine | lysine | ≥15 g |
| zolmitriptan | lysine | ≥1.75 g | capecitabine | lysine | ≥15 g |
| acetylcarnitine | lysine | ≥1.75 g | cefaclor | lysine | ≥15 g |
| capecitabine | lysine | ≥1.75 g | cefixime | lysine | ≥15 g |
| cefaclor | lysine | ≥1.75 g | cefmetazole | lysine | ≥15 g |
| cefixime | lysine | ≥1.75 g | cefpodoxime proxetil | lysine | ≥15 g |
| cefmetazole | lysine | ≥1.75 g | cefroxadine | lysine | ≥15 g |
| cefpodoxime proxetil | lysine | ≥1.75 g | alfoscerate | lysine | ≥15 g |
| cefroxadine | lysine | ≥1.75 g | cilazapril | lysine | ≥15 g |
| alfoscerate | lysine | ≥1.75 g | cimetropium bromide | lysine | ≥15 g |
| cilazapril | lysine | ≥1.75 g | diacerein | lysine | ≥15 g |
| cimetropium bromide | lysine | ≥1.75 g | erdosteine | lysine | ≥15 g |
| diacerein | lysine | ≥1.75 g | famciclovir | lysine | ≥15 g |
| erdosteine | lysine | ≥1.75 g | gemifloxacin | lysine | ≥15 g |
| famciclovir | lysine | ≥1.75 g | levosulpiride | lysine | ≥15 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| gemifloxacin | lysine | ≥1.75 g | nabumetone | lysine | ≥15 g |
| levosulpiride | lysine | ≥1.75 g | oxiracetam | lysine | ≥15 g |
| nabumetone | lysine | ≥1.75 g | phendimetrazine | lysine | ≥15 g |
| oxiracetam | lysine | ≥1.75 g | rabeprazole | lysine | ≥15 g |
| phendimetrazine | lysine | ≥1.75 g | roxatidine acetate | lysine | ≥15 g |
| rabeprazole | lysine | ≥1.75 g | tamsulosin | lysine | ≥15 g |
| roxatidine acetate | lysine | ≥1.75 g | terazosin | lysine | ≥15 g |
| tamsulosin | lysine | ≥1.75 g | thioctic | lysine | ≥15 g |
| terazosin | lysine | ≥1.75 g | tosufloxacin | lysine | ≥15 g |
| thioctic | lysine | ≥1.75 g | triflusal | lysine | ≥15 g |
| tosufloxacin | lysine | ≥1.75 g | zaltoprofen | lysine | ≥15 g |
| triflusal | lysine | ≥1.75 g | etidronic acid | lysine | ≥15 g |
| zaltoprofen | lysine | ≥1.75 g | zoledronic acid | lysine | ≥15 g |
| etidronic acid | lysine | ≥1.75 g | clodronic acid | lysine | ≥15 g |
| zoledronic acid | lysine | ≥1.75 g | tiludronic acid | lysine | ≥15 g |
| clodronic acid | lysine | ≥1.75 g | pamidronic acid | lysine | ≥15 g |
| tiludronic acid | lysine | ≥1.75 g | alendronic acid | lysine | ≥15 g |
| pamidronic acid | lysine | ≥1.75 g | risedronic acid | lysine | ≥15 g |
| alendronic acid | lysine | ≥1.75 g | ibandronic acid | lysine | ≥15 g |
| risedronic acid | lysine | ≥1.75 g | abacavir | glycine | ≥15 g |
| ibandronic acid | lysine | ≥1.75 g | acarbose | glycine | ≥15 g |
| abacavir | glycine | ≥1.75 g | acetazolamide | glycine | ≥15 g |
| acarbose | glycine | ≥1.75 g | acyclovir | glycine | ≥15 g |
| acetazolamide | glycine | ≥1.75 g | albuterol (salbutamol) | glycine | ≥15 g |
| acyclovir | glycine | ≥1.75 g | allopurinol | glycine | ≥15 g |
| albuterol (salbutamol) | glycine | ≥1.75 g | amiloride | glycine | ≥15 g |
| allopurinol | glycine | ≥1.75 g | amisulpride | glycine | ≥15 g |
| amiloride | glycine | ≥1.75 g | amlodipine | glycine | ≥15 g |
| amisulpride | glycine | ≥1.75 g | amoxicillin | glycine | ≥15 g |
| amlodipine | glycine | ≥1.75 g | amphetamine | glycine | ≥15 g |
| amoxicillin | glycine | ≥1.75 g | atenolol | glycine | ≥15 g |
| amphetamine | glycine | ≥1.75 g | atropine | glycine | ≥15 g |
| atenolol | glycine | ≥1.75 g | azathioprine | glycine | ≥15 g |
| atropine | glycine | ≥1.75 g | benserazide | glycine | ≥15 g |
| azathioprine | glycine | ≥1.75 g | benznidazole | glycine | ≥15 g |
| benserazide | glycine | ≥1.75 g | camostat | glycine | ≥15 g |
| benznidazole | glycine | ≥1.75 g | captopril | glycine | ≥15 g |
| camostat | glycine | ≥1.75 g | cefdinir | glycine | ≥15 g |
| captopril | glycine | ≥1.75 g | cefotiam hexetil hydrochloride | glycine | ≥15 g |
| cefdinir | glycine | ≥1.75 g | cefprozil | glycine | ≥15 g |
| cefotiam hexetil hydrochloride | glycine | ≥1.75 g | cefuroxime axetil | glycine | ≥15 g |
| cefprozil | glycine | ≥1.75 g | chloramphenicol | glycine | ≥15 g |
| cefuroxime axetil | glycine | ≥1.75 g | cimetidine | glycine | ≥15 g |
| chloramphenicol | glycine | ≥1.75 g | ciprofloxacin | glycine | ≥15 g |
| cimetidine | glycine | ≥1.75 g | codeine | glycine | ≥15 g |
| ciprofloxacin | glycine | ≥1.75 g | colchicine | glycine | ≥15 g |
| codeine | glycine | ≥1.75 g | cyclophosphamide | glycine | ≥15 g |
| colchicine | glycine | ≥1.75 g | dapsone | glycine | ≥15 g |
| cyclophosphamide | glycine | ≥1.75 g | dexamethasone | glycine | ≥15 g |
| dapsone | glycine | ≥1.75 g | didanosine | glycine | ≥15 g |
| dexamethasone | glycine | ≥1.75 g | diethylcarbamazine | glycine | ≥15 g |
| didanosine | glycine | ≥1.75 g | methionine | glycine | ≥15 g |
| diethylcarbamazine | glycine | ≥1.75 g | dolasetron | glycine | ≥15 g |
| methionine | glycine | ≥1.75 g | doxifluridine | glycine | ≥15 g |
| dolasetron | glycine | ≥1.75 g | doxycycline | glycine | ≥15 g |
| doxifluridine | glycine | ≥1.75 g | ergonovine | glycine | ≥15 g |
| doxycycline | glycine | ≥1.75 g | erythromycin ethylsuccinate | glycine | ≥15 g |
| ergonovine | glycine | ≥1.75 g | ethambutol | glycine | ≥15 g |
| erythromycin ethylsuccinate | glycine | ≥1.75 g | ethosuximide | glycine | ≥15 g |
| ethambutol | glycine | ≥1.75 g | famotidine | glycine | ≥15 g |
| ethosuximide | glycine | ≥1.75 g | fluconazole | glycine | ≥15 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| famotidine | glycine | ≥1.75 g | folic acid | glycine | ≥15 g |
| fluconazole | glycine | ≥1.75 g | furosemide | glycine | ≥15 g |
| folic acid | glycine | ≥1.75 g | fursultiamine | glycine | ≥15 g |
| furosemide | glycine | ≥1.75 g | gabapentin | glycine | ≥15 g |
| fursultiamine | glycine | ≥1.75 g | glipizide | glycine | ≥15 g |
| gabapentin | glycine | ≥1.75 g | granisetron | glycine | ≥15 g |
| glipizide | glycine | ≥1.75 g | griseofulvin | glycine | ≥15 g |
| granisetron | glycine | ≥1.75 g | hydralazine | glycine | ≥15 g |
| griseofulvin | glycine | ≥1.75 g | hydrochlorothiazide | glycine | ≥15 g |
| hydralazine | glycine | ≥1.75 g | imidapril | glycine | ≥15 g |
| hydrochlorothiazide | glycine | ≥1.75 g | isoniazid | glycine | ≥15 g |
| imidapril | glycine | ≥1.75 g | lamivudine | glycine | ≥15 g |
| isoniazid | glycine | ≥1.75 g | l-carbocysteine | glycine | ≥15 g |
| lamivudine | glycine | ≥1.75 g | levetiracetam | glycine | ≥15 g |
| l-carbocysteine | glycine | ≥1.75 g | levofloxacin | glycine | ≥15 g |
| levetiracetam | glycine | ≥1.75 g | linezolid | glycine | ≥15 g |
| levofloxacin | glycine | ≥1.75 g | lisinopril | glycine | ≥15 g |
| linezolid | glycine | ≥1.75 g | losartan | glycine | ≥15 g |
| lisinopril | glycine | ≥1.75 g | methotrexate | glycine | ≥15 g |
| losartan | glycine | ≥1.75 g | methyldopa | glycine | ≥15 g |
| methotrexate | glycine | ≥1.75 g | s-methylmethionine | glycine | ≥15 g |
| methyldopa | glycine | ≥1.75 g | metoclopramide | glycine | ≥15 g |
| s-methylmethionine | glycine | ≥1.75 g | metronidazole | glycine | ≥15 g |
| metoclopramide | glycine | ≥1.75 g | moxifloxacin | glycine | ≥15 g |
| metronidazole | glycine | ≥1.75 g | nalidixic acid | glycine | ≥15 g |
| moxifloxacin | glycine | ≥1.75 g | nicorandil | glycine | ≥15 g |
| nalidixic acid | glycine | ≥1.75 g | nifurtimox | glycine | ≥15 g |
| nicorandil | glycine | ≥1.75 g | nitrofurantoin | glycine | ≥15 g |
| nifurtimox | glycine | ≥1.75 g | nizatidine | glycine | ≥15 g |
| nitrofurantoin | glycine | ≥1.75 g | nystatin | glycine | ≥15 g |
| nizatidine | glycine | ≥1.75 g | ondansetron | glycine | ≥15 g |
| nystatin | glycine | ≥1.75 g | oseltamivir | glycine | ≥15 g |
| ondansetron | glycine | ≥1.75 g | oxcarbazepine | glycine | ≥15 g |
| oseltamivir | glycine | ≥1.75 g | penicillamine | glycine | ≥15 g |
| oxcarbazepine | glycine | ≥1.75 g | perindopril | glycine | ≥15 g |
| penicillamine | glycine | ≥1.75 g | phenobarbital | glycine | ≥15 g |
| perindopril | glycine | ≥1.75 g | phenoxymethylpenicillin | glycine | ≥15 g |
| phenobarbital | glycine | ≥1.75 g | pravastatin sodium | glycine | ≥15 g |
| phenoxymethylpenicillin | glycine | ≥1.75 g | prednisolone | glycine | ≥15 g |
| pravastatin sodium | glycine | ≥1.75 g | primaquine | glycine | ≥15 g |
| prednisolone | glycine | ≥1.75 g | procaterol | glycine | ≥15 g |
| primaquine | glycine | ≥1.75 g | propylthiouracil | glycine | ≥15 g |
| procaterol | glycine | ≥1.75 g | pseudoephedrine | glycine | ≥15 g |
| propylthiouracil | glycine | ≥1.75 g | pyrazinamide | glycine | ≥15 g |
| pseudoephedrine | glycine | ≥1.75 g | pyridostigmine bromide | glycine | ≥15 g |
| pyrazinamide | glycine | ≥1.75 g | pyridoxine hydrochloride | glycine | ≥15 g |
| pyridostigmine bromide | glycine | ≥1.75 g | ranitidine | glycine | ≥15 g |
| pyridoxine hydrochloride | glycine | ≥1.75 g | ribavirin | glycine | ≥15 g |
| ranitidine | glycine | ≥1.75 g | riboflavin | glycine | ≥15 g |
| ribavirin | glycine | ≥1.75 g | rizatriptan | glycine | ≥15 g |
| riboflavin | glycine | ≥1.75 g | stavudine | glycine | ≥15 g |
| rizatriptan | glycine | ≥1.75 g | sulfadiazine | glycine | ≥15 g |
| stavudine | glycine | ≥1.75 g | sulfamethoxazole | glycine | ≥15 g |
| sulfadiazine | glycine | ≥1.75 g | sultamicillin | glycine | ≥15 g |
| sulfamethoxazole | glycine | ≥1.75 g | sumatriptan | glycine | ≥15 g |
| sultamicillin | glycine | ≥1.75 g | taltirelin | glycine | ≥15 g |
| sumatriptan | glycine | ≥1.75 g | tegafur | glycine | ≥15 g |
| taltirelin | glycine | ≥1.75 g | tenofovir disoproxil | glycine | ≥15 g |
| tegafur | glycine | ≥1.75 g | theophylline | glycine | ≥15 g |
| tenofovir disoproxil | glycine | ≥1.75 g | thiamine | glycine | ≥15 g |
| theophylline | glycine | ≥1.75 g | trimetazidine | glycine | ≥15 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| thiamine | glycine | ≥1.75 g | trimethoprim | glycine | ≥15 g |
| trimetazidine | glycine | ≥1.75 g | voglibose | glycine | ≥15 g |
| trimethoprim | glycine | ≥1.75 g | zidovudine | glycine | ≥15 g |
| voglibose | glycine | ≥1.75 g | zolmitriptan | glycine | ≥15 g |
| zidovudine | glycine | ≥1.75 g | acetylcarnitine | glycine | ≥15 g |
| zolmitriptan | glycine | ≥1.75 g | capecitabine | glycine | ≥15 g |
| acetylcarnitine | glycine | ≥1.75 g | cefaclor | glycine | ≥15 g |
| capecitabine | glycine | ≥1.75 g | cefixime | glycine | ≥15 g |
| cefaclor | glycine | ≥1.75 g | cefmetazole | glycine | ≥15 g |
| cefixime | glycine | ≥1.75 g | cefpodoxime proxetil | glycine | ≥15 g |
| cefmetazole | glycine | ≥1.75 g | cefroxadine | glycine | ≥15 g |
| cefpodoxime proxetil | glycine | ≥1.75 g | alfoscerate | glycine | ≥15 g |
| cefroxadine | glycine | ≥1.75 g | cilazapril | glycine | ≥15 g |
| alfoscerate | glycine | ≥1.75 g | cimetropium bromide | glycine | ≥15 g |
| cilazapril | glycine | ≥1.75 g | diacerein | glycine | ≥15 g |
| cimetropium bromide | glycine | ≥1.75 g | erdosteine | glycine | ≥15 g |
| diacerein | glycine | ≥1.75 g | famciclovir | glycine | ≥15 g |
| erdosteine | glycine | ≥1.75 g | gemifloxacin | glycine | ≥15 g |
| famciclovir | glycine | ≥1.75 g | levosulpiride | glycine | ≥15 g |
| gemifloxacin | glycine | ≥1.75 g | nabumetone | glycine | ≥15 g |
| levosulpiride | glycine | ≥1.75 g | oxiracetam | glycine | ≥15 g |
| nabumetone | glycine | ≥1.75 g | phendimetrazine | glycine | ≥15 g |
| oxiracetam | glycine | ≥1.75 g | rabeprazole | glycine | ≥15 g |
| phendimetrazine | glycine | ≥1.75 g | roxatidine acetate | glycine | ≥15 g |
| rabeprazole | glycine | ≥1.75 g | tamsulosin | glycine | ≥15 g |
| roxatidine acetate | glycine | ≥1.75 g | terazosin | glycine | ≥15 g |
| tamsulosin | glycine | ≥1.75 g | thioctic | glycine | ≥15 g |
| terazosin | glycine | ≥1.75 g | tosufloxacin | glycine | ≥15 g |
| thioctic | glycine | ≥1.75 g | triflusal | glycine | ≥15 g |
| tosufloxacin | glycine | ≥1.75 g | zaltoprofen | glycine | ≥15 g |
| triflusal | glycine | ≥1.75 g | etidronic acid | glycine | ≥15 g |
| zaltoprofen | glycine | ≥1.75 g | zoledronic acid | glycine | ≥15 g |
| etidronic acid | glycine | ≥1.75 g | clodronic acid | glycine | ≥15 g |
| zoledronic acid | glycine | ≥1.75 g | tiludronic acid | glycine | ≥15 g |
| clodronic acid | glycine | ≥1.75 g | pamidronic acid | glycine | ≥15 g |
| tiludronic acid | glycine | ≥1.75 g | alendronic acid | glycine | ≥15 g |
| pamidronic acid | glycine | ≥1.75 g | risedronic acid | glycine | ≥15 g |
| alendronic acid | glycine | ≥1.75 g | ibandronic acid | glycine | ≥15 g |
| risedronic acid | glycine | ≥1.75 g | abacavir | lysine | 5 g to 20 g |
| ibandronic acid | glycine | ≥1.75 g | acarbose | lysine | 5 g to 20 g |
| abacavir | lysine | ≥2 g | acetazolamide | lysine | 5 g to 20 g |
| acarbose | lysine | ≥2 g | acyclovir | lysine | 5 g to 20 g |
| acetazolamide | lysine | ≥2 g | albuterol (salbutamol) | lysine | 5 g to 20 g |
| acyclovir | lysine | ≥2 g | allopurinol | lysine | 5 g to 20 g |
| albuterol (salbutamol) | lysine | ≥2 g | amiloride | lysine | 5 g to 20 g |
| allopurinol | lysine | ≥2 g | amisulpride | lysine | 5 g to 20 g |
| amiloride | lysine | ≥2 g | amlodipine | lysine | 5 g to 20 g |
| amisulpride | lysine | ≥2 g | amoxicillin | lysine | 5 g to 20 g |
| amlodipine | lysine | ≥2 g | amphetamine | lysine | 5 g to 20 g |
| amoxicillin | lysine | ≥2 g | atenolol | lysine | 5 g to 20 g |
| amphetamine | lysine | ≥2 g | atropine | lysine | 5 g to 20 g |
| atenolol | lysine | ≥2 g | azathioprine | lysine | 5 g to 20 g |
| atropine | lysine | ≥2 g | benserazide | lysine | 5 g to 20 g |
| azathioprine | lysine | ≥2 g | benznidazole | lysine | 5 g to 20 g |
| benserazide | lysine | ≥2 g | camostat | lysine | 5 g to 20 g |
| benznidazole | lysine | ≥2 g | captopril | lysine | 5 g to 20 g |
| camostat | lysine | ≥2 g | cefdinir | lysine | 5 g to 20 g |
| captopril | lysine | ≥2 g | cefotiam hexetil hydrochloride | lysine | 5 g to 20 g |
| cefdinir | lysine | ≥2 g | cefprozil | lysine | 5 g to 20 g |
| cefotiam hexetil hydrochloride | lysine | ≥2 g | cefuroxime axetil | lysine | 5 g to 20 g |
| cefprozil | lysine | ≥2 g | chloramphenicol | lysine | 5 g to 20 g |
| cefuroxime axetil | lysine | ≥2 g | cimetidine | lysine | 5 g to 20 g |
| chloramphenicol | lysine | ≥2 g | ciprofloxacin | lysine | 5 g to 20 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| cimetidine | lysine | ≥2 g | codeine | lysine | 5 g to 20 g |
| ciprofloxacin | lysine | ≥2 g | colchicine | lysine | 5 g to 20 g |
| codeine | lysine | ≥2 g | cyclophosphamide | lysine | 5 g to 20 g |
| colchicine | lysine | ≥2 g | dapsone | lysine | 5 g to 20 g |
| cyclophosphamide | lysine | ≥2 g | dexamethasone | lysine | 5 g to 20 g |
| dapsone | lysine | ≥2 g | didanosine | lysine | 5 g to 20 g |
| dexamethasone | lysine | ≥2 g | diethylcarbamazine | lysine | 5 g to 20 g |
| didanosine | lysine | ≥2 g | methionine | lysine | 5 g to 20 g |
| diethylcarbamazine | lysine | ≥2 g | dolasetron | lysine | 5 g to 20 g |
| methionine | lysine | ≥2 g | doxifluridine | lysine | 5 g to 20 g |
| dolasetron | lysine | ≥2 g | doxycycline | lysine | 5 g to 20 g |
| doxifluridine | lysine | ≥2 g | ergonovine | lysine | 5 g to 20 g |
| doxycycline | lysine | ≥2 g | erythromycin ethylsuccinate | lysine | 5 g to 20 g |
| ergonovine | lysine | ≥2 g | ethambutol | lysine | 5 g to 20 g |
| erythromycin ethylsuccinate | lysine | ≥2 g | ethosuximide | lysine | 5 g to 20 g |
| ethambutol | lysine | ≥2 g | famotidine | lysine | 5 g to 20 g |
| ethosuximide | lysine | ≥2 g | fluconazole | lysine | 5 g to 20 g |
| famotidine | lysine | ≥2 g | folic acid | lysine | 5 g to 20 g |
| fluconazole | lysine | ≥2 g | furosemide | lysine | 5 g to 20 g |
| folic acid | lysine | ≥2 g | fursultiamine | lysine | 5 g to 20 g |
| furosemide | lysine | ≥2 g | gabapentin | lysine | 5 g to 20 g |
| fursultiamine | lysine | ≥2 g | glipizide | lysine | 5 g to 20 g |
| gabapentin | lysine | ≥2 g | granisetron | lysine | 5 g to 20 g |
| glipizide | lysine | ≥2 g | griseofulvin | lysine | 5 g to 20 g |
| granisetron | lysine | ≥2 g | hydralazine | lysine | 5 g to 20 g |
| griseofulvin | lysine | ≥2 g | hydrochlorothiazide | lysine | 5 g to 20 g |
| hydralazine | lysine | ≥2 g | imidapril | lysine | 5 g to 20 g |
| hydrochlorothiazide | lysine | ≥2 g | isoniazid | lysine | 5 g to 20 g |
| imidapril | lysine | ≥2 g | lamivudine | lysine | 5 g to 20 g |
| isoniazid | lysine | ≥2 g | l-carbocysteine | lysine | 5 g to 20 g |
| lamivudine | lysine | ≥2 g | levetiracetam | lysine | 5 g to 20 g |
| l-carbocysteine | lysine | ≥2 g | levofloxacin | lysine | 5 g to 20 g |
| levetiracetam | lysine | ≥2 g | linezolid | lysine | 5 g to 20 g |
| levofloxacin | lysine | ≥2 g | lisinopril | lysine | 5 g to 20 g |
| linezolid | lysine | ≥2 g | losartan | lysine | 5 g to 20 g |
| lisinopril | lysine | ≥2 g | methotrexate | lysine | 5 g to 20 g |
| losartan | lysine | ≥2 g | methyldopa | lysine | 5 g to 20 g |
| methotrexate | lysine | ≥2 g | s-methylmethionine | lysine | 5 g to 20 g |
| methyldopa | lysine | ≥2 g | metoclopramide | lysine | 5 g to 20 g |
| s-methylmethionine | lysine | ≥2 g | metronidazole | lysine | 5 g to 20 g |
| metoclopramide | lysine | ≥2 g | moxifloxacin | lysine | 5 g to 20 g |
| metronidazole | lysine | ≥2 g | nalidixic acid | lysine | 5 g to 20 g |
| moxifloxacin | lysine | ≥2 g | nicorandil | lysine | 5 g to 20 g |
| nalidixic acid | lysine | ≥2 g | nifurtimox | lysine | 5 g to 20 g |
| nicorandil | lysine | ≥2 g | nitrofurantoin | lysine | 5 g to 20 g |
| nifurtimox | lysine | ≥2 g | nizatidine | lysine | 5 g to 20 g |
| nitrofurantoin | lysine | ≥2 g | nystatin | lysine | 5 g to 20 g |
| nizatidine | lysine | ≥2 g | ondansetron | lysine | 5 g to 20 g |
| nystatin | lysine | ≥2 g | oseltamivir | lysine | 5 g to 20 g |
| ondansetron | lysine | ≥2 g | oxcarbazepine | lysine | 5 g to 20 g |
| oseltamivir | lysine | ≥2 g | penicillamine | lysine | 5 g to 20 g |
| oxcarbazepine | lysine | ≥2 g | perindopril | lysine | 5 g to 20 g |
| penicillamine | lysine | ≥2 g | phenobarbital | lysine | 5 g to 20 g |
| perindopril | lysine | ≥2 g | phenoxymethylpenicillin | lysine | 5 g to 20 g |
| phenobarbital | lysine | ≥2 g | pravastatin sodium | lysine | 5 g to 20 g |
| phenoxymethylpenicillin | lysine | ≥2 g | prednisolone | lysine | 5 g to 20 g |
| pravastatin sodium | lysine | ≥2 g | primaquine | lysine | 5 g to 20 g |
| prednisolone | lysine | ≥2 g | procaterol | lysine | 5 g to 20 g |
| primaquine | lysine | ≥2 g | propylthiouracil | lysine | 5 g to 20 g |
| procaterol | lysine | ≥2 g | pseudoephedrine | lysine | 5 g to 20 g |
| propylthiouracil | lysine | ≥2 g | pyrazinamide | lysine | 5 g to 20 g |
| pseudoephedrine | lysine | ≥2 g | pyridostigmine bromide | lysine | 5 g to 20 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| pyrazinamide | lysine | ≥2 g | pyridoxine hydrochloride | lysine | 5 g to 20 g |
| pyridostigmine bromide | lysine | ≥2 g | ranitidine | lysine | 5 g to 20 g |
| pyridoxine hydrochloride | lysine | ≥2 g | ribavirin | lysine | 5 g to 20 g |
| ranitidine | lysine | ≥2 g | riboflavin | lysine | 5 g to 20 g |
| ribavirin | lysine | ≥2 g | rizatriptan | lysine | 5 g to 20 g |
| riboflavin | lysine | ≥2 g | stavudine | lysine | 5 g to 20 g |
| rizatriptan | lysine | ≥2 g | sulfadiazine | lysine | 5 g to 20 g |
| stavudine | lysine | ≥2 g | sulfamethoxazole | lysine | 5 g to 20 g |
| sulfadiazine | lysine | ≥2 g | sultamicillin | lysine | 5 g to 20 g |
| sulfamethoxazole | lysine | ≥2 g | sumatriptan | lysine | 5 g to 20 g |
| sultamicillin | lysine | ≥2 g | taltirelin | lysine | 5 g to 20 g |
| sumatriptan | lysine | ≥2 g | tegafur | lysine | 5 g to 20 g |
| taltirelin | lysine | ≥2 g | tenofovir disoproxil | lysine | 5 g to 20 g |
| tegafur | lysine | ≥2 g | theophylline | lysine | 5 g to 20 g |
| tenofovir disoproxil | lysine | ≥2 g | thiamine | lysine | 5 g to 20 g |
| theophylline | lysine | ≥2 g | trimetazidine | lysine | 5 g to 20 g |
| thiamine | lysine | ≥2 g | trimethoprim | lysine | 5 g to 20 g |
| trimetazidine | lysine | ≥2 g | voglibose | lysine | 5 g to 20 g |
| trimethoprim | lysine | ≥2 g | zidovudine | lysine | 5 g to 20 g |
| voglibose | lysine | ≥2 g | zolmitriptan | lysine | 5 g to 20 g |
| zidovudine | lysine | ≥2 g | acetylcarnitine | lysine | 5 g to 20 g |
| zolmitriptan | lysine | ≥2 g | capecitabine | lysine | 5 g to 20 g |
| acetylcarnitine | lysine | ≥2 g | cefaclor | lysine | 5 g to 20 g |
| capecitabine | lysine | ≥2 g | cefixime | lysine | 5 g to 20 g |
| cefaclor | lysine | ≥2 g | cefmetazole | lysine | 5 g to 20 g |
| cefixime | lysine | ≥2 g | cefpodoxime proxetil | lysine | 5 g to 20 g |
| cefmetazole | lysine | ≥2 g | cefroxadine | lysine | 5 g to 20 g |
| cefpodoxime proxetil | lysine | ≥2 g | alfoscerate | lysine | 5 g to 20 g |
| cefroxadine | lysine | ≥2 g | cilazapril | lysine | 5 g to 20 g |
| alfoscerate | lysine | ≥2 g | cimetropium bromide | lysine | 5 g to 20 g |
| cilazapril | lysine | ≥2 g | diacerein | lysine | 5 g to 20 g |
| cimetropium bromide | lysine | ≥2 g | erdosteine | lysine | 5 g to 20 g |
| diacerein | lysine | ≥2 g | famciclovir | lysine | 5 g to 20 g |
| erdosteine | lysine | ≥2 g | gemifloxacin | lysine | 5 g to 20 g |
| famciclovir | lysine | ≥2 g | levosulpiride | lysine | 5 g to 20 g |
| gemifloxacin | lysine | ≥2 g | nabumetone | lysine | 5 g to 20 g |
| levosulpiride | lysine | ≥2 g | oxiracetam | lysine | 5 g to 20 g |
| nabumetone | lysine | ≥2 g | phendimetrazine | lysine | 5 g to 20 g |
| oxiracetam | lysine | ≥2 g | rabeprazole | lysine | 5 g to 20 g |
| phendimetrazine | lysine | ≥2 g | roxatidine acetate | lysine | 5 g to 20 g |
| rabeprazole | lysine | ≥2 g | tamsulosin | lysine | 5 g to 20 g |
| roxatidine acetate | lysine | ≥2 g | terazosin | lysine | 5 g to 20 g |
| tamsulosin | lysine | ≥2 g | thioctic | lysine | 5 g to 20 g |
| terazosin | lysine | ≥2 g | tosufloxacin | lysine | 5 g to 20 g |
| thioctic | lysine | ≥2 g | triflusal | lysine | 5 g to 20 g |
| tosufloxacin | lysine | ≥2 g | zaltoprofen | lysine | 5 g to 20 g |
| triflusal | lysine | ≥2 g | etidronic acid | lysine | 5 g to 20 g |
| zaltoprofen | lysine | ≥2 g | zoledronic acid | lysine | 5 g to 20 g |
| etidronic acid | lysine | ≥2 g | clodronic acid | lysine | 5 g to 20 g |
| zoledronic acid | lysine | ≥2 g | tiludronic acid | lysine | 5 g to 20 g |
| clodronic acid | lysine | ≥2 g | pamidronic acid | lysine | 5 g to 20 g |
| tiludronic acid | lysine | ≥2 g | alendronic acid | lysine | 5 g to 20 g |
| pamidronic acid | lysine | ≥2 g | risedronic acid | lysine | 5 g to 20 g |
| alendronic acid | lysine | ≥2 g | ibandronic acid | lysine | 5 g to 20 g |
| risedronic acid | lysine | ≥2 g | abacavir | glycine | 5 g to 20 g |
| ibandronic acid | lysine | ≥2 g | acarbose | glycine | 5 g to 20 g |
| abacavir | glycine | ≥2 g | acetazolamide | glycine | 5 g to 20 g |
| acarbose | glycine | ≥2 g | acyclovir | glycine | 5 g to 20 g |
| acetazolamide | glycine | ≥2 g | albuterol (salbutamol) | glycine | 5 g to 20 g |
| acyclovir | glycine | ≥2 g | allopurinol | glycine | 5 g to 20 g |
| albuterol (salbutamol) | glycine | ≥2 g | amiloride | glycine | 5 g to 20 g |
| allopurinol | glycine | ≥2 g | amisulpride | glycine | 5 g to 20 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| amiloride | glycine | ≥2 g | amlodipine | glycine | 5 g to 20 g |
| amisulpride | glycine | ≥2 g | amoxicillin | glycine | 5 g to 20 g |
| amlodipine | glycine | ≥2 g | amphetamine | glycine | 5 g to 20 g |
| amoxicillin | glycine | ≥2 g | atenolol | glycine | 5 g to 20 g |
| amphetamine | glycine | ≥2 g | atropine | glycine | 5 g to 20 g |
| atenolol | glycine | ≥2 g | azathioprine | glycine | 5 g to 20 g |
| atropine | glycine | ≥2 g | benserazide | glycine | 5 g to 20 g |
| azathioprine | glycine | ≥2 g | benznidazole | glycine | 5 g to 20 g |
| benserazide | glycine | ≥2 g | camostat | glycine | 5 g to 20 g |
| benznidazole | glycine | ≥2 g | captopril | glycine | 5 g to 20 g |
| camostat | glycine | ≥2 g | cefdinir | glycine | 5 g to 20 g |
| captopril | glycine | ≥2 g | cefotiam hexetil hydrochloride | glycine | 5 g to 20 g |
| cefdinir | glycine | ≥2 g | cefprozil | glycine | 5 g to 20 g |
| cefotiam hexetil hydrochloride | glycine | ≥2 g | cefuroxime axetil | glycine | 5 g to 20 g |
| cefprozil | glycine | ≥2 g | chloramphenicol | glycine | 5 g to 20 g |
| cefuroxime axetil | glycine | ≥2 g | cimetidine | glycine | 5 g to 20 g |
| chloramphenicol | glycine | ≥2 g | ciprofloxacin | glycine | 5 g to 20 g |
| cimetidine | glycine | ≥2 g | codeine | glycine | 5 g to 20 g |
| ciprofloxacin | glycine | ≥2 g | colchicine | glycine | 5 g to 20 g |
| codeine | glycine | ≥2 g | cyclophosphamide | glycine | 5 g to 20 g |
| colchicine | glycine | ≥2 g | dapsone | glycine | 5 g to 20 g |
| cyclophosphamide | glycine | ≥2 g | dexamethasone | glycine | 5 g to 20 g |
| dapsone | glycine | ≥2 g | didanosine | glycine | 5 g to 20 g |
| dexamethasone | glycine | ≥2 g | diethylcarbamazine | glycine | 5 g to 20 g |
| didanosine | glycine | ≥2 g | methionine | glycine | 5 g to 20 g |
| diethylcarbamazine | glycine | ≥2 g | dolasetron | glycine | 5 g to 20 g |
| methionine | glycine | ≥2 g | doxifluridine | glycine | 5 g to 20 g |
| dolasetron | glycine | ≥2 g | doxycycline | glycine | 5 g to 20 g |
| doxifluridine | glycine | ≥2 g | ergonovine | glycine | 5 g to 20 g |
| doxycycline | glycine | ≥2 g | erythromycin ethylsuccinate | glycine | 5 g to 20 g |
| ergonovine | glycine | ≥2 g | ethambutol | glycine | 5 g to 20 g |
| erythromycin ethylsuccinate | glycine | ≥2 g | ethosuximide | glycine | 5 g to 20 g |
| ethambutol | glycine | ≥2 g | famotidine | glycine | 5 g to 20 g |
| ethosuximide | glycine | ≥2 g | fluconazole | glycine | 5 g to 20 g |
| famotidine | glycine | ≥2 g | folic acid | glycine | 5 g to 20 g |
| fluconazole | glycine | ≥2 g | furosemide | glycine | 5 g to 20 g |
| folic acid | glycine | ≥2 g | fursultiamine | glycine | 5 g to 20 g |
| furosemide | glycine | ≥2 g | gabapentin | glycine | 5 g to 20 g |
| fursultiamine | glycine | ≥2 g | glipizide | glycine | 5 g to 20 g |
| gabapentin | glycine | ≥2 g | granisetron | glycine | 5 g to 20 g |
| glipizide | glycine | ≥2 g | griseofulvin | glycine | 5 g to 20 g |
| granisetron | glycine | ≥2 g | hydralazine | glycine | 5 g to 20 g |
| griseofulvin | glycine | ≥2 g | hydrochlorothiazide | glycine | 5 g to 20 g |
| hydralazine | glycine | ≥2 g | imidapril | glycine | 5 g to 20 g |
| hydrochlorothiazide | glycine | ≥2 g | isoniazid | glycine | 5 g to 20 g |
| imidapril | glycine | ≥2 g | lamivudine | glycine | 5 g to 20 g |
| isoniazid | glycine | ≥2 g | l-carbocysteine | glycine | 5 g to 20 g |
| lamivudine | glycine | ≥2 g | levetiracetam | glycine | 5 g to 20 g |
| l-carbocysteine | glycine | ≥2 g | levofloxacin | glycine | 5 g to 20 g |
| levetiracetam | glycine | ≥2 g | linezolid | glycine | 5 g to 20 g |
| levofloxacin | glycine | ≥2 g | lisinopril | glycine | 5 g to 20 g |
| linezolid | glycine | ≥2 g | losartan | glycine | 5 g to 20 g |
| lisinopril | glycine | ≥2 g | methotrexate | glycine | 5 g to 20 g |
| losartan | glycine | ≥2 g | methyldopa | glycine | 5 g to 20 g |
| methotrexate | glycine | ≥2 g | s-methylmethionine | glycine | 5 g to 20 g |
| methyldopa | glycine | ≥2 g | metoclopramide | glycine | 5 g to 20 g |
| s-methylmethionine | glycine | ≥2 g | metronidazole | glycine | 5 g to 20 g |
| metoclopramide | glycine | ≥2 g | moxifloxacin | glycine | 5 g to 20 g |
| metronidazole | glycine | ≥2 g | nalidixic acid | glycine | 5 g to 20 g |
| moxifloxacin | glycine | ≥2 g | nicorandil | glycine | 5 g to 20 g |
| nalidixic acid | glycine | ≥2 g | nifurtimox | glycine | 5 g to 20 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| nicorandil | glycine | ≥2 g | nitrofurantoin | glycine | 5 g to 20 g |
| nifurtimox | glycine | ≥2 g | nizatidine | glycine | 5 g to 20 g |
| nitrofurantoin | glycine | ≥2 g | nystatin | glycine | 5 g to 20 g |
| nizatidine | glycine | ≥2 g | ondansetron | glycine | 5 g to 20 g |
| nystatin | glycine | ≥2 g | oseltamivir | glycine | 5 g to 20 g |
| ondansetron | glycine | ≥2 g | oxcarbazepine | glycine | 5 g to 20 g |
| oseltamivir | glycine | ≥2 g | penicillamine | glycine | 5 g to 20 g |
| oxcarbazepine | glycine | ≥2 g | perindopril | glycine | 5 g to 20 g |
| penicillamine | glycine | ≥2 g | phenobarbital | glycine | 5 g to 20 g |
| perindopril | glycine | ≥2 g | phenoxymethylpenicillin | glycine | 5 g to 20 g |
| phenobarbital | glycine | ≥2 g | pravastatin sodium | glycine | 5 g to 20 g |
| phenoxymethylpenicillin | glycine | ≥2 g | prednisolone | glycine | 5 g to 20 g |
| pravastatin sodium | glycine | ≥2 g | primaquine | glycine | 5 g to 20 g |
| prednisolone | glycine | ≥2 g | procaterol | glycine | 5 g to 20 g |
| primaquine | glycine | ≥2 g | propylthiouracil | glycine | 5 g to 20 g |
| procaterol | glycine | ≥2 g | pseudoephedrine | glycine | 5 g to 20 g |
| propylthiouracil | glycine | ≥2 g | pyrazinamide | glycine | 5 g to 20 g |
| pseudoephedrine | glycine | ≥2 g | pyridostigmine bromide | glycine | 5 g to 20 g |
| pyrazinamide | glycine | ≥2 g | pyridoxine hydrochloride | glycine | 5 g to 20 g |
| pyridostigmine bromide | glycine | ≥2 g | ranitidine | glycine | 5 g to 20 g |
| pyridoxine hydrochloride | glycine | ≥2 g | ribavirin | glycine | 5 g to 20 g |
| ranitidine | glycine | ≥2 g | riboflavin | glycine | 5 g to 20 g |
| ribavirin | glycine | ≥2 g | rizatriptan | glycine | 5 g to 20 g |
| riboflavin | glycine | ≥2 g | stavudine | glycine | 5 g to 20 g |
| rizatriptan | glycine | ≥2 g | sulfadiazine | glycine | 5 g to 20 g |
| stavudine | glycine | ≥2 g | sulfamethoxazole | glycine | 5 g to 20 g |
| sulfadiazine | glycine | ≥2 g | sultamicillin | glycine | 5 g to 20 g |
| sulfamethoxazole | glycine | ≥2 g | sumatriptan | glycine | 5 g to 20 g |
| sultamicillin | glycine | ≥2 g | taltirelin | glycine | 5 g to 20 g |
| sumatriptan | glycine | ≥2 g | tegafur | glycine | 5 g to 20 g |
| taltirelin | glycine | ≥2 g | tenofovir disoproxil | glycine | 5 g to 20 g |
| tegafur | glycine | ≥2 g | theophylline | glycine | 5 g to 20 g |
| tenofovir disoproxil | glycine | ≥2 g | thiamine | glycine | 5 g to 20 g |
| theophylline | glycine | ≥2 g | trimetazidine | glycine | 5 g to 20 g |
| thiamine | glycine | ≥2 g | trimethoprim | glycine | 5 g to 20 g |
| trimetazidine | glycine | ≥2 g | voglibose | glycine | 5 g to 20 g |
| trimethoprim | glycine | ≥2 g | zidovudine | glycine | 5 g to 20 g |
| voglibose | glycine | ≥2 g | zolmitriptan | glycine | 5 g to 20 g |
| zidovudine | glycine | ≥2 g | acetylcarnitine | glycine | 5 g to 20 g |
| zolmitriptan | glycine | ≥2 g | capecitabine | glycine | 5 g to 20 g |
| acetylcarnitine | glycine | ≥2 g | cefaclor | glycine | 5 g to 20 g |
| capecitabine | glycine | ≥2 g | cefixime | glycine | 5 g to 20 g |
| cefaclor | glycine | ≥2 g | cefmetazole | glycine | 5 g to 20 g |
| cefixime | glycine | ≥2 g | cefpodoxime proxetil | glycine | 5 g to 20 g |
| cefmetazole | glycine | ≥2 g | cefroxadine | glycine | 5 g to 20 g |
| cefpodoxime proxetil | glycine | ≥2 g | alfoscerate | glycine | 5 g to 20 g |
| cefroxadine | glycine | ≥2 g | cilazapril | glycine | 5 g to 20 g |
| alfoscerate | glycine | ≥2 g | cimetropium bromide | glycine | 5 g to 20 g |
| cilazapril | glycine | ≥2 g | diacerein | glycine | 5 g to 20 g |
| cimetropium bromide | glycine | ≥2 g | erdosteine | glycine | 5 g to 20 g |
| diacerein | glycine | ≥2 g | famciclovir | glycine | 5 g to 20 g |
| erdosteine | glycine | ≥2 g | gemifloxacin | glycine | 5 g to 20 g |
| famciclovir | glycine | ≥2 g | levosulpiride | glycine | 5 g to 20 g |
| gemifloxacin | glycine | ≥2 g | nabumetone | glycine | 5 g to 20 g |
| levosulpiride | glycine | ≥2 g | oxiracetam | glycine | 5 g to 20 g |
| nabumetone | glycine | ≥2 g | phendimetrazine | glycine | 5 g to 20 g |
| oxiracetam | glycine | ≥2 g | rabeprazole | glycine | 5 g to 20 g |
| phendimetrazine | glycine | ≥2 g | roxatidine acetate | glycine | 5 g to 20 g |
| rabeprazole | glycine | ≥2 g | tamsulosin | glycine | 5 g to 20 g |
| roxatidine acetate | glycine | ≥2 g | terazosin | glycine | 5 g to 20 g |
| tamsulosin | glycine | ≥2 g | thioctic | glycine | 5 g to 20 g |

TABLE 11-continued

Particular embodiments of unit dose pharmaceutical compositions of the present invention. As indicated in the columns 1-3 and 4-6 above, the compositions comprise an API and coformer, wherein the coformer is either present as a molecular complex coformer, an additional coformer or both a molecular complex coformer and additional coformer, with the total amount of coformer present in the unit dose indicated. Each three cell combination of API, coformer and amount of coformer represent an individual embodiment of the present invention.

| API | Amino Acid | Amount of Amino Acid per Unit Dose of API | API | Amino Acid | Amount of Amino Acid per Unit Dose of API |
|---|---|---|---|---|---|
| terazosin | glycine | ≥2 g | tosufloxacin | glycine | 5 g to 20 g |
| thioctic | glycine | ≥2 g | triflusal | glycine | 5 g to 20 g |
| tosufloxacin | glycine | ≥2 g | zaltoprofen | glycine | 5 g to 20 g |
| triflusal | glycine | ≥2 g | etidronic acid | glycine | 5 g to 20 g |
| zaltoprofen | glycine | ≥2 g | zoledronic acid | glycine | 5 g to 20 g |
| etidronic acid | glycine | ≥2 g | clodronic acid | glycine | 5 g to 20 g |
| zoledronic acid | glycine | ≥2 g | tiludronic acid | glycine | 5 g to 20 g |
| clodronic acid | glycine | ≥2 g | pamidronic acid | glycine | 5 g to 20 g |
| tiludronic acid | glycine | ≥2 g | alendronic acid | glycine | 5 g to 20 g |
| pamidronic acid | glycine | ≥2 g | risedronic acid | glycine | 5 g to 20 g |
| alendronic acid | glycine | ≥2 g | ibandronic acid | glycine | 5 g to 20 g |
| risedronic acid | glycine | ≥2 g | zoledronic acid | lysine | ≥2.5 g |
| ibandronic acid | glycine | ≥2 g | zoledronic acid | lysine | ≥2.6 g |
| zoledronic acid | lysine | ≥2.1 g | zoledronic acid | lysine | ≥2.7 g |
| zoledronic acid | lysine | ≥2.2 g | zoledronic acid | lysine | ≥2.8 g |
| zoledronic acid | lysine | ≥2.3 g | zoledronic acid | lysine | ≥2.9 g |
| zoledronic acid | lysine | ≥2.4 g | zoledronic acid | lysine | ≥3.5 g |

TABLE 12

| Bisphosphonic Acid | Molecular Complex Coformer | Additional Coformer as Excipient |
|---|---|---|
| zoledronic acid | sodium | L-lysine |
| alendronic acid | sodium | L-lysine |
| ibandronic acid | sodium | L-lysine |
| risedronic acid | sodium | L-lysine |
| tiludronic acid | sodium | L-lysine |
| zoledronic acid | sodium | DL-lysine |
| alendronic acid | sodium | DL-lysine |
| ibandronic acid | sodium | DL-lysine |
| risedronic acid | sodium | DL-lysine |
| tiludronic acid | sodium | DL-lysine |
| zoledronic acid | sodium | glycine |
| alendronic acid | sodium | glycine |
| ibandronic acid | sodium | glycine |
| risedronic acid | sodium | glycine |
| tiludronic acid | sodium | glycine |
| zoledronic acid | ammonium | L-lysine |
| alendronic acid | ammonium | L-lysine |
| ibandronic acid | ammonium | L-lysine |
| risedronic acid | ammonium | L-lysine |
| tiludronic acid | ammonium | L-lysine |
| zoledronic acid | ammonium | DL-lysine |
| alendronic acid | ammonium | DL-lysine |
| ibandronic acid | ammonium | DL-lysine |
| risedronic acid | ammonium | DL-lysine |
| tiludronic acid | ammonium | DL-lysine |
| zoledronic acid | ammonium | glycine |
| alendronic acid | ammonium | glycine |
| ibandronic acid | ammonium | glycine |
| risedronic acid | ammonium | glycine |
| tiludronic acid | ammonium | glycine |
| zoledronic acid | ammonia | L-lysine |
| alendronic acid | ammonia | L-lysine |
| ibandronic acid | ammonia | L-lysine |
| risedronic acid | ammonia | L-lysine |
| tiludronic acid | ammonia | L-lysine |
| zoledronic acid | ammonia | DL-lysine |
| alendronic acid | ammonia | DL-lysine |
| ibandronic acid | ammonia | DL-lysine |
| risedronic acid | ammonia | DL-lysine |
| tiludronic acid | ammonia | DL-lysine |
| zoledronic acid | ammonia | glycine |
| alendronic acid | ammonia | glycine |
| ibandronic acid | ammonia | glycine |
| risedronic acid | ammonia | glycine |
| tiludronic acid | ammonia | glycine |
| zoledronic acid | L-lysine | L-lysine |
| alendronic acid | L-lysine | L-lysine |
| ibandronic acid | L-lysine | L-lysine |
| risedronic acid | L-lysine | L-lysine |
| tiludronic acid | L-lysine | L-lysine |
| zoledronic acid | L-lysine | DL-lysine |
| alendronic acid | L-lysine | DL-lysine |
| ibandronic acid | L-lysine | DL-lysine |
| risedronic acid | L-lysine | DL-lysine |
| tiludronic acid | L-lysine | DL-lysine |
| zoledronic acid | L-lysine | glycine |
| alendronic acid | L-lysine | glycine |
| ibandronic acid | L-lysine | glycine |
| risedronic acid | L-lysine | glycine |
| tiludronic acid | L-lysine | glycine |
| zoledronic acid | DL-lysine | L-lysine |
| alendronic acid | DL-lysine | L-lysine |
| ibandronic acid | DL-lysine | L-lysine |
| risedronic acid | DL-lysine | L-lysine |
| tiludronic acid | DL-lysine | L-lysine |
| zoledronic acid | DL-lysine | DL-lysine |
| alendronic acid | DL-lysine | DL-lysine |
| ibandronic acid | DL-lysine | DL-lysine |
| risedronic acid | DL-lysine | DL-lysine |
| tiludronic acid | DL-lysine | DL-lysine |
| zoledronic acid | DL-lysine | glycine |
| alendronic acid | DL-lysine | glycine |
| ibandronic acid | DL-lysine | glycine |
| risedronic acid | DL-lysine | glycine |
| tiludronic acid | DL-lysine | glycine |
| zoledronic acid | nicotinamide | L-lysine |
| alendronic acid | nicotinamide | L-lysine |
| ibandronic acid | nicotinamide | L-lysine |

TABLE 12-continued

| Bisphosphonic Acid | Molecular Complex Coformer | Additional Coformer as Excipient |
|---|---|---|
| risedronic acid | nicotinamide | L-lysine |
| tiludronic acid | nicotinamide | L-lysine |
| zoledronic acid | nicotinamide | DL-lysine |
| alendronic acid | nicotinamide | DL-lysine |
| ibandronic acid | nicotinamide | DL-lysine |
| risedronic acid | nicotinamide | DL-lysine |
| tiludronic acid | nicotinamide | DL-lysine |
| zoledronic acid | nicotinamide | glycine |
| alendronic acid | nicotinamide | glycine |
| ibandronic acid | nicotinamide | glycine |
| risedronic acid | nicotinamide | glycine |
| tiludronic acid | nicotinamide | glycine |
| zoledronic acid | adenine | L-lysine |
| alendronic acid | adenine | L-lysine |
| ibandronic acid | adenine | L-lysine |
| risedronic acid | adenine | L-lysine |
| tiludronic acid | adenine | L-lysine |
| zoledronic acid | adenine | DL-lysine |
| alendronic acid | adenine | DL-lysine |
| ibandronic acid | adenine | DL-lysine |
| risedronic acid | adenine | DL-lysine |
| tiludronic acid | adenine | DL-lysine |
| zoledronic acid | adenine | glycine |
| alendronic acid | adenine | glycine |
| ibandronic acid | adenine | glycine |
| risedronic acid | adenine | glycine |
| tiludronic acid | adenine | glycine |
| zoledronic acid | glycine | L-lysine |
| alendronic acid | glycine | L-lysine |
| ibandronic acid | glycine | L-lysine |
| risedronic acid | glycine | L-lysine |
| tiludronic acid | glycine | L-lysine |
| zoledronic acid | glycine | DL-lysine |
| alendronic acid | glycine | DL-lysine |
| ibandronic acid | glycine | DL-lysine |
| risedronic acid | glycine | DL-lysine |
| tiludronic acid | glycine | DL-lysine |
| zoledronic acid | glycine | glycine |
| alendronic acid | glycine | glycine |
| ibandronic acid | glycine | glycine |
| risedronic acid | glycine | glycine |
| tiludronic acid | glycine | glycine |
| zoledronic acid | free acid | L-lysine |
| alendronic acid | free acid | L-lysine |
| ibandronic acid | free acid | L-lysine |
| risedronic acid | free acid | L-lysine |
| tiludronic acid | free acid | L-lysine |
| zoledronic acid | free acid | DL-lysine |
| alendronic acid | free acid | DL-lysine |
| ibandronic acid | free acid | DL-lysine |
| risedronic acid | free acid | DL-lysine |
| tiludronic acid | free acid | DL-lysine |
| zoledronic acid | free acid | glycine |
| alendronic acid | free acid | glycine |
| ibandronic acid | free acid | glycine |
| risedronic acid | free acid | glycine |
| tiludronic acid | free acid | glycine |

Particular embodiments of compositions of the present invention comprising: a bisphosphonic acid (left column), either in the form of a crystalline molecular complex (e.g., salt or cocrystal) with a coformer or in the form of a free acid (middle column), and an additional coformer (right column). Each row of the above table represents an individual embodiment of the present invention.

TABLE 13

| Bisphosphonic Acid | Molecular Complex Coformer | Additional Coformer | Mass Ratio of Additional Coformer:Bisphosphic Acid |
|---|---|---|---|
| zoledronic acid | sodium | L-lysine | ≥5:1 |
| zoledronic acid | sodium | L-lysine | ≥6:1 |
| zoledronic acid | sodium | L-lysine | ≥7:1 |
| zoledronic acid | sodium | L-lysine | ≥8:1 |
| zoledronic acid | sodium | L-lysine | ≥9:1 |
| zoledronic acid | sodium | L-lysine | ≥10:1 |
| zoledronic acid | sodium | L-lysine | ≥11:1 |
| zoledronic acid | sodium | L-lysine | ≥12:1 |
| zoledronic acid | sodium | L-lysine | ≥13:1 |
| zoledronic acid | sodium | L-lysine | ≥14:1 |
| zoledronic acid | sodium | L-lysine | ≥15:1 |
| zoledronic acid | sodium | L-lysine | ≥16:1 |
| zoledronic acid | sodium | L-lysine | ≥17:1 |
| zoledronic acid | sodium | L-lysine | ≥18:1 |
| zoledronic acid | sodium | L-lysine | ≥19:1 |
| zoledronic acid | sodium | L-lysine | ≥20:1 |
| zoledronic acid | sodium | L-lysine | ≥25:1 |
| zoledronic acid | sodium | L-lysine | ≥50:1 |
| zoledronic acid | sodium | L-lysine | ≥750:1 |
| zoledronic acid | sodium | L-lysine | ≥2500:1 |
| zoledronic acid | sodium | L-lysine | ≥5000:1 |
| zoledronic acid | sodium | DL-lysine | ≥5:1 |
| zoledronic acid | sodium | DL-lysine | ≥6:1 |
| zoledronic acid | sodium | DL-lysine | ≥7:1 |
| zoledronic acid | sodium | DL-lysine | ≥8:1 |
| zoledronic acid | sodium | DL-lysine | ≥9:1 |
| zoledronic acid | sodium | DL-lysine | ≥10:1 |
| zoledronic acid | sodium | DL-lysine | ≥11:1 |
| zoledronic acid | sodium | DL-lysine | ≥12:1 |
| zoledronic acid | sodium | DL-lysine | ≥13:1 |
| zoledronic acid | sodium | DL-lysine | ≥14:1 |
| zoledronic acid | sodium | DL-lysine | ≥15:1 |
| zoledronic acid | sodium | DL-lysine | ≥16:1 |
| zoledronic acid | sodium | DL-lysine | ≥17:1 |
| zoledronic acid | sodium | DL-lysine | ≥18:1 |
| zoledronic acid | sodium | DL-lysine | ≥19:1 |
| zoledronic acid | sodium | DL-lysine | ≥20:1 |
| zoledronic acid | sodium | DL-lysine | ≥25:1 |
| zoledronic acid | sodium | DL-lysine | ≥50:1 |
| zoledronic acid | sodium | DL-lysine | ≥750:1 |
| zoledronic acid | sodium | DL-lysine | ≥2500:1 |
| zoledronic acid | sodium | DL-lysine | ≥5000:1 |
| zoledronic acid | sodium | glycine | ≥5:1 |
| zoledronic acid | sodium | glycine | ≥50:1 |
| zoledronic acid | sodium | glycine | ≥750:1 |
| zoledronic acid | sodium | glycine | ≥2500:1 |
| zoledronic acid | sodium | glycine | ≥5000:1 |
| zoledronic acid | ammonium | L-lysine | ≥5:1 |
| zoledronic acid | ammonium | L-lysine | ≥50:1 |
| zoledronic acid | ammonium | L-lysine | ≥750:1 |
| zoledronic acid | ammonium | L-lysine | ≥2500:1 |
| zoledronic acid | ammonium | L-lysine | ≥5000:1 |
| zoledronic acid | ammonium | DL-lysine | ≥5:1 |
| zoledronic acid | ammonium | DL-lysine | ≥50:1 |
| zoledronic acid | ammonium | DL-lysine | ≥750:1 |
| zoledronic acid | ammonium | DL-lysine | ≥2500:1 |
| zoledronic acid | ammonium | DL-lysine | ≥5000:1 |
| zoledronic acid | ammonium | glycine | ≥5:1 |
| zoledronic acid | ammonium | glycine | ≥50:1 |
| zoledronic acid | ammonium | glycine | ≥750:1 |
| zoledronic acid | ammonium | glycine | ≥2500:1 |
| zoledronic acid | ammonium | glycine | ≥5000:1 |
| zoledronic acid | ammonia | L-lysine | ≥5:1 |
| zoledronic acid | ammonia | L-lysine | ≥50:1 |
| zoledronic acid | ammonia | L-lysine | ≥750:1 |
| zoledronic acid | ammonia | L-lysine | ≥2500:1 |
| zoledronic acid | ammonia | L-lysine | ≥5000:1 |
| zoledronic acid | ammonia | DL-lysine | ≥5:1 |
| zoledronic acid | ammonia | DL-lysine | ≥50:1 |
| zoledronic acid | ammonia | DL-lysine | ≥750:1 |
| zoledronic acid | ammonia | DL-lysine | ≥2500:1 |
| zoledronic acid | ammonia | DL-lysine | ≥5000:1 |
| zoledronic acid | ammonia | glycine | ≥5:1 |
| zoledronic acid | ammonia | glycine | ≥50:1 |
| zoledronic acid | ammonia | glycine | ≥750:1 |
| zoledronic acid | ammonia | glycine | ≥2500:1 |
| zoledronic acid | ammonia | glycine | ≥5000:1 |
| zoledronic acid | L-lysine | L-lysine | ≥5:1 |
| zoledronic acid | L-lysine | L-lysine | ≥6:1 |
| zoledronic acid | L-lysine | L-lysine | ≥7:1 |
| zoledronic acid | L-lysine | L-lysine | ≥8:1 |

TABLE 13-continued

| Bisphosphonic Acid | Molecular Complex Coformer | Additional Coformer | Mass Ratio of Additional Coformer:Bisphosphic Acid |
|---|---|---|---|
| zoledronic acid | L-lysine | L-lysine | ≥9:1 |
| zoledronic acid | L-lysine | L-lysine | ≥10:1 |
| zoledronic acid | L-lysine | L-lysine | ≥11:1 |
| zoledronic acid | L-lysine | L-lysine | ≥12:1 |
| zoledronic acid | L-lysine | L-lysine | ≥13:1 |
| zoledronic acid | L-lysine | L-lysine | ≥14:1 |
| zoledronic acid | L-lysine | L-lysine | ≥15:1 |
| zoledronic acid | L-lysine | L-lysine | ≥16:1 |
| zoledronic acid | L-lysine | L-lysine | ≥17:1 |
| zoledronic acid | L-lysine | L-lysine | ≥18:1 |
| zoledronic acid | L-lysine | L-lysine | ≥19:1 |
| zoledronic acid | L-lysine | L-lysine | ≥20:1 |
| zoledronic acid | L-lysine | L-lysine | ≥25:1 |
| zoledronic acid | L-lysine | L-lysine | ≥50:1 |
| zoledronic acid | L-lysine | L-lysine | ≥750:1 |
| zoledronic acid | L-lysine | L-lysine | ≥2500:1 |
| zoledronic acid | L-lysine | L-lysine | ≥5000:1 |
| zoledronic acid | L-lysine | DL-lysine | ≥5:1 |
| zoledronic acid | L-lysine | DL-lysine | ≥6:1 |
| zoledronic acid | L-lysine | DL-lysine | ≥7:1 |
| zoledronic acid | L-lysine | DL-lysine | ≥8:1 |
| zoledronic acid | L-lysine | DL-lysine | ≥9:1 |
| zoledronic acid | L-lysine | DL-lysine | ≥10:1 |
| zoledronic acid | L-lysine | DL-lysine | ≥11:1 |
| zoledronic acid | L-lysine | DL-lysine | ≥12:1 |
| zoledronic acid | L-lysine | DL-lysine | ≥13:1 |
| zoledronic acid | L-lysine | DL-lysine | ≥14:1 |
| zoledronic acid | L-lysine | DL-lysine | ≥15:1 |
| zoledronic acid | L-lysine | DL-lysine | ≥16:1 |
| zoledronic acid | L-lysine | DL-lysine | ≥17:1 |
| zoledronic acid | L-lysine | DL-lysine | ≥18:1 |
| zoledronic acid | L-lysine | DL-lysine | ≥19:1 |
| zoledronic acid | L-lysine | DL-lysine | ≥20:1 |
| zoledronic acid | L-lysine | DL-lysine | ≥25:1 |
| zoledronic acid | L-lysine | DL-lysine | ≥50:1 |
| zoledronic acid | L-lysine | DL-lysine | ≥750:1 |
| zoledronic acid | L-lysine | DL-lysine | ≥2500:1 |
| zoledronic acid | L-lysine | DL-lysine | ≥5000:1 |
| zoledronic acid | L-lysine | glycine | ≥5:1 |
| zoledronic acid | L-lysine | glycine | ≥50:1 |
| zoledronic acid | L-lysine | glycine | ≥750:1 |
| zoledronic acid | L-lysine | glycine | ≥2500:1 |
| zoledronic acid | L-lysine | glycine | ≥5000:1 |
| zoledronic acid | DL-lysine | L-lysine | ≥5:1 |
| zoledronic acid | DL-lysine | L-lysine | ≥6:1 |
| zoledronic acid | DL-lysine | L-lysine | ≥7:1 |
| zoledronic acid | DL-lysine | L-lysine | ≥8:1 |
| zoledronic acid | DL-lysine | L-lysine | ≥9:1 |
| zoledronic acid | DL-lysine | L-lysine | ≥10:1 |
| zoledronic acid | DL-lysine | L-lysine | ≥11:1 |
| zoledronic acid | DL-lysine | L-lysine | ≥12:1 |
| zoledronic acid | DL-lysine | L-lysine | ≥13:1 |
| zoledronic acid | DL-lysine | L-lysine | ≥14:1 |
| zoledronic acid | DL-lysine | L-lysine | ≥15:1 |
| zoledronic acid | DL-lysine | L-lysine | ≥16:1 |
| zoledronic acid | DL-lysine | L-lysine | ≥17:1 |
| zoledronic acid | DL-lysine | L-lysine | ≥18:1 |
| zoledronic acid | DL-lysine | L-lysine | ≥19:1 |
| zoledronic acid | DL-lysine | L-lysine | ≥20:1 |
| zoledronic acid | DL-lysine | L-lysine | ≥25:1 |
| zoledronic acid | DL-lysine | L-lysine | ≥50:1 |
| zoledronic acid | DL-lysine | L-lysine | ≥750:1 |
| zoledronic acid | DL-lysine | L-lysine | ≥2500:1 |
| zoledronic acid | DL-lysine | L-lysine | ≥5000:1 |
| zoledronic acid | DL-lysine | DL-lysine | ≥5:1 |
| zoledronic acid | DL-lysine | DL-lysine | ≥6:1 |
| zoledronic acid | DL-lysine | DL-lysine | ≥7:1 |
| zoledronic acid | DL-lysine | DL-lysine | ≥8:1 |
| zoledronic acid | DL-lysine | DL-lysine | ≥9:1 |
| zoledronic acid | DL-lysine | DL-lysine | ≥10:1 |
| zoledronic acid | DL-lysine | DL-lysine | ≥11:1 |
| zoledronic acid | DL-lysine | DL-lysine | ≥12:1 |
| zoledronic acid | DL-lysine | DL-lysine | ≥13:1 |
| zoledronic acid | DL-lysine | DL-lysine | ≥14:1 |
| zoledronic acid | DL-lysine | DL-lysine | ≥15:1 |
| zoledronic acid | DL-lysine | DL-lysine | ≥16:1 |
| zoledronic acid | DL-lysine | DL-lysine | ≥17:1 |
| zoledronic acid | DL-lysine | DL-lysine | ≥18:1 |
| zoledronic acid | DL-lysine | DL-lysine | ≥19:1 |
| zoledronic acid | DL-lysine | DL-lysine | ≥20:1 |
| zoledronic acid | DL-lysine | DL-lysine | ≥25:1 |
| zoledronic acid | DL-lysine | DL-lysine | ≥50:1 |
| zoledronic acid | DL-lysine | DL-lysine | ≥750:1 |
| zoledronic acid | DL-lysine | DL-lysine | ≥2500:1 |
| zoledronic acid | DL-lysine | DL-lysine | ≥5000:1 |
| zoledronic acid | DL-lysine | glycine | ≥5:1 |
| zoledronic acid | DL-lysine | glycine | ≥50:1 |
| zoledronic acid | DL-lysine | glycine | ≥750:1 |
| zoledronic acid | DL-lysine | glycine | ≥2500:1 |
| zoledronic acid | DL-lysine | glycine | ≥5000:1 |
| zoledronic acid | nicotinamide | L-lysine | ≥5:1 |
| zoledronic acid | nicotinamide | L-lysine | ≥50:1 |
| zoledronic acid | nicotinamide | L-lysine | ≥750:1 |
| zoledronic acid | nicotinamide | L-lysine | ≥2500:1 |
| zoledronic acid | nicotinamide | L-lysine | ≥5000:1 |
| zoledronic acid | nicotinamide | DL-lysine | ≥5:1 |
| zoledronic acid | nicotinamide | DL-lysine | ≥50:1 |
| zoledronic acid | nicotinamide | DL-lysine | ≥750:1 |
| zoledronic acid | nicotinamide | DL-lysine | ≥2500:1 |
| zoledronic acid | nicotinamide | DL-lysine | ≥5000:1 |
| zoledronic acid | nicotinamide | glycine | ≥5:1 |
| zoledronic acid | nicotinamide | glycine | ≥50:1 |
| zoledronic acid | nicotinamide | glycine | ≥750:1 |
| zoledronic acid | nicotinamide | glycine | ≥2500:1 |
| zoledronic acid | nicotinamide | glycine | ≥5000:1 |
| zoledronic acid | adenine | L-lysine | ≥5:1 |
| zoledronic acid | adenine | L-lysine | ≥50:1 |
| zoledronic acid | adenine | L-lysine | ≥750:1 |
| zoledronic acid | adenine | L-lysine | ≥2500:1 |
| zoledronic acid | adenine | L-lysine | ≥5000:1 |
| zoledronic acid | adenine | DL-lysine | ≥5:1 |
| zoledronic acid | adenine | DL-lysine | ≥50:1 |
| zoledronic acid | adenine | DL-lysine | ≥750:1 |
| zoledronic acid | adenine | DL-lysine | ≥2500:1 |
| zoledronic acid | adenine | DL-lysine | ≥5000:1 |
| zoledronic acid | adenine | glycine | ≥5:1 |
| zoledronic acid | adenine | glycine | ≥50:1 |
| zoledronic acid | adenine | glycine | ≥750:1 |
| zoledronic acid | adenine | glycine | ≥2500:1 |
| zoledronic acid | adenine | glycine | ≥5000:1 |
| zoledronic acid | glycine | L-lysine | ≥5:1 |
| zoledronic acid | glycine | L-lysine | ≥50:1 |
| zoledronic acid | glycine | L-lysine | ≥750:1 |
| zoledronic acid | glycine | L-lysine | ≥2500:1 |
| zoledronic acid | glycine | L-lysine | ≥5000:1 |
| zoledronic acid | glycine | DL-lysine | ≥5:1 |
| zoledronic acid | glycine | DL-lysine | ≥50:1 |
| zoledronic acid | glycine | DL-lysine | ≥750:1 |
| zoledronic acid | glycine | DL-lysine | ≥2500:1 |
| zoledronic acid | glycine | DL-lysine | ≥5000:1 |
| zoledronic acid | glycine | glycine | ≥5:1 |
| zoledronic acid | glycine | glycine | ≥50:1 |
| zoledronic acid | glycine | glycine | ≥750:1 |
| zoledronic acid | glycine | glycine | ≥2500:1 |
| zoledronic acid | glycine | glycine | ≥5000:1 |
| zoledronic acid | free acid | L-lysine | ≥5:1 |
| zoledronic acid | free acid | L-lysine | ≥6:1 |
| zoledronic acid | free acid | L-lysine | ≥7:1 |
| zoledronic acid | free acid | L-lysine | ≥8:1 |
| zoledronic acid | free acid | L-lysine | ≥9:1 |
| zoledronic acid | free acid | L-lysine | ≥10:1 |
| zoledronic acid | free acid | L-lysine | ≥11:1 |
| zoledronic acid | free acid | L-lysine | ≥12:1 |
| zoledronic acid | free acid | L-lysine | ≥13:1 |
| zoledronic acid | free acid | L-lysine | ≥14:1 |
| zoledronic acid | free acid | L-lysine | ≥15:1 |
| zoledronic acid | free acid | L-lysine | ≥16:1 |
| zoledronic acid | free acid | L-lysine | ≥17:1 |
| zoledronic acid | free acid | L-lysine | ≥18:1 |
| zoledronic acid | free acid | L-lysine | ≥19:1 |

TABLE 13-continued

| Bisphosphonic Acid | Molecular Complex Coformer | Additional Coformer | Mass Ratio of Additional Coformer:Bisphosphic Acid |
|---|---|---|---|
| zoledronic acid | free acid | L-lysine | ≥20:1 |
| zoledronic acid | free acid | L-lysine | ≥25:1 |
| zoledronic acid | free acid | L-lysine | ≥50:1 |
| zoledronic acid | free acid | L-lysine | ≥750:1 |
| zoledronic acid | free acid | L-lysine | ≥2500:1 |
| zoledronic acid | free acid | L-lysine | ≥5000:1 |
| zoledronic acid | free acid | DL-lysine | ≥5:1 |
| zoledronic acid | free acid | DL-lysine | ≥6:1 |
| zoledronic acid | free acid | DL-lysine | ≥7:1 |
| zoledronic acid | free acid | DL-lysine | ≥8:1 |
| zoledronic acid | free acid | DL-lysine | ≥9:1 |
| zoledronic acid | free acid | DL-lysine | ≥10:1 |
| zoledronic acid | free acid | DL-lysine | ≥11:1 |
| zoledronic acid | free acid | DL-lysine | ≥12:1 |
| zoledronic acid | free acid | DL-lysine | ≥13:1 |
| zoledronic acid | free acid | DL-lysine | ≥14:1 |
| zoledronic acid | free acid | DL-lysine | ≥15:1 |
| zoledronic acid | free acid | DL-lysine | ≥16:1 |
| zoledronic acid | free acid | DL-lysine | ≥17:1 |
| zoledronic acid | free acid | DL-lysine | ≥18:1 |
| zoledronic acid | free acid | DL-lysine | ≥19:1 |
| zoledronic acid | free acid | DL-lysine | ≥20:1 |
| zoledronic acid | free acid | DL-lysine | ≥25:1 |
| zoledronic acid | free acid | DL-lysine | ≥50:1 |
| zoledronic acid | free acid | DL-lysine | ≥750:1 |
| zoledronic acid | free acid | DL-lysine | ≥2500:1 |
| zoledronic acid | free acid | DL-lysine | ≥5000:1 |
| zoledronic acid | free acid | glycine | ≥5:1 |
| zoledronic acid | free acid | glycine | ≥50:1 |
| zoledronic acid | free acid | glycine | ≥750:1 |
| zoledronic acid | free acid | glycine | ≥2500:1 |
| zoledronic acid | free acid | glycine | ≥5000:1 |

Particular embodiments of compositions of the present invention comprising: (from left to right) a bisphosphonic acid (either in the form of a crystalline molecular complex (e.g., salt or cocrystal) with a coformer or in the form of a free acid), an additional coformer, and the ratio of the additional coformer to bisphosphonic acid (by mass). Each row of the above table represents an individual embodiment of the present invention.

TABLE 14

| Molecular Complex | Additional Coformer | Mass Ratio of Additional Coformer:Molecular Complex Coformer |
|---|---|---|
| zoledronic acid, sodium zoledronate and water complex characterized by an X-ray powder diffraction pattern having peaks at about 8.1, 13.3, 21.5, 24.6, and 25.6 ± 0.2 degrees two-theta | L-lysine | ≥5:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | L-lysine | ≥5:1 |
| zoledronic diammonia water complex characterized by an X-ray powder diffraction pattern having strong peaks at about 12.2, 13.0, 14.1, 17.1, and 19.3 ± 0.2 degrees two-theta | L-lysine | ≥5:1 |
| zoledronic acid, L-lysine, and water complex characterized by an X-ray powder diffraction pattern having peaks at about 9.0, 14.4, 18.1, 26.0, and 29.6 ± 0.2 degrees two-theta | L-lysine | ≥5:1 |
| zoledronic acid, L-lysine, and water complex characterized by an X-ray powder diffraction pattern comprising peaks at about 9.6, 10.7, 14.3, 21.4, and 23.5 ± 0.2 degrees two theta | L-lysine | ≥5:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | L-lysine | ≥5:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | L-lysine | ≥5:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | L-lysine | ≥5:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | L-lysine | ≥5:1 |
| zoledronic acid, adenine, and water complex characterized by an X-ray powder diffraction pattern comprising peaks at about 13.6, 15.9, 19.7, 27.9, and 29.5 ± 0.2 degrees two-theta | L-lysine | ≥5:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | L-lysine | ≥5:1 |
| zoledronic acid and glycine complex characterized by an X-ray powder diffraction pattern comprising peaks at about 10.2, 17.8, 19.9, 22.9, and 28.1 ± 0.2 degrees two-theta | L-lysine | ≥5:1 |

TABLE 14-continued

| Molecular Complex | Additional Coformer | Mass Ratio of Additional Coformer:Molecular Complex Coformer |
|---|---|---|
| zoledronic acid, sodium zoledronate and water complex characterized by an X-ray powder diffraction pattern having peaks at about 8.1, 13.3, 21.5, 24.6, and 25.6 ± 0.2 degrees two-theta | L-lysine | ≥40:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | L-lysine | ≥40:1 |
| zoledronic diammonia water complex characterized by an X-ray powder diffraction pattern having strong peaks at about 12.2, 13.0, 14.1, 17.1, and 19.3 ± 0.2 degrees two-theta | L-lysine | ≥40:1 |
| zoledronic acid, L-lysine, and water complex characterized by an X-ray powder diffraction pattern having peaks at about 9.0, 14.4, 18.1, 26.0, and 29.6 ± 0.2 degrees two-theta | L-lysine | ≥40:1 |
| zoledronic acid, L-lysine, and water complex characterized by an X-ray powder diffraction pattern comprising peaks at about 9.6, 10.7, 14.3, 21.4, 23.5 ± 0.2 degrees two theta | L-lysine | ≥40:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | L-lysine | ≥40:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | L-lysine | ≥40:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | L-lysine | ≥40:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | L-lysine | ≥40:1 |
| zoledronic acid, adenine, and water complex characterized by an X-ray powder diffraction pattern comprising peaks at about 13.6, 15.9, 19.7, 27.9, and 29.5 ± 0.2 degrees two-theta | L-lysine | ≥40:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | L-lysine | ≥40:1 |
| zoledronic acid and glycine complex characterized by an X-ray powder diffraction pattern comprising peaks at about 10.2, 17.8, 19.9, 22.9, and 28.1 ± 0.2 degrees two-theta | L-lysine | ≥40:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | L-lysine | ≥750:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | L-lysine | ≥750:1 |
| zoledronic diammonia water complex characterized by an X-ray powder diffraction pattern having strong peaks at about 12.2, 13.0, 14.1, 17.1, and 19.3 ± 0.2 degrees two-theta | L-lysine | ≥750:1 |
| zoledronic acid, L-lysine, and water complex characterized by an X-ray powder diffraction pattern having peaks at about 9.0, 14.4, 18.1, 26.0, and 29.6 ± 0.2 degrees two-theta | L-lysine | ≥750:1 |
| zoledronic acid, L-lysine, and water complex characterized by an X-ray powder diffraction pattern comprising peaks at about 9.6, 10.7, 14.3, 21.4, 23.5 ± 0.2 degrees two theta | L-lysine | ≥750:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | L-lysine | ≥750:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | L-lysine | ≥750:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | L-lysine | ≥750:1 |

TABLE 14-continued

| Molecular Complex | Additional Coformer | Mass Ratio of Additional Coformer:Molecular Complex Coformer |
|---|---|---|
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | L-lysine | ≥750:1 |
| zoledronic acid, adenine, and water complex characterized by an X-ray powder diffraction pattern comprising peaks at about 13.6, 15.9, 19.7, 27.9, and 29.5 ± 0.2 degrees two-theta | L-lysine | ≥750:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | L-lysine | ≥750:1 |
| zoledronic acid and glycine complex characterized by an X-ray powder diffraction pattern comprising peaks at about 10.2, 17.8, 19.9, 22.9, and 28.1 ± 0.2 degrees two-theta | L-lysine | ≥750:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | L-lysine | ≥1000:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | L-lysine | ≥1000:1 |
| zoledronic diammonia water complex characterized by an X-ray powder diffraction pattern having strong peaks at about 12.2, 13.0, 14.1, 17.1, and 19.3 ± 0.2 degrees two-theta | L-lysine | ≥1000:1 |
| zoledronic acid, L-lysine, and water complex characterized by an X-ray powder diffraction pattern having peaks at about 9.0, 14.4, 18.1, 26.0, and 29.6 ± 0.2 degrees two-theta | L-lysine | ≥1000:1 |
| zoledronic acid, L-lysine, and water complex characterized by an X-ray powder diffraction pattern comprising peaks at about 9.6, 10.7, 14.3, 21.4, 23.5 ± 0.2 degrees two theta | L-lysine | ≥1000:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | L-lysine | ≥1000:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | L-lysine | ≥1000:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | L-lysine | ≥1000:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | L-lysine | ≥1000:1 |
| zoledronic acid, adenine, and water complex characterized by an X-ray powder diffraction pattern comprising peaks at about 13.6, 15.9, 19.7, 27.9, and 29.5 ± 0.2 degrees two-theta | L-lysine | ≥1000:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | L-lysine | ≥1000:1 |
| zoledronic acid and glycine complex characterized by an X-ray powder diffraction pattern comprising peaks at about 10.2, 17.8, 19.9, 22.9, and 28.1 ± 0.2 degrees two-theta | L-lysine | ≥1000:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | L-lysine | ≥1000 ≥ 5000:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | L-lysine | ≥1000 ≥ 5000:1 |
| zoledronic diammonia water complex characterized by an X-ray powder diffraction pattern having strong peaks at about 12.2, 13.0, 14.1, 17.1, and 19.3 ± 0.2 degrees two-theta | L-lysine | ≥1000 ≥ 5000:1 |
| zoledronic acid, L-lysine, and water complex characterized by an X-ray powder diffraction pattern having peaks at about 9.0, 14.4, 18.1, 26.0, and 29.6 ± 0.2 degrees two-theta | L-lysine | ≥1000 ≥ 5000:1 |

TABLE 14-continued

| Molecular Complex | Additional Coformer | Mass Ratio of Additional Coformer:Molecular Complex Coformer |
|---|---|---|
| zoledronic acid, L-lysine, and water complex characterized by an X-ray powder diffraction pattern comprising peaks at about 9.6, 10.7, 14.3, 21.4, 23.5 ± 0.2 degrees two theta | L-lysine | ≥1000 ≥ 5000:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | L-lysine | ≥1000 ≥ 5000:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | L-lysine | ≥1000 ≥ 5000:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | L-lysine | ≥1000 ≥ 5000:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | L-lysine | ≥1000 ≥ 5000:1 |
| zoledronic acid, adenine, and water complex characterized by an X-ray powder diffraction pattern comprising peaks at about 13.6, 15.9, 19.7, 27.9, and 29.5 ± 0.2 degrees two-theta | L-lysine | ≥1000 ≥ 5000:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | L-lysine | ≥1000 ≥ 5000:1 |
| zoledronic acid and glycine complex characterized by an X-ray powder diffraction pattern comprising peaks at about 10.2, 17.8, 19.9, 22.9, and 28.1 ± 0.2 degrees two-theta | L-lysine | ≥1000 ≥ 5000:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | D,L-lysine | ≥5:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | D,L-lysine | ≥5:1 |
| zoledronic diammonia water complex characterized by an X-ray powder diffraction pattern having strong peaks at about 12.2, 13.0, 14.1, 17.1, and 19.3 ± 0.2 degrees two-theta | D,L-lysine | ≥5:1 |
| zoledronic acid, L-lysine, and water complex characterized by an X-ray powder diffraction pattern having peaks at about 9.0, 14.4, 18.1, 26.0, and 29.6 ± 0.2 degrees two-theta | D,L-lysine | ≥5:1 |
| zoledronic acid, L-lysine, and water complex characterized by an X-ray powder diffraction pattern comprising peaks at about 9.6, 10.7, 14.3, 21.4, 23.5 ± 0.2 degrees two theta | DL-lysine | ≥5:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | DL-lysine | ≥5:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | DL-lysine | ≥5:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | DL-lysine | ≥5:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | DL-lysine | ≥5:1 |
| zoledronic acid, adenine, and water complex characterized by an X-ray powder diffraction pattern comprising peaks at about 13.6, 15.9, 19.7, 27.9, and 29.5 ± 0.2 degrees two-theta | DL-lysine | ≥5:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | DL-lysine | ≥5:1 |
| zoledronic acid and glycine complex characterized by an X-ray powder diffraction pattern comprising peaks at about 10.2, 17.8, 19.9, 22.9, and 28.1 ± 0.2 degrees two-theta | DL-lysine | ≥5:1 |

TABLE 14-continued

| Molecular Complex | Additional Coformer | Mass Ratio of Additional Coformer:Molecular Complex Coformer |
|---|---|---|
| zoledronic acid, sodium zoledronate and water complex characterized by an X-ray powder diffraction pattern having peaks at about 8.1, 13.3, 21.5, 24.6, and 25.6 ± 0.2 degrees two-theta | DL-lysine | ≥40:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | DL-lysine | ≥40:1 |
| zoledronic diammonia water complex characterized by an X-ray powder diffraction pattern having strong peaks at about 12.2, 13.0, 14.1, 17.1, and 19.3 ± 0.2 degrees two-theta | DL-lysine | ≥40:1 |
| zoledronic acid, L-lysine, and water complex characterized by an X-ray powder diffraction pattern having peaks at about 9.0, 14.4, 18.1, 26.0, and 29.6 ± 0.2 degrees two-theta | DL-lysine | ≥40:1 |
| zoledronic acid, L-lysine, and water complex characterized by an X-ray powder diffraction pattern comprising peaks at about 9.6, 10.7, 14.3, 21.4, 23.5 ± 0.2 degrees two theta | DL-lysine | ≥40:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | DL-lysine | ≥40:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | DL-lysine | ≥40:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | DL-lysine | ≥40:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | DL-lysine | ≥40:1 |
| zoledronic acid, adenine, and water complex characterized by an X-ray powder diffraction pattern comprising peaks at about 13.6, 15.9, 19.7, 27.9, and 29.5 ± 0.2 degrees two-theta | DL-lysine | ≥40:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | DL-lysine | ≥40:1 |
| zoledronic acid and glycine complex characterized by an X-ray powder diffraction pattern comprising peaks at about 10.2, 17.8, 19.9, 22.9, and 28.1 ± 0.2 degrees two-theta | DL-lysine | ≥40:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | DL-lysine | ≥750:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | DL-lysine | ≥750:1 |
| zoledronic diammonia water complex characterized by an X-ray powder diffraction pattern having strong peaks at about 12.2, 13.0, 14.1, 17.1, and 19.3 ± 0.2 degrees two-theta | DL-lysine | ≥750:1 |
| zoledronic acid, L-lysine, and water complex characterized by an X-ray powder diffraction pattern having peaks at about 9.0, 14.4, 18.1, 26.0, and 29.6 ± 0.2 degrees two-theta | DL-lysine | ≥750:1 |
| zoledronic acid, L-lysine, and water complex characterized by an X-ray powder diffraction pattern comprising peaks at about 9.6, 10.7, 14.3, 21.4, 23.5 ± 0.2 degrees two theta | DL-lysine | ≥750:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | DL-lysine | ≥750:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | DL-lysine | ≥750:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | DL-lysine | ≥750:1 |

TABLE 14-continued

| Molecular Complex | Additional Coformer | Mass Ratio of Additional Coformer:Molecular Complex Coformer |
|---|---|---|
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | DL-lysine | ≥750:1 |
| zoledronic acid, adenine, and water complex characterized by an X-ray powder diffraction pattern comprising peaks at about 13.6, 15.9, 19.7, 27.9, and 29.5 ± 0.2 degrees two-theta | DL-lysine | ≥750:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | DL-lysine | ≥750:1 |
| zoledronic acid and glycine complex characterized by an X-ray powder diffraction pattern comprising peaks at about 10.2, 17.8, 19.9, 22.9, and 28.1 ± 0.2 degrees two-theta | DL-lysine | ≥750:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | DL-lysine | ≥1000:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | DL-lysine | ≥1000:1 |
| zoledronic diammonia water complex characterized by an X-ray powder diffraction pattern having strong peaks at about 12.2, 13.0, 14.1, 17.1, and 19.3 ± 0.2 degrees two-theta | DL-lysine | ≥1000:1 |
| zoledronic acid, L-lysine, and water complex characterized by an X-ray powder diffraction pattern having peaks at about 9.0, 14.4, 18.1, 26.0, and 29.6 ± 0.2 degrees two-theta | DL-lysine | ≥1000:1 |
| zoledronic acid, L-lysine, and water complex characterized by an X-ray powder diffraction pattern comprising peaks at about 9.6, 10.7, 14.3, 21.4, 23.5 ± 0.2 degrees two theta | DL-lysine | ≥1000:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | DL-lysine | ≥1000:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | DL-lysine | ≥1000:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | DL-lysine | ≥1000:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | DL-lysine | ≥1000:1 |
| zoledronic acid, adenine, and water complex characterized by an X-ray powder diffraction pattern comprising peaks at about 13.6, 15.9, 19.7, 27.9, and 29.5 ± 0.2 degrees two-theta | DL-lysine | ≥1000:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | DL-lysine | ≥1000:1 |
| zoledronic acid and glycine complex characterized by an X-ray powder diffraction pattern comprising peaks at about 10.2, 17.8, 19.9, 22.9, and 28.1 ± 0.2 degrees two-theta | DL-lysine | ≥1000:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | DL-lysine | ≥5000:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | DL-lysine | ≥5000:1 |
| zoledronic diammonia water complex characterized by an X-ray powder diffraction pattern having strong peaks at about 12.2, 13.0, 14.1, 17.1, and 19.3 ± 0.2 degrees two-theta | DL-lysine | ≥5000:1 |
| zoledronic acid, L-lysine, and water complex characterized by an X-ray powder diffraction pattern having peaks at about 9.0, 14.4, 18.1, 26.0, and 29.6 ± 0.2 degrees two-theta | DL-lysine | ≥5000:1 |

TABLE 14-continued

| Molecular Complex | Additional Coformer | Mass Ratio of Additional Coformer:Molecular Complex Coformer |
|---|---|---|
| zoledronic acid, L-lysine, and water complex characterized by an X-ray powder diffraction pattern comprising peaks at about 9.6, 10.7, 14.3, 21.4, 23.5 ± 0.2 degrees two theta | DL-lysine | ≥5000:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | DL-lysine | ≥5000:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | DL-lysine | ≥5000:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | DL-lysine | ≥5000:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | DL-lysine | ≥5000:1 |
| zoledronic acid, adenine, and water complex characterized by an X-ray powder diffraction pattern comprising peaks at about 13.6, 15.9, 19.7, 27.9, and 29.5 ± 0.2 degrees two-theta | DL-lysine | ≥5000:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | DL-lysine | ≥5000:1 |
| zoledronic acid and glycine complex characterized by an X-ray powder diffraction pattern comprising peaks at about 10.2, 17.8, 19.9, 22.9, and 28.1 ± 0.2 degrees two-theta | DL-lysine | ≥5000:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | glycine | ≥5:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | glycine | ≥5:1 |
| zoledronic diammonia water complex characterized by an X-ray powder diffraction pattern having strong peaks at about 12.2, 13.0, 14.1, 17.1, and 19.3 ± 0.2 degrees two-theta | glycine | ≥5:1 |
| zoledronic acid, L-lysine, and water complex characterized by an X-ray powder diffraction pattern having peaks at about 9.0, 14.4, 18.1, 26.0, and 29.6 ± 0.2 degrees two-theta | glycine | ≥5:1 |
| zoledronic acid, L-lysine, and water complex characterized by an X-ray powder diffraction pattern comprising peaks at about 9.6, 10.7, 14.3, 21.4, 23.5 ± 0.2 degrees two theta | glycine | ≥5:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | glycine | ≥5:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | glycine | ≥5:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | glycine | ≥5:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | glycine | ≥5:1 |
| zoledronic acid, adenine, and water complex characterized by an X-ray powder diffraction pattern comprising peaks at about 13.6, 15.9, 19.7, 27.9, and 29.5 ± 0.2 degrees two-theta | glycine | ≥5:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | glycine | ≥5:1 |
| zoledronic acid and glycine complex characterized by an X-ray powder diffraction pattern comprising peaks at about 10.2, 17.8, 19.9, 22.9, and 28.1 ± 0.2 degrees two-theta | glycine | ≥5:1 |

TABLE 14-continued

| Molecular Complex | Additional Coformer | Mass Ratio of Additional Coformer:Molecular Complex Coformer |
|---|---|---|
| zoledronic acid, sodium zoledronate and water complex characterized by an X-ray powder diffraction pattern having peaks at about 8.1, 13.3, 21.5, 24.6, and 25.6 ± 0.2 degrees two-theta | glycine | ≥40:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | glycine | ≥40:1 |
| zoledronic diammonia water complex characterized by an X-ray powder diffraction pattern having strong peaks at about 12.2, 13.0, 14.1, 17.1, and 19.3 ± 0.2 degrees two-theta | glycine | ≥40:1 |
| zoledronic acid, L-lysine, and water complex characterized by an X-ray powder diffraction pattern having peaks at about 9.0, 14.4, 18.1, 26.0, and 29.6 ± 0.2 degrees two-theta | glycine | ≥40:1 |
| zoledronic acid, L-lysine, and water complex characterized by an X-ray powder diffraction pattern comprising peaks at about 9.6, 10.7, 14.3, 21.4, 23.5 ± 0.2 degrees two theta | glycine | ≥40:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | glycine | ≥40:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | glycine | ≥40:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | glycine | ≥40:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | glycine | ≥40:1 |
| zoledronic acid, adenine, and water complex characterized by an X-ray powder diffraction pattern comprising peaks at about 13.6, 15.9, 19.7, 27.9, and 29.5 ± 0.2 degrees two-theta | glycine | ≥40:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | glycine | ≥40:1 |
| zoledronic acid and glycine complex characterized by an X-ray powder diffraction pattern comprising peaks at about 10.2, 17.8, 19.9, 22.9, and 28.1 ± 0.2 degrees two-theta | glycine | ≥40:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | glycine | ≥750:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | glycine | ≥750:1 |
| zoledronic diammonia water complex characterized by an X-ray powder diffraction pattern having strong peaks at about 12.2, 13.0, 14.1, 17.1, and 19.3 ± 0.2 degrees two-theta | glycine | ≥750:1 |
| zoledronic acid, L-lysine, and water complex characterized by an X-ray powder diffraction pattern having peaks at about 9.0, 14.4, 18.1, 26.0, and 29.6 ± 0.2 degrees two-theta | glycine | ≥750:1 |
| zoledronic acid, L-lysine, and water complex characterized by an X-ray powder diffraction pattern comprising peaks at about 9.6, 10.7, 14.3, 21.4, 23.5 ± 0.2 degrees two theta | glycine | ≥750:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | glycine | ≥750:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | glycine | ≥750:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | glycine | ≥750:1 |

TABLE 14-continued

| Molecular Complex | Additional Coformer | Mass Ratio of Additional Coformer:Molecular Complex Coformer |
|---|---|---|
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | glycine | ≥750:1 |
| zoledronic acid, adenine, and water complex characterized by an X-ray powder diffraction pattern comprising peaks at about 13.6, 15.9, 19.7, 27.9, and 29.5 ± 0.2 degrees two-theta | glycine | ≥750:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | glycine | ≥750:1 |
| zoledronic acid and glycine complex characterized by an X-ray powder diffraction pattern comprising peaks at about 10.2, 17.8, 19.9, 22.9, and 28.1 ± 0.2 degrees two-theta | glycine | ≥750:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | glycine | ≥1000:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | glycine | ≥1000:1 |
| zoledronic diammonia water complex characterized by an X-ray powder diffraction pattern having strong peaks at about 12.2, 13.0, 14.1, 17.1, and 19.3 ± 0.2 degrees two-theta | glycine | ≥1000:1 |
| zoledronic acid, L-lysine, and water complex characterized by an X-ray powder diffraction pattern having peaks at about 9.0, 14.4, 18.1, 26.0, and 29.6 ± 0.2 degrees two-theta | glycine | ≥1000:1 |
| zoledronic acid, L-lysine, and water complex characterized by an X-ray powder diffraction pattern comprising peaks at about 9.6, 10.7, 14.3, 21.4, 23.5 ± 0.2 degrees two theta | glycine | ≥1000:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | glycine | ≥1000:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | glycine | ≥1000:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | glycine | ≥1000:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | glycine | ≥1000:1 |
| zoledronic acid, adenine, and water complex characterized by an X-ray powder diffraction pattern comprising peaks at about 13.6, 15.9, 19.7, 27.9, and 29.5 ± 0.2 degrees two-theta | glycine | ≥1000:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | glycine | ≥1000:1 |
| zoledronic acid and glycine complex characterized by an X-ray powder diffraction pattern comprising peaks at about 10.2, 17.8, 19.9, 22.9, and 28.1 ± 0.2 degrees two-theta | glycine | ≥1000:1 |
| zoledronic acid, sodium zoledronate and water complex characterized by an X-ray powder diffraction pattern having peaks at about 8.1, 13.3, 21.5, 24.6, and 25.6 ± 0.2 degrees two-theta | glycine | ≥5000:1 |
| ammonium zoledronic acid salt and water complex characterized by an X-ray powder diffraction pattern having strong peaks at about 11.0, 14.6, 15.4, 19.9, and 29.4 ± 0.2 degrees two-theta | glycine | ≥5000:1 |
| zoledronic diammonia water complex characterized by an X-ray powder diffraction pattern having strong peaks at about 12.2, 13.0, 14.1, 17.1, and 19.3 ± 0.2 degrees two-theta | glycine | ≥5000:1 |
| zoledronic acid, L-lysine, and water complex characterized by an X-ray powder diffraction pattern having peaks at about 9.0, 14.4, 18.1, 26.0, and 29.6 ± 0.2 degrees two-theta | glycine | ≥5000:1 |

TABLE 14-continued

| Molecular Complex | Additional Coformer | Mass Ratio of Additional Coformer:Molecular Complex Coformer |
|---|---|---|
| zoledronic acid, L-lysine, and water complex characterized by an X-ray powder diffraction pattern comprising peaks at about 9.6, 10.7, 14.3, 21.4, 23.5 ± 0.2 degrees two theta | glycine | ≥5000:1 |
| zoledronic acid DL-lysine and water complex characterized by an X-ray powder diffraction pattern comprising peaks at about 8.3, 11.8, 12.3, 15.8, and 20.8 ± 0.2 degrees two-theta | glycine | ≥5000:1 |
| zoledronic acid, DL-lysine, and water complex characterized by an X-ray powder diffraction pattern comprising peaks at about 9.1, 14.7, 18.0, 21.2, and 26.0 ± 0.2 degrees two-theta | glycine | ≥5000:1 |
| zoledronic acid, DL-lysine, and water complex characterized by an X-ray powder diffraction pattern comprising peaks at about 9.7, 10.8, 14.4, 18.9, 21.4 ± 0.2 degrees two theta | glycine | ≥5000:1 |
| zoledronic acid, zoledronic, DL-lysine, ethanol, and water complex characterized by an X-ray powder diffraction pattern comprising peaks at about 8.8, 9.7, 17.6, 23.1, and 26.5 ± 0.2 degrees two-theta | glycine | ≥5000:1 |
| zoledronic acid, adenine, and water complex characterized by an X-ray powder diffraction pattern comprising peaks at about 13.6, 15.9, 19.7, 27.9, and 29.5 ± 0.2 degrees two-theta | glycine | ≥5000:1 |
| zoledronic acid, nicotinamide, and water complex characterized by an X-ray powder diffraction pattern comprising peaks at about 13.1, 15.2, 21.0, 23.9, and 26.5 ± 0.2 degrees two-theta | glycine | ≥5000:1 |
| zoledronic acid and glycine complex characterized by an X-ray powder diffraction pattern comprising peaks at about 10.2, 17.8, 19.9, 22.9, and 28.1 ± 0.2 degrees two-theta | glycine | ≥5000:1 |

Particular embodiments of compositions of the present invention comprising: a crystalline molecular complex (left column), an additional coformer (middle column), and the ratio of the additional coformer to molecular complex coformer (by mass) is indicated in the far right column. Each row of the above table represents an individual embodiment of the present invention.

TABLE 15

| Bisphosphonic Acid | Amount of Bisphosphonic Acid per Unit Dose of | Amino Acid | Amount of Amino Acid per Unit Dose of Bisphosphonic Acid |
|---|---|---|---|
| zoledronic acid | 40-120 mg | lysine | ≥500 mg |
| zoledronic acid | 40-120 mg | lysine | ≥750 mg |
| zoledronic acid | 40-120 mg | lysine | ≥1000 mg |
| zoledronic acid | 40-120 mg | lysine | ≥1250 mg |
| zoledronic acid | 40-120 mg | lysine | ≥1500 mg |
| zoledronic acid | 40-120 mg | lysine | ≥1750 mg |
| zoledronic acid | 40-120 mg | lysine | ≥2000 mg |
| zoledronic acid | 40-120 mg | lysine | ≥2250 mg |
| zoledronic acid | 40-120 mg | lysine | ≥2500 mg |
| zoledronic acid | 40-120 mg | lysine | ≥2750 mg |
| zoledronic acid | 40-120 mg | lysine | ≥3000 mg |
| zoledronic acid | 40-120 mg | L-lysine | ≥500 mg |
| zoledronic acid | 40-120 mg | L-lysine | ≥750 mg |
| zoledronic acid | 40-120 mg | L-lysine | ≥1000 mg |
| zoledronic acid | 40-120 mg | L-lysine | ≥1250 mg |
| zoledronic acid | 40-120 mg | L-lysine | ≥1500 mg |
| zoledronic acid | 40-120 mg | L-lysine | ≥1750 mg |
| zoledronic acid | 40-120 mg | L-lysine | ≥2000 mg |
| zoledronic acid | 40-120 mg | L-lysine | ≥2250 mg |
| zoledronic acid | 40-120 mg | L-lysine | ≥2500 mg |
| zoledronic acid | 40-120 mg | L-lysine | ≥2750 mg |
| zoledronic acid | 40-120 mg | L-lysine | ≥3000 mg |
| zoledronic acid | 40-120 mg | DL-lysine | ≥500 mg |
| zoledronic acid | 40-120 mg | DL-lysine | ≥750 mg |
| zoledronic acid | 40-120 mg | DL-lysine | ≥1000 mg |
| zoledronic acid | 40-120 mg | DL-lysine | ≥1250 mg |
| zoledronic acid | 40-120 mg | DL-lysine | ≥1500 mg |
| zoledronic acid | 40-120 mg | DL-lysine | ≥1750 mg |
| zoledronic acid | 40-120 mg | DL-lysine | ≥2000 mg |
| zoledronic acid | 40-120 mg | DL-lysine | ≥2250 mg |
| zoledronic acid | 40-120 mg | DL-lysine | ≥2500 mg |
| zoledronic acid | 40-120 mg | DL-lysine | ≥2750 mg |
| zoledronic acid | 40-120 mg | DL-lysine | ≥3000 mg |
| zoledronic acid | 40-120 mg | glycine | ≥500 mg |
| zoledronic acid | 40-120 mg | glycine | ≥750 mg |
| zoledronic acid | 40-120 mg | glycine | ≥1000 mg |
| zoledronic acid | 40-120 mg | glycine | ≥1250 mg |
| zoledronic acid | 40-120 mg | glycine | ≥1500 mg |
| zoledronic acid | 40-120 mg | glycine | ≥1750 mg |
| zoledronic acid | 40-120 mg | glycine | ≥2000 mg |
| zoledronic acid | 40-120 mg | glycine | ≥2250 mg |
| zoledronic acid | 40-120 mg | glycine | ≥2500 mg |
| zoledronic acid | 40-120 mg | glycine | ≥2750 mg |
| zoledronic acid | 40-120 mg | glycine | ≥3000 mg |
| zoledronic acid | 50-250 mg | lysine | ≥500 mg |
| zoledronic acid | 50-250 mg | lysine | ≥750 mg |
| zoledronic acid | 50-250 mg | lysine | ≥1000 mg |
| zoledronic acid | 50-250 mg | lysine | ≥1250 mg |
| zoledronic acid | 50-250 mg | lysine | ≥1500 mg |
| zoledronic acid | 50-250 mg | lysine | ≥1750 mg |
| zoledronic acid | 50-250 mg | lysine | ≥2000 mg |
| zoledronic acid | 50-250 mg | lysine | ≥2250 mg |
| zoledronic acid | 50-250 mg | lysine | ≥2500 mg |
| zoledronic acid | 50-250 mg | lysine | ≥2750 mg |
| zoledronic acid | 50-250 mg | lysine | ≥3000 mg |
| zoledronic acid | 50-250 mg | L-lysine | ≥500 mg |
| zoledronic acid | 50-250 mg | L-lysine | ≥750 mg |
| zoledronic acid | 50-250 mg | L-lysine | ≥1000 mg |
| zoledronic acid | 50-250 mg | L-lysine | ≥1250 mg |
| zoledronic acid | 50-250 mg | L-lysine | ≥1500 mg |
| zoledronic acid | 50-250 mg | L-lysine | ≥1750 mg |
| zoledronic acid | 50-250 mg | L-lysine | ≥2000 mg |
| zoledronic acid | 50-250 mg | L-lysine | ≥2250 mg |
| zoledronic acid | 50-250 mg | L-lysine | ≥2500 mg |

TABLE 15-continued

| Bisphosphonic Acid | Amount of Bisphosphonic Acid per Unit Dose of | Amino Acid | Amount of Amino Acid per Unit Dose of Bisphosphonic Acid |
|---|---|---|---|
| zoledronic acid | 50-250 mg | L-lysine | ≥2750 mg |
| zoledronic acid | 50-250 mg | L-lysine | ≥3000 mg |
| zoledronic acid | 50-250 mg | DL-lysine | ≥500 mg |
| zoledronic acid | 50-250 mg | DL-lysine | ≥750 mg |
| zoledronic acid | 50-250 mg | DL-lysine | ≥1000 mg |
| zoledronic acid | 50-250 mg | DL-lysine | ≥1250 mg |
| zoledronic acid | 50-250 mg | DL-lysine | ≥1500 mg |
| zoledronic acid | 50-250 mg | DL-lysine | ≥1750 mg |
| zoledronic acid | 50-250 mg | DL-lysine | ≥2000 mg |
| zoledronic acid | 50-250 mg | DL-lysine | ≥2250 mg |
| zoledronic acid | 50-250 mg | DL-lysine | ≥2500 mg |
| zoledronic acid | 50-250 mg | DL-lysine | ≥2750 mg |
| zoledronic acid | 50-250 mg | DL-lysine | ≥3000 mg |
| zoledronic acid | 50-250 mg | glycine | ≥500 mg |
| zoledronic acid | 50-250 mg | glycine | ≥750 mg |
| zoledronic acid | 50-250 mg | glycine | ≥1000 mg |
| zoledronic acid | 50-250 mg | glycine | ≥1250 mg |
| zoledronic acid | 50-250 mg | glycine | ≥1500 mg |
| zoledronic acid | 50-250 mg | glycine | ≥1750 mg |
| zoledronic acid | 50-250 mg | glycine | ≥2000 mg |
| zoledronic acid | 50-250 mg | glycine | ≥2250 mg |
| zoledronic acid | 50-250 mg | glycine | ≥2500 mg |
| zoledronic acid | 50-250 mg | glycine | ≥2750 mg |
| zoledronic acid | 50-250 mg | glycine | ≥3000 mg |
| zoledronic acid | 40-120 mg | lysine | 500 mg-1000 mg |
| zoledronic acid | 40-120 mg | lysine | 750 mg-1250 |
| zoledronic acid | 40-120 mg | lysine | 1000 mg-1500 mg |
| zoledronic acid | 40-120 mg | lysine | 1250 mg-1750 mg |
| zoledronic acid | 40-120 mg | lysine | 1500 mg-2000 mg |
| zoledronic acid | 40-120 mg | lysine | 1750 mg-2250 mg |
| zoledronic acid | 40-120 mg | lysine | ≥2000 mg-2500 mg |
| zoledronic acid | 40-120 mg | lysine | ≥2250 mg-2750 mg |
| zoledronic acid | 40-120 mg | lysine | ≥2500 mg-3000 mg |
| zoledronic acid | 1-100 mg | lysine | 500 mg-1000 mg |
| zoledronic acid | 1-100 mg | lysine | 750 mg-1250 |
| zoledronic acid | 1-100 mg | lysine | 1000 mg-1500 mg |
| zoledronic acid | 1-100 mg | lysine | 1250 mg-1750 mg |
| zoledronic acid | 1-100 mg | lysine | 1500 mg-2000 mg |
| zoledronic acid | 1-100 mg | lysine | 1750 mg-2250 mg |
| zoledronic acid | 1-100 mg | lysine | ≥2000 mg-2500 mg |
| zoledronic acid | 1-100 mg | lysine | ≥2250 mg-2750 mg |
| zoledronic acid | 1-100 mg | lysine | ≥2500 mg-3000 mg |
| zoledronic acid | 100-200 mg | lysine | 500 mg-1000 mg |
| zoledronic acid | 100-200 mg | lysine | 750 mg-1250 |
| zoledronic acid | 100-200 mg | lysine | 1000 mg-1500 mg |
| zoledronic acid | 100-200 mg | lysine | 1250 mg-1750 mg |
| zoledronic acid | 100-200 mg | lysine | 1500 mg-2000 mg |
| zoledronic acid | 100-200 mg | lysine | 1750 mg-2250 mg |
| zoledronic acid | 100-200 mg | lysine | ≥2000 mg-2500 mg |
| zoledronic acid | 100-200 mg | lysine | ≥2250 mg-2750 mg |
| zoledronic acid | 100-200 mg | lysine | ≥2500 mg-3000 mg |
| zoledronic acid | 200-300 mg | lysine | 500 mg-1000 mg |
| zoledronic acid | 200-300 mg | lysine | 750 mg-1250 |
| zoledronic acid | 200-300 mg | lysine | 1000 mg-1500 mg |
| zoledronic acid | 200-300 mg | lysine | 1250 mg-1750 mg |
| zoledronic acid | 200-300 mg | lysine | 1500 mg-2000 mg |
| zoledronic acid | 200-300 mg | lysine | 1750 mg-2250 mg |
| zoledronic acid | 200-300 mg | lysine | ≥2000 mg-2500 mg |
| zoledronic acid | 200-300 mg | lysine | ≥2250 mg-2750 mg |
| zoledronic acid | 200-300 mg | lysine | ≥2500 mg-3000 mg |
| zoledronic acid | 40-120 mg | glycine | 500 mg-1000 mg |
| zoledronic acid | 40-120 mg | glycine | 750 mg-1250 |
| zoledronic acid | 40-120 mg | glycine | 1000 mg-1500 mg |
| zoledronic acid | 40-120 mg | glycine | 1250 mg-1750 mg |
| zoledronic acid | 40-120 mg | glycine | 1500 mg-2000 mg |
| zoledronic acid | 40-120 mg | glycine | 1750 mg-2250 mg |
| zoledronic acid | 40-120 mg | glycine | ≥2000 mg-2500 mg |
| zoledronic acid | 40-120 mg | glycine | ≥2250 mg-2750 mg |
| zoledronic acid | 40-120 mg | glycine | ≥2500 mg-3000 mg |
| zoledronic acid | 100-200 mg | glycine | 500 mg-1000 mg |
| zoledronic acid | 100-200 mg | glycine | 750 mg-1250 |
| zoledronic acid | 100-200 mg | glycine | 1000 mg-1500 mg |
| zoledronic acid | 100-200 mg | glycine | 1250 mg-1750 mg |
| zoledronic acid | 100-200 mg | glycine | 1500 mg-2000 mg |
| zoledronic acid | 100-200 mg | glycine | 1750 mg-2250 mg |
| zoledronic acid | 100-200 mg | glycine | ≥2000 mg-2500 mg |
| zoledronic acid | 100-200 mg | glycine | ≥2250 mg-2750 mg |
| zoledronic acid | 100-200 mg | glycine | ≥2500 mg-3000 mg |
| zoledronic acid | 200-300 mg | glycine | 500 mg-1000 mg |
| zoledronic acid | 200-300 mg | glycine | 750 mg-1250 |
| zoledronic acid | 200-300 mg | glycine | 1000 mg-1500 mg |
| zoledronic acid | 200-300 mg | glycine | 1250 mg-1750 mg |
| zoledronic acid | 200-300 mg | glycine | 1500 mg-2000 mg |
| zoledronic acid | 200-300 mg | glycine | 1750 mg-2250 mg |
| zoledronic acid | 200-300 mg | glycine | ≥2000 mg-2500 mg |
| zoledronic acid | 200-300 mg | glycine | ≥2250 mg-2750 mg |
| zoledronic acid | 200-300 mg | glycine | ≥2500 mg-3000 mg |

Particular embodiments of unit doses of a pharmaceutical composition of the present invention comprising: a bisphosphonic acid (left column), an amino acid, present as either a molecular complex coformer, additional coformer or both molecular complex coformer and additional coformer (middle column), and amount of the amino acid in a unit dose of bisphosphonic acid (right column). Each row of the above table represents an individual embodiment of the present invention.

The invention claimed is:
1. A composition comprising at least one API and at least one coformer:
   wherein said at least one coformer is a molecular complex coformer and/or an additional coformer;
   wherein said API and said molecular complex coformer form a molecular complex;
   wherein said API is a bisphosphonic acid and said at least one coformer is selected from the group consisting of sodium, ammonium, ammonia, lysine, nicotinamide, adenine, and glycine; and
   wherein said molecular complex is a crystalline molecular complex selected from the group consisting of:
   a) a crystalline zoledronic acid, sodium zoledronate and water molecular complex characterized by an X-ray powder diffraction pattern having peaks at about 8.1, 13.3, 21.5, 24.6, and 25.6±0.2 degrees two-theta;
   b) a crystalline ammonium zoledronic acid salt and water molecular complex characterized by an X-ray powder diffraction pattern having strong peaks at about 11.0, 14.6, 15.4, 19.9, and 29.4±0.2 degrees two-theta;
   c) a crystalline zoledronic diammonia water molecular complex characterized by an X-ray powder diffraction pattern having strong peaks at about 12.2, 13.0, 14.1, 17.1, and 19.3±0.2 degrees two-theta;
   d) a crystalline zoledronic acid, L-lysine, and water molecular complex characterized by an X-ray powder diffraction pattern comprising peaks at about 9.0, 14.4, 18.1, 26.0, and 29.6±0.2 degrees two-theta;
   e) a crystalline zoledronic acid, L-lysine, and water molecular complex characterized by an X-ray powder diffraction pattern comprising peaks at about 9.6, 10.7, 14.3, 21.4, 23.5±0.2 degrees two-theta;
   f) a crystalline zoledronic acid DL-lysine and water molecular complex characterized by an X-ray powder diffraction pattern comprising peaks at about 8.3, 11.8, 12.3, 15.8, and 20.8±0.2 degrees two-theta;
   g) a crystalline zoledronic acid, DL-lysine, and water molecular complex characterized by an X-ray powder diffraction pattern comprising peaks at about 9.1, 14.7, 18.0, 21.2, and 26.0±0.2 degrees two-theta;

h) a crystalline zoledronic acid, DL-lysine, and water molecular complex characterized by an X-ray powder diffraction pattern comprising peaks at about 9.7, 10.8, 14.4, 18.9, 21.4±0.2 degrees two-theta;

i) a crystalline zoledronic acid, zoledronic, DL-lysine, ethanol, and water complex characterized by an X-ray powder diffraction pattern comprising peaks at about 8.8, 9.7, 17.6, 23.1, and 26.5±0.2 degrees two-theta;

j) a crystalline zoledronic acid, adenine, and water molecular complex characterized by an X-ray powder diffraction pattern comprising peaks at about 13.6, 15.9, 19.7, 27.9, and 29.5±0.2 degrees two-theta;

k) a crystalline zoledronic acid, nicotinamide, and water molecular complex characterized by an X-ray powder diffraction pattern comprising peaks at about 13.1, 15.2, 21.0, 23.9, and 26.5±0.2 degrees two-theta; and l) a crystalline zoledronic acid and glycine molecular complex characterized by an X-ray powder diffraction pattern comprising peaks at about 10.2, 17.8, 19.9, 22.9, and 28.1±0.2 degrees two-theta.

2. A pharmaceutical composition comprising the composition of claim 1 and a pharmaceutically acceptable excipient.

3. The pharmaceutical composition of claim 2, wherein said coformer:
 a) increases the intestinal permeability of the API;
 b) increases the $C_{max}$ of the API;
 c) increases the aqueous solubility of the API;
 d) increases the stability of the API under ambient conditions; and/or
 e) increases the oral bioavailability of the API.

4. The pharmaceutical composition of claim 2, wherein the pharmaceutical composition is an oral dosage form.

5. A unit dose of the pharmaceutical composition of claim 2, wherein said unit dose comprises at least about 250 mg of the coformer.

6. The unit dose of claim 5, wherein the coformer is lysine or glycine.

7. A method for enhancing the oral bioavailability or permeability of a bisphosphonic acid, said method comprising the step of combining said bisphosphonic acid with a coformer selected from the group consisting of sodium, ammonium, ammonia, lysine, nicotinamide, adenine, and glycine, to form the pharmaceutical composition of claim 2.

8. A method of treating a disease state for which a bisphosphonic acid is indicated, said method comprising the step of administering to a patient in need of said bisphosphonic acid a therapeutically effective amount of said pharmaceutical composition of claim 2.

9. The method of claim 8, wherein said disease state is associated with osteoporosis, hypercalcemia, cancer induced bone metastasis, Paget's disease, or adjuvant or neoadjuvant cancer therapies.

* * * * *